US011091518B2

(12) United States Patent
Weiner et al.

(10) Patent No.: US 11,091,518 B2
(45) Date of Patent: Aug. 17, 2021

(54) FILOVIRUS CONSENSUS ANTIGENS, NUCLEIC ACID CONSTRUCTS AND VACCINES MADE THEREFROM, AND METHODS OF USING SAME

(71) Applicants: The Trustees of the University of Pennsylvania, Philadelphia, PA (US); THE WISTAR INSTITUTE OF ANATOMY AND BIOLOGY, Philadelphia, PA (US); Inovio Pharmaceuticals, Inc., Plymouth Meeting, PA (US)

(72) Inventors: David B. Weiner, Merion, PA (US); Ami Patel, Philadelphia, PA (US); Jian Yan, Wallingford, PA (US)

(73) Assignees: The Trustees of the University of Pennsylvania, Philadelphia, PA (US); THE WISTAR INSTITUTE OF ANATOMY AND BIOLOGY, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 0 days.

(21) Appl. No.: 16/098,912

(22) PCT Filed: May 5, 2017

(86) PCT No.: PCT/US2017/031215
§ 371 (c)(1),
(2) Date: Nov. 5, 2018

(87) PCT Pub. No.: WO2017/192947
PCT Pub. Date: Nov. 9, 2017

(65) Prior Publication Data
US 2019/0153040 A1    May 23, 2019

Related U.S. Application Data

(60) Provisional application No. 62/332,372, filed on May 5, 2016, provisional application No. 62/402,519, filed on Sep. 30, 2016, provisional application No. 62/483,979, filed on Apr. 11, 2017.

(51) Int. Cl.
| C07K 14/005 | (2006.01) |
| A61K 31/12 | (2006.01) |
| A61K 39/12 | (2006.01) |
| A61K 38/00 | (2006.01) |
| A61P 31/12 | (2006.01) |
| A61K 9/00 | (2006.01) |
| A61K 39/39 | (2006.01) |
| C07K 14/54 | (2006.01) |
| A61K 39/00 | (2006.01) |

(52) U.S. Cl.
CPC ........... *C07K 14/005* (2013.01); *A61K 9/0009* (2013.01); *A61K 39/12* (2013.01); *A61K 39/39* (2013.01); *A61P 31/12* (2018.01); *C07K 14/54* (2013.01); *C07K 14/5434* (2013.01); *C07K 14/5443* (2013.01); *A61K 38/00* (2013.01); *A61K 2039/53* (2013.01); *A61K 2039/54* (2013.01); *A61K 2039/545* (2013.01); *A61K 2039/55527* (2013.01); *A61K 2039/55538* (2013.01); *A61K 2039/58* (2013.01); *A61K 2039/70* (2013.01); *C07K 2319/02* (2013.01); *C12N 2760/14122* (2013.01); *C12N 2760/14134* (2013.01)

(58) Field of Classification Search
None
See application file for complete search history.

(56) References Cited

U.S. PATENT DOCUMENTS

| 9,597,388 B2 * | 3/2017 | Weiner ................. A61P 31/14 |
| 2011/0182938 A1 | 7/2011 | Weiner |
| 2015/0335726 A1 | 11/2015 | Weiner |
| 2016/0045589 A1 | 2/2016 | Weiner |

FOREIGN PATENT DOCUMENTS

| WO | 2013155441 A1 | 10/2013 |
| WO | 2016054003 A1 | 4/2016 |

OTHER PUBLICATIONS

Carroll et al., Journal of Virology, 2013, 87(5):2608-2616. (Year: 2013).*
GenBank Accession No. KC242796.1 (2014). (Year: 2014).*
GenBank Accession No. AGB56794.1 (2014) (Year: 2014).*
Ami Patel et al: "450. A Single Immunization With Optimized DNA Vaccines Protects Against Lethal Ebola Virus Challenge in Mice and Induces Seroconversion in Non-Human Primates Following a DNA Prime-DNA Boost Approach", Molecular Therapy : The Journal of the American Society of Gene Therapy, vol. 23, May 1, 2015 (May 1, 2015), pp. S178-S179, XP055652495, US, ISSN: 1525-0016, DOI: 10.1016/S1525-0016(16)34059-X.
Rebecca J Grant-Klein et al: "Codon-optimized filovirus DNA vaccines delivered by intramuscular electroporation protect cynomolgus macaques from lethal Ebola and Marburg virus challenges", Human Vaccines and Immunotherapeutics, vol. 11, No. 8, Aug. 3, 2015 (Aug. 3, 2015), pp. 1991-2004, XP055652512, US ISSN: 2164-5515, DOI: 10.1080/21645515.2015.1039757.

(Continued)

*Primary Examiner* — Stacy B Chen
(74) *Attorney, Agent, or Firm* — Riverside Law LLP

(57) ABSTRACT

Nucleic acid molecules and compositions comprising one or more nucleic acid sequences that encode a consensus *Ebolavirus* glycoproteinimmunogens are disclosed. The coding sequences optionally include operable linked coding sequence that encode a signal peptide. Immunomodulatory methods and methods of inducing an immune response against *Ebolavirus* are disclosed. Method of preventing *Ebolavirus* and methods of treating individuals infected with *Ebolavirus* are disclosed. Consensus *Ebolavirus* proteins are disclosed.

24 Claims, 60 Drawing Sheets

Specification includes a Sequence Listing.

(56) References Cited

OTHER PUBLICATIONS

Shedlock DJ, et al. Induction of broad cytotoxic T cells by protective DNA vaccination against marburg and ebola. Mol Ther 2013;21:1432-1444.

\* cited by examiner

Figure 3A-3C

Experimental vaccines against Ebola

The Ebola viral glycoprotein (GP) is the major antigenic target for vaccines: Antibody & T cell target Vaccines currently in clinical trials

- rVSVΔG/ZEBOVGP
- ChAd3 prime + MVA boost — Advantages: immunogenic, protective in NHPs, single dose protection
- MVA pan-filovirus Drawbacks:
- development of anti-vector immunity
- duration of memory response uncertain
- adverse reactions in human clinical trials
- may not be suitable for all populations An additional platform with a cleaner safety profile that can induce strong immune responses against heterologous Zaire Ebola viruses would be very beneficial

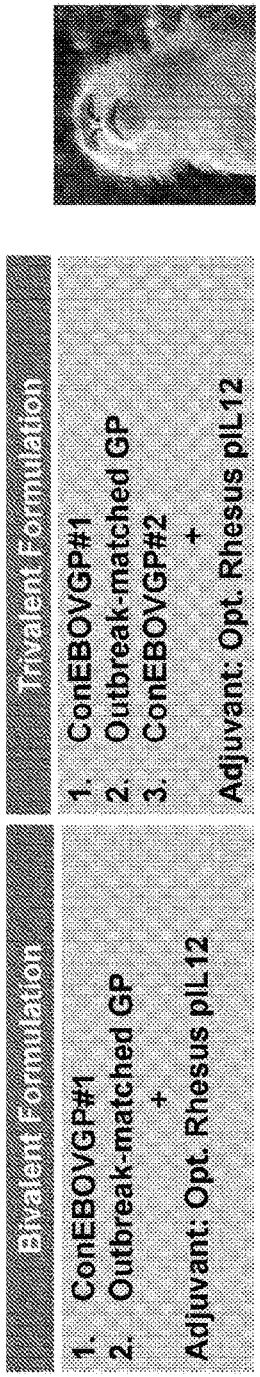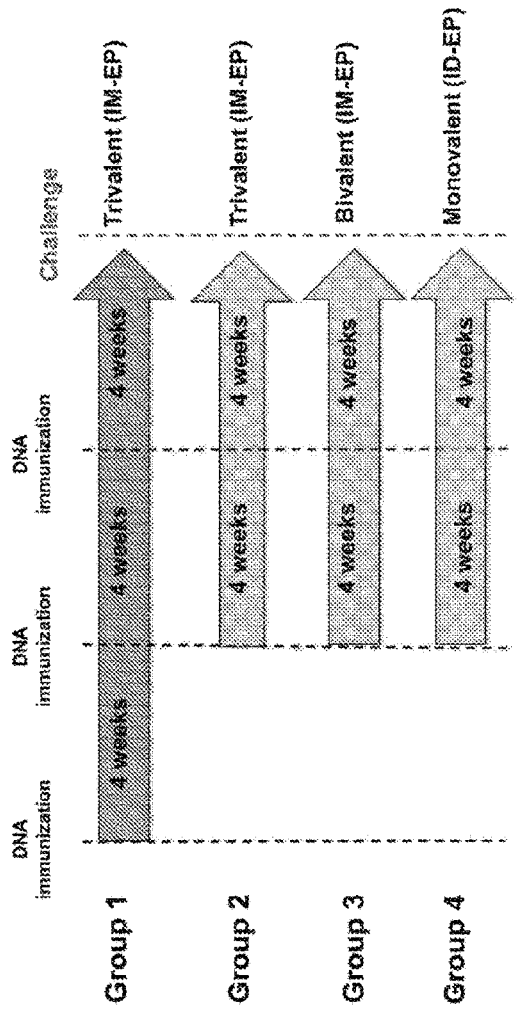
Figure 14

GP DNA formulation vaccines protect against lethal Zaire Ebola virus (Makona) challenge Challenge dose = 1000 TCID50 Guinea-Makona 2014 C07 virus (7-U reference strain), 28 days post-final DNA immunization Animals were monitored for 28 days post-challenge.

Surviving animals did not have any significant signs of disease. They also maintained normal CBC and enzyme levels

Figure 16

EBOV-001 phase I clinical (NCT02464670)

Open-Label Study of INO-4212 With or Without INO-9012, Administered IM or ID Followed by Electroporation in Healthy Volunteers Primary outcome: safety assessment
Secondary outcome: immunological assessment
Other: intradermal (ID) delivery vs intramuscular (IM) delivery

| Cohort | Vaccine | Schedule | Route | Dose (mg) |
|---|---|---|---|---|
| 1 | ConEBOVGP#1 | 0-4-12 weeks | IM | 2 |
| 2 | Guinea-GP | 0-4-12 weeks | IM | 2 |
| 3 | ConEBOVGP#1 | 0-4-12 weeks | ID | 2 |
| 4 | ConEBOVGP#1 + Guinea-GP | 0-4-12 weeks | IM | 4 |
| 5 | ConEBOVGP#1 + Guinea-GP + plasmid IL12 | 0-4-12 weeks | IM | 4+1 |

Figure 17

EBOV-001 seroconversion

Figure 18

69 subjects total

ELISA analysis:
- baseline
- week 2
- week 6
- week 14

Seropositive = + IgG antibody response to Ebola Zaire glycoprotein

Week 14: IgG GMT = $10^3$-$10^5$

Comparison with other Ebola vaccine platforms currently in clinical trials

| | ChAd3/MVA-GP | rVSV/ZEBOVGP | GP DNA Vaccine |
|---|---|---|---|
| | NIAID VRC/GSK | PHAC/Newlink/Merck | Inovio |
| Transgene | 1976 GP | 1995 GP | Consensus GP 2014 GP |
| Route of administration | I.M. | I.M. | I.M. or I.D. |
| Regimen | ChAd3 prime (60-90% sero), MVA boost | Single injection | 2 injection (100% sero. ID) 3 injection (100% sero. IM) |
| Side Effects | Fever, Fatigue, Arthralgia Lymphopenia | Fever, Fatigue, Arthralgia | None |
| Injection Site Pain | Yes | Yes | Yes |
| Antibody titers | >$10^3$ | >$10^3$ | $10^3$-$10^5$ |
| T cell responses | Yes | N/A | Yes |
| Cold-chain | -20C | -20C | 4C |
| Other notes | Need MVA boost to generate long-term memory | Ring-vaccine trial, long-term memory not confirmed | Can be re-administered Memory study ongoing |

***Rampling et al 2015, Legenwood et al 2014, Agnandji et al 2015, Henao-Restrepo et al 2015, Tapia et al 2015

Some of the side effects of rVSV/ZEBOVGP and ChAd3/MVAGP overlap with symptoms of Ebola

Figure 20

EBOV001 ELISA

- 69 subjects from all cohorts (1-5) are included in analysis.
- ELISA analysis from baseline, week 2, week 6, week 14.
- Protein used was Ebola Zaire

Cohort descriptions

| Cohort | Vaccine | Plasmids included in vaccine | Schedule | Route | Dose (mg) |
|---|---|---|---|---|---|
| 1 | INO-4201 | pGX4201 | 0-4-12 weeks | IM | 2 |
| 2 | INO-4202 | pGX4202 | 0-4-12 weeks | IM | 2 |
| 3 | INO-4201 | pGX4201 | 0-4-12 weeks | ID | 2 |
| 4 | INO-4212 | pGX4201 and pGX4202 | 0-4-12 weeks | IM | 4 |
| 5 | INO-4212 +INO-9012 | pGX4201, pGX4202, and pGX6001 | 0-4-12 weeks | IM | 4+1 |

| | | Ethnicity | | Race | | | | | |
|---|---|---|---|---|---|---|---|---|---|
| | | Hispanic | Not Hispanic | Black | White | Asian | BI-RACIAL | West African Origin | |
| Number subjects | 74 | 8 | 66 | 34 | 37 | 2 | 1 | 1 | Sierra Leone |
| Male | 25 | 4 | 21 | 9 | 15 | 1 | 0 | | Subject 4201-007, Cohort 1 |
| Female | 49 | 4 | 45 | 25 | 22 | 1 | 1 | | |

Figure 21

EBOV001 ELISpot

- 75 subjects from all cohorts (1-5) are included in analysis.
- ELISpot analysis from baseline, week 2, week 6, week 14.
- 4 peptide pools (Zaire) used for stimulation:
  - Pool 1 (pp1-28)
  - Pool 2 (pp29-56)
  - Pool 3 (pp57-84)
  - Pool 4 (pp85-112)

| Cohort | Vaccine | Plasmids included in vaccine | Schedule | Route | Dose (mg) |
|---|---|---|---|---|---|
| 1 | INO-4201 | pGX4201 | 0-4-12 weeks | IM | 2 |
| 2 | INO-4202 | pGX4202 | 0-4-12 weeks | IM | 2 |
| 3 | INO-4201 | pGX4201 | 0-4-12 weeks | ID | 2 |
| 4 | INO-4212 | pGX4201 and pGX4202 | 0-4-12 weeks | IM | 4 |
| 5 | INO-4212+INO-9012 | pGX4201, pGX4202 and pGX6001 | 0-4-12 weeks | IM | 4+1 |

Figure 25

Responder Analysis

Vaccine Responders – All Subjects

| All Subjects | Responder | Total | % Responders |
|---|---|---|---|
| EBOV | 4 | 75 | 5.3% |
| GP Pool 1 | 31 | 75 | 41.3% |
| GP Pool 2 | 22 | 75 | 29.3% |
| GP Pool 3 | 5 | 75 | 6.7% |
| GP Pool 4 | 3 | 75 | 4.0% |

| | Response by pool | | | | |
|---|---|---|---|---|---|
| | Cohort 1 | Cohort 2 | Cohort 3 | Cohort 4 | Cohort 5 |
| EBOV | 0/15 | 1/15 | 2/15 | 1/15 | 0/15 |
| GP pool 1 | 6/15 | 8/15 | 4/15 | 7/15 | 6/15 |
| GP pool 2 | 5/15 | 4/15 | 3/15 | 5/15 | 5/15 |
| GP pool 3 | 0/15 | 1/15 | 2/15 | 2/15 | 0/15 |
| GP pool 4 | 0/15 | 0/15 | 2/15 | 1/15 | 0/15 |

| | Response by Cohort | | | | |
|---|---|---|---|---|---|
| | Cohort 1 | Cohort 2 | Cohort 3 | Cohort 4 | Cohort 5 |
| EBOV | 0/15 | 1/15 | 2/15 | 1/15 | 0/15 |
| Any Pool | 7/15 | 8/15 | 6/15 | 8/15 | 7/15 |

| All Subjects | Responder | Total | % Responders |
|---|---|---|---|
| EBOV | 4 | 75 | 5.3% |
| Any Pool | 36 | 75 | 48.0% |

| | % Response by pool | | | | |
|---|---|---|---|---|---|
| | Cohort 1 | Cohort 2 | Cohort 3 | Cohort 4 | Cohort 5 |
| EBOV | 0.0% | 6.7% | 13.3% | 6.7% | 0.0% |
| GP pool 1 | 40.0% | 53.3% | 26.7% | 46.7% | 40.0% |
| GP pool 2 | 33.3% | 26.7% | 20.0% | 33.3% | 33.3% |
| GP pool 3 | 0.0% | 6.7% | 13.3% | 13.3% | 0.0% |
| GP pool 4 | 0.0% | 0.0% | 13.3% | 6.7% | 0.0% |

| | % Response by Cohort | | | | |
|---|---|---|---|---|---|
| | Cohort 1 | Cohort 2 | Cohort 3 | Cohort 4 | Cohort 5 |
| EBOV | 0.0% | 6.7% | 13.3% | 6.7% | 0.0% |
| Any Pool | 46.7% | 53.3% | 40.0% | 53.3% | 46.7% |

Figure 33

Responder Analysis

Vaccine Responders – Baseline Outliers (n=8) Removed

All Subjects

|         | Responder | Total | % Responders |
|---------|-----------|-------|--------------|
| EBOV    | 19        | 67    | 28.4%        |
| GP Pool 1 | 44      | 67    | 65.7%        |
| GP Pool 2 | 33      | 67    | 49.3%        |
| GP Pool 3 | 6       | 67    | 9.0%         |
| GP Pool 4 | 4       | 67    | 6.0%         |

All Subjects

|          | Responder | Total | % Responders |
|----------|-----------|-------|--------------|
| EBOV     | 19        | 67    | 28.4%        |
| Any Pool | 46        | 67    | 68.7%        |

Response by pool

|          | Cohort 1 | Cohort 2 | Cohort 3 | Cohort 4 | Cohort 5 |
|----------|----------|----------|----------|----------|----------|
| EBOV     | 2/12     | 5/13     | 3/14     | 5/13     | 4/15     |
| GP pool 1| 7/12     | 11/13    | 8/14     | 10/13    | 8/15     |
| GP pool 2| 6/12     | 9/13     | 7/14     | 5/13     | 6/15     |
| GP pool 3| 0/12     | 4/13     | 1/14     | 0/13     | 1/15     |
| GP pool 4| 0/12     | 2/13     | 1/14     | 0/13     | 1/15     |

% Response by pool

|          | Cohort 1 | Cohort 2 | Cohort 3 | Cohort 4 | Cohort 5 |
|----------|----------|----------|----------|----------|----------|
| EBOV     | 16.7%    | 38.5%    | 21.4%    | 38.5%    | 26.7%    |
| GP pool 1| 58.3%    | 84.6%    | 57.1%    | 76.9%    | 53.3%    |
| GP pool 2| 50.0%    | 69.2%    | 50.0%    | 38.5%    | 40.0%    |
| GP pool 3| 0.0%     | 30.8%    | 7.1%     | 0.0%     | 6.7%     |
| GP pool 4| 0.0%     | 15.4%    | 7.1%     | 0.0%     | 6.7%     |

Response by Cohort

|          | Cohort 1 | Cohort 2 | Cohort 3 | Cohort 4 | Cohort 5 |
|----------|----------|----------|----------|----------|----------|
| EBOV     | 2/12     | 5/13     | 3/14     | 5/13     | 4/15     |
| Any Pool | 8/12     | 11/13    | 9/14     | 10/13    | 8/15     |

% Response by Cohort

|          | Cohort 1 | Cohort 2 | Cohort 3 | Cohort 4 | Cohort 5 |
|----------|----------|----------|----------|----------|----------|
| EBOV     | 16.7%    | 38.5%    | 21.4%    | 38.5%    | 26.7%    |
| Any Pool | 66.7%    | 84.6%    | 64.3%    | 76.9%    | 53.3%    |

Figure 34

EBOV001 ICS

- 47 subjects from all cohorts (1-5) are included in analysis. Cohort 5 is currently underrepresented.
- ICS analysis performed at baseline and week 14
- A single EBOV peptide pool composed of Pools 1-4 is used for stimulation Cohort descriptions

| Cohort | Vaccine | Plasmids included in vaccine | Schedule | Route | Dose (mg) |
|---|---|---|---|---|---|
| 1 | INO-4201 | pGX4201 | 0-4-12 weeks | IM | 2 |
| 2 | INO-4202 | pGX4202 | 0-4-12 weeks | IM | 2 |
| 3 | INO-4201 | pGX4201 | 0-4-12 weeks | ID | 2 |
| 4 | INO-4212 | pGX4201 and pGX4202 | 0-4-12 weeks | IM | 4 |
| 5 | INO-4212+INO-9012 | pGX4201, pGX4202, and pGX6001 | 0-4-12 weeks | IM | 4+1 |

Figure 35

EBOV001 ICS

Wilcoxon Paired analysis based on cohort

|  | Cohort 1 (2-tailed) | Cohort 2 (2-tailed) | Cohort 3 (2-tailed) | Cohort 4 (2-tailed) | Cohort 5 (2-tailed) |
|---|---|---|---|---|---|
| CD4 IFNg and TNFa | .770 | .252 | .695 | .438 | |
| CD4 IFNg | .688 | .105 | .713 | .063 | |
| CD4 IFNg and/or TNFa | .945 | .121 | .0039 | .547 | |
| CD4 TNFa | .945 | .301 | .0078 | .406 | |
| CD8 IFNg and TNFa | .770 | .922 | .027 | .164 | |
| CD8 IFNg | .844 | .133 | .221 | .125 | |
| CD8 IFNg and/or TNFa | .945 | .695 | .0010 | .844 | |
| CD8 TNFa | .910 | .734 | .0010 | .742 | |

Evaluated subjects

| Cohort | n= |
|---|---|
| 1 | 12 |
| 2 | 12 |
| 3 | 11 |
| 4 | 9 |
| 5 | |

Yellow = significant
Red = unevaluable due to N

Figure 36

Vaccine Responders: All (n=75) subjects by cohort

- Vaccine responder is defined as meeting the threshold and having more SFUs post day 0
- Threshold = Mean + 2 x STDEV of total population's response on Day 0 for each pool

| Cohort | 4201-003 | 4201-004 | 4201-007 | 4201-008 | 4202-006 | 4202-013 | 4202-025 | 4203-001 | 4203-006 | 4203-011 | 4203-016 | 4203-019 | 4203-020 | 4203-029 | 4203-031 | 4204-004 |
|---|---|---|---|---|---|---|---|---|---|---|---|---|---|---|---|---|
| | 1 | 1 | 1 | 1 | 1 | 1 | 1 | 1 | 1 | 1 | 1 | 1 | 1 | 1 | 1 | 1 |
| GP1 | Non | Response | Response | Non | Response | Response | Response | Non | Non | Response | Non | Non | Response | Non | Non | Non |
| GP2 | Non | Response | Response | Non | Response | Response | Non | Non | Non | Non | Response | Non | Non | Non | Non | Non |
| GP3 | Non | Non | Non | Non | Non | N | Non | Non | Non | Non | Non | Non | Response | Non | Non | Non |
| GP4 | Non | Non | Non | Non | Non | Non | Non | Non | Non | Non | Non | Non | Non | Non | Non | Non |
| Any pool | Non | Response | Response | Non | Response | Response | Response | Non | Non | Response | Response | Non | Response | Non | Non | Non |

| Cohort | 4201-001 | 4201-005 | 4201-010 | 4202-006 | 4202-014 | 4202-015 | 4202-016 | 4202-020 | 4203-003 | 4203-005 | 4203-007 | 4203-013 | 4203-015 | 4203-018 | 4203-021 | 4203-026 | 4203-029 | 4203-032 | 4203-035 |
|---|---|---|---|---|---|---|---|---|---|---|---|---|---|---|---|---|---|---|---|
| | 2 | 2 | 2 | 2 | 2 | 2 | 2 | 2 | 2 | 2 | 2 | 2 | 2 | 2 | 2 | 2 | 2 | 2 | 2 |
| GP1 | Non | Response | Response | Response | Response | Response | Non | Response | Non | Non | Response | Response | Non | Non | Non | Response | Non | Non | Non |
| GP2 | Non | Non | Response | Non | Non | Response | Non | Non | Non | Non | Non | Non | Non | Non | Non | Response | Non | Non | Non |
| GP3 | Non | Non | Response | Non | Non | Response | Non | Non | Non | Non | Non | Response | Non | Non | Non | Non | Non | Non | Non |
| GP4 | Non | Non | Non | Non | Non | Non | Non | Non | Non | Non | Non | Non | Non | Non | Non | Non | Non | Non | Non |
| Any pool | Non | Response | Response | Response | Response | Response | Non | Response | Non | Non | Response | Response | Non | Non | Non | Response | Non | Non | Non |

| Cohort | 4201-002 | 4201-006 | 4201-012 | 4202-007 | 4202-015 | 4202-017 | 4202-026 | 4203-003 | 4203-009 | 4203-013 | 4203-015 | 4203-023 | 4203-024 | 4203-028 | 4203-030 | 4203-037 |
|---|---|---|---|---|---|---|---|---|---|---|---|---|---|---|---|---|
| | 3 | 3 | 3 | 3 | 3 | 3 | 3 | 3 | 3 | 3 | 3 | 3 | 3 | 3 | 3 | 3 |
| GP1 | Non | Non | Non | Response | Response | Non | Response | Non | Non | Non | Non | Non | Response | Non | Non | Non |
| GP2 | Non | Non | Non | Response | Response | Non | Non | Non | Non | Non | Non | Non | Non | Non | Non | Non |
| GP3 | Non | Response | Non | Non | Non | Response | Yes | Non | Non | Non | Non | Non | Non | Non | Non | Non |
| GP4 | Non | Response | Non | Non | Non | Non | Yes | Non | Non | Non | Non | Non | Non | Non | Non | Non |
| Any pool | Non | Response | Non | Response | Response | Response | Response | Non | Non | Non | Non | Non | Response | Non | Non | Non |

Figure 39

Vaccine Responders: All (n=75) subjects by cohort

- Vaccine responders is defined as meeting the threshold and having more SFUs post day 0
- Threshold = Mean + 2 x STDEV of total population's response on Day 0 for each pool

| Cohort | 4201-009 | 4201-011 | 4201-014 | 4201-017 | 4202-011 | 4202-027 | 4202-028 | 4202-030 | 4202-031 | 4203-014 | 4203-017 | 4203-040 | 4203-042 | 4203-043 |
|---|---|---|---|---|---|---|---|---|---|---|---|---|---|---|
|  | 4 | 4 | 4 | 4 | 4 | 4 | 4 | 4 | 4 | 4 | 4 | 4 | 4 | 4 |
| GP1 | Response | Non | Non | Response | Response | Response | Response | Response | Non | Response | Non | Non | Non | Non |
| GP2 | Response | Non | Non | Res | Non | Response | Res | Non | Non | Non | Non | Response | Non | Non |
| GP3 | Non | Non | Non | Res | Non | Non | Res | Non | Non | Non | Non | Non | Non | Non |
| GP4 | Non | Non | Non | Non | Non | Non | Response | Response | Non | Response | Non | Response | Non | Non |
| Any pool | Response | Non | Non | Response | Response | Response | Response | Response | Non | Response | Non | Response | Non | Non |

| Cohort | 4201-018 | 4201-019 | 4201-020 | 4201-021 | 4201-022 | 4202-023 | 4202-024 | 4202-033 | 4203-034 | 4203-044 | 4203-045 | 4203-046 | 4203-047 | 4203-049 | 4203-050 |
|---|---|---|---|---|---|---|---|---|---|---|---|---|---|---|---|
|  | 5 | 5 | 5 | 5 | 5 | 5 | 5 | 5 | 5 | 5 | 5 | 5 | 5 | 5 | 5 |
| GP1 | Non | Response | Non | Response | Non | Response | Non | Non | Response | Non | Non | Non | Response | Non | Response |
| GP2 | Response | Response | Non | Response | Non | Response | Non | Non | Response | Non | Non | Non | Non | Non | Non |
| GP3 | Non | Non | Non | Non | Non | Non | Non | Non | Non | Non | Non | Non | Non | Non | Non |
| GP4 | Non | Non | Non | Response | Non | Response | Non | Non | Non | Non | Non | Non | Response | Non | Response |
| Any pool | Response | Response | Non | Response | Non | Response | Non | Non | Response | Non | Non | Non | Response | Non | Response |

Figure 40

Median responses by cohort and pool (n=75)

| Cohort | \multicolumn{6}{c}{Median ELISpot Response} |
|---|---|---|---|---|---|---|
| | 1 | 2 | 3 | 4 | 5 | All Subjects |
| EBOV-Baseline | 26.7 | 25.0 | 20.8 | 27.9 | 13.3 | 21.7 |
| EBOV-Wk2 | 33.3 | 8.3 | 20.0 | 21.7 | 15.0 | 19.2 |
| EBOV-Wk6 | 60.0 | 83.3 | 133.3 | 102.5 | 90.8 | 83.3 |
| EBOV-Wk14 | 58.3 | 75.4 | 77.5 | 105.8 | 58.3 | 77.5 |
| GP pool 1 -Baseline | 6.7 | 3.3 | 5.0 | 6.3 | 1.7 | 4.2 |
| GP pool 1 -Wk2 | 6.7 | 3.3 | 5.0 | 3.3 | 1.7 | 5.0 |
| GP pool 1 -Wk6 | 17.5 | 30.0 | 23.3 | 25.8 | 13.3 | 23.3 |
| GP pool 1 -Wk14 | 28.3 | 18.3 | 23.3 | 29.2 | 23.3 | 25.0 |
| GP pool 2 -Baseline | 6.7 | 3.3 | 3.3 | 10.8 | 3.3 | 6.3 |
| GP pool 2 -Wk2 | 0.8 | 3.3 | 3.3 | 9.2 | 3.3 | 5.0 |
| GP pool 2 -Wk6 | 11.7 | 30.0 | 28.3 | 21.7 | 15.8 | 18.3 |
| GP pool 2 -Wk14 | 13.3 | 18.3 | 16.7 | 23.3 | 16.7 | 19.2 |
| GP pool 3 -Baseline | 0.0 | 5.0 | 0.0 | 3.3 | 3.3 | 3.3 |
| GP pool 3 -Wk2 | 3.3 | 0.0 | 3.3 | 3.3 | 1.7 | 2.5 |
| GP pool 3 -Wk6 | 5.0 | 16.7 | 10.0 | 8.3 | 1.7 | 8.3 |
| GP pool 3 -Wk14 | 3.3 | 5.0 | 10.0 | 12.5 | 1.7 | 5.8 |
| GP pool 4 -Baseline | 1.7 | 6.7 | 5.0 | 5.8 | 1.7 | 3.3 |
| GP pool 4 -Wk2 | 5.0 | 3.3 | 8.3 | 5.0 | 5.0 | 5.0 |
| GP pool 4 -Wk6 | 8.3 | 29.2 | 36.7 | 30.0 | 19.2 | 21.7 |
| GP pool 4 -Wk14 | 21.7 | 14.2 | 31.7 | 26.7 | 13.3 | 21.7 |

EBOV response = summed response of pools 1-4

Figure 41

Mean responses by cohort and pool (n=75)

| | Mean ELISpot Response | | | | | |
|---|---|---|---|---|---|---|
| Cohort | 1 | 2 | 3 | 4 | 5 | All Subjects |
| EBOV-Baseline | 124.6 | 116.3 | 85.6 | 148.9 | 44.6 | 103.4 |
| EBOV-Wk2 | 112.5 | 66.9 | 158.7 | 154.1 | 41.7 | 107.2 |
| EBOV-Wk6 | 147.1 | 206.0 | 295.3 | 291.3 | 88.3 | 203.5 |
| EBOV-Wk14 | 128.3 | 121.8 | 160.6 | 280.1 | 128.1 | 163.9 |
| | | | | | | |
| GP pool 1 -Baseline | 17.9 | 8.9 | 5.8 | 7.2 | 2.7 | 8.5 |
| GP pool 1 -Wk2 | 21.9 | 6.0 | 8.4 | 11.4 | 3.1 | 10.3 |
| GP pool 1 -Wk6 | 29.4 | 62.4 | 22.1 | 47.1 | 24.0 | 37.5 |
| GP pool 1 -Wk14 | 38.7 | 33.8 | 25.3 | 69.6 | 31.7 | 40.3 |
| | | | | | | |
| GP pool 2-Baseline | 8.8 | 17.4 | 9.2 | 18.5 | 5.8 | 11.8 |
| GP pool 2-Wk2 | 4.2 | 20.7 | 9.8 | 23.7 | 6.6 | 12.6 |
| GP pool 2-Wk6 | 26.4 | 52.7 | 27.8 | 40.2 | 26.2 | 34.9 |
| GP pool 2-Wk14 | 24.0 | 31.0 | 21.9 | 58.7 | 53.4 | 37.8 |
| | | | | | | |
| GP pool 3-Baseline | 27.8 | 8.2 | 26.6 | 44.8 | 12.0 | 23.6 |
| GP pool 3-Wk2 | 21.1 | 15.0 | 46.6 | 43.6 | 13.4 | 28.1 |
| GP pool 3-Wk6 | 25.0 | 35.5 | 80.5 | 66.0 | 5.2 | 41.6 |
| GP pool 3-Wk14 | 19.1 | 27.2 | 36.1 | 60.6 | 6.7 | 30.0 |
| | | | | | | |
| GP pool 4-Baseline | 69.9 | 81.8 | 44.1 | 78.4 | 24.1 | 59.4 |
| GP pool 4-Wk2 | 65.3 | 25.2 | 93.9 | 75.4 | 18.6 | 56.2 |
| GP pool 4-Wk6 | 66.2 | 55.4 | 164.9 | 137.9 | 32.9 | 89.6 |
| GP pool 4-Wk14 | 46.6 | 29.9 | 77.2 | 91.2 | 36.3 | 55.8 |

EBOV response = summed response of pools 1-4

Figure 47

EBOV GP DNA Vaccine Memory Study: IM Delivery

| Group | Vaccine | Constructs | Schedule | n | Dose |
|---|---|---|---|---|---|
| 1 | Trivalent | pGX4201 + pGX4202 + pGX4203 + opt IL-12 (pGX6006) | 0-4-8 (3 injections) | 5 | 3 mg + 3 mg + 3 mg + 0.2 mg |
| 2 | Trivalent | pGX4201 (old con) + pGX4202 (Guinea-GP) + pGX4203 (new con) + opt IL-12 (pGX6006) | 0-4 (2 injections) | 5 | 3 mg + 3 mg + 3 mg + 0.2 mg |
| 3 | Bivalent | pGX4201 + pGX4202 + opt IL-12 (pGX6006) | 0-4 (2 injections) | 5 | 4.5 mg + 4.5 mg + 0.2 mg |
| 4 | Trivalent | pGX4201 + pGX4202 + pGX4203 + opt IL-12 (pGX6006) | 0 (1 injection) | 5 | 3 mg + 3 mg + 3 mg + 0.2 mg |

* immunized animals Jan-March 2016
* followed immune responses over 12 months following final dose
* gave a 1-year boost February 2017

Figure 48

Increase in total IgG antibody responses following the 1 year boost

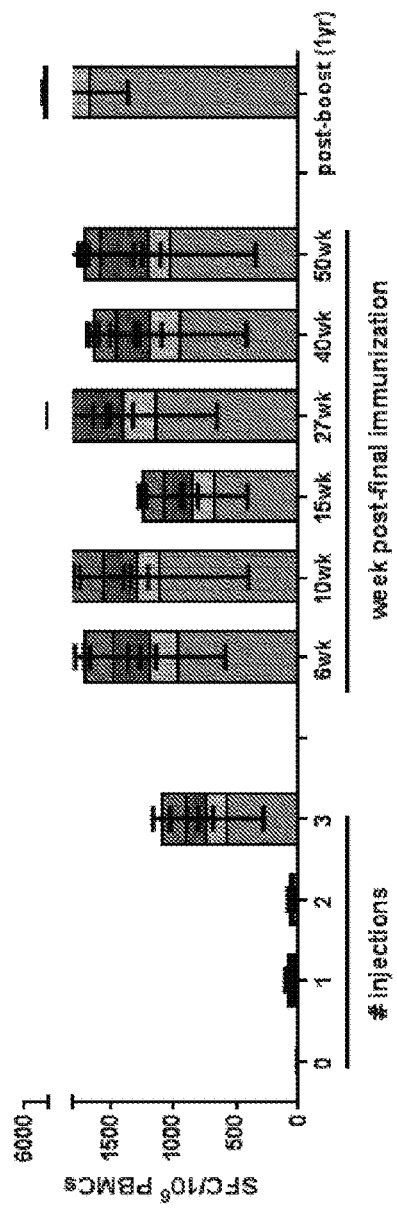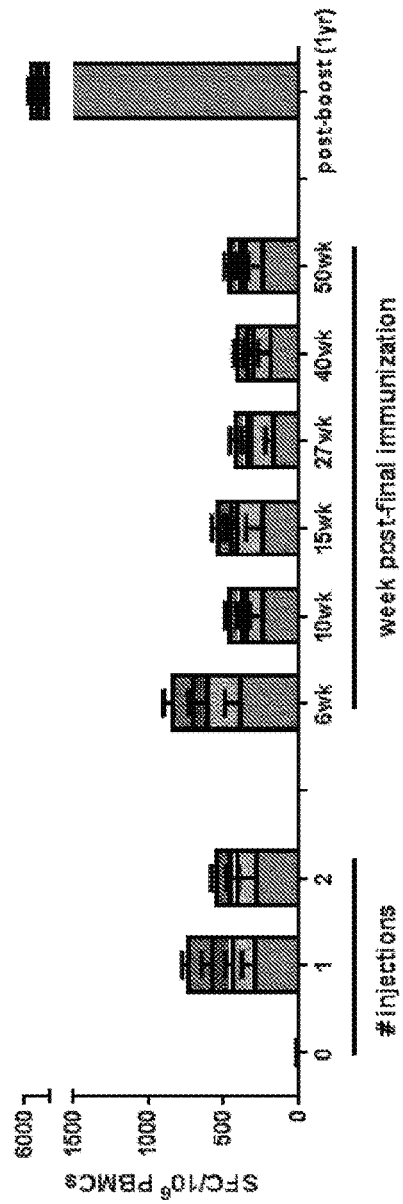
Figure 51
Increase IFNγ ELISPOT responses following the 1 year boost. Magnitude of boost is not as high in the 3 injection group.

Summary – Long Term Memory

- EBOV-GP DNA vaccine elicits long-term immune responses
- Strong recall response following a 1 year boost
  - This response is remarkably high in the group that received a single IM injection
- Next steps: memory study with intradermal delivery
  - Working on securing a challenge slot for this study

Figure 56

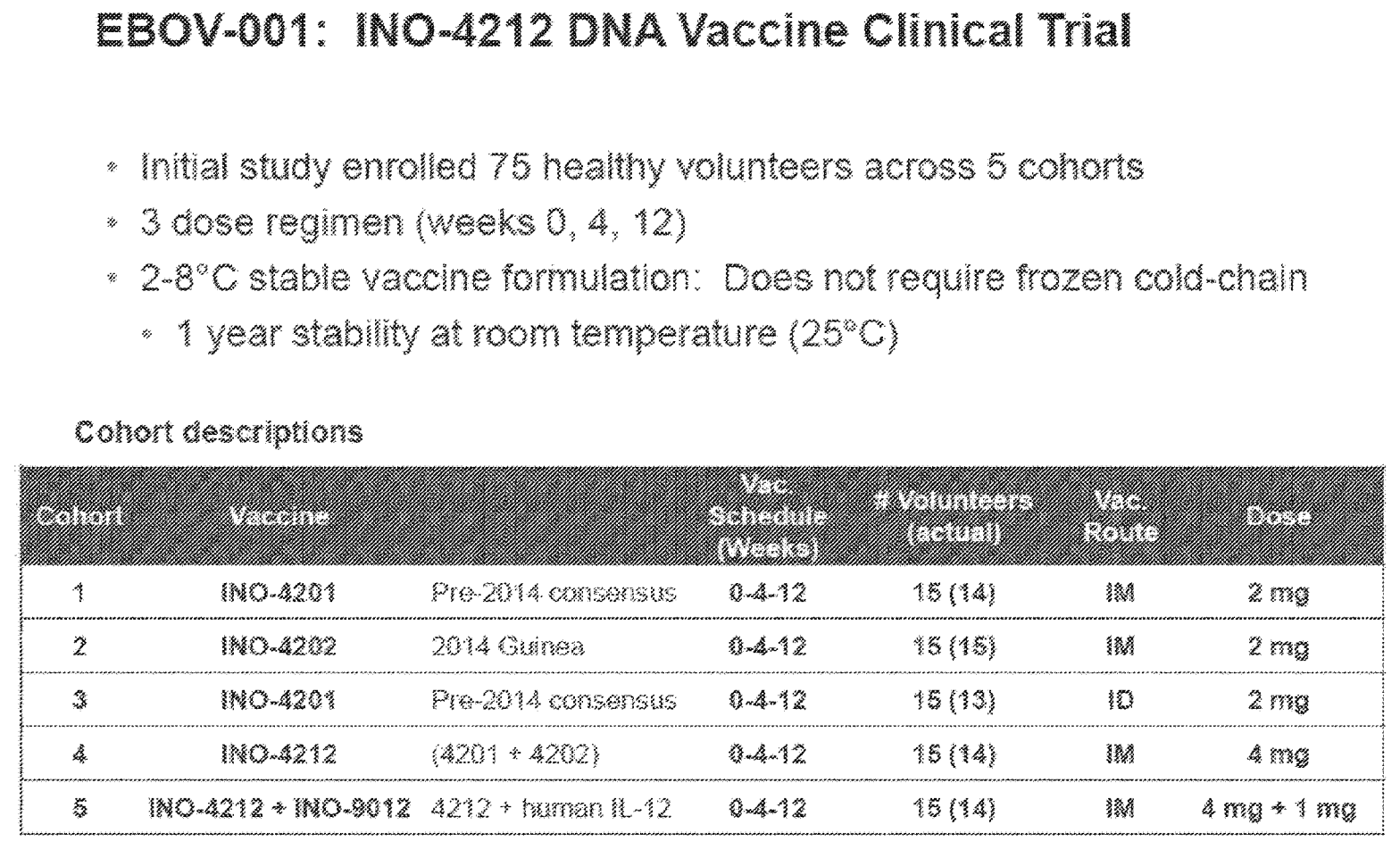

EBOV-001: INO-4212 DNA Vaccine Clinical Trial

- Initial study enrolled 75 healthy volunteers across 5 c

Figure 58

EBOV-001: ID Delivery Expansion Cohorts

Based on the seroconversion observed cohort 3 (ID delivery) 6 additional ID cohorts were added to explore different doses, dose regimens and impact of IL-12 DNA as an immuno-adjuvant

| Cohort | Vaccine | Dose Schedule (Weeks) | # Volunteers | Vac. Route | Dose (mg) |
|---|---|---|---|---|---|
| 1 | INO-4201 | 0-4-12 | 15 | IM | 2 |
| 2 | INO-4202 | 0-4-12 | 15 | IM | 2 |
| 3 | INO-4201 | 0-4-12 | 20* | ID | 2 |
| 4 | INO-4212 | 0-4-12 | 15 | IM | 4 |
| 5 | INO-4212 + INO-9012 | 0-4-12 | 15 | IM | 4 + 1 |
| 6 | INO-4201 | 0-4-12 | 20 | ID | 1 |
| 7 | INO-4201 | 0-4 | 20 | ID | 2 |
| 8 | INO-4201 | 0-4 | 20 | ID | 1 |
| 9 | INO-4201 + INO-9012 | 0-4-12 | 20 | ID | 1.6 + 0.4 |
| 10 | INO-4201 + INO-9012 | 0-4 | 20 | ID | 1.6 + 0.4 |
| 11 | INO-4201 + INO-9012 | 0-4-12 | 20 | ID | 0.8 + 0.2 |
| | | TOTAL | 200 | | |

* Part 2 enrolled an additional 5 subjects will be enrolled in cohort 5

Figure 59

FILOVIRUS CONSENSUS ANTIGENS, NUCLEIC ACID CONSTRUCTS AND VACCINES MADE THEREFROM, AND METHODS OF USING SAME

CROSS-REFERENCE TO RELATED APPLICATIONS

This application is the U.S. national stage application filed under 35 U.S.C. § 371 claiming benefit to International Patent Application No. PCT/US17/31215, filed May 5, 2017, which claims priority to U.S. Provisional Application No. 62/332,372, filed May 5, 2016, U.S. Provisional Application No. 62/402,519, filed Sep. 30, 2016, and U.S. Provisional Application No. 62/483,979, filed Apr. 11, 2017, each of which is incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: 206108-0059-00US_Sequence_Listing.txt; created on Dec. 9, 2020, 90,446 bytes, is hereby incorporated by reference.

FIELD OF THE INVENTION

The present invention relates to vaccines for inducing immune responses and preventing filovirus infection and/or treating individuals infected with filovirus, particularly infection by *Ebolavirus*. The present invention relates to consensus *Ebolavirus* proteins and nucleic acid molecules which encode the same.

BACKGROUND OF THE INVENTION

The *Filoviridae* are non-segmented, single stranded RNA viruses which contain two divergent genera, *Marburgvirus* (MARV) and *Ebolavirus* (EBOV). Members from each can cause severe and highly lethal hemorrhagic fever disease to which there is no cure or licensed vaccine (Bradfute S. B., et al. (2011) Filovirus vaccines. Hum Vaccin 7: 701-711; Falzarano D., et al. (2011) Progress in filovirus vaccine development: evaluating the potential for clinical use. Expert Rev Vaccines 10: 63-77; Fields B. N., et al. (2007) Fields' virology. Philadelphia: Lippincott Williams & Wilkins. 2 v. (xix, 3091, I-3086 p.); Richardson J. S., et al. (2009) Enhanced protection against Ebola virus mediated by an improved adenovirus-based vaccine. PLoS One 4: e5308; and Towner J. S., et al. (2006) *Marburgvirus* genomics and association with a large hemorrhagic fever outbreak in Angola. J Virol 80: 6497-6516).

Due to lethality rates of up to 90% they have been described as "one of the most virulent viral diseases known to man" by the World Health Organization. The US Centers for Disease Control and Prevention has classified them as 'Category A Bioterrorism Agents' due in part to their potential threat to national security if weaponized (Burki T. K. (2011) USA focuses on Ebola vaccine but research gaps remain. Lancet 378: 389). These 'high priority' agents could in theory be easily transmitted, result in high mortality rates, cause major public health impact and panic, and require special action for public health preparedness (CDC (2011) Bioterrorism Agents/Diseases. Atlanta: Centers for Disease Control and Prevention).

The haemorrhagic fever diseases are acute infectious with no carrier state, although they are easily transmissible among humans and nonhuman primates by direct contact with contaminated bodily fluids, blood, and tissue (Feldmann H., et al. (2003) Ebola virus: from discovery to vaccine. Nat Rev Immunol 3: 677-685). During outbreak situations, reuse of medical equipment, health care facilities with limited resources, and untimely application of prevention measures escalate transmission of the disease, allowing amplification of infections in medical settings.

Since the natural reservoirs of these zoonotic pathogens are likely to be African bats and pigs (Kobinger G. P., et al. (2011) Replication, pathogenicity, shedding, and transmission of *Zaire ebolivirus* in pigs. J Infect Dis 204: 200-208), the latter possibly being more of an amplifying host, the manner in which the virus first appears at the start of an outbreak is thought to occur through human contact with an infected animal. Unpredictable endemic surfacing in the Philippines, potentially Europe, and primarily Africa of this disease further constitutes a major public health concern (Outbreak news. (2009) Ebola Reston in pigs and humans, Philippines. Wkly Epidemiol Rec 84: 49-50).

Experiments have been performed to determine the capacity of the vaccine for inducing protective efficacy and broad CTL including experiments in rodent preclinical studies. (Fenimore P W, et al. (2012). Designing and testing broadly-protective filoviral vaccines optimized for cytotoxic T-lymphocyte epitope coverage. PLoS ONE 7: e44769; Hensley L E, et al. (2010). Demonstration of cross-protective vaccine immunity against an emerging pathogenic Ebolavirus Species. PLoS Pathog 6: e1000904; Zahn R, et al (2012). Ad35 and ad26 vaccine vectors induce potent and cross-reactive antibody and T-cell responses to multiple filovirus species. PLoS ONE 7: e44115; Geisbert T W, Feldmann H (2011). Recombinant vesicular stomatitis virus-based vaccines against Ebola and Marburg virus infections. *J Infect Dis* 204 Suppl 3: S1075-1081; and Grant-Klein R J, Van Deusen N M, Badger C V, Hannaman D, Dupuy L C, Schmaljohn C S (2012). A multiagent filovirus DNA vaccine delivered by intramuscular electroporation completely protects mice from ebola and Marburg virus challenge. Hum Vaccin Immunother 8; Grant-Klein R J, Altamura L A, Schmaljohn C S (2011). Progress in recombinant DNA-derived vaccines for Lassa virus and filoviruses. Virus Res 162: 148-161).

Vaccine-induced adaptive immune responses have been described in numerous preclinical animal models (Blaney J E, et al. (2011). Inactivated or live-attenuated bivalent vaccines that confer protection against rabies and Ebola viruses. J Virol 85: 10605-10616; Dowling W, et al. (2007). Influences of glycosylation on antigenicity, immunogenicity, and protective efficacy of ebola virus GP DNA vaccines. J Virol 81: 1821-1837; Jones S M, et al. (2005). Live attenuated recombinant vaccine protects nonhuman primates against Ebola and Marburg viruses. Nat Med 11: 786-790; Kalina W V, Warfield K L, Olinger G G, Bavari S (2009). Discovery of common marburgvirus protective epitopes in a BALB/c mouse model. Virol J 6: 132; Kobinger G P, et al. (2006). Chimpanzee adenovirus vaccine protects against Zaire Ebola virus. Virology 346: 394-401; Olinger G G, et al. (2005). Protective cytotoxic T-cell responses induced by Venezuelan equine encephalitis virus replicons expressing Ebola virus proteins. *J Virol* 79: 14189-14196; Rao M, Bray M, Alving C R, Jahrling P, Matyas G R (2002). Induction of immune responses in mice and monkeys to Ebola virus after immunization with liposome-encapsulated irradiated Ebola virus: protection in mice requires CD4(+) T cells. *J Virol* 76: 9176-9185; Rao M, Matyas G R, Grieder F, Anderson K, Jahrling P B, Alving C R (1999). Cytotoxic T lymphocytes to Ebola Zaire virus are induced in mice by immunization with liposomes containing lipid A. *Vaccine* 17: 2991-2998; Richardson J S, et al. (2009). Enhanced protection against Ebola virus mediated by an improved adenovirus-based vaccine. *PLoS One* 4: e5308; Vanderzanden L, et al (1998). DNA vaccines expressing either the GP or NP genes of Ebola virus protect mice from lethal challenge. *Virology* 246: 134-144; Warfield K L, et al. (2005). Induction of humoral and CD8+ T cell responses are required for protection against lethal Ebola virus infection. *J Immunol* 175: 1184-1191; Jones S M, et al. (2007). Assessment of a vesicular stomatitis virus-based vaccine by use of the mouse model of Ebola virus hemorrhagic fever. *J Infect Dis* 196 Supp12: S404-412 Grant-Klein R J, Van Deusen N M, Badger C V, Hannaman D, Dupuy L C, Schmaljohn C S (2012). A multiagent filovirus DNA vaccine delivered by intramuscular electroporation completely protects mice from ebola and Marburg virus challenge. *Hum Vaccin Immunother* 8; Geisbert T W, et al. (2010). Vector choice determines immunogenicity and potency of genetic vaccines against Angola Marburg virus in nonhuman primates. *J Virol* 84: 10386-10394.) Viral vaccines have shown promise and include mainly the recombinant adenoviruses and vesicular stomatitis viruses. Non-infectious strategies such as recombinant DNA and Ag-coupled virus-like particle (VLP) vaccines have also demonstrated levels of preclinical efficacy and are generally considered to be safer than virus-based platforms. Virus-specific Abs, when applied passively, can be protective when applied either before or immediately after infection (Gupta M, Mahanty S, Bray M, Ahmed R, Rollin P E (2001). Passive transfer of antibodies protects immunocompetent and immunodeficient mice against lethal Ebola virus infection without complete inhibition of viral replication. *J Virol* 75: 4649-4654; Marzi A, et al. (2012). Protective efficacy of neutralizing monoclonal antibodies in a nonhuman primate model of Ebola hemorrhagic fever. *PLoS ONE* 7: e36192; Parren P W, Geisbert T W, Maruyama T, Jahrling P B, Burton D R (2002). Pre- and postexposure prophylaxis of Ebola virus infection in an animal model by passive transfer of a neutralizing human antibody. *J Virol* 76: 6408-6412; Qiu X, et al. (2012). Ebola GP-Specific Monoclonal Antibodies Protect Mice and Guinea Pigs from Lethal Ebola Virus Infection. *PLoSNegl Trop Dis* 6: e1575; Wilson J A, et al. (2000). Epitopes involved in antibody-mediated protection from Ebola virus. *Science* 287: 1664-1666; Sullivan N J, et al. (2011). CD8(+) cellular immunity mediates rAd5 vaccine protection against Ebola virus infection of nonhuman primates. *Nat Med* 17: 1128-1131; Bradfute S B, Warfield K L, Bavari S (2008). Functional CD8+ T cell responses in lethal Ebola virus infection. *J Immunol* 180: 4058-4066; Warfield K L, Olinger G G (2011). Protective role of cytotoxic T lymphocytes in filovirus hemorrhagic fever. *J Biomed Biotechnol* 2011: 984241). T cells have also been shown to provide protection based on studies performed in knockout mice, depletion studies in NHPs, and murine adoptive transfer studies where efficacy was greatly associated with the lytic function of adoptively-transferred CD8+ T cells. However, little detailed analysis of this response as driven by a protective vaccine has been reported.

Countermeasure development will ultimately require an improved understanding of protective immune correlates and how they are modulated during infection. This proves difficult when infected individuals who succumb to filoviral disease fail to mount an early immune response. These fast-moving hemorrhagic fever diseases result in immune dysregulation, as demonstrated by the lack of a virus-specific Ab response and a great reduction in gross T cell numbers, leading to uncontrolled viral replication and multi-organ infection and failure. Conversely, survivors of Ebola virus (EBOV) disease exhibit an early and transient IgM response, which is quickly followed by increasing levels of virus-specific IgG and CTL. These observations suggest that humoral and cell-mediated immune responses play a role in conferring protection against disease. These data are also supported by numerous preclinical efficacy studies demonstrating the contribution of vaccine-induced adaptive immunity to protection against lethal challenge. However, mounting evidence has demonstrated a critical role for T cells in providing protection where efficacy was greatly associated with the functional phenotype of CD8+ T cells. While these recent studies highlight the importance of T cells in providing protection, their precise contributions remain uncharacterized and controversial. Furthermore, little detailed analysis of this response driven by a protective vaccine has been reported.

SUMMARY OF THE INVENTION

Isolated nucleic acid molecules comprising on or more nucleic acid sequences encoding a a first consensus *Zaire ebolivirus* envelope glycoprotein immunogen (ZEBOVCON), a nucleic acid encoding a second consensus *Zaire ebolivirus* envelope glycoprotein immunogen (ZEBOVCON2), or a nucleic acid encoding a ZEBOV Guinea 2014 Outbreak envelope glycoprotein immunogen (ZEBOVGUI) are provided.

In one embodiment, the the ZEBOVCON comprises an amino acid sequence that is at least 95% homologous to SEQ ID NO:1, a fragment of an amino acid sequence that is at least 95% homologous to SEQ ID NO:1, an amino acid sequence that is at least 99% homologous to SEQ ID NO:1, a fragment of an amino acid sequence that is at least 99% homologous to SEQ ID NO:1, an amino acid sequence of SEQ ID NO:1, or a fragment of SEQ ID NO:1.

In one embodiment, the ZEBOVCON2 comprises an amino acid sequence that is at least 95% homologous to SEQ ID NO:68, a fragment of an amino acid sequence that is at least 95% homologous to SEQ ID NO:68, an amino acid sequence that is at least 99% homologous to SEQ ID NO: 68, a fragment of an amino acid sequence that is at least 99% homologous to SEQ ID NO: 68, an amino acid sequence of SEQ ID NO: 68, or a fragment of SEQ ID NO: 68.

In one embodiment, the ZEBOVGUI comprises an amino acid sequence that is at least 95% homologous to SEQ ID NO:67, a fragment of an amino acid sequence that is at least 95% homologous to SEQ ID NO:67, an amino acid sequence that is at least 99% homologous to SEQ ID NO: 67, a fragment of an amino acid sequence that is at least 99% homologous to SEQ ID NO: 67, an amino acid sequence of SEQ ID NO: 67, or a fragment of SEQ ID NO: 67.

In some embodiments, the fragments comprise at least 600 amino acids, at least 630 amino acids, or at least 660 amino acids.

In one embodiment, ZEBOVCON is linked to an IgE signal peptide. In one embodiment, ZEBOVCON2 is linked to an IgE signal peptide. In one embodiment, ZEBOVGUI is linked to an IgE signal peptide.

In one embodiment, the nucleic acid encoding ZEBOVCON comprises a nucleic acid sequence at least 95% homologous SEQ ID NO:69, or a fragment thereof. In one embodiment, the nucleic acid encoding ZEBOVGUI comprises a nucleic acid sequence at least 95% homologous SEQ ID NO:72, or a fragment thereof. In one embodiment, the nucleic acid encoding ZEBOVCON2 comprises a nucleic acid sequence at least 95% homologous SEQ ID NO:70, or a fragment thereof.

In one embodiment, the nucleic acid encoding ZEBOVCON comprises a nucleic acid transcribed from a DNA sequence at least 95% homologous SEQ ID NO:69, or a fragment thereof. In one embodiment, the nucleic acid encoding ZEBOVGUI comprises a nucleic acid transcribed from a DNA sequence at least 95% homologous SEQ ID NO:72, or a fragment thereof. In one embodiment, the nucleic acid encoding ZEBOVCON2 comprises a nucleic acid transcribed from a DNA sequence at least 95% homologous SEQ ID NO:70, or a fragment thereof.

A composition comprising one or more nucleic acid sequence encoding one or more of ZEBOVCON, ZEBOVCON2 and ZEBOVGUI is also provided. In one embodiment, the composition comprises two or more nucleic acid sequence encoding two or more of ZEBOVCON, ZEBOVCON2 and ZEBOVGUI. In one embodiment, the composition comprises two nucleic acid molecules. In one embodiment, the composition comprises three or more nucleic acid sequence encoding ZEBOVCON, ZEBOVCON2 and ZEBOVGUI. In one embodiment, the composition comprises three nucleic acid molecules.

The invention also provides novel sequence for producing immunogens in mammailian cells or viral vectors.

A composition comprising a nucleic acid sequence that encodes a consensus *Zaire ebolavirus* envelope glycoprotein immunogen, a nucleic acid sequence that encodes a consensus *Sudan ebolavirus* envelope glycoprotein immunogen, and a nucleic acid sequence that encodes a *Marburg marburgvirus* Angola 2005 envelope glycoprotein immunogen is provided. The amino acid sequence of the consensus *Zaire ebolivirus* envelope glycoprotein immunogen may be SEQ ID NO:1 (ZEBOV CON), a fragment of SEQ ID NO:1, an amino acid sequence that is homologous to SEQ ID NO:1, or a fragment of an amino acid sequence that is homologous to SEQ ID NO:1. Amino acid sequences that are homologous to SEQ ID NO:1 are typically 95% or more, 96% or more, 97% or more, 99% or more, or 99% or more, homologous to SEQ ID NO:1. Fragments of SEQ ID NO:1 or fragments of amino acid sequences that are homologous to SEQ ID NO:1 are typically 600 or more, 630 or more, or 660 or more amino acids. The amino acid sequence of the consensus *Sudan ebolavirus* envelope glycoprotein immunogen may be SEQ ID NO:2 (SUDV CON), a fragment of SEQ ID NO:2, an amino acid sequence that is homologous to SEQ ID NO:2, or a fragment of an amino acid sequence that is homologous to SEQ ID NO:2. Amino acid sequences that are homologous to SEQ ID NO:1 are typically 95% or more, 96% or more, 97% or more, 99% or more, or 99% or more, homologous to SEQ ID NO:2. Fragments of SEQ ID NO:2 or fragments of amino acid sequences that are homologous to SEQ ID NO:2 are typically 600 or more, 630 or more, or 660 or more amino acids. The amino acid sequence of the *Marburg marburgvirus* Angola 2005 envelope glycoprotein immunogen may be SEQ ID NO:3 (MARV ANG), a fragment of SEQ ID NO:3, an amino acid sequence that is homologous to SEQ ID NO:3, or a fragment of an amino acid sequence that is homologous to SEQ ID NO:3. Amino acid sequences that are homologous to SEQ ID NO:3 are typically 95% or more, 96% or more, 97% or more, 99% or more, or 99% or more, homologous to SEQ ID NO:3. Fragments of SEQ ID NO:3 or fragments of amino acid sequences that are homologous to SEQ ID NO:3 are typically 600 or more, 637 or more, or 670 or more amino acids. The amino acid sequence may optionally comprise a leader sequences such as the IgE leader.

A composition comprising a nucleic acid sequence that encodes a consensus *Zaire ebolavirus* envelope glycoprotein immunogen, a nucleic acid sequence that encodes a consensus *Sudan ebolavirus* envelope glycoprotein immunogen, a nucleic acid sequence that encodes a *Marburg marburgvirus* first consensus envelope glycoprotein immunogen, a nucleic acid sequence that encodes a *Marburg marburgvirus* second consensus envelope glycoprotein immunogen, and a nucleic acid sequence that encodes a *Marburg marburgvirus* third consensus envelope glycoprotein immunogen is also provided. The amino acid sequence of the consensus *Zaire ebolivirus* envelope glycoprotein immunogen may be SEQ ID NO:1 (ZEBOV CON), a fragment of SEQ ID NO:1, an amino acid sequence that is homologous to SEQ ID NO:1, or a fragment of an amino acid sequence that is homologous to SEQ ID NO:1. Amino acid sequences that are homologous to SEQ ID NO:1 are typically 95% or more, 96% or more, 97% or more, 99% or more, or 99% or more, homologous to SEQ ID NO:1. Fragments of SEQ ID NO:1 or fragments of amino acid sequences that are homologous to SEQ ID NO:1 are typically 600 or more, 630 or more, or 660 or more amino acids. The amino acid sequence of the consensus *Sudan ebolavirus* envelope glycoprotein immunogen may be SEQ ID NO:2 (SUDV CON), a fragment of SEQ ID NO:2, an amino acid sequence that is homologous to SEQ ID NO:2, or a fragment of an amino acid sequence that is homologous to SEQ ID NO:2. Amino acid sequences that are homologous to SEQ ID NO:1 are typically 95% or more, 96% or more, 97% or more, 99% or more, or 99% or more, homologous to SEQ ID NO:2. Fragments of SEQ ID NO:2 or fragments of amino acid sequences that are homologous to SEQ ID NO:2 are typically 600 or more, 630 or more, or 660 or more amino acids. The amino acid sequence of the *Marburg marburgvirus* first consensus envelope glycoprotein immunogen may be SEQ ID NO:4 (MARV RAV), a fragment of SEQ ID NO:4, an amino acid sequence that is homologous to SEQ ID NO:4, or a fragment of an amino acid sequence that is homologous to SEQ ID NO:4. Amino acid sequences that are homologous to SEQ ID NO:4 are typically 95% or more, 96% or more, 97% or more, 99% or more, or 99% or more, homologous to SEQ ID NO:4. Fragments of SEQ ID NO:4 or fragments of amino acid sequences that are homologous to SEQ ID NO:4 are typically 600 or more, 637 or more, or 670 or more amino acids. The amino acid sequence of the *Marburg marburgvirus* second consensus envelope glycoprotein immunogen may be SEQ ID NO:5 (MARV OZO), a fragment of SEQ ID NO:5, an amino acid sequence that is homologous to SEQ ID NO:5, or a fragment of an amino acid sequence that is homologous to SEQ ID NO:5. Amino acid sequences that are homologous to SEQ ID NO:5 are typically 95% or more, 96% or more, 97% or more, 99% or more, or 99% or more, homologous to SEQ ID NO:4. Fragments of SEQ ID NO:5 or fragments of amino acid sequences that are homologous to SEQ ID NO:5 are typically 600 or more, 637 or more, or 670 or more amino acids. The amino acid sequence of the *Marburg marburgvirus* third consensus envelope glycoprotein immunogen may be SEQ ID NO:6 (MARV MUS), a fragment of SEQ ID NO:6, an amino acid sequence that is homologous to SEQ ID NO:6, or a fragment of an amino acid sequence that is homologous to SEQ ID NO:6. Amino acid sequences that are homologous to SEQ ID NO:6 are typically 95% or more, 96% or more, 97% or more, 99% or more, or 99% or more, homologous to SEQ ID NO:6. Fragments of SEQ ID NO:6 or fragments of amino acid sequences that are homologous to SEQ ID NO:6 are typically 600 or more, 637 or more, or 670 or more amino acids. The amino acid sequence may optionally comprise a leader sequences such as the IgE leader. In some embodiments, the composition further comprises a nucleic acid sequence that encodes the *Marburg marburgvirus* Angola 2005 envelope glycoprotein immunogen. The amino acid sequence of the *Marburg marburgvirus* Angola 2005 envelope glycoprotein immunogen may be SEQ ID NO:3 (MARV ANG), a fragment of SEQ ID NO:3, an amino acid sequence that is homologous to SEQ ID NO:3, or a fragment of an amino acid sequence that is homologous to SEQ ID NO:3. Amino acid sequences that are homologous to SEQ ID NO:3 are typically 95% or more, 96% or more, 97% or more, 99% or more, or 99% or more, homologous to SEQ ID NO:3. Fragments of SEQ ID NO:3 or fragments of amino acid sequences that are homologous to SEQ ID NO:3 are typically 600 or more, 637 or more, or 670 or more amino acids. The amino acid sequence may optionally comprise a leader sequences such as the IgE leader.

Also provided is a composition comprising a nucleic acid sequence that encodes a consensus *Zaire ebolivirus* envelope glycoprotein immunogen, and a nucleic acid sequence that encodes a consensus *Sudan ebolavirus* envelope glycoprotein immunogen. The amino acid sequence of the consensus *Zaire ebolivirus* envelope glycoprotein immunogen may be SEQ ID NO:1 (ZEBOV CON), a fragment of SEQ ID NO:1, an amino acid sequence that is homologous to SEQ ID NO:1, or a fragment of an amino acid sequence that is homologous to SEQ ID NO:1. Amino acid sequences that are homologous to SEQ ID NO:1 are typically 95% or more, 96% or more, 97% or more, 99% or more, or 99% or more, homologous to SEQ ID NO:1. Fragments of SEQ ID NO:1 or fragments of amino acid sequences that are homologous to SEQ ID NO:1 are typically 600 or more, 630 or more, or 660 or more amino acids. The amino acid sequence of the consensus *Sudan ebolavirus* envelope glycoprotein immunogen may be SEQ ID NO:2 (SUDV CON), a fragment of SEQ ID NO:2, an amino acid sequence that is homologous to SEQ ID NO:2, or a fragment of an amino acid sequence that is homologous to SEQ ID NO:2. Amino acid sequences that are homologous to SEQ ID NO:1 are typically 95% or more, 96% or more, 97% or more, 99% or more, or 99% or more, homologous to SEQ ID NO:2. Fragments of SEQ ID NO:2 or fragments of amino acid sequences that are homologous to SEQ ID NO:2 are typically 600 or more, 630 or more, or 660 or more amino acids. The amino acid sequence may optionally comprise a leader sequences such as the IgE leader.

A composition comprising a nucleic acid sequence that encodes a consensus *Zaire ebolivirus* envelope glycoprotein immunogen, a nucleic acid sequence that encodes a consensus *Sudan ebolavirus* envelope glycoprotein immunogen, and a nucleic acid sequence that encodes a *Marburg marburgvirus* Angola 2005 envelope glycoprotein immunogen is provided. The nucleic acid sequence that encodes a consensus *Zaire ebolivirus* envelope glycoprotein immunogen may be SEQ ID NO:64, a fragment of SEQ ID NO:64, a nucleic acid sequence that is homologous to SEQ ID NO:64, or a fragment of a nucleotide sequence that is homologous to SEQ ID NO:64. Nucleic acid sequences that are homologous to SEQ ID NO:64 are typically 95% or more, 96% or more, 97% or more, 99% or more, or 99% or more, homologous to SEQ ID NO:64. Fragments of SEQ ID NO:64 or fragments of amino acid sequences that are homologous to SEQ ID NO:64 typically encode 600 or more, 630 or more, or 660 or more amino acids of the consensus *Zaire ebolavirus* envelope glycoprotein immunogen encoded by SEQ ID NO:64. The nucleic acid sequence that encodes a consensus *Sudan ebolavirus* envelope glycoprotein immunogen may be SEQ ID NO:65, a fragment of SEQ ID NO:65, a nucleic acid sequence that is homologous to SEQ ID NO:65, or a fragment of a nucleotide sequence that is homologous to SEQ ID NO:65. Nucleic acid sequences that are homologous to SEQ ID NO:65 are typically 95% or more, 96% or more, 97% or more, 99% or more, or 99% or more, homologous to SEQ ID NO:65. Fragments of SEQ ID NO:65 or fragments of amino acid sequences that are homologous to SEQ ID NO:65 typically encode 600 or more, 630 or more, or 660 or more amino acids of the consensus *Sudan ebolavirus* envelope glycoprotein immunogen encoded by SEQ ID NO:65. The nucleic acid sequence that encodes *Marburg marburgvirus* Angola 2005 envelope glycoprotein immunogen may be SEQ ID NO:66, a fragment of SEQ ID NO:66, a nucleic acid sequence that is homologous to SEQ ID NO:66, or a fragment of a nucleotide sequence that is homologous to SEQ ID NO:66. Nucleic acid sequences that are homologous to SEQ ID NO:66 are typically 95% or more, 96% or more, 97% or more, 99% or more, or 99% or more, homologous to SEQ ID NO:66. Fragments of SEQ ID NO:66 or fragments of amino acid sequences that are homologous to SEQ ID NO:66 typically encode 600 or more, 630 or more, or 670 or more amino acids of the *Marburg marburgvirus* Angola 2005 envelope glycoprotein immunogen encoded by SEQ ID NO:66. The nucleic acid sequences may optionally include sequences that encode leader sequences such as the IgE leader linked to the sequences encoding the immunogens.

Each of the different nucleic acid sequences may be on a single nucleic acid molecule, may each be on a separate nucleic acid molecules or various permutations. Nucleic acid molecules may be plasmids.

The composition may be formulated for delivery to an individual using electroporation.

The composition may further comprise nucleic acid sequences that encode one or more proteins selected from the group consisting of: IL-12, IL-15 and IL-28.

The composition may be used in methods of inducing an immune response against a filovirus. The filovirus may be selected from the group consisting of: *Marburgvirus, Ebolavirus Sudan* and *Ebolavirus* Zaire.

Methods of treating an individual who has been diagnosed with filovirus comprising administering a therapeutically effective amount of the composition to an individual are provided. The filovirus may be selected from the group consisting of: *Marburgvirus, Ebolavirus Sudan* and *Ebolavirus* Zaire.

Method of preventing filovirus infection in an individual are provided. The methods comprise administering a prophylactically effective amount of the composition to an individual. The filovirus may be selected from the group consisting of: *Marburgvirus, Ebolavirus Sudan* and *Ebolavirus* Zaire.

Compositions comprising two or more proteins selected from the group consisting of: a consensus *Zaire ebolivirus* envelope glycoprotein immunogen, a consensus *Sudan ebolavirus* envelope glycoprotein immunogen, a *Marburg marburgvirus* Angola 2005 envelope glycoprotein immunogen, a first consensus *Marburg marburgvirus* envelope glycoprotein immunogen, a second consensus *Marburg marburgvirus envelope glycoprotein immunogen and a third consensus *Marburg marburgvirus* envelope glycoprotein immunogen are provided.

BRIEF DESCRIPTION OF THE DRAWINGS

FIG. 1A shows phylogenetic trees for MGP (top), SGP (lower right), and ZGP (lower left). Significant support values are indicated (*) as verified by bootstrap analysis. A consensus strategy was adopted for the ZGP and SGP immunogens (CON VACCINE). Scale bars signify distance of amino acids per site and analyses were conducted using MEGA version 5 software. GP transgenes were commercially synthesized, genetically optimized, and subcloned into modified pVAX1 mammalian expression vectors. Antigen expression was analyzed following transfection of HEK 293T cells by Western immunoblotting and FACS. Western immunoblotting results are shown in FIG. 1B and FACS in FIG. 1C. For a comparative control, rVSV expressing MGP, SGP, or ZGP was run concurrently with each GP sample and species-specific anti-GP1 mAbs were used for detection. Size is indicated (kDa). For FACS, transfected cells were indirectly stained with mouse-derived GP-specific serum reagents followed by extensive washing and goat anti-mouse IgG and MHC class I. Western immunoblotting and FACS experiments were repeated at least three times with similar results. Significance for unrooted phylogenetic trees was determined by maximum-likelihood method and verified by bootstrap analysis and significant support values (≥80%; 1,000 bootstrap replicates) were determined by MEGA version 5 software.

FIG. 2A shows trivalent vaccinated animals survived post MARV challenge while control animals all died by day 10. FIG. 2E shows trivalent vaccinated animals survived post ZEBOV challenge while control animals all died by day 7. Data for % change in body weight for vaccinated and control animal are displayed in FIG. 2B for vaccinated challenged with MARV. The y axis indicates change in body weight as shown in FIG. 2F. The light solid line is for Trivalent vaccinated animals. The light dashed line is for TriAVE, the average results of the Trivalent vaccinated animals. The dark solid line is for control animals. The dark dashed line is for Control AVE, the average result for the control animals. The light solid lines and light dashed lines remain steady on the graph in the days post challenge showing no significant weight loss among vaccinated animals. The dark solid lines and dark dashed lines decline on the graph from days 0-9 post challenge ending with the dagger denote animals that succumbed to disease by day 10. Data for % change in body weight for vaccinated and control animal are displayed in FIG. 2F for vaccinated challenged with ZEBOV. The y axis shows change in body weight as a percent. The light solid line is for Trivalent vaccinated animals. The light dashed line is for TriAVE, the average results of the Trivalent vaccinated animals. The dark solid line is for control animals. The dark dashed line is for Control AVE, the average result for the control animals. The light solid lines and light dashed lines remain steady on the graph in the days post challenge showing no significant weight loss among vaccinated animals. The dark solid lines and dark dashed lines decline on the graph from days 0-6 post challenge ending with the dagger denote animals that succumbed to disease before day 8. (n=3 for gpMARV and n=6 for gpZEBOV). Binding Abs (FIG. 2C and FIG. 2G) and NAbs (FIG. 2D and FIG. 2H) were measured in serum from vaccinated animals before (Pre) and after the first (1×) and second (2×) immunizations. Analysis was conducted on pooled serum (FIG. 2H). *p<0.1; *p<0.001; **p<0.0001.

FIGS. 3A-3C show results from Example 1 demonstrating induction of neutralizing Abs. B cell responses were assessed in mice (n=5/group) 20 days following each of two vaccinations, spaced three weeks between injections with 40 μg of E-DNA vaccination. FIG. 3A shows serum GP-specific IgG responses from vaccinated (solid lines) mice or pre-bled (dotted lines) mice were measured by ELISA. The data is summarized in FIG. 3B. All responses from pEBOS- and pEBOZ-immunized animals were measured against sucrose-purified ZGP since SGP was not available for this study. IgG responses from pMARV-immunized mice were measured against MARV-Ozolin GP or with negative control sucrose-purified Nipah G protein, Neutralization activity of serum samples was measured against ZEBOV-EGFP, SUDV-Boniface and MARV-Angola in a BSL-4 facility and NAb titers are shown in FIG. 3C. NAbs against SUDV-Boniface were assayed based on cytopathic effect (CPE) on CV-1 cells and those against MARV-Angola were assayed using an immunofluorescent assay. Averages are shown in FIG. 3B and FIG. 3C and error bars represent SEM. Group analyses were completed by matched, two-tailed, unpaired t test. Experiments were repeated at least two times with similar results and *p<0.1; p<0.01;*p<0.001.

In FIG. 4A H-$2^b$ (light bars) and H-$2^d$ (dark bars) mice (n=5/group) were immunized twice with either pMARV, pEBOS or pEBOZ DNA, and IFNγ responses were measured by IFNγ ELISPOT assay. Splenocytes harvested 8 days after the second immunization were incubated in the presence of individual GP peptides (15-mers overlapping by 9 amino acids) and results are shown in stacked bar graphs. Epitope-containing peptides were identified (≥10 AVE spots AND ≤80% response rate), confirmed by flow cytometry and characterized in the population of total activated IFNγ+ and CD44+ CD4+ and/or CD8+ T cells (Tables 1-6), and peptide numbers of positive inducers are indicated above the bars. Peptides containing CD4+ epitopes alone, CD8+ epitopes alone (*), and dual CD4+ and CD8+ epitopes (**) are numbered. Putative shared and/or partial epitopes were explored for contiguous positive peptide responses (Tables 1-6). FIG. 4B shows amino acid similarity plots comparing GP sequences from MARV, SUDV, and ZEBOV viruses displayed in FIG. 1A. FIG. 4C is a diagram showing putative domains within the ZEBOV GP (GenBank #VGP_EBOZM). SP, signal peptide; RB, receptor binding; MUC, mucin-like region; FC, furin cleavage site; TM, transmembrane region. In FIG. 4D, total subdominant (darker shade) and immunodominant (lighter shade) T cell epitopic responses are displayed as a percentage of the total IFNγ response generated by each vaccine. Experiments were repeated at least two times with similar results.

FIG. 5B shows data for % change in body weight in challenged animals. Data from immunized animals is shown as a solid light line; the average data for immunized animals is shown as a dashed light line. Data from control animals is shown as a solid dark line; the average data for control animals is shown as a dashed dark line. The light solid lines and light dashed lines remain steady within the range of about 85%-120% on the graph in the days post challenge showing no significant weight loss among vaccinated animals. The dark solid lines and dark dashed lines decline on the graph from days 0-6 post challenge ending with the dagger denote animals that succumbed to disease by day 7. NAbs measured prior to challenge; the data shown in FIG. 5C. T cell responses after a single pEBOZ immunization as measured by FACS are summarized as AVE % of total CD44+/IFNγ+ CD4+ (dark) or CD8+ (light) cells in FIG. 5D. $T_h$1-type effector markers were assessed (TNF and T-bet) and data for CD44+/IFNγ+CD4+ and CD8+ T cells were compared with total T cell data which was as follows: For Total Cells: TNF 2.9±0.8, Tbet 13.0±1.1. For CD4+/CD44+/IFNγ+ Cells: TNF 61.4±3.1, Tbet 72.6±2.0. For CD8+/CD44+/IFNγ+ Cells: TNF 33.0±3.3, Tbet 992.1±1.4 (*$p<0.1$; *$p<0.001$; **$p<0.0001$). Group analyses were completed by matched, two-tailed, unpaired t test and survival curves were analyzed by log-rank (Mantel-Cox) test. Experiments were performed twice with similar results and error bars represent SEM.

FIG. 9 depicts the vaccination strategy against Ebola. Ebola viral glycoproteins are the major target for vaccines. Currently, three vaccines are currently in clinical trials which are immunogenic protective in non-human primates (NHPs) and have single dose protection. However, these vaccines develop anti-vector immunity, show adverse reactions in human clinical trials, have uncertain duration of memory response and may not be suitable for all populations.

Figures 44A, 44B, 44C:
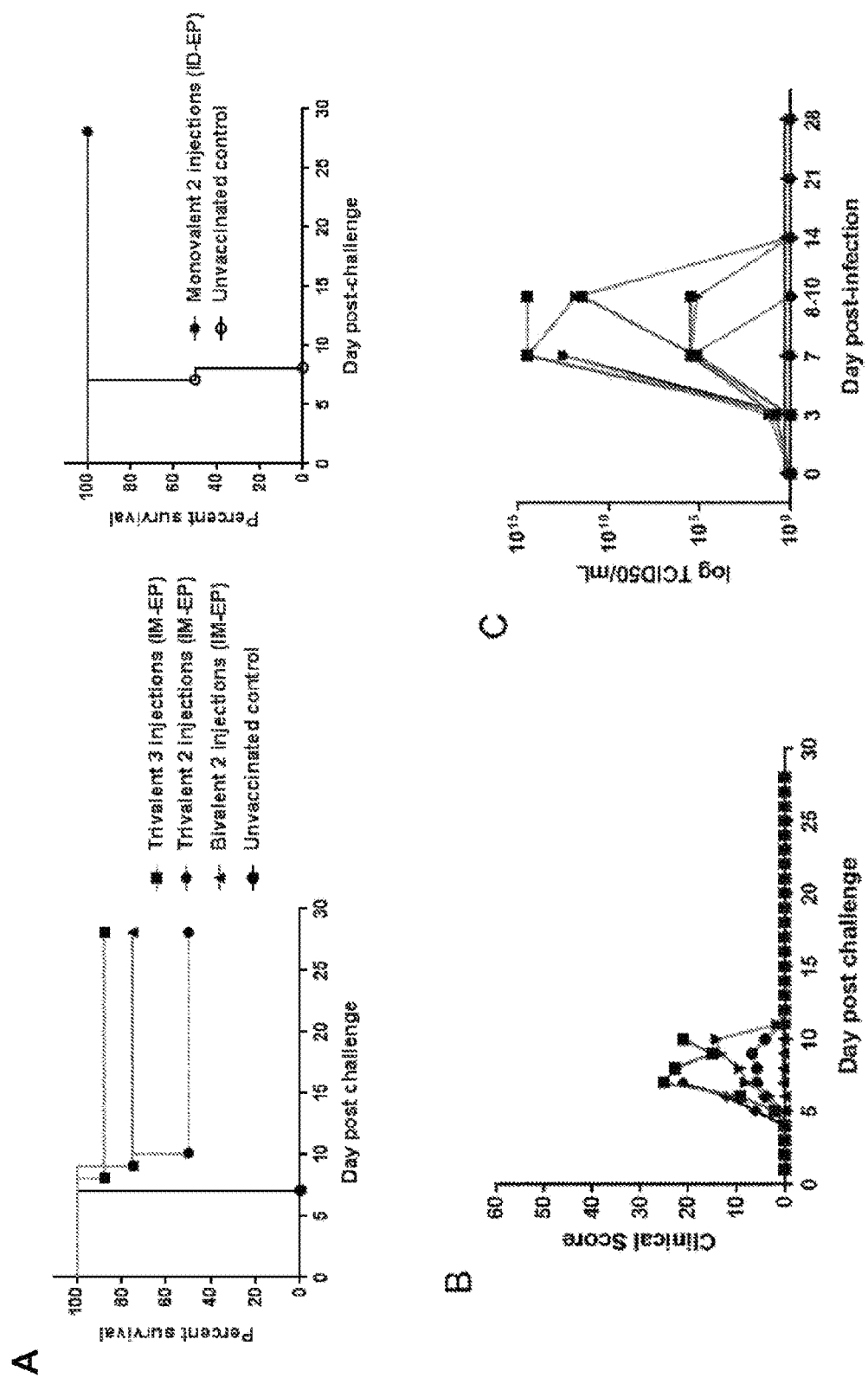

FIG.

lenged with 1000TCID50 of lethal Guinea Makona C07 EBOV and survival was monitored for 28 days post-challenge, FIG. 44B) Clinical score. Clinical signs of disease were monitored throughout the course of infection. FIG. 44C) Viral load. Viremia during the course of infection was assayed from blood by TCID50 assay.

Figure 45:
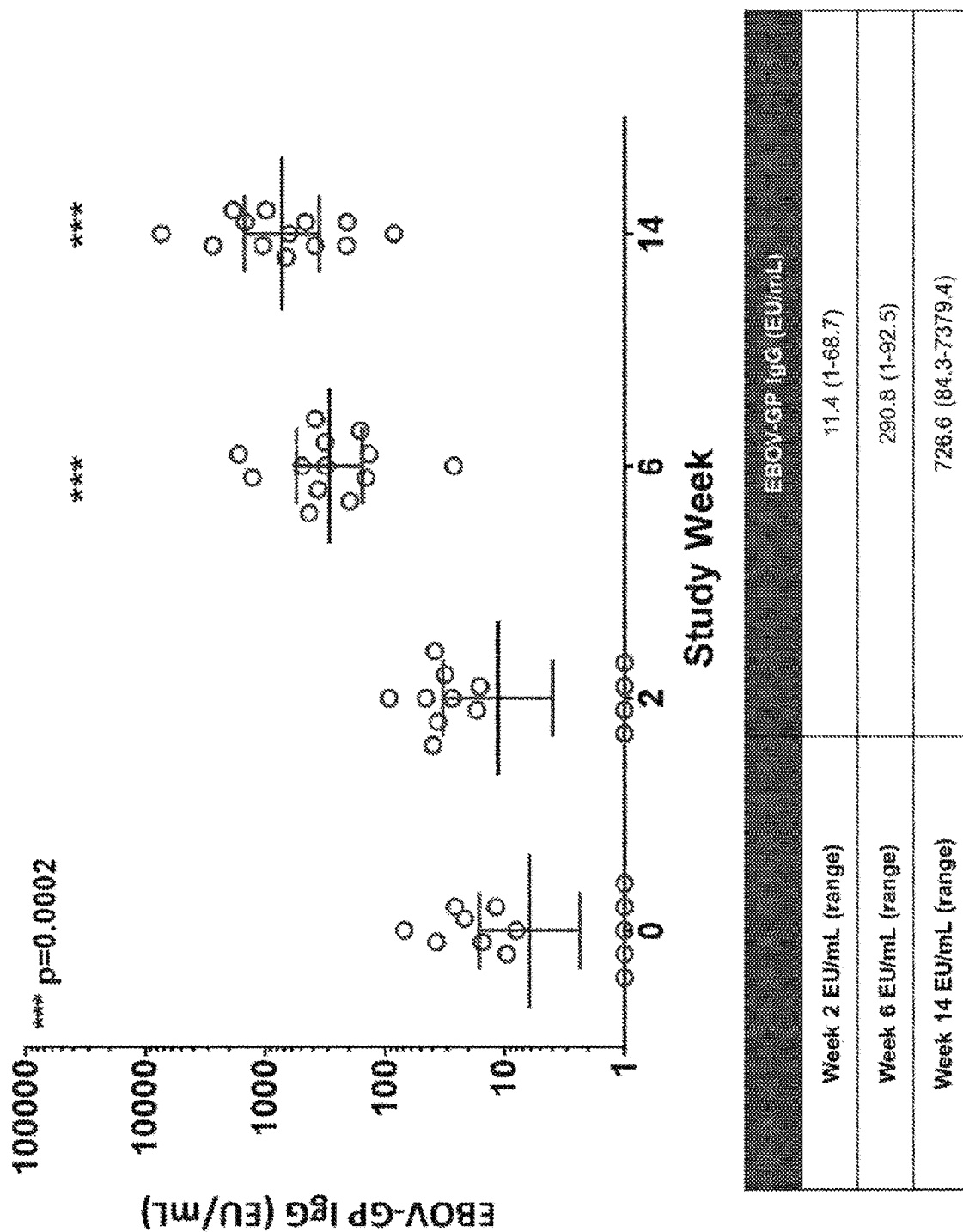

FIG. 45 shows a quantification ELISA using the ADI human anti-Zaire Ebola virus glycoprotein IgG kit to assess the amount of ZEBOV specific IgG antibody in the sera of each vaccinated subject at study entry and 2 weeks post each immunization. Statistical analyses were performed using two tailed Wilcoxon Sign Rank test.

Figure 46:
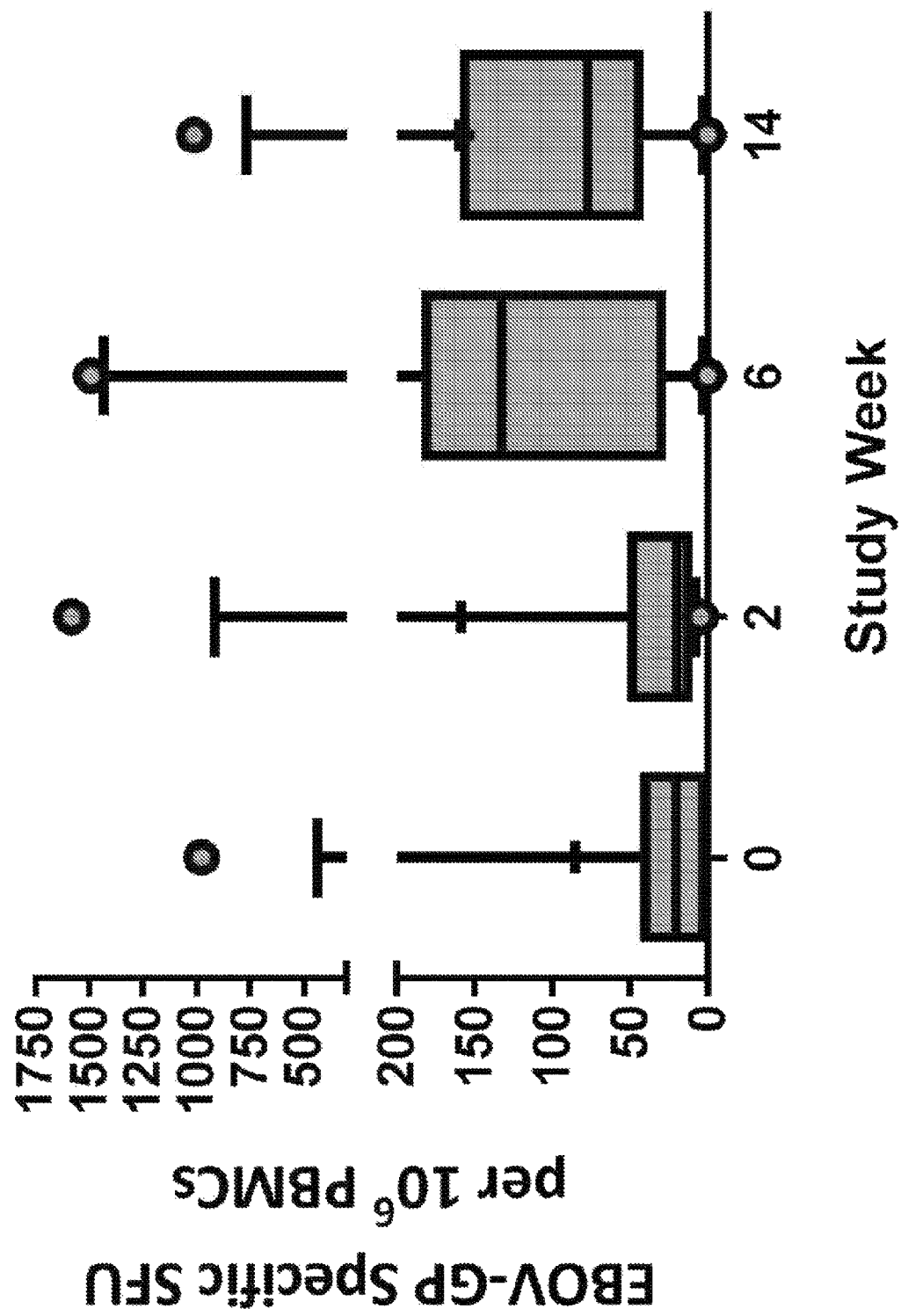

FIG. 46 shows an Interferon Gamma ELISpot response. PBMCs were isolated from vaccinated subjects at study entry and 2 weeks post each immunization and stimulated with Ebola peptides spanning the full length GP in an IFNg ELISpot assay. The graph represents EBOV-GP specific spot forming units per million PBMCs. Lines within boxes represent Median response. Individual dots represent outlier data.

Figure 47:
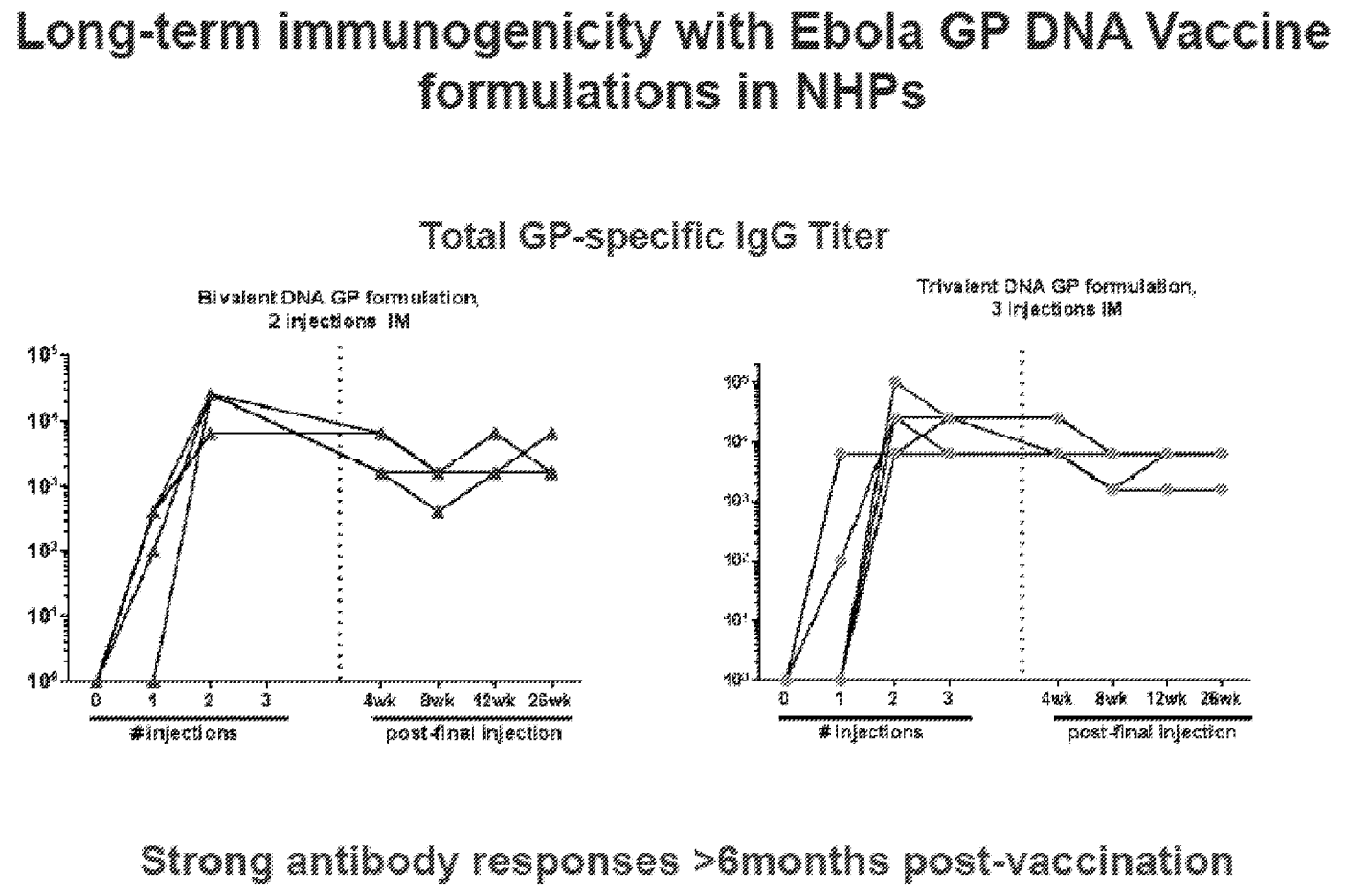

FIG. 47 depicts experimental results demonstrating long-term immunogenicity with Ebola GP DNA vaccine formulations in non-human primates (NHPs). Strong antibody responses are observed greater than 6 months post-vaccination.

FIG. 48 depicts the Memory study of intramuscular delivery of EBOV GP DNA vaccine. NHPs were immunized over a 3 month period with bivalent or trivalent EBOV GP DNA vaccine formulations. The immune responses were followed over a 12 months following the final dose. A 1 year boost was given at month 13.

Figure 49:
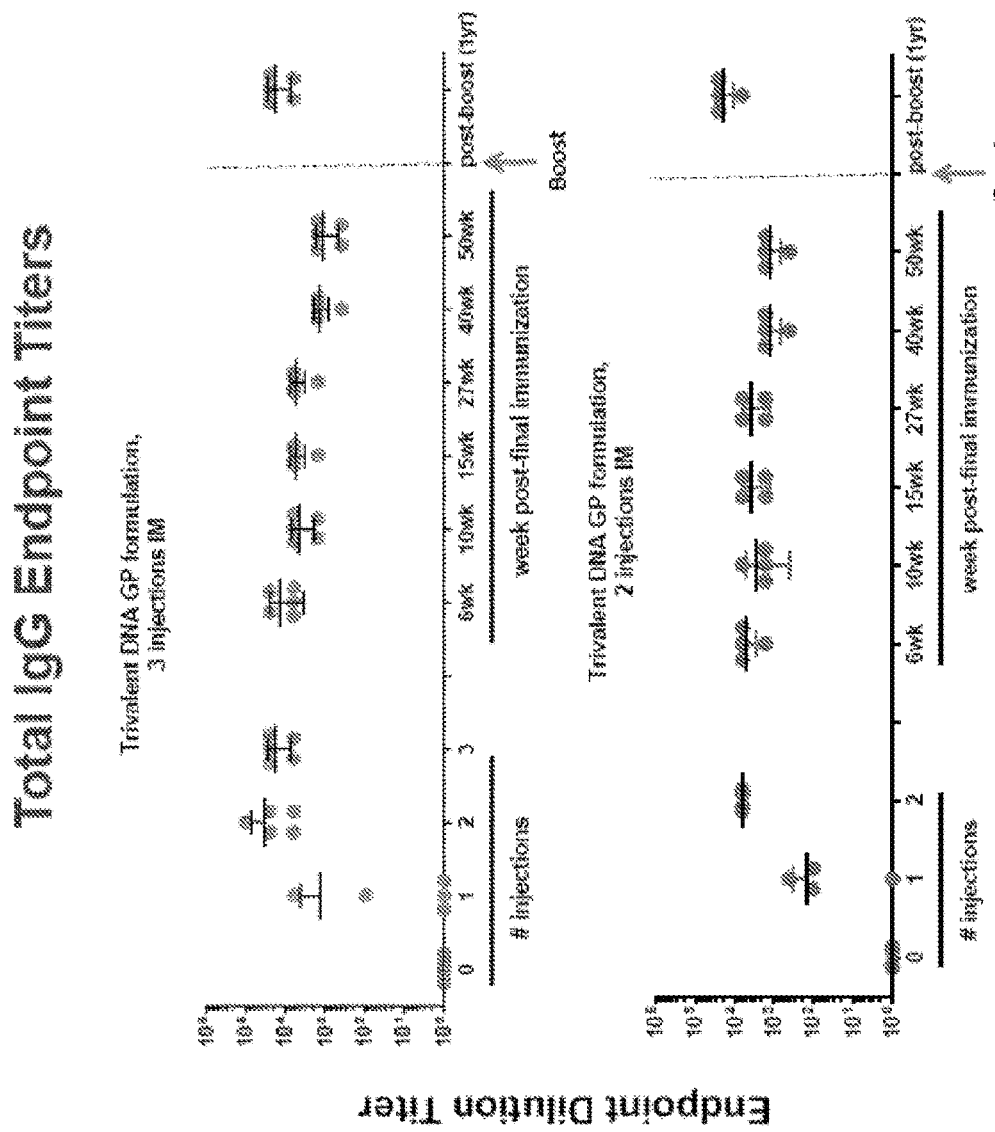

FIG. 49 depicts the total IgG endpoint titers of animals receiving a trivalent DNA GP formulation. An increase in total IgG antibody response was observed following the 1-year boost.

Figure 50:
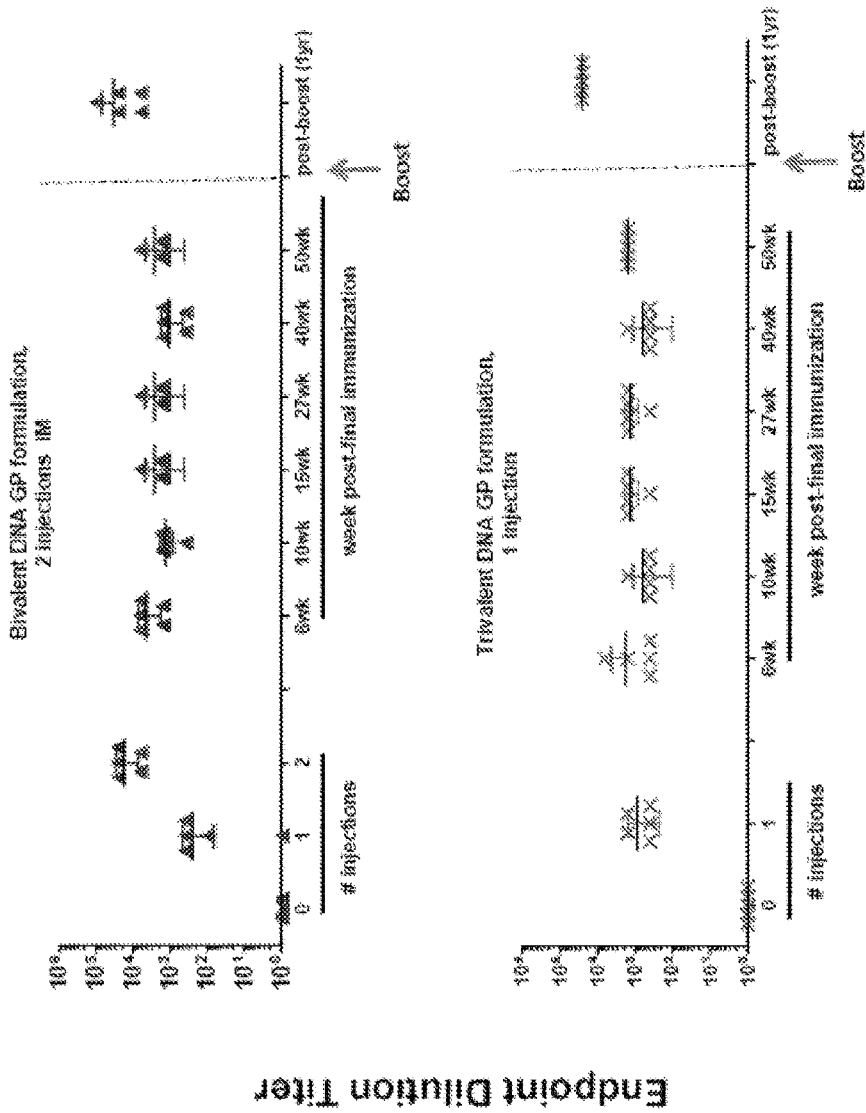

FIG. 50 depicts the total IgG endpoint titers of animals receiving a bivalent or trivalent DNA GP formulation. An increase in total IgG antibody response was observed following the 1-year boost.

FIG. 51 depicts the ELISPOT of trivalent DNA GP formulations. Increase IFNγ ELISPOT responses following the 1 year boost. Magnitude of boost is not as high in the 3 injection group.

Figure 52:
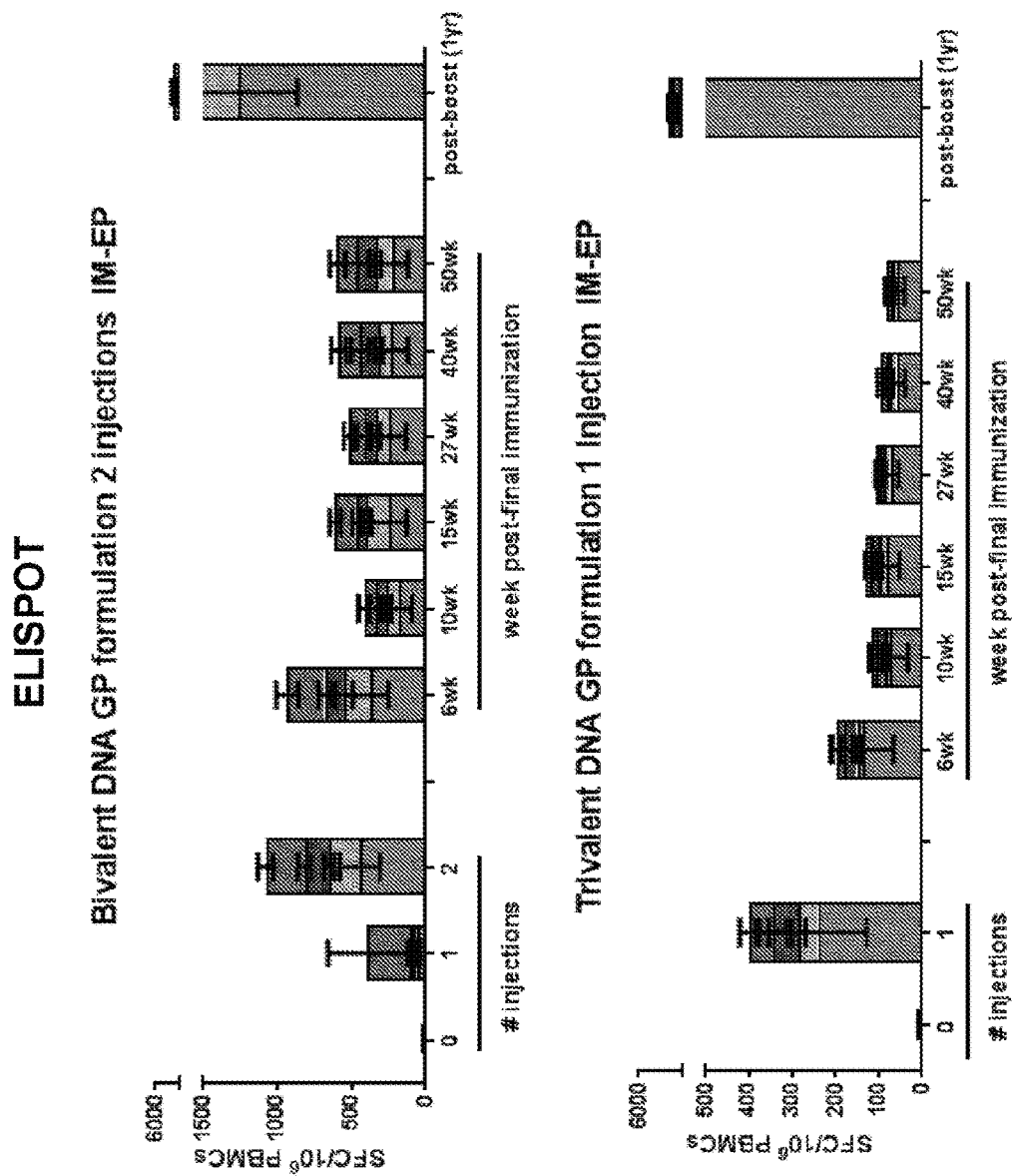

FIG. 52 depicts the ELISPOT of bivalent or trivalent DNA GP formulations. Increase IFNγ ELISPOT responses following the 1 year boost. There was a remarkably strong boost in single immunization group.

Figure 53:
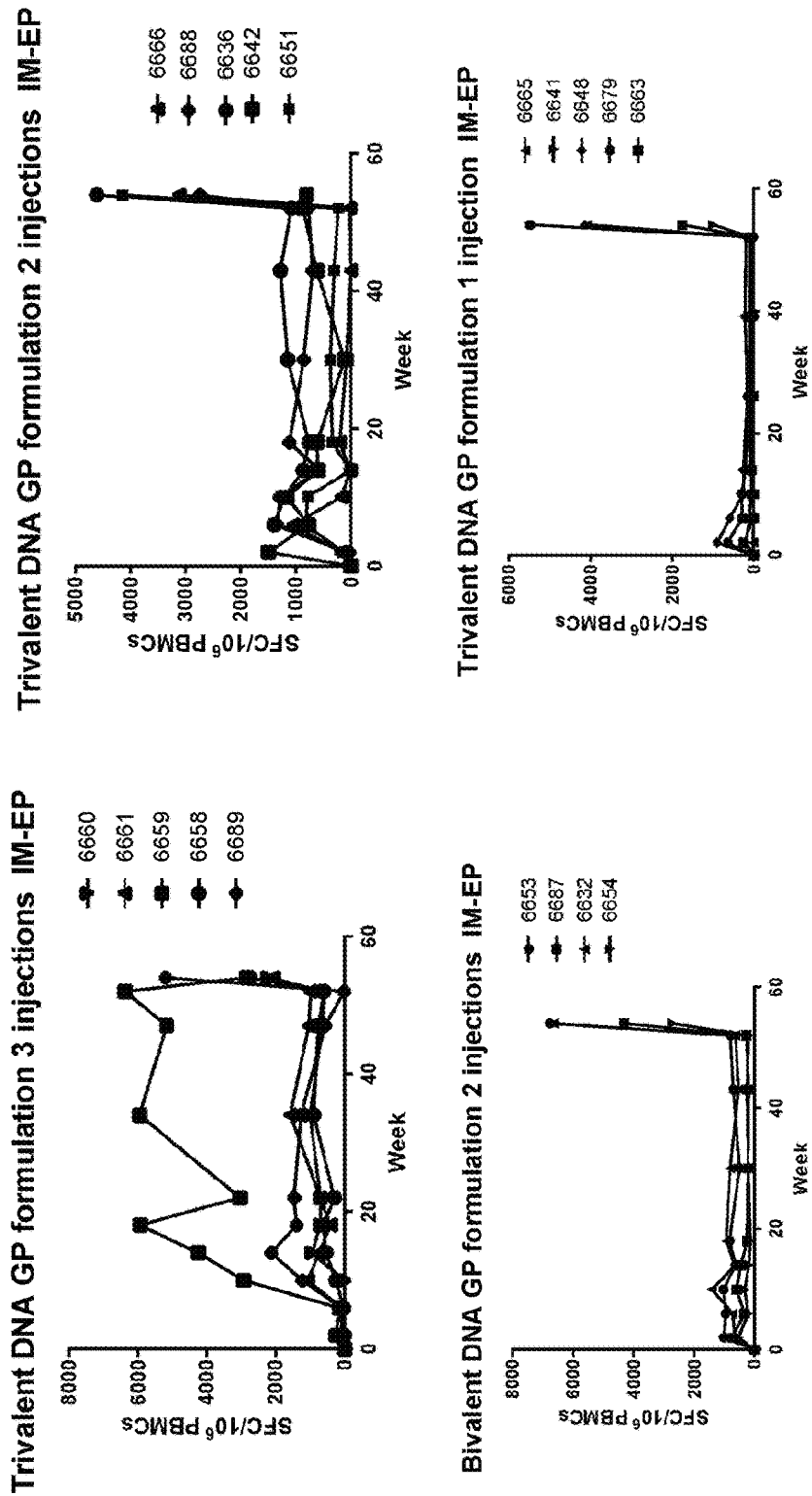

FIG. 53 depicts a summary of IFNγ ELISPOT results. 17/19 animals had increased T cell responses following the boost. 1/19 animals maintained the same level of T cell responses. 1/19 animals had worse T cell responses following the boost, however this animal was consistently high over the past year in the 3 injection group.

Figure 54:
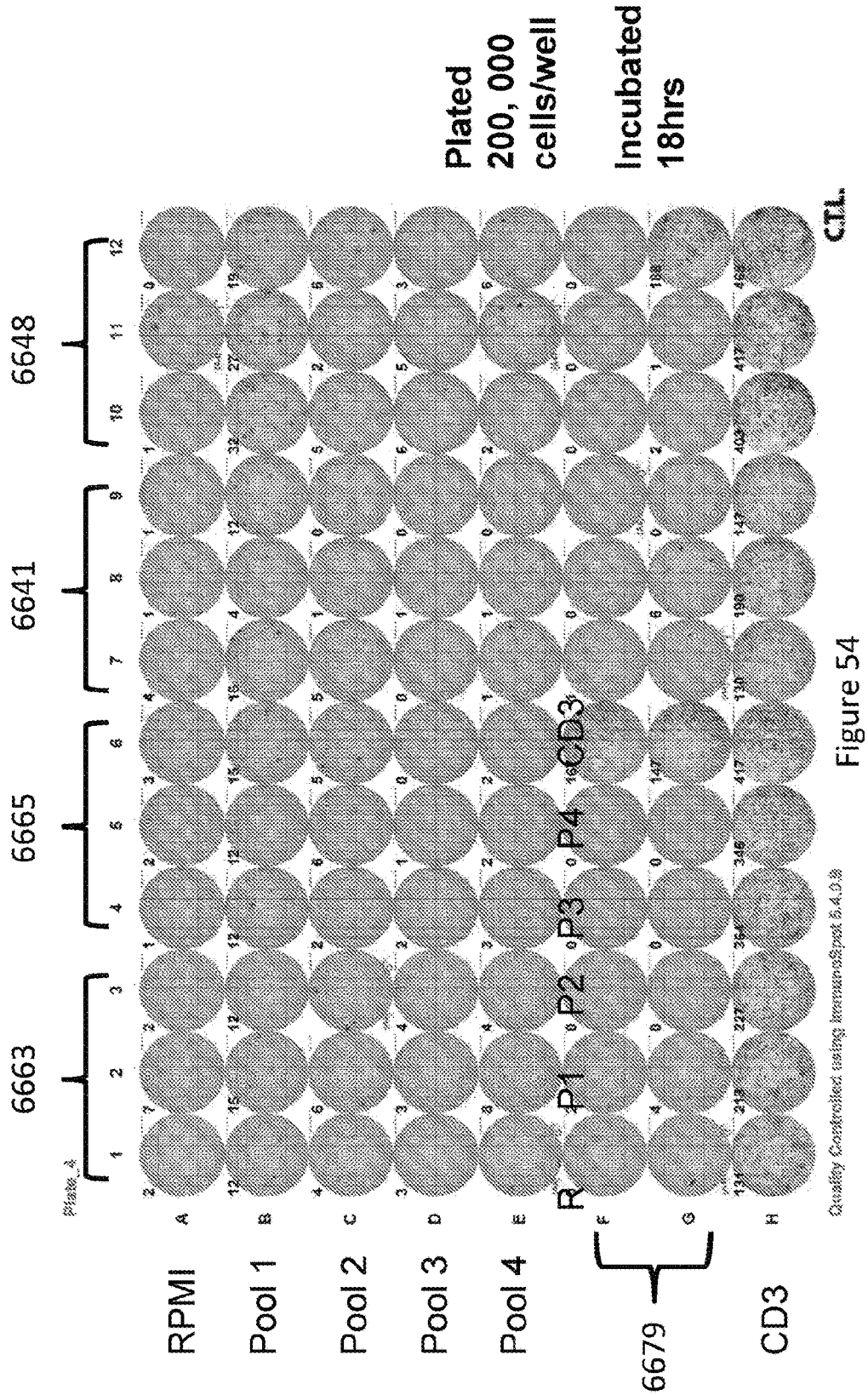

FIG. 54 depicts an exemplary IFNγ ELISPOT for animals in the single immunization group at the 12 month time point, before the 1-year boost.

Figure 55:
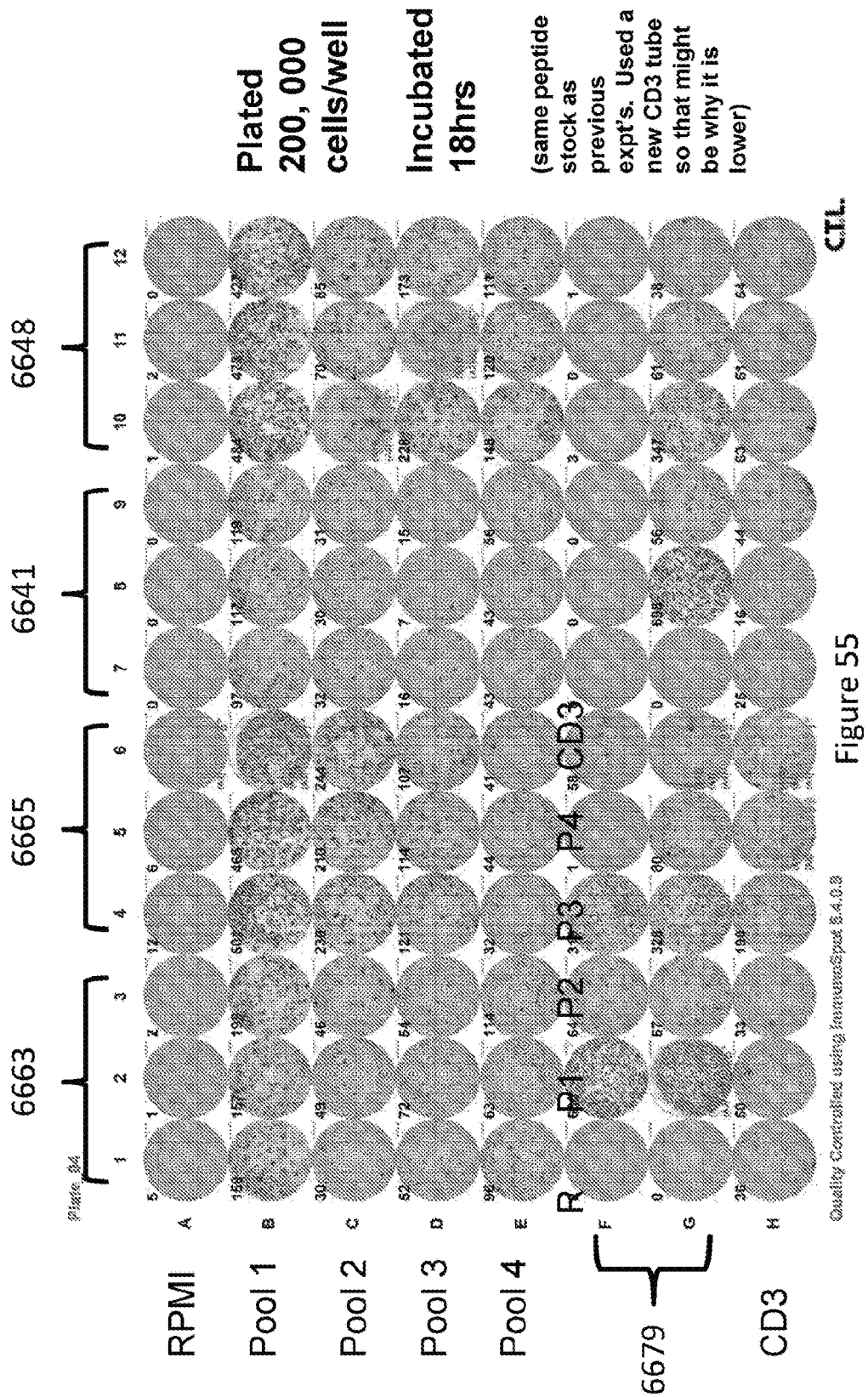

FIG. 55 depicts an exemplary IFNγ ELISPOT for animals in the single immunization group after the 1-year boost.

FIG. 56 depicts the results of the IM memory study. The EBOV GP DNA vaccines elicit long term immune response with a strong recall following a 1 year boost. Intradermal delivery studies are carried out to study the immune response of intradermal EBOV GP DNA vaccines.

FIG. 57 depicts a summary of the EBOV DNA vaccine clinical trial (EBOV-001). Healthy volunteers receive a 3 dose regimen of INO-4201, INO-4202, INO-4212 or INO-4212 and INO-9021.

Figure 58:
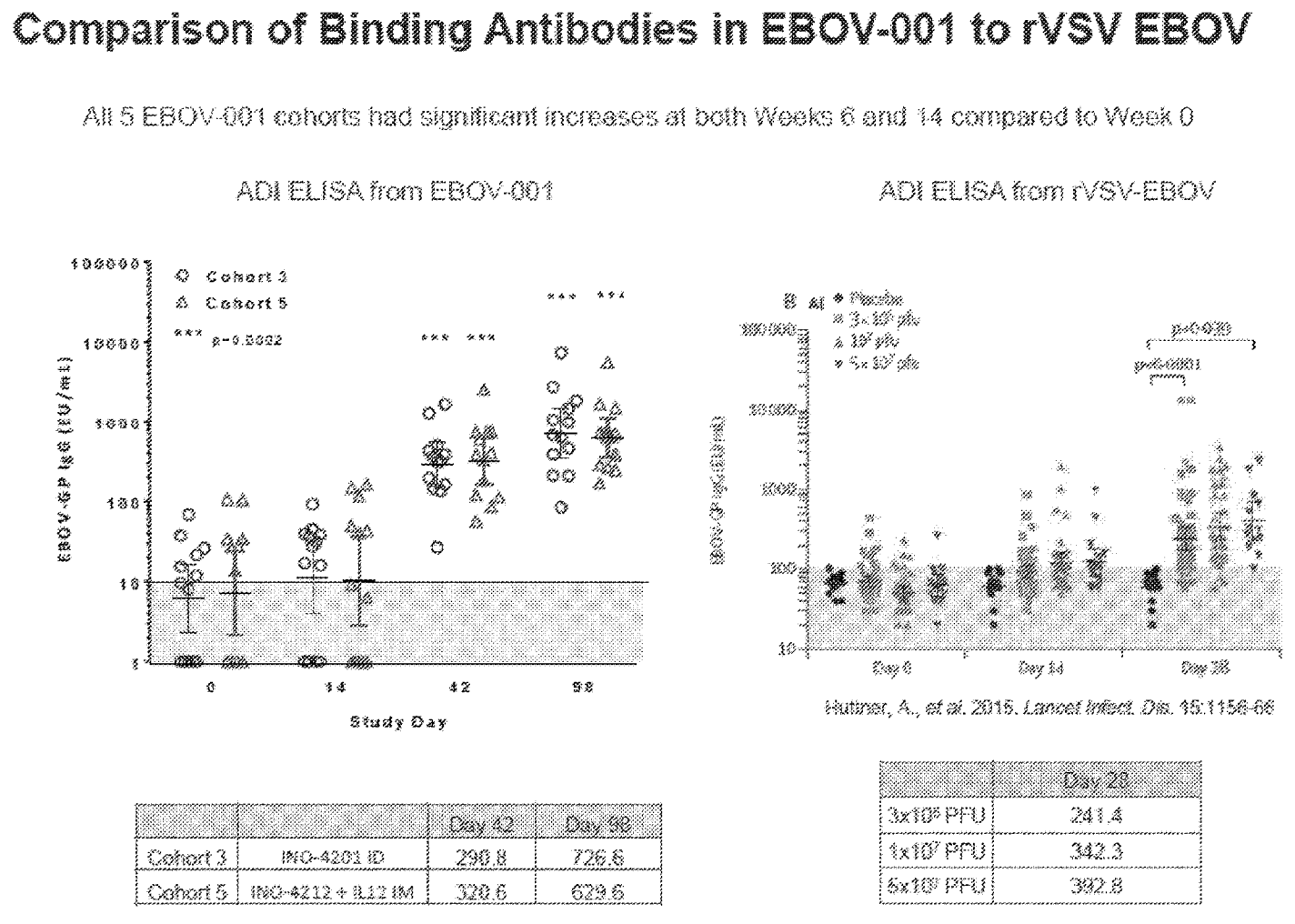

FIG. 58 depicts a comparison of binding antibodies in EBOV-001 to rVSV EBOV. All EBOV-001 cohorts had significant increases at both weeks 6 and 14 compared to week 0.

FIG. 59 depicts a summary of the Intradermal Delivery of EBOV GP DNA vaccine study. Cohorts were added to explore dosing, dose regimens and use of IL-12 DNA as an immuno-adjuvant.

Figure 60:
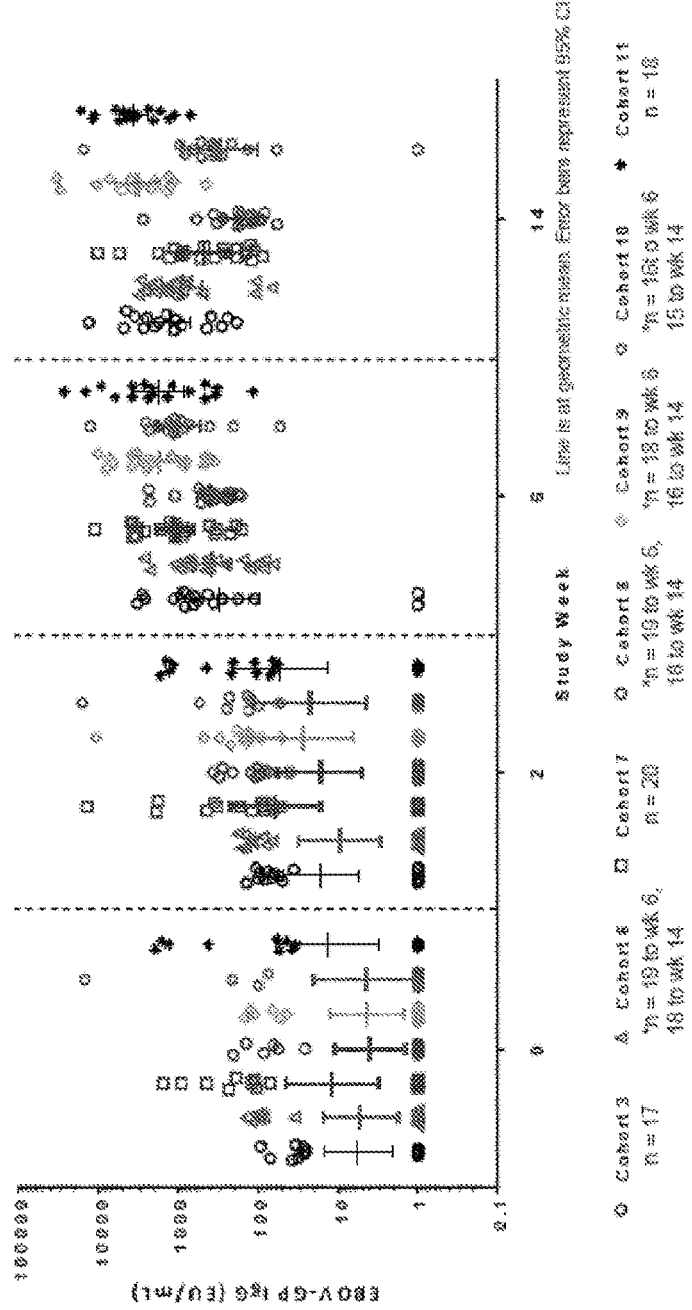

FIG. 60 depicts the results of ID cohorts at week 14. Sereoreactivity was observed in 125/127 (98.4%) subjects in all ID cohorts.

DETAILED DESCRIPTION OF PREFERRED EMBODIMENTS

In one aspect of the invention, it is desired that the consensus antigen provides for improved transcription and translation, including having one or more of the following: low GC content leader sequence to increase transcription; mRNA stability and codon optimization; eliminating to the extent possible cis-acting sequence motifs (i.e., internal TATA-boxes).

In some aspects of the invention, it is desired to generate a consensus antigen that generates a broad immune response across multiple strains, including having one or more of the following: incorporate all available full-length sequences; computer generate sequences that utilize the most commonly occurring amino acid at each position; and increase cross-reactivity between strains.

Diversity among the *Filoviridae* is relatively high. Intensive efforts have been aimed at developing a universal and broadly-reactive filovirus vaccine that would ideally provide protection against multiple species responsible for the highest human case-fatality rates. However, this proves difficult due to the relative high level of diversity among the *Filovirida*. The EBOV are currently classified into five distinct species, *Zaire ebolivirus* (ZEBOV), *Sudan ebolavirus* (SUDV), *Reston ebolavirus* (RESTV), *Bundibugyo ebolavirus* (BDBV) and *Tai Forest ebolavirus* (TAFV; formerly *Cote d'Ivoire ebolavirus*), the first two responsible for the highest lethality rates and the most likely candidates for weaponization. Diversity is lower among the Marburg viruses (MARV) of which can also be up to 90% lethal. Currently, there is only one classified species, *Marburg marburgvirus* (formerly *Lake Victoria marburgvirus*), although a recent amendment proposes that it contain two viruses including the Ravn virus (RAVV). Adding to the complexity for polyvalent-vaccine development, the MARV and EBOV are highly divergent, in which there exists about 67% divergence at the nucleotide level. Furthermore, phylogenetic diversity among the filoviral GP is also very high (82% overall). These allude to the potential of the filoviruses to evolve, as demonstrated by the recent emergence of BDBV in 2007. Therefore, due to relative divergence among the *Filoviridae*, we hypothesized that development of an effective polyvalent-filovirus vaccine will likely require a cocktail of immunogenic components.

A synthetic polyvalent-filovirus DNA vaccine against *Marburg marburgvirus* (MARV), *Zaire ebolivirus* (ZEBOV), and *Sudan ebolavirus* (SUDV) was developed. The novel polyvalent-filovirus vaccine comprised by three DNA plasmids encoding the envelope glycoprotein (GP) genes of *Marburg marburgvirus* (MARV), *Sudan ebolavirus* (SUDV) or *Zaire ebolivirus* (ZEBOV), adopting the multiagent approach. As a filoviral vaccine candidate, an enhanced DNA (DNA)-based platform exhibits many advantages given recent advances in genetic optimization and delivery techniques (Bagarazzi M L, et al. (2012). Immunotherapy Against HPV16/18 Generates Potent TH1 and Cytotoxic Cellular Immune Responses. *Sci Transl Med* 4: 155ra138; Kee S T, Gehl J, W. L E (2011). *Clinical Aspects of Electroporation*, Springer, New York, N.Y.; Hirao L A, et al. (2011). Multivalent smallpox DNA vaccine delivered by intradermal electroporation drives protective immunity in nonhuman primates against lethal monkeypox challenge. *J Infect Dis* 203: 95-102). As such, each GP was genetically-optimized, subcloned into modified mammalian expression vectors, and then delivered using in vivo electroporation (EP).

Preclinical efficacy studies were performed in guinea pigs and mice using rodent-adapted viruses, while murine T cell responses were extensively analyzed using a novel modified assay described herein. T cell responses were extensively analyzed including the use of a novel method for epitope identification and characterization described herein. This model provides an important preclinical tool for studying protective immune correlates that could be applied to existing platforms.

Vaccination in preclinical rodent studies was highly potent, elicited robust neutralizing antibodies (NAbs) and CTL expressing $T_h1$-type markers, and completely protected against MARV and ZEBOV challenge. Comprehensive T cell analysis as extensively analyzed using a novel modified assay described herein (Shedlock D J, et al. (2012). Vaccination with synthetic constructs expressing cytomegalovirus immunogens is highly T cell immunogenic in mice. *Hum Vaccin Immunother* 8: 1668-1681) revealed cytotoxic T lymphocytes of great magnitude, epitopic breadth, and $T_h1$-type marker expression. In total, 52 novel T cell epitopes from two different mouse genetic backgrounds were identified (19 of 20 MARV epitopes, 15 of 16 SUDV, and 18 of 22 ZEBOV) and occurred primarily in highly conserved regions of their respective glycoproteins (GPs). These data represent the most comprehensive report of preclinical glycoprotein epitopes to date.

Figure 1A:
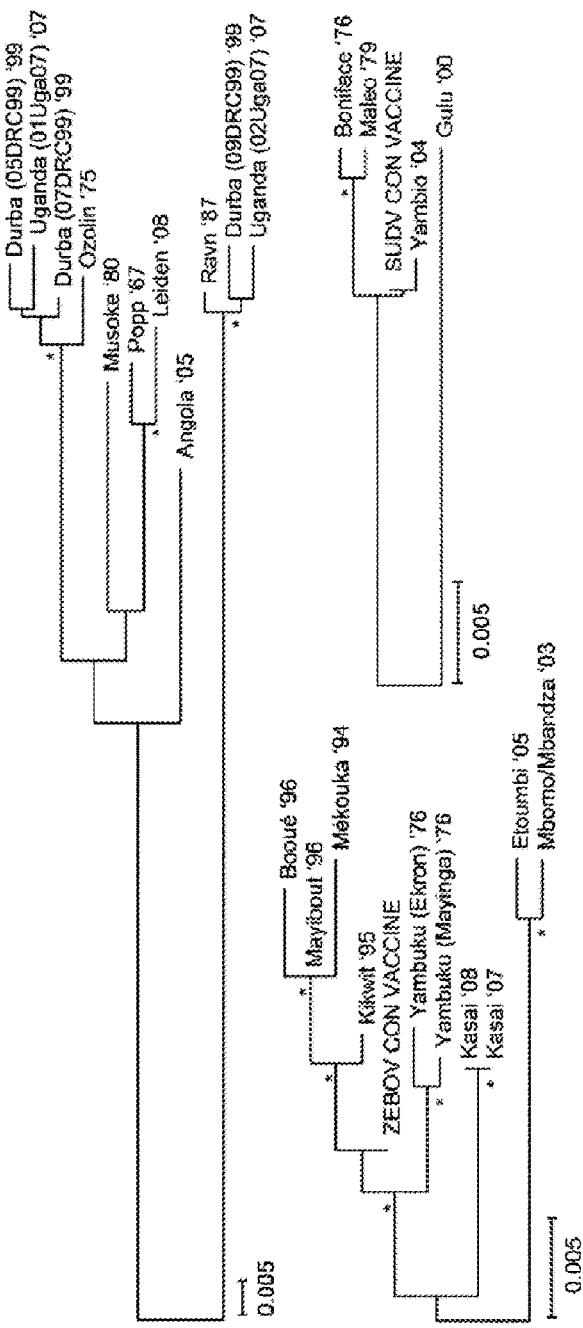
FIGS. 1A-1C refer to the polyvalent-vaccine construction strategy and expression experiments in Example 1.

In developing a strategy to provide protection against multiple species responsible for the highest human case-fatality rates, we focused on MARV, SUDV, and ZEBOV. Due to their relative divergence, we hypothesized that development of a polyvalent-filovirus vaccine would require a cocktail of components that can be quickly and easily adapted in response to future outbreak strains and/or species. While overall diversity among the EBOV is about 33%, amino acid identity increases substantially when SUDV and ZEBOV are analyzed separately (~94% identity within each species). Therefore, as shown in FIG. 1A, a two component strategy for coverage of the most lethal EBOV, one plasmid GP vaccine for SUDV and another for ZEBOV was designed. Since GP diversity among each species was relatively low (5.6% for SUDV and 7.1% for ZEBOV), consensus immunogens were developed increase inter-species coverage, a strategy shown previously to enhance protection among divergent strains of influenza and HIV. These GP sequences were consensus for all reported outbreak sequences (GenBank) as determined by alignment using Vector NTI software (Invitrogen, Calif., USA). Non-consensus residues, 4 amino acids each in SUDV (95, 203, 261, and 472) and ZEBOV (314, 377, 430, and 440), were weighted towards Gulu and Mbomo/Mbanza, respectively. Gulu was chosen since it was responsible for the highest human case-fatality rate of any *Filoviridae* outbreak (n=425), while Mbomo/Mbanza was chosen since they were the most recent and lethal outbreaks with published sequence data. The consensus GP for SUDV (SUDV CON VACCINE) and ZEBOV (ZEBOV CON VACCINE) were phylogenetically intermediary their parentally aligned strains.

Identification of proteins in FIG. 1A are as follows: MARV Durba (05DRC99) '99: ABE27085; Uganda (01Uga07) '07: ACT79229; Durba (07DRC99) '99: ABE27078; Ozolin '75: VGP_MABVO; Musoke '80: VGP_ MABVM; Popp '67: VGP_MABVP; Leiden '08: AEW11937; Angola '05: VGP_MABVA; Ravn '87: VGP_MABVR; Durba (09DRC99) '99; ABE27092; Uganda (02Uga07) '07: ACT79201. SUDV: Boniface '76: VGP_EBOSB; Maleo '79:VGP_EBOSM; Yambio '04: ABY75325; Gulu '00: VGP_EBOSU. ZEBOV: Booue '96: AAL25818; Mayibout '96: AEK25495; Mekouka '94: AAC57989, VGP_EBOG4; Kikwit '95: VGP_EBOZ5; Yambuku (Ekron) '76: VGP_EBOEC; Yambuku (Mayinga) '76: VGP_EBOZM; Kasai '08: AER59712; Kassai '07: AER59718; Etoumbi '05: ABW34742; Mbomo/Mbandza '03: ABW34743.

A sequence listing provided herewith contains a list of 72 sequences including the following SEQ ID NO:1 is the amino acid sequence of ZEBOV CON (CONGP1), which is a consensus *Zaire ebolivirus* envelope glycoprotein immunogen.

SEQ ID NO:2 is the amino acid sequence of SUDV CON, which is a consensus Sudan ebolavirus envelope glycoprotein immunogen.

SEQ ID NO:3 is the amino acid sequence of MARV or MARV ANG, which the amino acid sequence of the *Marburg marburgvirus* Angola 2005 envelope glycoprotein and a *Marburg marburgvirus* Angola 2005 envelope glycoprotein immunogen.

SEQ ID NO:4 is the amino acid sequence of MARV CON1, which is the first consensus *Marburg marburgvirus* envelope glycoprotein immunogen.

SEQ ID NO:5 is the amino acid sequence of MARV CON2, which is the second consensus *Marburg marburgvirus* envelope glycoprotein immunogen.

SEQ ID NO:6 is the amino acid sequence of MARV CON3, which is the third consensus *Marburg marburgvirus* envelope glycoprotein immunogen.

SEQ ID NOs:7-25 are peptides derived from MARV ANG.

SEQ ID NO:26-41 are peptides derived from SUDV CON.

SEQ ID NO: 42-62 are peptides derived from ZEBOV CON.

SEQ ID NO:63 is the sequence of the IgE signal peptide: MDWTWILFLVAAATRVHS.

SEQ ID NO:64 is the nucleotide sequence insert in plasmid pEBOZ which encodes consensus *Zaire ebolivirus* envelope glycoprotein immunogen.

SEQ ID NO:65 is the nucleotide sequence insert in plasmid pEBOS which encodes consensus *Sudan ebolavirus* envelope glycoprotein immunogen.

SEQ ID NO:66 is the nucleotide sequence insert in plasmid pMARZ ANG which encodes the *Marburg marburgvirus* Angola 2005 envelope glycoprotein.

SEQ ID NO:67 is the amino acid sequence of ZEBOVGUI (GuineaGP), which is a consensus *Zaire ebolivirus* envelope glycoprotein immunogen isolated from the 2014 Outbreak in Guinea.

SEQ ID NO:68 is the amino acid sequence of ZEBOVCON2 (CONGP2), which is a second consensus *Zaire ebolivirus* envelope glycoprotein.

SEQ ID NO:69 is the nucleotide sequence insert in plasmid pZEBOVGUI which encodes consensus *Zaire ebolivirus* envelope glycoprotein immunogen isolated from the 2014 Outbreak in Guinea.

SEQ ID NO:70 is the nucleotide sequence insert in plasmid pEBOZCON2 which encodes a second consensus *Zaire ebolivirus* envelope glycoprotein.

SEQ ID NO:71 is the nucleotide sequence of plasmid pEBOZCON2 which encodes a second consensus *Zaire ebolivirus* envelope glycoprotein.

SEQ ID NO:72 is the nucleotide sequence insert in plasmid pZEBOVGUI which encodes a *Zaire ebolivirus* envelope glycoprotein immunogen isolated from the 2014 Outbreak in Guinea.

In some embodiments, the strategy employs coding sequences for three filovirus immunogens selected from: MARV, SUDV, ZEBOV, ZEBOVGUI and ZEBOVCON2. MARV immunogen is the glycoprotein of the Angola 2005 isolate. For SUDV ZEBOV, ZEBOVGUI, and ZEBOVCON2 concensus glycoprotein sequences were designed.

In some embodiments, the strategy employs coding sequences for five filovirus immunogens. Three MARV immunogens are provided. Consensus glycoprotein Ozolin, Musoke, or Ravn derived from three clusters, were designed. These three MARV immunogens are targets for immune responses together the SUDV, ZEBOV or ZEBOVCON2, ZEBOVGUI consensus glycoprotein sequences that were designed.

In some embodiments, the strategy employs coding sequences for six filovirus immunogens. Four MARV immunogens are provided: three consensus glycoproteins derived from three clusters were designed. These three MARV immunogens are targets for immune responses together the SUDV, ZEBOV and ZEBOVCON2, ZEBOVGUI consensus glycoprotein sequences that were designed, the MARV immunogen is the glycoprotein of the Angola 2005 isolate.

As a candidate for filoviral vaccines, DNA vaccines exhibit a multitude of advantages including rapid and inexpensive up-scale production, stability at room temperature, and ease of transport, all of which further enhance this platform from an economic and geographic perspective. Due to the synthetic nature of the plasmids, Ag sequences can be quickly and easily modified in response to newly emergent species and/or expanded to include additional vaccine components and/or regimen for rapid response during outbreak settings. For example, the MARV strategies herein can be easily expanded for greater coverage by the co-administration of additional plasmids encoding consensus MARV GP (MGP) immunogens for other phylogenetic clusters.

While 'first-generation' DNA vaccines were poorly immunogenic, recent technological advances have dramatically improved their immunogenicity in clinical trials. Optimization of plasmid DNA vectors and their encoded Ag genes have led to increases in in vivo immunogenicity. Cellular uptake and subsequent Ag expression are substantially amplified when highly-concentrated plasmid vaccine formulations are administered with in vivo electroporation, a technology that uses brief square-wave electric pulses within the vaccination site to drive plasmids into transiently permeabilized cells. In theory, a cocktail of DNA plasmids could be assembled for directing a highly-specialized immune response against any number of variable Ags. Immunity can be further directed by co-delivery with plasmid molecular adjuvants encoding species-specific cytokine genes as well as 'consensus-engineering' of the Ag amino acid sequences to help bias vaccine-induced immunity towards particular strains. This strategy has been shown to enhance protection among divergent strains of influenza virus and HIV. Due in parts to these technological advancements, immunization regimens including these DNA vaccines are highly versatile and extremely customizable.

1. Definitions.

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

a. Adjuvant

"Adjuvant" as used herein may mean any molecule added to the DNA plasmid vaccines described herein to enhance antigenicity of the one or more consensus filovirus immunogens encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. In some embodiments, the coding sequence may optionally further comprise a start codon that encodes an N terminal methionine or a signal peptide such as an IgE or IgG signal peptide.

d. Genetic Construct

Genetic construct" as used herein refers to the DNA or RNA molecules that comprise a nucleotide sequence which encodes a protein, such as an immunogen. The genetic construct may also refer to a DNA molecule which transcribes RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

e. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

f. Consensus or Consensus Sequence

"Consensus" or "consensus sequence" as used herein may mean a synthetic nucleic acid sequence, or corresponding polypeptide sequence, constructed based on analysis of an alignment of multiple subtypes of a particular filovirus antigen, that can be used to induce broad immunity against multiple subtypes or serotypes of a particular filovirus antigen.

Consensus *Zaire ebolivirus* envelope glycoprotein immunogen refers to SEQ ID NO:1, fragments of SEQ ID NO:1, variants of SEQ ID NO:1 and fragment of variants of SEQ ID NO:1. (ZEBOV or ZEBOV CON or ZEBOV CON VACCINE). Plasmids comprising coding sequences of SEQ ID NO:1 may be referred to as pZEBOV or pEBOZ. Coding sequences for consensus *Zaire ebolivirus* envelope glycoprotein immunogen include SEQ ID NO:64, fragments of SEQ ID NO:64, variants of SEQ ID NO:64 and fragment of variants of SEQ ID NO:64. Plasmid pEBOZ comprises SEQ ID NO:64.

Consensus *Sudan ebolavirus* envelope glycoprotein immunogen refers to SEQ ID NO:2, fragments of SEQ ID NO:2, variants of SEQ ID NO:2 and fragment of variants of SEQ ID NO:2. (SUDV or SUDV CON or SUDV CON VACCINE) Plasmids comprising coding sequences of SEQ ID NO:2 may be referred to as pSUDV or pEBOS. Coding sequences for consensus *Sudan ebolavirus* envelope glycoprotein immunogen include SEQ ID NO:65, fragments of SEQ ID NO:65, variants of SEQ ID NO:65 and fragment of variants of SEQ ID NO:65. Plasmid pEBOS comprises SEQ ID NO:65.

*Marburg marburgvirus* Angola 2005 envelope glycoprotein is not a consensus but a protein sequence derived from an isolate. It has sequence SEQ ID NO:3. *Marburg marburgvirus* Angola 2005 envelope glycoprotein immunogen refers to SEQ ID NO:3, fragments of SEQ ID NO:3, variants of SEQ ID NO:3 and fragment of variants of SEQ ID NO:3. (MARV or MARV ANG or MARV ANG or MARV ANG VACCINE) Plasmids comprising coding sequences of SEQ ID NO:3 may be referred to as pMARV or pMARV-ANG. Coding sequences for *Marburg marburgvirus* Angola 2005 envelope glycoprotein immunogen include SEQ ID NO:66, fragments of SEQ ID NO:66, variants of SEQ ID NO:66 and fragment of variants of SEQ ID NO:66. Plasmid pMARV ANG comprises SEQ ID NO:66.

The first consensus *Marburg marburgvirus* envelope glycoprotein immunogen refers to SEQ ID NO:4, fragments of SEQ ID NO:4, variants of SEQ ID NO:4 and fragment of variants of SEQ ID NO:4. SEQ ID NO:4 is a *Marburg marburgvirus* consensus sequence from the Ravn cluster consensus (Ravn, Durba (09DRC99) and Uganda (02Uga07Y). (MARV CON1 or MARV-RAV CON or MARV-RAV CON VACCINE) Plasmids comprising coding sequences of SEQ ID NO:4 may be referred to as pMARV-RAV.

The second consensus *Marburg marburgvirus* envelope glycoprotein immunogen refers to SEQ ID NO:5, fragments of SEQ ID NO:5, variants of SEQ ID NO:5 and fragment of variants of SEQ ID NO:5. SEQ ID NO:5 is a *Marburg marburgvirus* consensus sequence from the Ozolin cluster consensus (Ozolin, Uganda (01Uga07), and Durba (05 and 07DRC99)). (MARV CON2 or MARV-OZO CON or MARV-OZO CON VACCINE) Plasmids comprising coding sequences of SEQ ID NO:5 may be referred to as pMARV-OZO.

The third consensus *Marburg marburgvirus* envelope glycoprotein immunogen refers to SEQ ID NO:6, fragments of SEQ ID NO:6, variants of SEQ ID NO:6 and fragment of variants of SEQ ID NO:6. SEQ ID NO:6 is a *Marburg marburgvirus* consensus sequence from the Musoke cluster consensus (Musoke, Popp, and Leiden). (MARV CON1 or MARV-MUS CON or MARV-MUS CON VACCINE) Plasmids comprising coding sequences of SEQ ID NO:6 may be referred to as pMARV-MUS.

Consensus *Zaire ebolivirus* GP envelope glycoprotein immunogen refers to SEQ ID NO:67, fragments of SEQ ID NO:67, variants of SEQ ID NO:67 and fragment of variants of SEQ ID NO:67. (ZEBOVGUI or ZEBOVGUI VACCINE). Plasmids comprising coding sequences of SEQ ID NO:67 may be referred to as pZEBOVGUI or pEBOZGUI. Coding sequences for consensus *Zaire ebolivirus* Guinea 2014 envelope glycoprotein immunogen include SEQ ID NO:69, fragments of SEQ ID NO:69, variants of SEQ ID NO:69 and fragment of variants of SEQ ID NO:69. Plasmid pEBOZGUI comprises SEQ ID NO:69.

A second consensus *Zaire ebolivirus* envelope glycoprotein immunogen refers to SEQ ID NO:68 fragments of SEQ ID NO:68, variants of SEQ ID NO:68 and fragment of variants of SEQ ID NO:68. (ZEBOV2 or ZEBOVCON2 or ZEBOVCON2 VACCINE) Plasmids comprising coding sequences of SEQ ID NO: 68 may be referred to as pEBOVCON2. Coding sequences for second consensus *Zaire ebolivirus* envelope glycoprotein immunogen include SEQ ID NO:70, fragments of SEQ ID NO:70, variants of SEQ ID NO:70 and fragment of variants of SEQ ID NO:70. Plasmid pEBOVCON2 comprises SEQ ID NO:70.

g. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

h. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

i. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

j. Electroporation

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

k. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

l. Fragment "Fragment" may mean a polypeptide fragment of a filovirus immunogen that is capable of eliciting an immune response in a mammal against filovirus by recognizing the particular filovirus antigen. The filovirus envelope glycoprotein immunogen may optionally include a signal peptides and/or a methionine at position 1, proteins 98% or more homologous to the consensus sequences set forth herein, proteins 99% or more homologous to the consensus sequences set forth herein, and proteins 100% identical to the consensus sequences set forth herein, in each case with or without signal peptides and/or a methionine at position 1. A fragment may or may not for example comprise a fragment of a filovirus immunogen linked to a signal peptide such as an immunoglobulin signal peptide for example IgE signal peptide or IgG signal peptide.

Fragments of any of ZEBOV CON, SUDV CON, MARV ANG, MARV-RAV CON, MARV-OZO CON, MARV-MUS CON, ZEBOVGUI or ZEBOVCON2 or variants thereof, in each case with or without signal peptides and/or a methionine at position 1, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length ZEBOV CON, SUDV CON, MARV ANG, MARV-RAV CON, MARV-OZO CON, MARV-MUS CON, ZEBOVGUI or ZEBOVCON2 or variants thereof. Fragments refer to fragments polypeptides 100% identical to the sequences ZEBOV CON, SUDV CON, MARV ANG, MARV-RAV CON, MARV-OZO CON, MARV-MUS CON, ZEBOVGUI or ZEBOVCON2 in each case with or without signal peptides and/or a methionine at position 1. Fragments also refer to fragments of variants, i.e. polypeptides that 95% or more, 98% or more, or 99% or more homologous to the sequences ZEBOV CON, SUDV CON, MARV ANG, MARV-RAV CON, MARV-OZO CON, MARV-MUS CON, ZEBOVGUI or ZEBOVCON2, in each case with or without signal peptides and/or a methionine at position 1. The fragment may comprise a fragment of a polypeptide that is 98% or more homologous, 99% or more homologous, or 100% identical to the Filovirus immunogens set forth in SEQ ID NOs: 1-6, 67-68 and additionally comprise a signal peptide such as an immunoglobulin signal peptide which is not included when calculating percent homology. In some embodiments, a fragment of SEQ ID NOs: 1-6, 67-68 linked to a signal peptide such as an immunoglobulin signal peptide for example IgE signal peptide or IgG signal peptide. The fragment may comprise fragments of SEQ ID NOs: 1-6, 67-68including the N terminal methionine. Fragments also refer to fragments of a polypeptide that is 95% or more, 98% or more, or 99% or more homologous to the sequence disclosed in SEQ ID NOs: 1-6, 67-68. If a signal peptide is present it is not included when calculating percent homology.

In some embodiments, fragments of SEQ ID NOs: 1-6, 67-68 or variants thereof may comprise 10, 15, 20, 30, 40, 50, 75, 100, 150, 200, 250, 300, 350, 400, 450, 500, 550, 600, 610, 620, 630, 640, 650, 660, 670 or more contiguous amino acids of any of SEQ ID NOs:1-6 or variants thereof. In some embodiments, fragments of SEQ ID NOs:1-6 or variants thereof may comprise 15, 20, 30, 40, 50, 75, 100, 150, 200, 250, 300, 350, 400, 450, 500, 550, 600, 610, 620, 630, 640, 650, 660, 670, 675 or less contiguous amino acids of any of SEQ ID NOs: 1-6, 67-68 or variants thereof.

"Fragment" may also mean a fragment of a nucleic acid sequence that encodes a filovirus immunogen, the nucleic acid fragment encoding a fragment of filovirus immunogen that is capable of eliciting an immune response in a mammal against filovirus by recognizing the particular filovirus antigen. Fragments of nucleic acid fragment encoding a filovirus immunogen or variants thereof, in each case with or without signal peptides and/or a methionine at position 1, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length nucleic acid sequence that encodes a filovirus immunogen or variants thereof. The fragment may comprise a fragment of nucleotide sequence that encodes polypeptide that is 98% or more homologous, 99% or more homologous, or 100% identical to the filovirus immunogens set forth in SEQ ID NOs: 1-6, 67-68 and additionally comprise a signal peptide such as an immunoglobulin signal peptide which is not included when calculating percent homology. In some embodiments, fragment of nucleotide sequence that encodes a fragment of SEQ ID NOs: 1-6, 67-68 linked to a signal peptide such as an immunoglobulin signal peptide for example IgE signal peptide or IgG signal peptide. Coding sequences of a signal peptide sis present it is not included when calculating percent homology. In some embodiments, fragment of nucleotide sequence that encodes fragments of SEQ ID NOs:1-6 or variants thereof may comprises sequences that encode 10, 15, 20, 30, 40, 50, 75, 100, 150, 200, 250, 300, 350, 400, 450, 500, 550, 600, 610, 620, 630, 640, 650, 660, 670 or more contiguous amino acids of any of SEQ ID NOs: 1-6, 67-68 or variants thereof. In some embodiments, fragment of nucleotide sequence that encodes fragments of SEQ ID NOs:1-6, 67-68 or variants thereof may sequences that encode comprise 15, 20, 30, 40, 50, 75, 100, 150, 200, 250, 300, 350, 400, 450, 500, 550, 600, 610, 620, 630, 640, 650, 660, 670, 675 or less contiguous amino acids of any of SEQ ID NOs:1-6, 67-68 or variants thereof.

In some embodiments, fragments are fragments of SEQ ID NO:64, SEQ ID NO:65, SEQ ID NO:66, SEQ ID NO:69, SEQ ID NO:70, or SEQ ID NO:72. Fragments of SEQ ID NO:64, SEQ ID NO:65, SEQ ID NO:66, SEQ ID NO:69, SEQ ID NO:70, or SEQ ID NO:72, in each case with or without signal peptides and/or a methionine at position 1, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length nucleic acid sequence that encodes a filovirus immunogen or variants thereof. The fragment of SEQ ID NO:64, SEQ ID NO:65, SEQ ID NO:66, SEQ ID NO:69, SEQ ID NO:70, or SEQ ID NO:72 may comprise a fragment of nucleotide sequence that encodes polypeptide that is 98% or more homologous, 99% or more homologous, or 100% identical to the filovirus immunogens encoded by of SEQ ID NO:64, SEQ ID NO:65, SEQ ID NO:66, SEQ ID NO:69, SEQ ID NO:70, or SEQ ID NO:72 and additionally comprise a signal peptide such as an immunoglobulin signal peptide which is not included when calculating percent homology. Fragments of SEQ ID NO:64, SEQ ID NO:65, SEQ ID NO:66, SEQ ID NO:69, SEQ ID NO:70, or SEQ ID NO:72 may comprises sequences that encode 10, 15, 20, 30, 40, 50, 75, 100, 150, 200, 250, 300, 350, 400, 450, 500, 550, 600, 610, 620, 630, 640, 650, 660, 670 or more contiguous amino acids of SEQ ID NO:64, SEQ ID NO:65, SEQ ID NO:66, SEQ ID NO:69, SEQ ID NO:70, or SEQ ID NO:72 or variants thereof. Fragments of SEQ ID NO:64, SEQ ID NO:65, SEQ ID NO:66, SEQ ID NO:69, SEQ ID NO:70, or SEQ ID NO:72 may comprises sequences that encode 15, 20, 30, 40, 50, 75, 100, 150, 200, 250, 300, 350, 400, 450, 500, 550, 600, 610, 620, 630, 640, 650, 660, 670, 675 or less contiguous amino acids of SEQ ID NO:64, SEQ ID NO:65, SEQ ID NO:66, SEQ ID NO:69, SEQ ID NO:70, or SEQ ID NO:72 or variants thereof. In some embodiments, fragments are fragments of RNA transcribed from or encoded by SEQ ID NO:64, SEQ ID NO:65, SEQ ID NO:66, SEQ ID NO:69, SEQ ID NO:70, or SEQ ID NO:72 m. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

n. Impedance

"Impedance" as used herein may be used when discussing the feedback mechanism and can be converted to a current value according to Ohm's law, thus enabling comparisons with the preset current.

o. Immune Response

"Immune response" as used herein may mean the activation of a host's immune system, e.g., that of a mammal, in response to the introduction of one or more filovirus consensus antigen via the provided DNA plasmid vaccines. The immune response can be in the form of a cellular or humoral response, or both.

p. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

q. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

r. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

s. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

t. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

u. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

v. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. Variants are preferably homologous to SEQ ID NO:1-6,67-68 by 95% or more, 96% or more, 97% or more, 98% or more or 99% or more.

"Variant" with respect to a nucleic acid sequence that encodes the same specific amino acid sequence differs in nucleotide sequence by use of different codons. Variants of SEQ ID NO:64, SEQ ID NO:65, SEQ ID NO:66, SEQ ID NO:69, SEQ ID NO:70, or SEQ ID NO:72 that encode the same amino acid sequence as those encoded by SEQ ID NO:64, SEQ ID NO:65, SEQ ID NO:66, SEQ ID NO:69, SEQ ID NO:70, or SEQ ID NO:72 may be any degree of homology, preferably 80% or more, 85% or more, 90% or more, 95% or more, 96% or more, 97% or more, 98% or more or 99% or more. Variants of RNA transcribed by SEQ ID NO:64, SEQ ID NO:65, SEQ ID NO:66, SEQ ID NO:69, SEQ ID NO:70, or SEQ ID NO:72 that encode the same amino acid sequence as those encoded by SEQ ID NO:64, SEQ ID NO:65, SEQ ID NO:66, SEQ ID NO:69, SEQ ID NO:70, or SEQ ID NO:72 may be any degree of homology, preferably 80% or more, 85% or more, 90% or more, 95% or more, 96% or more, 97% or more, 98% or more or 99% or more.Variant may also be variants of SEQ ID NO:64, SEQ ID NO:65, SEQ ID NO:66, SEQ ID NO:69, SEQ ID NO:70, or SEQ ID NO:72 that encode protein which are variants of the proteins encoded by SEQ ID NO:64, SEQ ID NO:65, SEQ ID NO:66, SEQ ID NO:69, SEQ ID NO:70, or SEQ ID NO:72 with an amino acid sequence that is substantially identical to a referenced protein with an amino acid sequence that retains at least one biological activity, typically the amino acid sequences are homologous by 95% or more, 96% or more, 97% or more, 98% or more or 99% or more. Variant may also be variants of RNA transcribed by SEQ ID NO:64, SEQ ID NO:65, SEQ ID NO:66, SEQ ID NO:69, SEQ ID NO:70, or SEQ ID NO:72 that encode protein which are variants of the proteins encoded the RNA transcribed by SEQ ID NO:64, SEQ ID NO:65, SEQ ID NO:66, SEQ ID NO:69, SEQ ID NO:70, or SEQ ID NO:72 with an amino acid sequence that is substantially identical to a referenced protein with an amino acid sequence that retains at least one biological activity, typically the amino acid sequences are homologous by 95% or more, 96% or more, 97% or more, 98% or more or 99% or more w. Vector "Vector" used herein may mean a nucleic acid sequence containing an origin of replication. A vector may be a plasmid, bacteriophage, bacterial, viral vector, artificial chromosome or yeast artificial chromosome. A vector may be a DNA or RNA vector. A vector may be either a self-replicating extrachromosomal vector or a vector which integrates into a host genome.

2. Proteins

Provided herein are filovirus immunogens that can be used to induce broad immunity against multiple subtypes or serotypes of a particular filovirus antigen. Consensus filovirus antigens may include consensus amino acid sequences of *Marburgvirus* filovirus glycoprotein MARV RAV immunogen, consensus amino acid sequences of *Marburgvirus* filovirus glycoprotein MARV OZO immunogen, consensus amino acid sequences of *Marburgvirus filovirus* glycoprotein MARV MUS immunogen, isolate amino acid sequences of *Marburgvirus filovirus* glycoprotein MARV ANG immunogen, consensus amino acid sequences of *Zaire ebolavirus* glycoprotein ZEBOV immunogen, consensus amino acid sequences of *Zaire ebolavirus* glycoprotein ZEBOV2014 immunogen, isolate amino acid sequences of *Zaire ebolavirus* glycoprotein ZEBOVCON2 immunogen, and consensus amino acid sequences of *Sudan ebolavirus* glycoprotein SUDV immunogen, respectively. In some embodiments, the immunogens may comprise a signal peptide from a different protein such as an immunoglobulin protein, for example an IgE signal peptide or an IgG signal peptide.

The amino acid sequence for immunogens include SEQ ID NO:1-6,67-68 variants thereof and fragments of SEQ ID NO:1-6, 67-68 and variants thereof, optionally including a signal peptide such as for example an IgE or IgG signal peptide.

3. Coding Sequences Encoding Proteins

Coding sequences encoding the proteins set forth herein may be generated using routine methods. Composition comprising a nucleic acid sequence that encodes a consensus *Zaire ebolavirus* envelope glycoprotein immunogen, comprising a nucleic acid sequence that encodes a second consensus *Zaire ebolivirus* envelope glycoprotein immunogen, a nucleic acid sequence that encodes a Consensus *Zaire ebolivirus* Guinea envelope glycoprotein immunogen envelope glycoprotein immunogen, a nucleic acid sequence that encodes a consensus *Sudan ebolavirus* envelope glycoprotein immunogen, a nucleic acid sequence that encodes a *Marburg marburgvirus* Angola 2005 envelope glycoprotein immunogen are provided and a nucleic acid sequence that encodes a first consensus *Marburg marburgvirus* envelope glycoprotein immunogen, a nucleic acid sequence that encodes a second consensus *Marburg marburgvirus* envelope glycoprotein immunogen, and a nucleic acid sequence that encodes a third consensus *Marburg marburgvirus* envelope glycoprotein immunogen can be generated based upon the amino acid sequences disclosed.

Nucleic acid sequence may encodes a full length consensus *Zaire ebolivirus* envelope glycoprotein immunogen, a full length second consensus *Zaire ebolivirus* envelope glycoprotein immunogen, a full length consensus Consensus *Zaire ebolivirus* Guinea envelope glycoprotein immunogen envelope glycoprotein immunogen, a full length consensus Sudan ebolavirus envelope glycoprotein immunogen, a full length *Marburg marburgvirus* Angola 2005 envelope glycoprotein immunogen, a full length first consensus *Marburg marburgvirus* envelope glycoprotein immunogen, a full length second consensus *Marburg marburgvirus* envelope glycoprotein immunogen, or a full length third consensus *Marburg marburgvirus* envelope glycoprotein immunogen. Nucleic acid sequences may comprise a sequence that encodes SEQ ID NO:1, SEQ ID NO:2, SEQ ID NO:3, SEQ ID NO:4, SEQ ID NO:5, SEQ ID NO:6, SEQ ID NO:67, or SEQ ID NO:68. Nucleic acid sequence may comprise SEQ ID NO:64, SEQ ID NO:65, SEQ ID NO:66, SEQ ID NO:69 SEQ ID NO:70, or SEQ ID NO:72. In one embodiment the nucleotide sequence comprises an RNA sequence transcribed from a DNA sequence described herein. For example, nucleic acids may comprise an RNA sequence transcribed by the DNA sequence of SEQ ID NOs: 64, 65, 66, 69, 70 or 72, a fragment thereof or a variant thereof. Nucleic acid sequence may optionally comprise coding sequences that encode a signal peptide such as for example an IgE or IgG signal peptide.

Nucleic acid sequence may encode a fragment of a full length consensus *Zaire ebolavirus* envelope glycoprotein immunogen, a fragment of a full length second consensus *Zaire ebolavirus* envelope glycoprotein immunogen, a fragment of a full length *Consensus Zaire ebolavirus Guinea* envelope glycoprotein immunogen envelope glycoprotein immunogen, a fragment of a full length consensus *Sudan ebolavirus* envelope glycoprotein immunogen, a fragment of a full length *Marburg marburgvirus* Angola 2005 envelope glycoprotein immunogen, a fragment of a full length first consensus *Marburg marburgvirus* envelope glycoprotein immunogen, a fragment of a full length second consensus *Marburg marburgvirus* envelope glycoprotein immunogen, or a fragment of a full length third consensus *Marburg marburgvirus* envelope glycoprotein immunogen. Nucleic acid sequence may comprise a sequence that encodes a fragment of SEQ ID NO:1, SEQ ID NO:2, SEQ ID NO:3, SEQ ID NO:4, SEQ ID NO:5, SEQ ID NO:6, SEQ ID NO:67, or SEQ ID NO:68. Nucleic acid sequence may comprise a fragment of SEQ ID NO:64, SEQ ID NO:65, SEQ ID NO:66, SEQ ID NO:69 SEQ ID NO:70, or SEQ ID NO:72. Fragment sizes are disclosed herein as set forth in section entitled "Fragments". Nucleic acid sequence may optionally comprise coding sequences that encode a signal peptide such as for example an IgE or IgG signal peptide.

Nucleic acid sequences may encode a protein homologous to a full length consensus *Zaire ebolivirus* envelope glycoprotein immunogen, a full length second consensus Zaire ebolavirus envelope glycoprotein immunogen, a full length *Consensus Zaire ebolavirus Guinea* envelope glycoprotein immunogen envelope glycoprotein immunogen, a protein homologous to a full length consensus *Sudan ebolavirus* envelope glycoprotein immunogen, a protein homologous to a full length *Marburg marburgvirus* Angola 2005 envelope glycoprotein immunogen, a protein homologous to a full length first consensus *Marburg marburgvirus* envelope glycoprotein immunogen, a protein homologous to a full length second consensus *Marburg marburgvirus* envelope glycoprotein immunogen, or a protein homologous to a full length third consensus *Marburg marburgvirus* envelope glycoprotein immunogen. Nucleic acid sequence may comprise a sequence that encodes a protein homologous to SEQ ID NO:1, SEQ ID NO:2, SEQ ID NO:3, SEQ ID NO:4, SEQ ID NO:5, SEQ ID NO:6, SEQ ID NO:67, or SEQ ID NO:68. Nucleic acid sequence may be homologous to SEQ ID NO:64, SEQ ID NO:65, SEQ ID NO:66, SEQ ID NO:69 SEQ ID NO:70, or SEQ ID NO:72. Degrees of homology are discussed herein such as in the section referring to Variants. Nucleic acid sequence may optionally comprise coding sequences that encode a signal peptide such as for example an IgE or IgG signal peptide.

Nucleic acid sequence may encode a protein homologous to fragment of a full length consensus *Zaire ebolivirus* envelope glycoprotein immunogen, a protein homologous to fragment of a full length second consensus *Zaire ebolivirus* envelope glycoprotein immunogen, a protein homologous to fragment of a full length Consensus *Zaire ebolivirus* Guinea envelope glycoprotein immunogen envelope glycoprotein immunogen, a protein homologous to a fragment of a full length consensus *Sudan ebolavirus* envelope glycoprotein immunogen, a protein homologous to a fragment of a full length *Marburg marburgvirus* Angola 2005 envelope glycoprotein immunogen, a protein homologous to a fragment of a full length first consensus *Marburg marburgvirus* envelope glycoprotein immunogen, a protein homologous to a fragment of a full length second consensus *Marburg marburgvirus* envelope glycoprotein immunogen, or a protein homologous to a fragment of a full length third consensus *Marburg marburgvirus* envelope glycoprotein immunogen. Nucleic acid sequence may comprise a sequence that encodes a protein homologous to a fragment of SEQ ID NO:1, SEQ ID NO:2, SEQ ID NO:3, SEQ ID NO:4, SEQ ID NO:5, SEQ ID NO:6, SEQ ID NO:67, or SEQ ID NO:68. Nucleic acid sequence may comprise a fragment homologous to SEQ ID NO:64, SEQ ID NO:65, SEQ ID NO:66, SEQ ID NO:69 SEQ ID NO:70, or SEQ ID NO:72. Degrees of homology are discussed herein such as in the section referring to Variants. Nucleic acid sequence may optionally comprise coding sequences that encode a signal peptide such as for example an IgE or IgG signal peptide.

SEQ ID NO:64 is the nucleotide sequence insert in plasmid pEBOZ which encodes consensus *Zaire ebolivirus* envelope glycoprotein immunogen.

SEQ ID NO:65 is the nucleotide sequence insert in plasmid pEBOS which encodes consensus *Sudan ebolavirus* envelope glycoprotein immunogen.

SEQ ID NO:66 is the nucleotide sequence insert in plasmid pMARZ ANG which encodes the *Marburg marburgvirus* Angola 2005 envelope glycoprotein.

SEQ ID NO:69 is the nucleotide sequence insert in plasmid pEBOZGUI which encodes consensus *Zaire ebolivirus* GP envelope glycoprotein immunogen SEQ ID NO:70 is the nucleotide sequence insert in plasmid pEBOZCON2 which encodes a second consensus *Zaire ebolivirus* envelope glycoprotein 4. Vectors Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

a. Plasmid

Plasmid may comprise a nucleic acid sequence that encodes one or more of the various immunogens disclosed above including coding sequences that encode synthetic, consensus antigen capable of eliciting an immune response against filoproteins.

A single plasmid may contain coding sequence for a single filoprotein immunogen, coding sequence for two filoprotein immunogens, coding sequence for three filoprotein immunogens, coding sequence for four filoprotein immunogens, coding sequence for five filoprotein immunogens or coding sequence for six filoprotein immunogens. A single plasmid may contain a coding sequence for a single filoprotein immunogen which can be formulated together. In some embodiments, a plasmid may comprise coding sequence that encodes IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in Escherichia coli (E.coli). The plasmid may also be pYES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

b. RNA Vectors

In one embodiment, the nucleic acid is an RNA molecule. Accordingly, in one embodiment, the invention provides an RNA molecule encoding one or more of the envelope glycoprotein (GP) genes of *Marburg marburgvirus* (MARV), *Sudan ebolavirus* (SUDV) or *Zaire ebolavirus* (ZEBOV). The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded.

c. Linear Vectors

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid may be pVAX, pcDNA3.0, or provax, or any other expression vector capable of expressing the DNA and enabling a cell to translate the sequence to an antigen that is recognized by the immune system.

The LEC may be derived from any plasmid capable of being linearized. The plasmid may be capable of expressing the antigen. The plasmid may be pVAX, pcDNA3.0, or provax, or any other expression vector capable of expressing the DNA and enabling a cell to translate the sequence to a antigen that is recognized by the immune system.

d. Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

5. Compositions

Compositions are provided which comprise nucleic acid molecules. The compositions may comprise a plurality of copies of a single nucleic acid molecule such a single plasmid, a plurality of copies of two or more different nucleic acid molecules such as two or more different plasmids. For example a composition may comprise plurality of two, three, four, five, six, seven, eight, nine or ten or more different nucleic acid molecules. Such compositions may comprise plurality of two, three, four, five, six, or more different plasmids.

Compositions may comprise nucleic acid molecules, such as plasmids, that collectively contain coding sequence for a single filoprotein immunogen selected from the group consisting of one or more a consensus *Zaire ebolivirus* envelope glycoprotein immunogen, a second consensus *Zaire ebolivirus* envelope glycoprotein immunogen, a Consensus *Zaire ebolavirus* Guinea envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen.

Composition comprise nucleic acid sequence that encode the combination of: a consensus *Zaire ebolivirus* envelope glycoprotein immunogen and a consensus *Sudan ebolavirus* envelope glycoprotein immunogen; or a consensus *Zaire ebolivirus* envelope glycoprotein immunogen and a second consensus *Zaire ebolivirus* envelope glycoprotein immunogen; or a consensus *Zaire ebolivirus* envelope glycoprotein immunogen and a *Consensus Zaire ebolivirus Guinea* envelope glycoprotein immunogen; or a consensus *Zaire ebolivirus* envelope glycoprotein immunogen, a consensus *Sudan ebolavirus* envelope glycoprotein immunogen and the Marburg marburgvirus Angola 2005 envelope glycoprotein; or a consensus *Zaire ebolivirus* envelope glycoprotein immunogen, a consensus *Sudan ebolavirus* envelope glycoprotein immunogen and the second consensus *Zaire ebolivirus* envelope glycoprotein immunogen; or a consensus Zaire ebolavirus envelope glycoprotein immunogen, a consensus *Sudan ebolavirus* envelope glycoprotein immunogen and the *Consensus Zaire ebolivirus* Guinea envelope glycoprotein immunogen; or a consensus *Zaire ebolivirus* envelope glycoprotein immunogen, a second consensus *Zaire ebolivirus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen; or a consensus *Zaire ebolivirus* envelope glycoprotein immunogen, a Consensus *Zaire ebolivirus* Guinea envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen; or a consensus *Zaire ebolivirus* envelope glycoprotein immunogen, a consensus *Sudan ebolavirus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen; or a consensus *Zaire ebolivirus* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen; or a consensus *Zaire ebolivirus* envelope glycoprotein immunogen, a consensus *Sudan ebolavirus* envelope glycoprotein immunogen, a Consensus *Zaire ebolavirus* Guinea envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen; or a consensus *Zaire ebolivirus* envelope glycoprotein immunogen, a consensus *Sudan ebolavirus* envelope glycoprotein immunogen, a second consensus *Zaire ebolivirus* envelope glycoprotein immunogen the *Marburg marburgvirus* Angola 2005 envelope glycoprotein, the first consensus *Marburg marburgvirus* envelope glycoprotein immunogen and the third consensus *Marburg marburgvirus* envelope glycoprotein immunogen.

Each coding sequence for each filoprotein immunogens is preferably included on a separate plasmid.

Accordingly, compositions that comprise nucleic acid sequence that encode a consensus *Zaire ebolivirus* envelope glycoprotein immunogen and a consensus *Sudan ebolavirus* envelope glycoprotein immunogen; a consensus *Zaire ebolivirus* envelope glycoprotein immunogen and a second consensus *Zaire ebolivirus* envelope glycoprotein immunogen; or a consensus *Zaire ebolavirus* envelope glycoprotein immunogen and the Consensus *Zaire ebolivirus* Guinea envelope glycoprotein immunogen, may be on a single plasmid but are preferably on two separate plasmids.

Compositions that comprise nucleic acid sequence that encode a consensus *Zaire ebolavirus* envelope glycoprotein immunogen, a consensus *Sudan ebolavirus* envelope glycoprotein immunogen and the *Marburg marburgvirus* Angola 2005 envelope glycoprotein; or a consensus *Zaire ebolivirus* envelope glycoprotein immunogen, a consensus *Sudan ebolavirus* envelope glycoprotein immunogen and the second consensus *Zaire ebolivirus* envelope glycoprotein immunogen; or a consensus *Zaire ebolivirus* envelope glycoprotein immunogen, a consensus *Sudan ebolavirus* envelope glycoprotein immunogen and the Consensus *Zaire ebolavirus* Guinea envelope glycoprotein immunogen; may be on a single plasmid or on two plasmids in any permutation but are preferably on three separate plasmids.

Compositions that comprise nucleic acid sequence that encode a consensus *Zaire ebolavirus* envelope glycoprotein immunogen, a consensus *Sudan ebolavirus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation but are preferably on five separate plasmids.

Compositions that comprise nucleic acid sequence that encode a consensus *Zaire ebolavirus* envelope glycoprotein immunogen, a second consensus *Zaire ebolivirus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation but are preferably on five separate plasmids.

Compositions that comprise nucleic acid sequence that encode a consensus *Zaire ebolavirus* envelope glycoprotein immunogen, a Consensus *Zaire ebolivirus* Guinea envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation but are preferably on five separate plasmids.

Compositions that comprise nucleic acid sequence that encode a consensus *Zaire ebolavirus* envelope glycoprotein immunogen, a consensus *Sudan ebolavirus* envelope glycoprotein immunogen, a second consensus *Zaire ebolivirus* envelope glycoprotein immunogen the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation or on four plasmids in any permutation but are preferably on six separate plasmids.

Compositions that comprise nucleic acid sequence that encode a consensus *Zaire ebolavirus* envelope glycoprotein immunogen, a consensus *Sudan ebolavirus* envelope glycoprotein immunogen, the Consensus *Zaire ebolivirus* Guinea envelope glycoprotein immunogen the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation or on four plasmids in any permutation but are preferably on six separate plasmids.

Compositions that comprise nucleic acid sequence that encode a consensus *Zaire ebolavirus* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation or on five plasmids in any permutation but are preferably on six separate plasmids.

Compositions that comprise nucleic acid sequence that encode a consensus *Zaire ebolavirus* envelope glycoprotein immunogen, a second consensus *Zaire ebolivirus* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation or on five plasmids in any permutation or on six plasmids in any permutation but are preferably on seven separate plasmids.

Compositions that comprise nucleic acid sequence that encode a consensus *Zaire ebolavirus* envelope glycoprotein immunogen, the *Consensus Zaire ebolivirus Guinea* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus Marburg marburgvirus envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation or on five plasmids in any permutation or on six plasmids in any permutation but are preferably on seven separate plasmids.

Likewise, compositions that comprise nucleic acid sequence that encode a consensus *Zaire ebolivirus* envelope glycoprotein immunogen, a second consensus *Zaire ebolavirus* envelope glycoprotein immunogen, the *Consensus Zaire ebolivirus Guinea* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen may be on a single plasmid or on two plasmids in any permutation, or on three plasmids in any permutation or on four plasmids in any permutation or on five plasmids in any permutation or on six plasmids in any permutation or on seven plasmids in any permutation but are preferably on eight separate plasmids.

6. Vaccine

Provided herein is a vaccine capable of generating in a mammal an immune response against Filovirus, particularly *Marburgvirus, Ebolavirus Sudan* and/or *Ebolavirus Zaire*. The vaccine may comprise each plasmid as discussed above. The vaccine may comprise a plurality of the plasmids, or combinations thereof. The vaccine may be provided to induce a therapeutic or prophylactic immune response.

Vaccines may be used to deliver nucleic acid molecules that encode a consensus *Zaire ebolavirus* envelope glycoprotein immunogen and a consensus *Sudan ebolavirus* envelope glycoprotein immunogen. Vaccines may be used to deliver nucleic acid molecules that encode a consensus *Zaire ebolivirus* envelope glycoprotein immunogen and a *Consensus Zaire ebolavirus Guinea* envelope glycoprotein immunogen. Vaccines may be used to deliver nucleic acid molecules that encode a consensus *Zaire ebolivirus* envelope glycoprotein immunogen and a second consensus *Zaire ebola virus* envelope glycoprotein immunogen. Vaccines may be used to deliver nucleic acid molecules that encode a consensus *Zaire ebolivirus* envelope glycoprotein immunogen, a consensus *Sudan ebolavirus* envelope glycoprotein immunogen and a second consensus *Zaire ebola virus* envelope glycoprotein immunogen. Vaccines may be used to deliver nucleic acid molecules that encode a consensus *Zaire ebolivirus* envelope glycoprotein immunogen, a consensus *Sudan ebolavirus* envelope glycoprotein immunogen and the *Consensus Zaire ebolivirus Guinea* envelope glycoprotein immunogen. Vaccines may be used to deliver nucleic acid molecules that encode a consensus *Zaire ebolivirus* envelope glycoprotein immunogen, a consensus *Sudan ebolavirus* envelope glycoprotein immunogen and the *Marburg marburgvirus* Angola 2005 envelope glycoprotein. Vaccines may be used to deliver nucleic acid molecules that encode a consensus *Zaire ebolivirus* envelope glycoprotein immunogen, a second consensus *Zaire ebola virus* envelope glycoprotein immunogen and the *Marburg marburgvirus* Angola 2005 envelope glycoprotein. Vaccines may be used to deliver nucleic acid molecules that encode a consensus *Zaire ebolivirus* envelope glycoprotein immunogen, a *Consensus Zaire ebolavirus Guinea* envelope glycoprotein immunogen and the *Marburg marburgvirus* Angola 2005 envelope glycoprotein. Vaccines may be used to deliver nucleic acid molecules that encode a consensus *Zaire ebolivirus* envelope glycoprotein immunogen, a consensus *Sudan ebolavirus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines may be used to deliver nucleic acid molecules that encode a consensus *Zaire ebolavirus* envelope glycoprotein immunogen, a second consensus *Zaire ebola virus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines may be used to deliver nucleic acid molecules that encode a consensus *Zaire ebolivirus* envelope glycoprotein immunogen, a Consensus *Zaire ebolivirus Guinea* envelope glycoprotein immunogen, a consensus *Sudan ebolavirus* envelope glycoprotein immunogen, the first consensus *Marburg marburgvirus* envelope glycoprotein immunogen, the second consensus *Marburg marburgvirus* envelope glycoprotein immunogen and the third consensus Marburg marburgvirus envelope glycoprotein immunogen. Vaccines may be used to deliver nucleic acid molecules that encode a consensus *Zaire ebolivirus* envelope glycoprotein immunogen, a *Zaire ebolavirus* 2014 envelope glycoprotein immunogen, a consensus *Sudan ebolavirus* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines may be used to deliver nucleic acid molecules that encode a consensus *Zaire ebolivirus* envelope glycoprotein immunogen, a Consensus *Zaire ebolivirus Guinea* envelope glycoprotein immunogen, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines may be used to deliver nucleic acid molecules that encode a consensus *Zaire ebolivirus* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines may be used to deliver nucleic acid molecules that encode a consensus *Zaire ebolivirus* envelope glycoprotein immunogen, a second consensus *Zaire ebola virus* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus Marburg marburgvirus envelope glycoprotein immunogen and the third consensus Marburg marburgvirus envelope glycoprotein immunogen. Vaccines may be used to deliver nucleic acid molecules that encode a consensus *Zaire ebolivirus* envelope glycoprotein immunogen, the *Consensus Zaire ebolavirus Guinea* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines may be used to deliver nucleic acid molecules that encode a consensus *Zaire ebolivirus* envelope glycoprotein immunogen, a second consensus *Zaire ebola virus* envelope glycoprotein immunogen, the *Consensus Zaire ebolavirus Guinea* envelope glycoprotein immunogen, a consensus *Sudan ebolavirus* envelope glycoprotein immunogen, the *Marburg marburgvirus* Angola 2005 envelope glycoprotein, the first consensus *Marburg marburgvirus* envelope glycoprotein immunogen, the second consensus *Marburg marburgvirus* envelope glycoprotein immunogen and the third consensus *Marburg marburgvirus* envelope glycoprotein immunogen. Vaccines are preferably compositions comprising plasmids.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the vaccine. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof. In some embodiments adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The vaccine may further comprise a genetic vaccine facilitator agent as described in U.S. Ser. No. 021,579 filed Apr. 1, 1994, which is fully incorporated by reference.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

The vaccine may be stable for is stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the vaccine is stable under refrigeration (2-8° C.). Accordingly, in one embodiment, the vaccine does not require frozen cold-chain. A vaccine is stable if it retains its biological activity for a sufficient period to allow its intended use (e.g., to generate an immune response in a subject). For example, for vaccines that are to be stored, shipped, etc., it may be desired that the vaccines remain stable for months to years.

7. Methods of Delivery the Vaccine

Provided herein is a method for delivering the vaccine for providing genetic constructs and proteins of the consensus antigen which comprise epitopes that make them particular effective against immunogens of filovirus, particularly *Marburgvirus, Ebolavirus Sudan* and/or *Ebolavirus Zaire*, against which an immune response can be induced. The method of delivering the vaccine or vaccination may be provided to induce a therapeutic and prophylactic immune response. The vaccination process may generate in the mammal an immune response against filovirus, particularly *Marburgvirus, Ebolavirus Sudan* and/or *Ebolavirus Zaire*. The vaccine may be delivered to an individual to modulate the activity of the mammal's immune system and enhance the immune response. The delivery of the vaccine may be the transfection of the consensus antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against filovirus, particularly *Marburgvirus, Ebolavirus Sudan* and/or *Ebolavirus Zaire* by administering to the mammals the vaccine as discussed above.

Upon delivery of the vaccine and plasmid into the cells of the mammal, the transfected cells will express and secrete consensus antigens for each of the plasmids injected from the vaccine. These proteins will be recognized as foreign by the immune system and antibodies will be made against them. These antibodies will be maintained by the immune system and allow for an effective response to subsequent infections by filovirus, particularly *Marburgvirus, Ebolavirus Sudan* and/or *Ebolavirus Zaire*.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The vaccine may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application, Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing DNA Plasmids

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Example. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Methods

Plasmid Vaccine Construction

The pMARV, pEBOS, and pEBOZ plasmid DNA constructs encode full-length GP proteins. An amino acid consensus strategy was used for the pEBOS and pEBOZ, while a type-matched sequence from the 2005 Angola outbreak strain was used (GenBank #VGP_MABVR) for pMARV (Towner J S, et al. (2006). *Marburgvirus* genomics and association with a large hemorrhagic fever outbreak in Angola. *J Virol* 80: 6497-6516). Consensus sequences were determined by alignment of the prevailing ZEBOV and SUDV GP amino acid sequences and generating a consensus for each. Each vaccine GP gene was genetically optimized for expression in humans (including codon- and RNA-optimization for enhancing protein expression (GenScript, Piscataway, N.J.)), synthesized commercially, and then subcloned (GenScript, Piscataway, N.J.) into modified pVAX1 mammalian expression vectors (Invitrogen, Carlsbad, Calif.) under the control of the cytomegalovirus immediate-early (CMV) promoter; modifications include 2A>C, 3C>T, 4T>G, 241C>G, 1,942C>T, 2,876A>-, 3,277C>T, and 3,753G>C. Phylogenetic analysis was performed by multiple-alignment with ClustalW using MEGA version 5 software. Alternatively, GP diversity among the MARV was much higher (~70% identity) in comparison, so a consensus strategy was not adopted. For coverage of MARV, we chose to utilize the MGP sequence from the 2005 outbreak in Angola (GenBank #VGP_MABVR) since it was solely responsible for the largest and deadliest MARV outbreak to date. This sequence was greater than 10% divergent from either of its closest cluster of relative strains including Musoke, Popp and Leiden (10.6% divergence), or Uganda (01Uga07), Durba (05DRC99 and 07DRC99) and Ozolin (10.3% divergence). Altogether, a three-plasmid strategy formed the foundation for our novel trivalent polyvalent-filovirus vaccine strategy.

Transfections and Immunoblotting

Figure 1B:
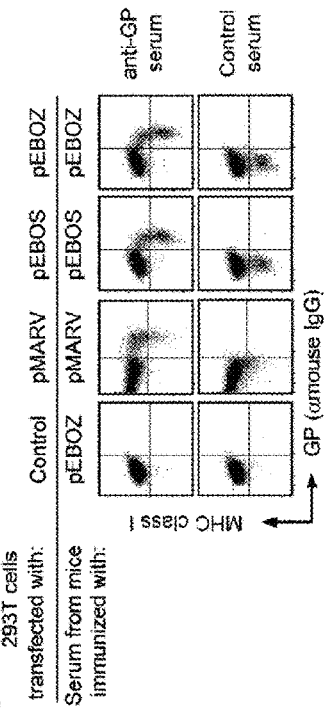
Figure 1C:
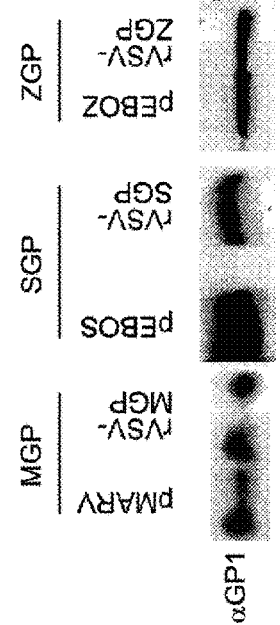

Human Embryonic Kidney (HEK) 293T cells were cultured, transfected, and harvested. Briefly, cells were grown in DMEM with 10% FBS, 1% Pen-strep, sodium pyruvate, and L-glutamine. Cells were cultured in 150 mm Corning dishes and grown to 70% confluence overnight in a 37° incubator with 5% $CO_2$. Dishes were transfected with 10-25 μg of Filoviridae pDNA using either a Calphos™ Mammalian Transfection Kit protocol (Clonetech) or Lipofectamine™ 2000 reagent (Invitrogen) per the manufacturer's protocol and then incubated for 24-48 h. Cells were harvested with ice cold PBS, centrifuged and washed, and then pelleted for Western immunoblot or FACS analysis. Standard Western blotting was used and GP-specific MAbs for GP1 detection were generated. Data from Western immunoblotting experiments is shown in FIG. 1B. Data from FACS analysis is shown in FIG. 1C.

Animals, Vaccinations, and Challenge

Adult female C57BL/6 ($H-2^b$), BALB/cJ ($H-2^d$), and B10.Br ($H-2^k$) mice were purchased from The Jackson Laboratory (Bar Harbor, Me.) while Hartley guinea pigs were from Charles River (Wilmington, Mass.). All animal experimentation was conducted following UPenn IACUC and School of Medicine Animal Facility, or NML Institutional Animal Care Committee of the PHAC and the Canadian Council on Animal Care guidelines for housing and care of laboratory animals and performed in accordance with recommendations in the Guide for the Care and Use of Laboratory Animals of NIH after pertinent review and approval by the abovementioned institutions. UPenn and NML comply with NIH policy on animal welfare, the Animal Welfare Act, and all other applicable federal, state and local laws.

Mice were immunized i.m. by needle injection with 40 μg of plasmid resuspended in water, while guinea pigs were immunized i.d., with 200 μg of each into three separate vaccination sites. Vaccinations were immediately followed by EP at the same site. Briefly, a three-pronged CELLECTRA® adaptive constant current Minimally Invasive Device was inserted approximately 2 mm i.d. (Inovio Pharmaceuticals, Inc., Blue Bell, Pa.). Square-wave pulses were delivered through a triangular 3-electrode array consisting of 26-gauge solid stainless steel electrodes and two constant-current pulses of 0.1 Amps were delivered for 52 msec/pulse separated by a 1 sec delay.

For lethal challenge studies, challenges were limited to rodent-adapted ZEBOV and MARV. Guinea pigs were challenged 28 days after the final vaccination by i.p. injection with 1,000 $LD_{50}$ of guinea pig-adapted ZEBOV (21.3 FFU/animal) (Richardson J S, Abou M C, Tran K N, Kumar A, Sahai B M, Kobinger G P (2011). Impact of systemic or mucosal immunity to adenovirus on ad-based Ebola virus vaccine efficacy in guinea pigs. *J Infect Dis* 204 Suppl 3: S1032-1042) or 1,000 $LD_{50}$ MARV-Angola (681 TCID50/animal). Briefly, the guinea-pig adapted MARV was made by the serial passage of wild-type MARV-Angola in outbred adult female Hartley guinea pigs. Seven days after inoculation, the animals were euthanized and livers were harvested and homogenized. This homogenate was then injected i.p. into naive adult guinea pigs and the process repeated until animals lost weight, gloss of hair, and succumbed to infection similar to EBOV adaptation in guinea pigs. For mouse lethal challenge studies (Kobinger G P, et al. (2006). Chimpanzee adenovirus vaccine protects against Zaire Ebola virus. *Virology* 346: 394-401), mice were injected i.p. with 200 μl of a 1,000 $LD_{50}$ (10 FFU/animal) of mouse-adapted ZEBOV. All animals were weighed daily and monitored for disease progression using an approved score sheet for at least 18 days for mice and 22 days for guinea pigs. All infectious work was performed in a 'Biosafety Level 4' (BSL4) facility at NML, PHAC.

ELISA and Neutralization Assays

Antibody (Ab) titers were determined using 96-well ELISA plates coated with either sucrose-purified MARV Ozolin GP or ZGP, or with negative control sucrose-purified Nipah G protein at a concentration of 1:2,000. Briefly, the plates were then incubated for 18 h at 4° C., washed with PBS and 0.1% Tween-20, and 100 μl/sample of the sera were tested in triplicate (at dilutions 1:100, 1:400, 1:1,600, and 1:6,400 in PBS with 5% skim milk and 0.5% Tween-20). Following an incubation at 37° C. for 1 h in a moist container, the plates were washed and then 100 μl of goat anti-mouse IgG-conjugated HRP antibody (Cedarlane) was added (1:2,000 dilution) and incubated for another 37° C. for 1 h in a moist container. After a wash, 100 μl of the ABST (2,2'-azino-bis(3-ethylbenthiazoline-6-sulphonic acid) and peroxidase substrate (Cedarlane) was added to visualize Ab binding. Again in a moist container, the plate was incubated for 30 min at 37° C. and then later read at 405 nm. Positive binding results were characterized by being >3 SD when subtracting the positive control from the negative control serum.

The ZEBOV neutralization assay was performed. Briefly, Sera collected from immunized mice and guinea pigs were inactivated at 56° C. for 45 minutes and serial dilutions of each sample (1:20, 1:40, etc. . . . , for mice and 1:50 for guinea pigs, in 50 μl of DMEM) was mixed with equal volume of ZEBOV expressing the EGFP reporter gene (ZEBOV-EGFP) (100 transducing units/well, according to EGFP expression) and incubated at 37° C. for 90 minutes. The mixture was then transferred onto sub-confluent VeroE6 cells in 96-well flat-bottomed plates and incubated for 5-10 minutes at RT. Control wells were infected with equal amounts of the ZEBOV-EGFP virus without addition of serum or with non-immune serum. 100 μl of DMEM supplemented with 20% FBS was then added to each well and plates were incubated at 37° C. in 5% $CO_2$ for 48 h.

Alternatively, neutralization of MARV-Angola 368 was assessed using an immunofluorescent assay. A primary rabbit anti-MARV Ab and secondary goat anti-rabbit IgG FITC-conjugated Ab was used for detection. Neutralizing Abs (NAbs) against SUDV Boniface were assayed based on cytopathic effect (CPE) on CV-1 cells. Cells were incubated with equal parts of immunized sera and SUDV Boniface for 10 days before subsequently fixed with 10% buffered formalin for 24 hours and examined under a light microscope. EGFP and FITC positive cells were counted in each well and sample dilutions showing >50% reduction in the number of green cells compared to controls scored positive for NAb. Alternatively, NAbs against SUDV-Boniface were assayed based on cytopathic effect (CPE) on CV-1 cells. All infectious work was performed in the BSL4 laboratory of NML, PHAC.

Splenocyte Isolation

Mice were sacrificed 8-11 days following the final immunization and the spleens were harvested. Briefly, spleens were placed in RPMI 1640 medium (Mediatech Inc., Manassas, Va.) supplemented with 10% FBS, 1× Anti-anti (Invitrogen), and 1× β-ME (Invitrogen). Splenocytes were isolated by mechanical disruption of the spleen using a Stomacher machine (Seward Laboratory Systems Inc., Bohemia, N.Y.), and the resulting product was filtered using a 40 μm cell strainer (BD Falcon). The cells were then treated for 5 min with ACK lysis buffer (Lonza, Switzerland) for lysis of RBCs, washed in PBS, and then resuspended in RPMI medium for use in ELISPOT or FACS assay.

ELISPOT Assays

Standard IFNγ ELISPOT assay was performed. Briefly, 96-well plates (Millipore, Billerica, Mass.) were coated with anti-mouse IFN-γ capture antibody and incubated for 24 h at 4° C. (R&D Systems, Minneapolis, Minn.). The following day, plates were washed with PBS and then blocked for 2 h with blocking buffer (1% BSA and 5% sucrose in PBS). Splenocytes ($1\text{-}2\times10^5$ cells/well) were plated in triplicate and stimulated overnight at 37° C. in 5% $CO_2$ and in the presence of either RPMI 1640 (negative control), Con A (positive control), or GP peptides either individually (15-mers overlapping by 9 amino acids and spanning the lengths of their respective GP) or whole pooled (2.5 μg/ml final). After 18-24 h of stimulation, the plates were washed in PBS and then incubated for 24 h at 4° C. with biotinylated anti-mouse IFN-γ mAb (R&D Systems, Minneapolis, Minn.). Next, the plates were washed again in PBS, and streptavidin-alkaline phosphatase (MabTech, Sweden) was added to each well and incubated for 2 h at RT. Lastly, the plates were washed again in PBS and then BCIP/NBT Plus substrate (MabTech) was added to each well for 5-30 min for spot development. As soon as the development process was complete upon visual inspection, the plate were rinsed with distilled water and then dried overnight at RT. Spots were enumerated using an automated ELISPOT reader (Cellular Technology Ltd., Shaker Heights, Ohio).

For comprehensive analysis of T cell breadth, standard IFNγ ELISPOT was modified herein as previously described in Shedlock D J, et al. (2012). SUPRA. Identification and measurement of subdominant and immunodominant T cell epitopes were assessed by stimulating splenocytes with individual peptides as opposed to whole or matrix peptide pools; the traditional practice of pooling peptides for the sake of sample preservation, such as the use of matrix array pools, results in a reduction of assay sensitivity since total functional responses in pools containing multiple epitope-displaying peptides will effectively lower assay resolution, i.e. 'drown-out' those of lower magnitude. Thus, modified ELISPOT was performed with individual peptides (15-mers overlapping by 9 amino acids; 2.5 μg/ml final) spanning each GP immunogen. Peptides containing T cell epitopes were identified (≥10 AVE IFNγ+ spots AND 80% animal response rate; summarized in Tables 1-6) and then later confirmed functionally and phenotypically by FACS. No shared or partial epitopes were identified, nor did FACS data or web-based epitope prediction software suggest the presence of a CD4+ or CD8+ T cell epitope that was preserved within consecutive peptides. Here, possible shared/partial T cell epitopes were addressed for all instances of contiguous peptide responses as identified by modified ELISPOT assay. Cells were stimulated individually with each of the contiguous peptides, as well as paired in combination for direct comparison, and were defined as 'shared/partial' if the combined response was not greater than either of the two individual responses. Also, it must be noted, that the epitopic response presented herein may not have been completely comprehensive since the '15-mer overlapping by 9 amino acids' algorithm for generating peptides is biased towards complete coverage of CD8 T cell epitopes which may underestimate CD4 T cell responses due to the nature of class II-restricted epitopes being longer than 15 amino acids. Lastly, amino acid similarity plots were generated using Vector NTI software and the results are shown in FIG. 4B.

Flow Cytometry

Splenocytes were added to a 96-well plate ($1\times10^6$ cells/well) and stimulated for 5-6 h with either individual peptides or 'Minimal Peptide Pools' (2.5 μg/ml final). Individual peptides stimulation was used for functional confirmation of all peptides identified by modified ELISPOT (Tables 1-6) as well as phenotypic characterization. Splenocytes and transfected 293Ts were first pre-stained with LIVE/DEAD® Fixable Violet Dead Cell Stain Kit (Invitrogen). For splenocytes, cells were surface-stained for CD19 (V450; clone 1D3), CD4 (PE-Cy7; clone RM4-5), CD8a (APC-Cy7; clone 53-6.7) and CD44 (PE-Cy5; clone IM7) (BD Biosciences, San Jose, Calif.), washed three times in PBS+1% FBS, permeabilized with BD Cytofix/Cytoperm™ kit, and then stained intracellularly with IFNγ (APC; clone XMG1.2), TNF (FITC; clone MP6-XT22), CD3 (PE-cy5.5; clone 145-2C11), and T-bet (PE; clone 4B10) (eBioscience, San Diego, Calif.). GP expression in transfected 293T cells was assessed 24 h post-transfection. Indirect staining was performed following a 30 min incubation at 4° C. in PBS+1% FBS containing the indicated mouse-derived GP-specific polyclonal serum reagent (1:200 dilution), each produced by pooling serum from H-$2^b$ mice immunized three times with their respective DNA vaccine or pVAX1 empty vector control. Cells were then stained with FITC-conjugated goat anti-mouse IgG (BioLegend, San Diego, Calif.), washed extensively, and then stained for MHC class I (HLA-ABC; PE-Cy7; clone G46-2.6; BD). All cells were fixed in 1% paraformaldehyde. All data was collected using a LSRII flow cytometer (BD) and analyzed using FlowJo software (Tree Star, Ashland, Oreg.). Splenocytes were gated for activated IFNy-producing T cells that were CD3+CD44+, CD4+ or CD8+, and negative for the B cell marker CD19 and viability dye.

FIG. 6 shows a GP-specific T cell gating. Functional and phenotypic analysis for peptides containing T cell epitopes as identified by ELISPOT was performed by FACS gating of total lymphocytes, live (LD) CD3+ cells that were negative for CD 19 and LIVE-DEAD (dump channel), singlets (excludes cell doublets), CD4+ and CD8+ cells, activated cells (CD44+), and peptide-specific IFNγ-producing T cells.

Statistical Analysis

Significance for unrooted phylogenetic trees was determined by maximum-likelihood method and verified by bootstrap analysis and significant support values (≥80%; 1,000 bootstrap replicates) were determined by MEGA version 5 software. Group analyses were completed by matched, two-tailed, unpaired t test and survival curves were analyzed by log-rank (Mantel-Cox) test. All values are mean±SEM and statistical analyses were performed by GraphPad Prism (La Jolla, Calif.).

Results

Vaccine Construction and Expression

Phylogenetic analysis revealed relative conservation among the EBOV GPs (94.4% for SUDV and 92.9% for ZEBOV), whereas the MARV GP (MGP) were more divergent (~70% conserved). Thus, a consensus strategy, as determined by alignment of the prevailing ZEBOV and SUDV GP amino acid sequences, was adopted for the EBOV GPs, while a type-matched strategy was used for MARV employing the 2005 Angola outbreak sequence which was solely responsible for the largest and deadliest MARV outbreak. Each GP transgene was genetically optimized, synthesized commercially, and then subcloned into modified pVAX1 mammalian expression vector. Altogether, a three-plasmid strategy formed the foundation for our novel polyvalent-filovirus vaccine strategy.

HEK 293T cells were transfected separately with each plasmid and GP expression was assessed by Western immunoblotting and FACS. A ~130 kDa protein was observed for each in cell lysates harvested 48 h post-transfection using species-specific anti-GP1 mAbs for detection Results shown in FIG. 1B. For a comparative control, recombinant vesicular stomatitis viruses (rVSV) expressing the respective GPs were loaded in concurrent lanes. Next, GP expression on the cell surface was analyzed 24 h post-transfection by indirect staining with GP-specific or control polyclonal serum by FACS. Results are shown in FIG. 1C. Cell surface expression was detected for all vaccine plasmids while little non-specific binding was observed; control serum did not react with GP-transfected cells nor did the positive sera with pVAX1-transfected cells (data shown for pEBOZ). As expected for the EBOV GPs, cell surface expression sterically occluded recognition of surface MHC class I, as well as β1-integrin (Francica J R, Varela-Rohena A, Medvec A, Plesa G, Riley J L, Bates P (2010). Steric shielding of surface epitopes and impaired immune recognition induced by the ebola virus glycoprotein. *PLoS Pathog* 6: e1001098).

Complete Protection Against MARV and ZEBOV Challenge

To determine protective efficacy, we employed the guinea pig preclinical challenge model. Preclinical immunogenicity and efficacy studies were performed herein using the guinea pig and mouse models. The guinea pig preclinical model has been extensively used as a screening and 'proof-of-concept' tool for filoviral vaccine development. Although primary isolates of MARV and EBOV cause non-fatal illness in guinea pigs, a small number of passages in this host results in selection of variants able to cause fatal disease with pathological features similar to those seen in filovirus-infected primates. Similarly, mice have also been widely used for filoviral vaccine development, however, unlike the guinea pig model, immunodetection reagents for assessing immunity and T cell responses are extensively available. Infection with a murine-adapted ZEBOV (mZEBOV) results in disease characterized by high levels of virus in target organs and pathologic changes in livers and spleens akin to those found in EBOV-infected primates.

Figures 2A, 2B, 2C, 2D, 2E, 2F, 2G, 2H:
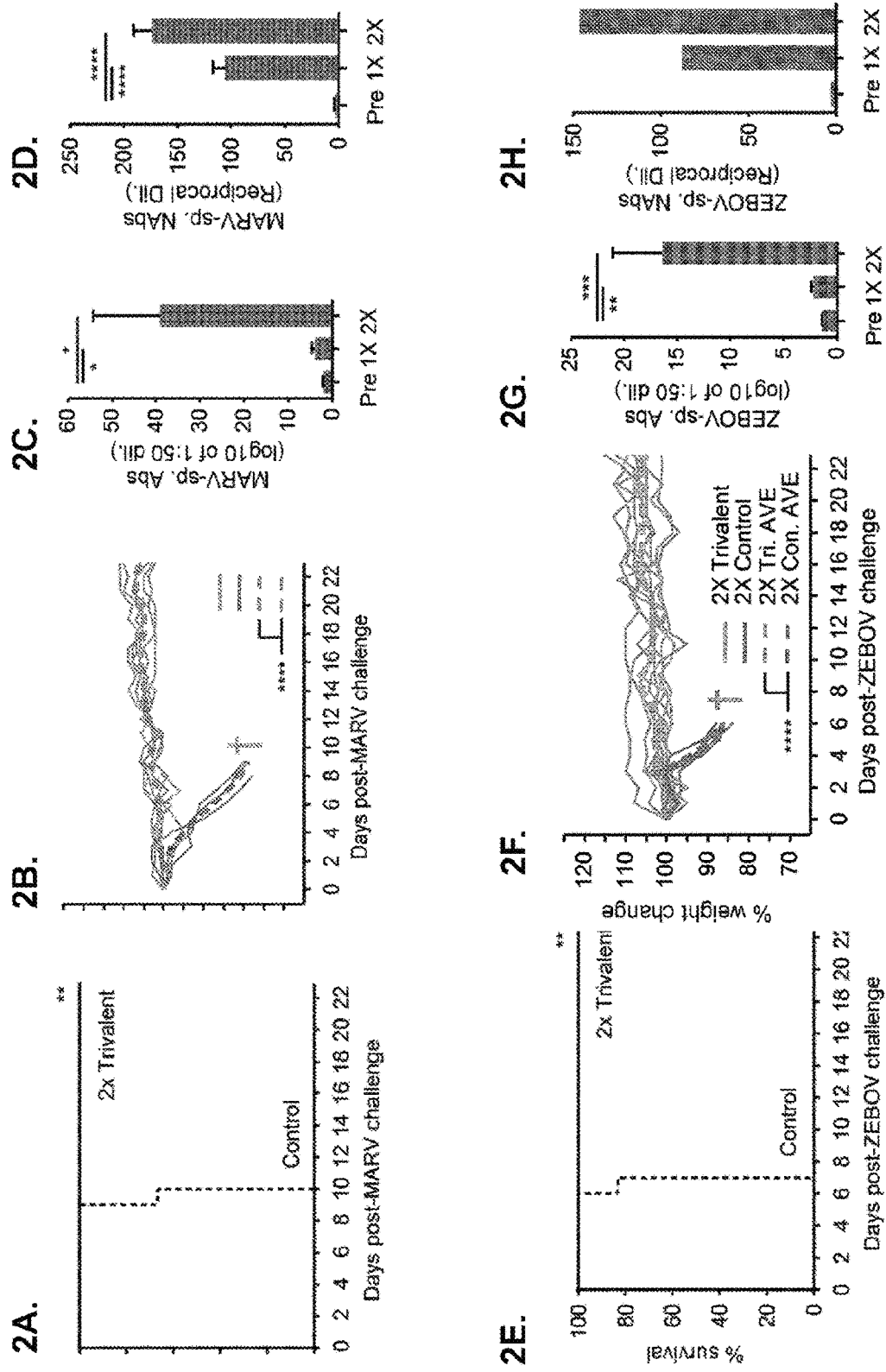
FIGS. 2A-2H show results from experiments in Example 1 in which complete protection against MARV and ZEBOV challenge was observed. Animal survival data is shown in FIG. 2A and FIG. 2E.

Guinea pigs (n=24) were immunized i.d. two times with 200 μg of each plasmid (pEBOZ, pEBOS and pMARV) into three separate vaccination sites or with pVAX1 empty vector control (n=9), and then boosted with the same vaccines one month later. Animals were challenged 28 days following the second immunization with 1,000 $LD_{50}$ of a guinea pig-adapted MARV-Angola (gpMARV) (n=9) or ZEBOV (gpZEBOV) (n=15) in a BSL-4 facility, and then observed and weighed daily. Results are shown in FIGS. 2A-2H. Vaccinated animals were completely protected while control-vaccinated animals succumbed to gpMARV by 10 days post-challenge (n=3; P=0.0052) or to gpZEBOV by day 7 post-challenge (n=6; P=0.0008) (FIG. 2A and FIG. 2E). Additionally, vaccinated animals were protected from weight loss (FIG. 2B and FIG. 2F; P<0.0001). It is likely that vaccine-induced Abs may have contributed to protection since GP-specific Abs in pooled serum exhibited a significant increase in binding (FIG. 2C and FIG. 2G) and neutralization (FIG. 2D and FIG. 2H) titers. Experiments were performed in a BSL-4 facility and repeated twice with similar results and error bars in FIGS. A-2H represent SEM. Group analyses were completed by matched, two-tailed, unpaired t test and survival curves were analyzed by log-rank (Mantel-Cox) test.

Plasmid Vaccines were Highly Immunogenic

Figures 3A, 3B, 3C:
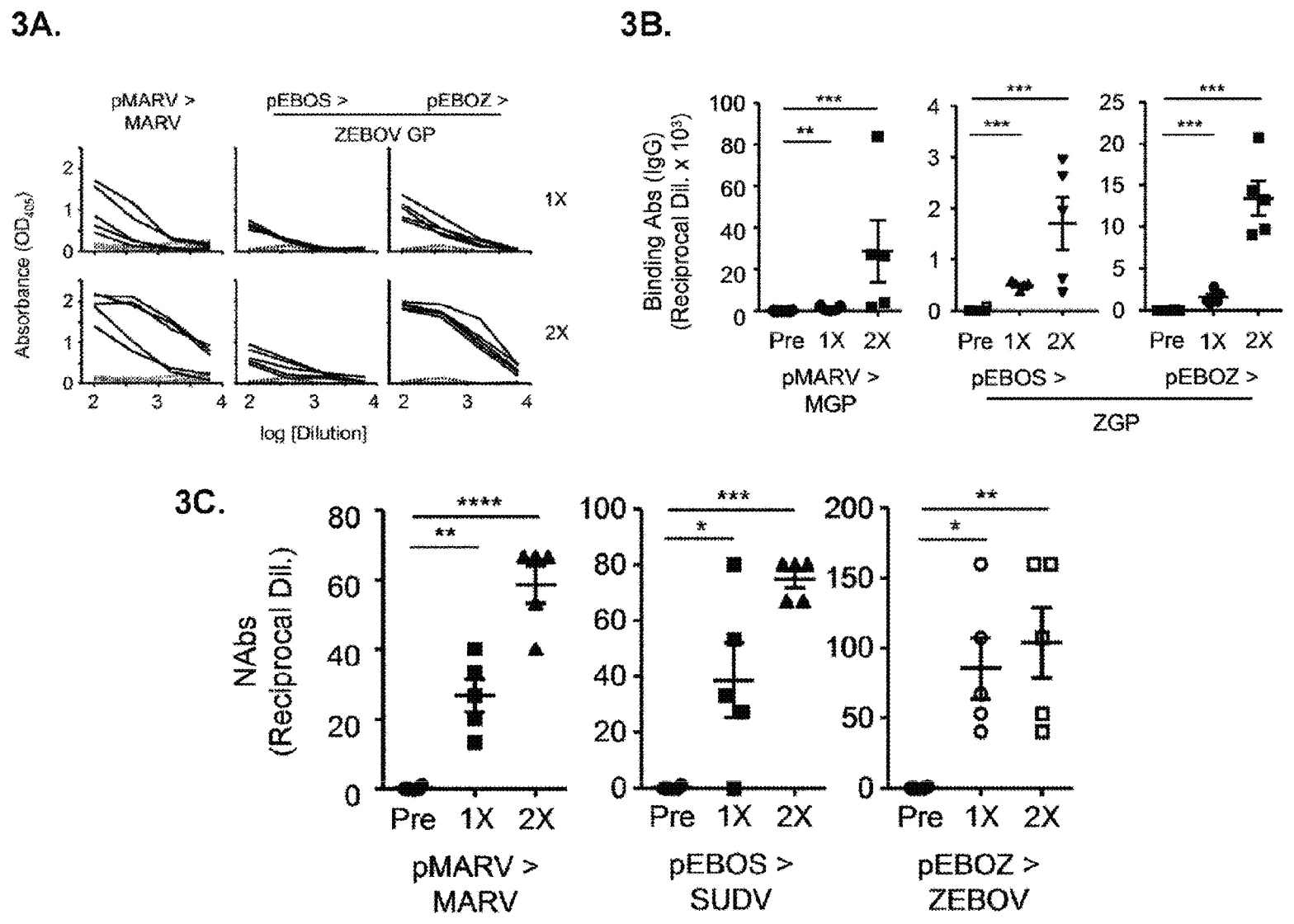

To better characterize immune correlates as driven by the protective DNA vaccine (plasmids pEBOZ, pEBOS and pMARV, also referred to as trivalent DNA vaccine), we next employed the mouse model which has been widely used as a screening and 'proof-of-concept' tool for filoviral vaccine development and in which extensive immunodetection reagents are available. First, B cell responses were assessed in $H-2^d$ mice (n=5/group) 20 days following each of two vaccinations, three weeks between injections with 40 μg of respective monovalent DNA vaccine. Data from these experiments is shown in FIGS. 3A-3C. While little GP-specific IgG was observed in pre-bleed control samples, as shown in FIG. 3A and FIG. 3B, a significant increase was detected in all animals following vaccination. Since purified SGP was not available, purified ZGP was used as a surrogate. IgG in SUDV-vaccinated mice bound ZGP, demonstrating the ability for vaccine-induced Ab generation as well as its capability for cross-species recognition. Additionally, seroconversion occurred in 100% of vaccinated animals after only one immunization, after which responses were significantly increased by homologous boost; AVE reciprocal endpoint dilution titres were boosted 22.1-fold in pMARV-immunized mice, and 3.4-fold and 8.6-fold in pEBOS- and pEBOZ-vaccinated animals, respectively. Samples were next assayed for neutralization of ZEBOV, SUDV-Boniface, and MARV-Angola in a BSL-4 facility. The results of the neutralization assay are shown in FIG. 3C. Significant increases in NAb titres were detected following vaccination in all animals.

Figure 4A:
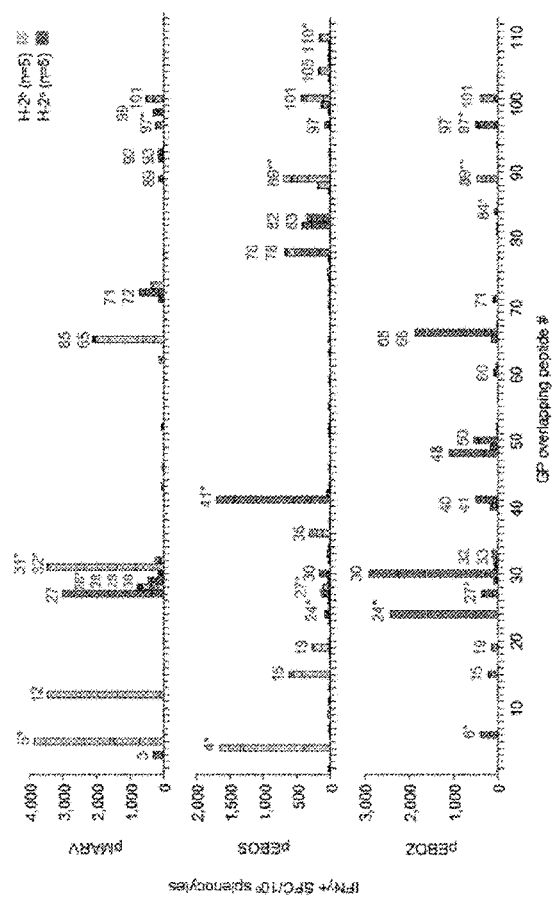
FIGS. 4A-4D shows refer to broad T cells responses generated by vaccination.

Mice from two different genetic backgrounds ($H-2^d$ and $H-2^b$; n=5/group) were immunized with 40 μg of respective plasmids pEBOZ, pEBOS and pMARV, homologous boosted after two weeks, and then sacrificed 8 days later for T cell analysis Results from a novel modified ELISPOT assay to assess the comprehensive vaccine-induced T cell response, in which splenocytes were stimulated using individual peptides as opposed to matrix pools are shown in FIG. 4A. DNA vaccination induced robust IFNγ+ responses that recognized a diversity of T-cell epitopes (Tables 1-6). All positive epitope-comprising peptides were subsequently gated (See FIG. 6), confirmed, and further characterized by FACS. This modified ELISPOT approach proved extremely sensitive since background responses from control wells were low (7.2±0.2 IFNγ-producing SFC/$10^6$ splenocytes in $H-2^b$ and 9.2±0.5 in $H-2^d$ mice). Results as shown in FIG. 4A revealed that vaccination with pMARV induced 9 measurable epitopes in $H-2^b$ mice and 11 in $H-2^d$, pEBOS induced 9 and 8, and pEBOZ generated 10 and 12, in these respective strains. While five of nine (55.6%) of the epitopes from pMARV-immunized H-$2^b$ mice were CD8+, they accounted for about 57.3% of the total MGP-specific IFNγ+ response as measured by both ELISPOT and FACS confirmation and phenotypic analysis. Similarly, only 33% and 38% of confirmed epitopes were CD8-restricted in pEBOS-immunized H-$2^b$ and H-$2^d$ mice, respectively. However these epitopes comprised roughly 50-90% of the total response; CD8+ T cell responses were estimated to be approximately 56% in both mouse strains while FACS estimates were 51% and 90% in H-$2^b$ and H-$2^d$ mice, respectively. Total CD8+ responses were lower in pEBOZ-vaccinated animals and measured between 33% and 57% (33% for both strains by ELISPOT and 6% and 57% for H-$2^b$ and H-$2^d$ mice, respectively, by FACS).

Figure 4B:
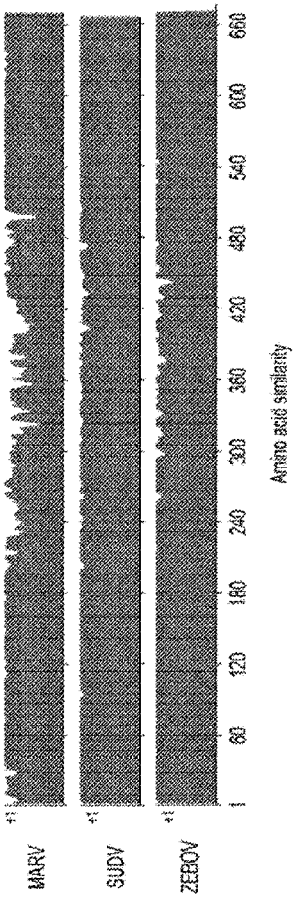
Figure 4C:
Figure 4D:
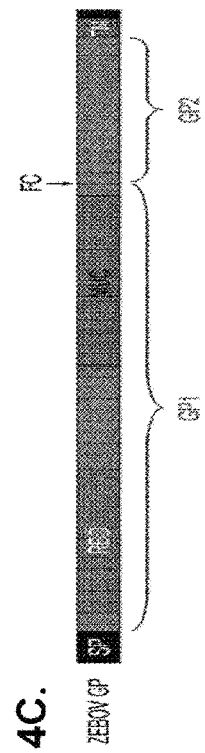

A single immunodominant epitope was detected in both mouse strains receiving pEBOS where an immunodominant epitope was loosely defined as generating an IFNγ response at least two-fold over the highest subdominant epitope; pMARV induced four H-$2^b$-restricted immunodominant CD8+ epitopes within peptides $MGP_{25-39}$ (#5), $MGP_{67-81}$ (#12), $MGP_{181-195}$ (#31) and $MGP_{385-399}$ (#65), and an H-$2^d$-restricted CD4+ epitope in $MGP_{151-171}$ (#27). Four of these epitopes occurred within highly conserved regions of MARV GP1, including three of which were located within the putative receptor binding domain, while only one occurred within the variable mucin-like region ($MGP_{385-399}$ (#65)) as shown in FIG. 4B and FIG. 4C. pEBOS stimulated CD8+ epitopes occurring in SUDV GP $(SGP)_{19-33}$ (#4) and $SGP_{241-255}$ (#41) in H-$2^b$ and H-$2^d$ mice, respectively, both in highly conserved regions of GP1. However, pEBOZ immunization revealed three immunodominant epitopes in H-$2^d$ mice (a CD8-restricted epitope located in the ZEBOV GP receptor binding domain $(GP)_{139-153}$ (#24), and two CD4-restricted epitopes $ZGP_{175-189}$ (#30) and $ZGP_{391-405}$ (#66)), occurring within the receptor binding domain and the mucin-like region, respectively. Only one immunodominant epitope was defined in H-$2^b$ mice which contained both a CD4+ and a CD8+ epitope (#89) and occurred in a highly conserved region of GP2. Overall, diverse epitope hierarchies were consistent and reproducible in each vaccine group. Furthermore, as shown in FIG. 4D, the subdominant response comprised a significant proportion of the total response; the total AVE subdominant response as measured by the modified ELISPOT assay was approximately 12%, 62%, and 74% in pMARV-, pEBOS- and pEBOZ-immunized H-$2^b$ mice, respectively, while responses in H-$2^d$ mice were 47%, 50% and 34%, respectively.

Lastly, total GP-specific T cell responses were measured by FACS using stimulation with minimal peptide pools containing only confirmed epitope-comprising peptides identified. Robust responses were detected in each of the vaccinated animals and were, in a majority of cases, comprised by both activated CD4+ and CD8+ T cells. Responses were GP-specific, since little IFNγ production was observed with a control peptide (h-Clip), and correlated well with ELISPOT data. The only instance where immunization did not induce remarkable CTL as measured by FACS was in H-$2^d$ mice vaccinated with pMARV in which no epitope identified by ELISPOT was confirmed to be CD8-restricted. Altogether, these data show that each of the vaccine plasmids was highly immunogenic in mice and yielded robust GP-specific T cell responses recognizing a diverse array of T cell epitopes including immunodominant epitopes within highly conserved regions of the GP. Furthermore, the highly diverse subdominant T cell response characterized herein might have otherwise been overlooked using traditional matrix array peptide pools for epitope identification.

Figure 7A:
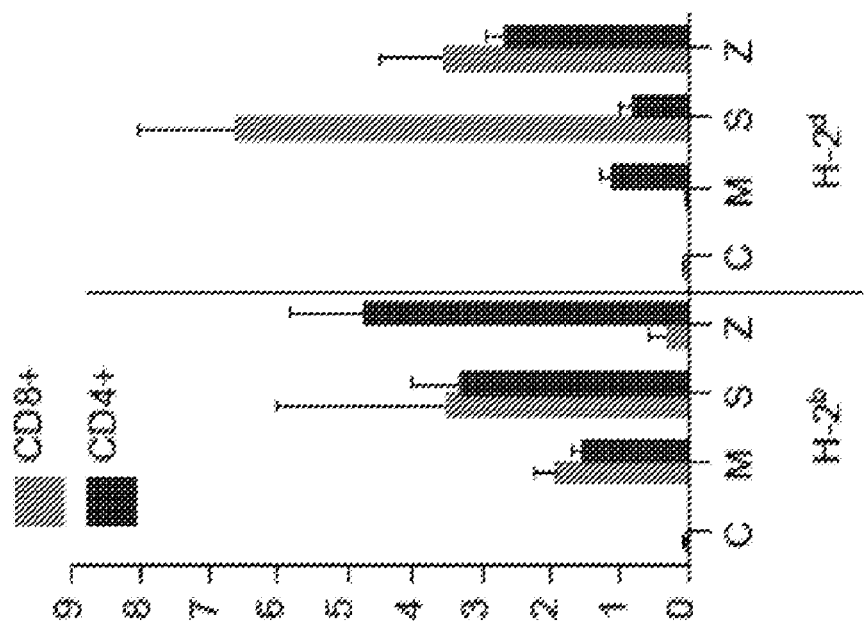
FIGS. 7A and 7B show that vaccination experiments in Example 1 generated robust T cells.
Figure 7B:
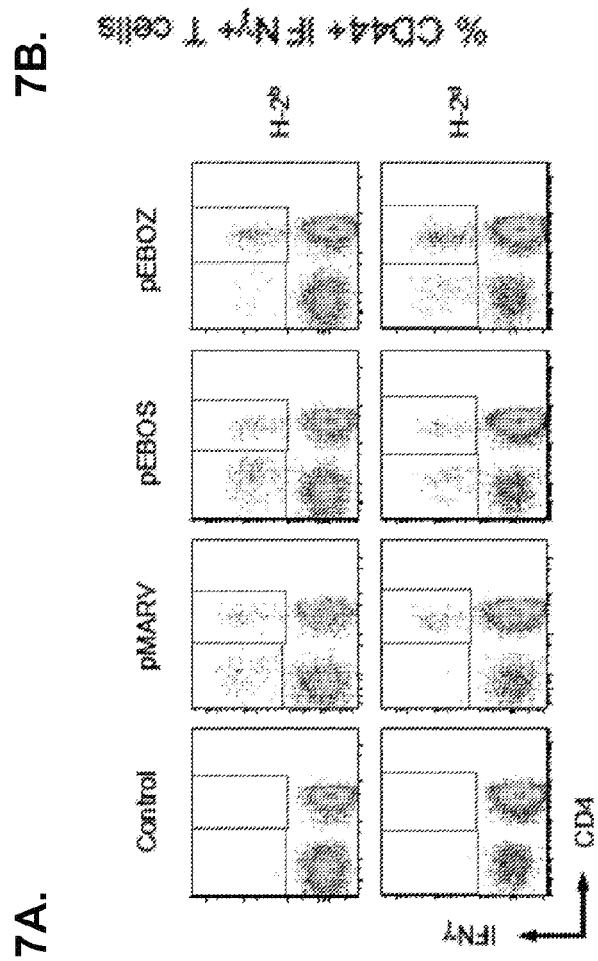

T cell responses were measured for reactivity against minimal peptide pools comprised by all positively identified peptides for each respective GP by FACS. FIG. 7A shows DNA vaccine-induced T cell responses are shown from a representative animal and IFNy-producing CD4+ (right) and CD8+ (left) cells are gated. FACS plots are shown. Incubation with h-CLIP peptide served as a negative control (Control). FIG. 7B shows results of gated cells in FIG. 7A are summarized as average % of total CD44+/IFNγ+CD4+ or CD8+ cells and error bars represent SEM. Experiments were repeated at least two times with similar results.

'Single-Dose' Protection in Mice

Figures 5A, 5B, 5C, 5D:
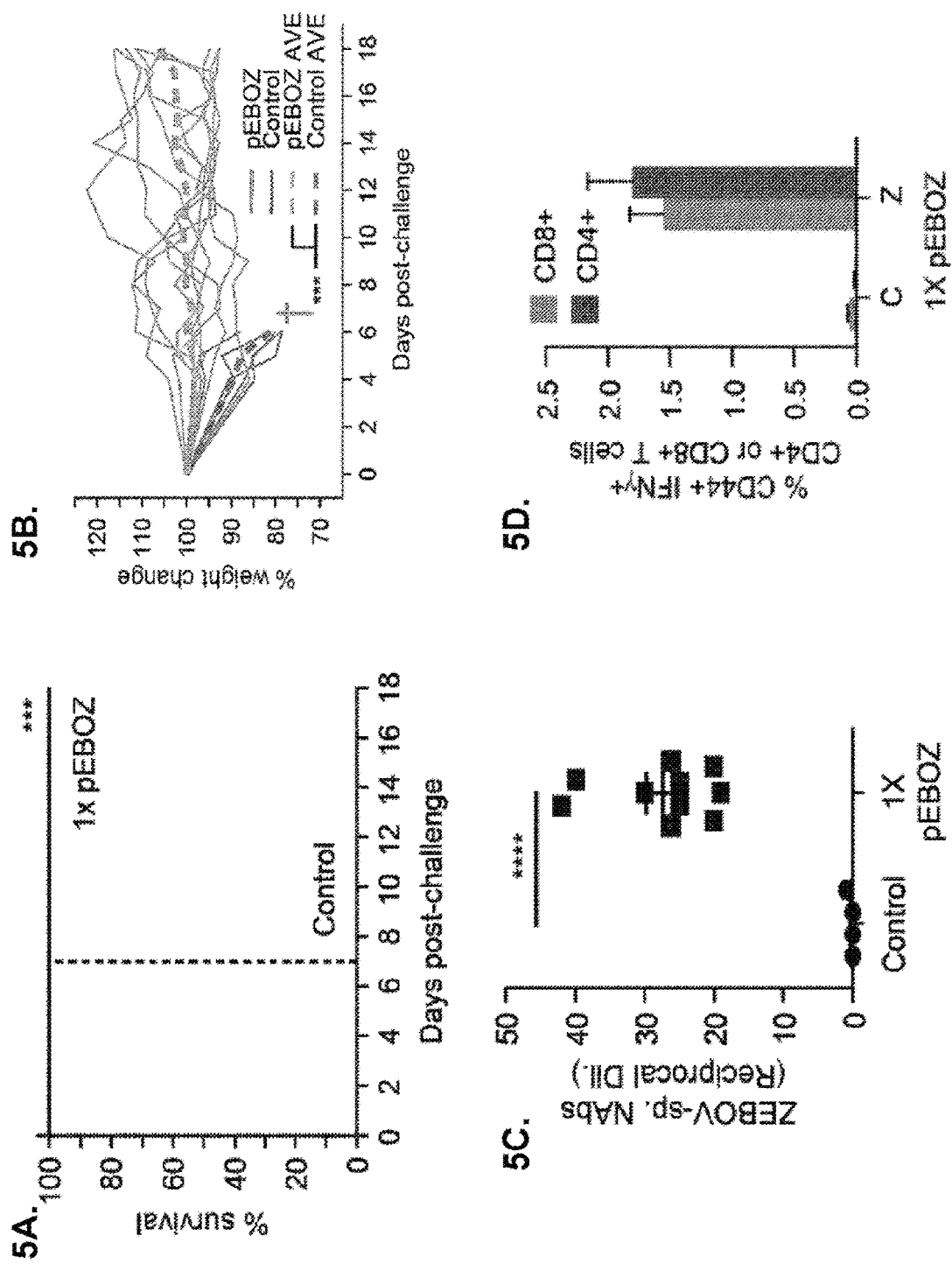
FIGS. 5A-5D show data from experiment assessing protective 'single-dose' vaccination induced neutralizing Abs and CTL. H-$2^k$ mice (n=10/group) were vaccinated once i.m. with pEBOZ E-DNA and then challenged 28 days later with 1,000 $LD_{50}$ of mZEBOV in a BSL-4 facility. Mice were weighed daily and monitored for disease progression. Animal survival data in FIG. 5A. Vaccinated animals survived challenge while control animals died by day 7.

Vaccine efficacy against ZEBOV challenge was next assessed in the preclinical murine model. Mice were vaccinated only once due to strong NAb induction and protection data observed. Mice (H-$2^k$; n=10/group) were immunized with 40 μg of the pEBOZ DNA and protection was evaluated 28 days later by challenge with 1,000 $LD_{50}$ of mouse-adapted ZEBOV (mZEBOV) in a BSL4 facility. While all control animals succumbed to infection by day 7 post-challenge, FIG. 5A shows DNA-vaccinated mice were completely protected (P=0.0002). In addition, as shown in FIG. 5B, control mice exhibited progressive loss of body weight until death (P<0.0001).

To better understand the mechanisms of DNA-induced protection in a 'single-dose' model, we next assessed NAb and T cell generation. NAbs were assessed 25 days post-vaccination, 3 days prior to challenge, and, as shown in FIG. 5C, a significant (P<0.0001) increase was detected in all vaccinated animals (n=10/group); reciprocal endpoint dilution titers ranged from 19 to 42, 27.3±2.5.

We next evaluated the generation of ZGP-specific T cells and increased the scope of our analysis to compare responses in mice immunized with either the pEBOZ alone, or in a trivalent formulation IFN-γ production (n=5) was assessed 11 days later by FACS using whole ZGP peptide pools; the data is shown in FIG. 5D. IFNγ-producing T cells were detected in all animals and were specific for ZGP peptides since stimulation with a control peptide did not induce cytokine production. Immunization with either the monovalent or trivalent formulation induced robust IFNy T cell responses that, when compared, were not significantly different P=0.0920).

Since CTL may be important in eliminating virus-infected cells (Warfield K L, et al. (2005). Induction of humoral and CD8+ T cell responses are required for protection against lethal Ebola virus infection. *J Immunol* 175: 1184-1191; Kalina W V, Warfield K L, Olinger G G, Bavari S (2009). Discovery of common marburgvirus protective epitopes in a BALB/c mouse model. *Virol J* 6: 132; Olinger G G, et al. (2005). Protective cytotoxic T-cell responses induced by venezuelan equine encephalitis virus replicons expressing Ebola virus proteins. *J Virol* 79: 14189-14196; Sullivan N J, et al. (2011). CD8(+) cellular immunity mediates rAd5 vaccine protection against Ebola virus infection of nonhuman primates. *Nat Med* 17: 1128-1131; and Geisbert T W, et al. (2010). Vector choice determines immunogenicity and potency of genetic vaccines against Angola Marburg virus in nonhuman primates. *J Virol* 84: 10386-10394), production of an additional effector cytokine, TNF, as well as a developmental restriction factor, T-box transcription factor TBX21 (T-bet), known to correlate with $T_h$1-type CTL immunity and cytotoxicity were measured and the results were as follows. For Total Cells: TNF 2.9±0.8, Tbet 13.0±1.1. For CD4+/CD44+/IFNγ+ Cells: TNF 61.4±3.1, Tbet 72.6±2.0. For CD8+/CD44+/IFNγ+ Cells: TNF 33.0±3.3, Tbet 992.1±1.4 (*p<0.1; ***p<0.001;

****p<0.0001). We found that ~61% and ~33% of activated CD4+ and CD8+ T cells, respectively, also produced TNF in addition to IFNγ. Furthermore, a majority of IFNγ-producing T cells expressed high levels of T-bet; about 73% and 92% of CD8+ and CD4+ T cells, respectively, were CD44+ and produced IFNγ following ZGP peptide stimulation.

Figures 8A, 8B:
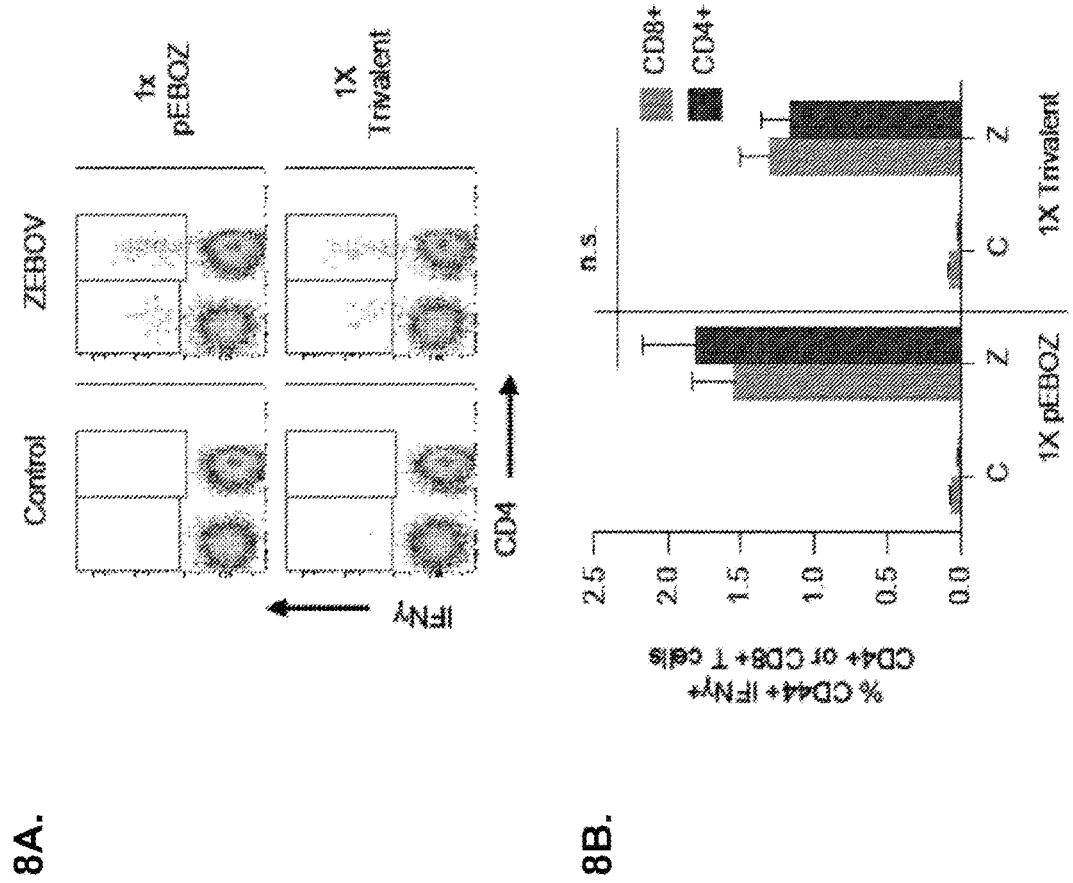
FIGS. 8A and 8B show T cell induction by 'single-dose' vaccination disclosed in Example 1.

FIGS. 8A and 8B show T cell induction by 'single-dose' vaccination. T cell responses in H-$2^k$ mice after a single pEBOZ immunization or a single trivalent vaccination, comprised by the three vaccine plasmids in separate sites, as measured by FACS are shown (a) and summarized (b) as AVE % of total CD44+/IFNγ+CD4+ (purple) or CD8+ (orange) cells. Pseudocolor FACS plots are from a representative animal and IFNγ-producing CD4+ (right) and CD8+ (left) cells are gated. Incubation with h-CLIP peptide served as a negative control (Control). Experiments were performed twice with similar results, error bars represent SEM; ns, no significance.

Discussion

We report development and evaluation of a polyvalent-filoviral vaccine in preclinical rodent immunogenicity and efficacy studies. Complete protection against challenge with gpMARV and gpZEBOV was observed following two DNA vaccine doses in guinea pigs, as well as with a 'single-dose' DNA vaccine in mice against mZEBOV. To date, genetic vaccination of guinea pigs has included either injection of naked DNA (Sullivan N J, Sanchez A, Rollin P E, Yang Z Y, Nabel G J (2000). Development of a preventive vaccine for Ebola virus infection in primates. *Nature* 408: 605-609) or DNA delivered by gene gun (Dowling W, et al. (2006). The influences of glycosylation on the antigenicity, immunogenicity, and protective efficacy of Ebola virus GP DNA vaccines. *J Virol* 81: 1821-1837; Vanderzanden L, et al. (1998). DNA vaccines expressing either the GP or NP genes of Ebola virus protect mice from lethal challenge. *Virology* 246: 134-144; and Riemenschneider J, et al (2003). Comparison of individual and combination DNA vaccines for *B. anthracis, Ebola* virus, *Marburg* virus and *Venezuelan* equine encephalitis virus. *Vaccine* 21: 4071-4080), however, either method required at least three vaccinations to achieve complete protection. Improved protection herein may be due to the induction of robust Abs since a single DNA vaccination generated GP-specific IgG binder titers that were comparable in magnitude to titers in protected animals following gene gun administration; DNA vaccination induced 3.85 and 2.18 log 10 ZGP and MGP-specific Ab titers, respectively, after a single administration versus 2.7 and 3.0 after three gene gun vaccinations. For comparison with an alternative 'single-dose' protective strategy in guinea pigs, an Ag-coupled virus-like particle (VLP) platform generated Ab titers that were only slightly higher than observed following DNA vaccination (Swenson D L, Warfield K L, Negley D L, Schmaljohn A, Aman M J, Bavari S (2005). Virus-like particles exhibit potential as a pan-filovirus vaccine for both Ebola and Marburg viral infections. *Vaccine* 23: 3033-3042). Furthermore, a recombinant adenovirus (rAd) approach induced ZGP-specific NAb titers that were lower than those from a single DNA vaccination (53 reciprocal endpoint dilution titer verses 88 herein) (Kobinger G P, et al. (2006). Chimpanzee adenovirus vaccine protects against *Zaire* Ebola virus. *Virology* 346: 394-401). Vaccination with rVSV (Jones S M, et al (2007). Assessment of a vesicular stomatitis virus-based vaccine by use of the mouse model of Ebola virus hemorrhagic fever. *J Infect Dis* 196 Suppl 2: S404-412) generated ZGP-specific Ab titers that were similar to the current platform. Altogether, these data demonstrate that DNA vaccination was capable of inducing binding and neutralizing Abs that were comparable to non-replicating viral platforms and that these data may help, in part, to explain strong guinea pig survival data herein.

The generation of NAbs by protective DNA vaccination may have benefitted by transgene-expressed mature GP structures. In vitro transfection studies confirmed that the vaccine-encoded GP were highly expressed, post-translationally cleaved (FIG. 1B), transported to the cell surface, and sterically occluded the immunodetection of cell surface molecules (FIG. 1C). Therefore, it was highly likely that the vaccine immunogens formed herein matured into heterotrimeric spikes that would otherwise be functional upon virion assembly during infection. This may be important for the generation and display of virologically-relevant neutralizing determinants which would be subsequently critical for the induction of conformation-dependent Nabs (Dowling W, et al. (2007). Influences of glycosylation on antigenicity, immunogenicity, and protective efficacy of ebola virus GP DNA vaccines. *J Virol* 81: 1821-1837; Shedlock D J, Bailey M A, Popernack P M, Cunningham J M, Burton D R, Sullivan N J (2010). Antibody-mediated neutralization of Ebola virus can occur by two distinct mechanisms. *Virology* 401: 228-235). Thus, in this regard, the expression of native anchored structures may be superior to soluble derivatives in the capacity for generating NAbs (Sullivan N J, et al. (2006). Immune protection of nonhuman primates against Ebola virus with single low-dose adenovirus vectors encoding modified GPs. *PLoS Med* 3: e177; Xu L, et al. (1998). Immunization for Ebola virus infection. *Nat Med* 4: 37-42).

To better characterize T cells responses as driven by a protective vaccine, we performed immunogenicity and efficacy studies in mice and determined 'single-dose' complete protection against mZEBOV with DNA vaccination (FIGS. 5A-5D). To date, the most effective platforms conferring complete protection in this model are VLP, either with (Warfield K L, et al. (2005). Induction of humoral and CD8+ T cell responses are required for protection against lethal Ebola virus infection. *J Immunol* 175: 1184-1191; Warfield K L, Swenson D L, Olinger G G, Kalina W V, Aman M J, Bavari S (2007). Ebola virus-like particle-based vaccine protects nonhuman primates against lethal Ebola virus challenge. *J Infect Dis* 196 Suppl 2: S430-437) or without (Sun Y, et al. (2009). Protection against lethal challenge by Ebola virus-like particles produced in insect cells. *Virology* 383: 12-21) adjuvant, rAd vaccination ((Kobinger G P, et al. (2006) SUPRA; Choi J H, et al. (2012). A single sublingual dose of an adenovirus-based vaccine protects against lethal Ebola challenge in mice and guinea pigs. *Mol Pharm* 9: 156-167; Richardson J S, et al. (2009). Enhanced protection against Ebola virus mediated by an improved adenovirus-based vaccine. *PLoS One* 4: e5308), or rRABV vaccination (Blaney J E, et al. (2011). Inactivated or live-attenuated bivalent vaccines that confer protection against rabies and Ebola viruses. *J Virol* 85: 10605-10616). However, characterization of T cell responses were severely limited in these studies and were restricted to splenocyte stimulation with either two (Warfield K L, (2007), SUPRA) or one (Warfield K L, et al. (2005) SUPRA) peptides previously described to contain ZGP T cell epitopes (Warfield K L, et al. (2005) SUPRA. Olinger G G, et al. (2005) SUPRA; Kobinger G P, et al. (2006), SUPRA; Sun Y, et al. (2009). Choi, J H, et al. (2012). Herein, we report induction of robust and broad CTL by protective vaccination as extensively analyzed by a novel modified T cell assay (FIG. 4A and Tables 1-6). In total, 52 novel T cell epitopes were identified including numerous immunodominant epitopes occurring primarily in highly conserved regions of GP. Of the 22 total ZGP epitopes identified, only 4 have been previously reported. Moreover, only one of the 20 MGP (Kalina W V, Warfield K L, Olinger G G, Bavari S (2009). Discovery of common marburgvirus protective epitopes in a BALB/c mouse model. *Virol J* 6: 132) and one of 16 SGP epitopes were previously described. As such, this the most comprehensive report of preclinical GP epitopes to date, describing GP epitopes from multiple filoviruses in two different mouse genetic backgrounds.

Another novel finding resulting from these analyses was the assessment of the vaccine-induced subdominant T cell responses, which we show comprised a significant percentage of the total T cell response, widely ranging between 12%-74% (FIG. 4D). This may be particularly important since subdominant responses can significantly contribute to protection. Thus, it may prove informative in the future to determine the specific contributions of the subdominant and immunodominant epitopic T cell responses to protection. Notably, these responses may have otherwise been overlooked using traditional matrix array peptide pools for epitope identification. As such, limited epitope detection in previous studies may have been directly related to lower levels of vaccine-induced immunity, the use of less sensitive standard assays, and/or the use of peptide arrangements and/or algorithms favoring detection of immunodominant CD8+ epitopes.

Although immune correlates of protection against the filoviruses remain controversial, data generated by this highly immunogenic approach provides a unique opportunity with which to study T cell immunity as driven by a protective vaccine. DNA vaccination herein induced strong ZGP-specific T cells, a large part of which were characterized by $T_h1$-type multifunctional CTL expressing high levels of T-bet, also shown to correlate with T cell cytotoxicity in humans. It is clear that previous stand-alone DNA vaccine platforms capable of generating mainly humoral immune responses and cellular immunity skewed towards CD4+ T cells may likely benefit from in vivo EP delivery which has been recently demonstrated to induce potent CD8+ T cells in NHPs and the clinic. Thus, data herein are consistent with this approach as a stand-alone or prime-boost modality in NHP immunogenicity and efficacy studies. This approach offers an attractive vaccination strategy that can be quickly and inexpensively modified and/or produced for rapid response during Filoviridae bio-threat situations and outbreaks. In addition, this model approach provides an important tool for studying protective immune correlates against filoviral disease and could be applied to existing platforms to guide future strategies.

Example 2

A trivalent vaccine is provided which comprises three plasmids. The first plasmid comprises a nucleic acid sequence that encodes a *Zaire ebolivirus* consensus immunogen which is based upon ZEBOV CON, SEQ ID NO:1, modified to include an IgE signal peptide at the N terminus of the *Zaire ebolivirus* consensus immunogen. The second plasmid comprises a nucleic acid sequence that encodes a *Sudan ebolavirus* consensus immunogen which is based upon SUDV CON, SEQ ID NO:2, modified to include an IgE signal peptide at the N terminus of the *Sudan ebolavirus* consensus immunogen. The third plasmid comprises a nucleic acid sequence that encodes a *Marburg marburgvirus* Angola (MARV immunogen which is based upon MARV ANG, SEQ ID NO:3, modified to include an IgE signal peptide at the N terminus of the *Marburg marburgvirus* Angola immunogen.

Example 3

A five plasmid vaccine is provided. The first plasmid comprises a nucleic acid sequence that encodes a *Zaire ebolivirus* consensus immunogen which is ZEBOV CON, SEQ ID NO:1. The second plasmid comprises a nucleic acid sequence that encodes a Sudan ebolavirus consensus immunogen which is SUDV CON, SEQ ID NO:2. The third plasmid comprises a nucleic acid sequence that encodes SEQ IDNO:4, a *Marburg marburgvirus*—Ravn cluster consensus (MARV-RAV CON) using *Marburg marburgvirus* Ravn, Durba (09DRC99) and Uganda (02Uga07Y). The fourth plasmid comprises a nucleic acid sequence that encodes SEQ IDNO:5, a *Marburg marburgvirus*—Ozolin cluster consensus (MARV-OZO CON) using Ozolin, Uganda (01Uga07), and Durba (05 and 07DRC99). The fifth plasmid comprises a nucleic acid sequence that encodes SEQ IDNO:6, a *Marburg marburgvirus*—Musoke cluster consensus (MARV-MUS CON) using (Musoke, Popp, and Leiden).

Example 4

A five plasmid vaccine is provided. The first plasmid comprises a nucleic acid sequence that encodes a *Zaire ebolivirus* consensus immunogen which is based upon ZEBOV CON, SEQ ID NO:1, modified to include an IgE signal peptide at the N terminus of the *Zaire ebolivirus* consensus immunogen. The second plasmid comprises a nucleic acid sequence that encodes a *Sudan ebolavirus* consensus immunogen which is based upon SUDV CON, SEQ ID NO:2, modified to include an IgE signal peptide at the N terminus of the *Sudan ebolavirus* consensus immunogen. The third plasmid comprises a nucleic acid sequence that encodes *Marburg marburgvirus* Rav consensus based upon SEQ IDNO:4, a *Marburg marburgvirus*—Ravn cluster consensus (MARV-RAV CON) using *Marburg marburgvirus* Ravn Durba (09DRC99) and Uganda (02Uga07Y) and modified to include an IgE signal peptide at the N terminus of the consensus *Marburg marburgvirus*—Rav immunogen. The fourth plasmid comprises a nucleic acid sequence that encodes *Marburg marburgvirus* Ozo consensus based upon SEQ IDNO:5, a *Marburg marburgvirus*—Ozolin cluster consensus (MARV-OZO CON) using Ozolin,Uganda (01Uga07), and Durba (05 and 07DRC99) and modified to include an IgE signal peptide at the N terminus of the consensus *Marburg marburgvirus*—Ozo immunogen. The fifth plasmid comprises a nucleic acid sequence that encodes *Marburg marburgvirus* Mus consensus based upon SEQ IDNO:6, a *Marburg marburgvirus*—Musoke cluster consensus (MARV-MUS CON) using (Musoke, Popp, and Leiden) and modified to include an IgE signal peptide at the N terminus of the consensus *Marburg marburgvirus*—Mus immunogen.

Example 5

A six plasmid vaccine is provided. The first plasmid comprises a nucleic acid sequence that encodes a *Zaire ebolivirus* consensus immunogen which is ZEBOV CON, SEQ ID NO:1. The second plasmid comprises a nucleic acid sequence that encodes a *Sudan ebolavirus* consensus immunogen which is SUDV CON, SEQ ID NO:2. The third plasmid comprises a nucleic acid sequence that encodes SEQ IDNO:4, a *Marburg marburgvirus*—Ravn cluster consensus (MARV-RAV CON) using *Marburg marburgvirus*—Ravn, Durba (09DRC99) and Uganda (02Uga07Y). The fourth plasmid comprises a nucleic acid sequence that encodes SEQ IDNO:5, a *Marburg marburgvirus*—Ozolin cluster consensus (MARV-OZO CON) using Ozolin, Uganda (01Uga07), and Durba (05 and 07DRC99). The fifth plasmid comprises a nucleic acid sequence that encodes SEQ IDNO:6, a *Marburg marburgvirus*—Musoke cluster consensus (MARV-MUS CON) using (Musoke, Popp, and Leiden). The sixth plasmid comprises a nucleic acid sequence that encodes SEQ IDNO:3, a *Marburg marburgvirus* Angola 2005 isolate glycoproteins immunogen.

Example 6

A five plasmid vaccine is provided. The first plasmid comprises a nucleic acid sequence that encodes a *Zaire ebolivirus* consensus immunogen which is based upon ZEBOV CON, SEQ ID NO:1, modified to include an IgE signal peptide at the N terminus of the *Zaire ebolavirus* consensus immunogen. The second plasmid comprises a nucleic acid sequence that encodes a *Sudan ebolavirus* consensus immunogen which is based upon SUDV CON, SEQ ID NO:2, modified to include an IgE signal peptide at the N terminus of the *Sudan ebolavirus* consensus immunogen. The third plasmid comprises a nucleic acid sequence that encodes *Marburg marburgvirus* Rav consensus based upon SEQ IDNO:4, a *Marburg marburgvirus*—Ravn cluster consensus (MARV-RAV CON) using *Marburg marburgvirus* Ravn Durba (09DRC99) and Uganda (02Uga07Y) and modified to include an IgE signal peptide at the N terminus of the consensus *Marburg marburgvirus*—Rav immunogen. The fourth plasmid comprises a nucleic acid sequence that encodes *Marburg marburgvirus* Ozo consensus based upon SEQ IDNO:5, a *Marburg marburgvirus*—Ozolin cluster consensus (MARV-OZO CON) using Ozolin,Uganda (01Uga07), and Durba (05 and 07DRC99) and modified to include an IgE signal peptide at the N terminusof the consensus *Marburg marburgvirus*—Ozo immunogen. The fifth plasmid comprises a nucleic acid sequence that encodes *Marburg marburgvirus* Mus consensus based upon SEQ IDNO:6, a *Marburg marburgvirus*—Musoke cluster consensus (MARV-MUS CON) using (Musoke, Popp, and Leiden) and modified to include an IgE signal peptide at the N terminusof the consensus *Marburg marburgvirus*—Mus immunogen. The sixth plasmid comprises a nucleic acid sequence that encodes a *Marburg marburgvirus* Angola 2005 isolate glycoproteins immunogen which is based upon MARV ANG, SEQ ID NO:3, modified to include an IgE signal peptide at the N terminus of the *Marburg marburgvirus* Angola immunogen.

Example 7

Described herein is a DNA vaccine formulation expressing 3 synthetic *Zaire* Ebola virus (EBOV) glycoproteins (GP): 2 designed based on GP sequence alignments (1976-2014) and a 3rd construct matched to a 2014 outbreak strain. Plasmid IL-12 (pIL-12) was also included as an adjuvant to further enhance cellular immune responses. The multivalent GP DNA vaccine formulation was administered in macaques following a DNA-DNA prime-boost immunization regimen. Macaques (n=3 or 4/group) received the multivalent GP DNA formulation+pIL-12 by intramuscular delivery followed by electroporation. Differences in immunogenicity were assayed and protection between different doses, regimens (2, 3, 4, and 5 injections), and different spacing intervals between subsequent doses were monitored. Both antibody and T cell responses were observed in 83% of animals 2 weeks following the first injection and 100% of animals after the 2nd injection. The macaques were challenged with a lethal dose of the EBOV Guinea-Makona outbreak strain (1000 pfu, 7-U virus) and monitored for 28 days following infection. 100% of animals receiving at least 3 injections at 4 week intervals survived lethal challenge. Animals were fully protected against signs of disease and did not exhibit elevated blood chemistry. Interestingly, 50% of animals receiving 2 injections survived lethal challenge. The surviving animals exhibited minimal signs of disease, suggesting that with further optimization complete protection with 2 injections is potentially achievable. In additional optimization studies in mice, single injections were found to be 100% protective and long-term immune responses 8 months post vaccination were induced.

Methods

Developing an EBOV GP DNA Vaccine Formulation

Vaccines currently in clinical trials include rVSVAG/ZEBOVGP, ChAd3 prime+MVA boost, and MVA pan-filovirus. While these vaccines are immunogenic, protective in non-human primates (NHPs), and provide single dose protection, they develop anti-vector immunity, have uncertain duration of memory response, give adverse reactions in human clinical trials and may not be suitable for all populations. Thus, an additional platform with a cleaner safety profile that can induce strong immune responses against heterologous Zaire Ebola viruses would be very beneficial (FIG. 9).

Figure 10:
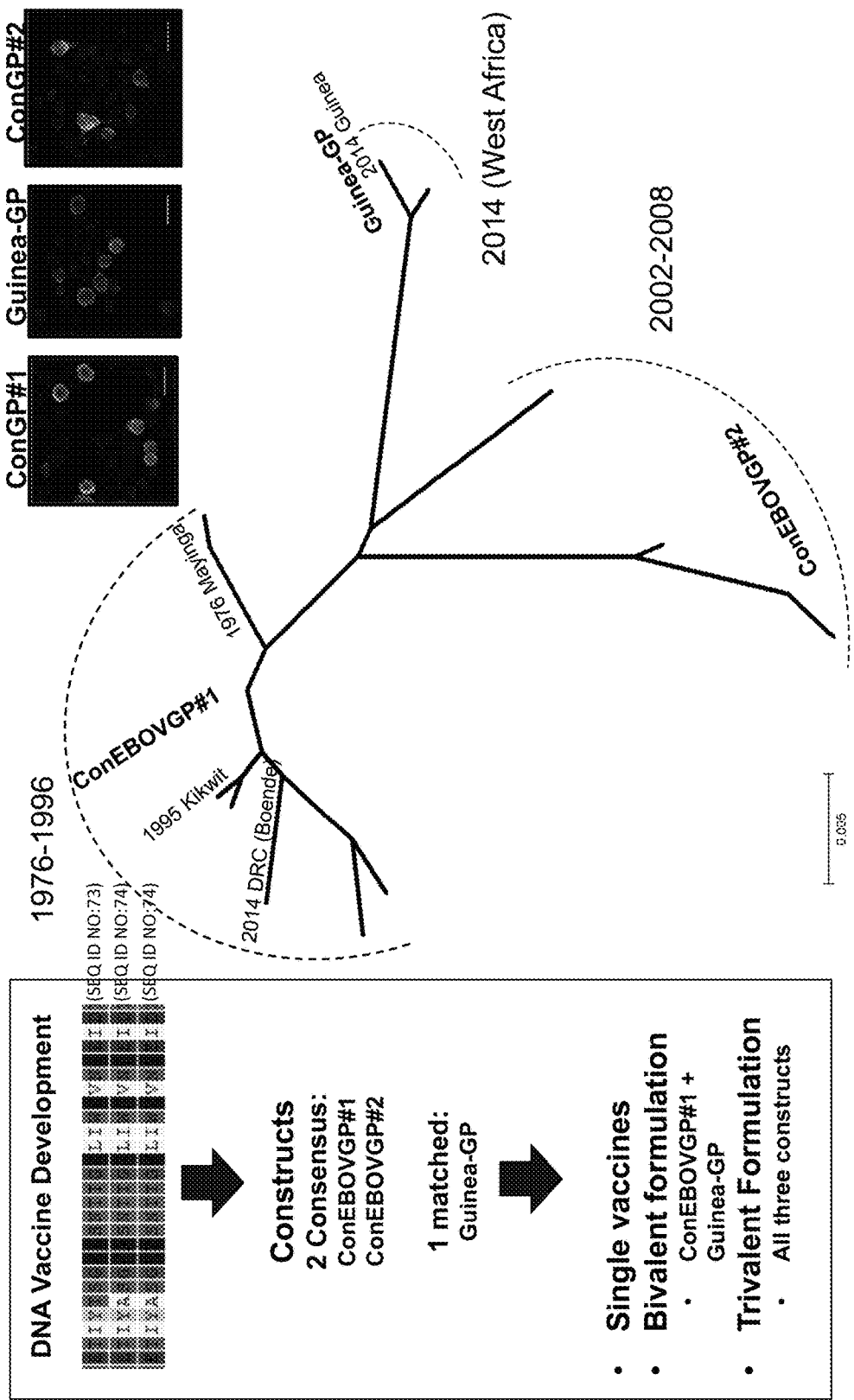

Three EBOV DNA constructs were designed: a consensus sequence of ZEBOV (1976-1996) (ConEBOVGP #1), ZEBOV (2002-2008) (ConEBOVGP #2), and a matched ZEBOV sequence from the 2014 Guinea outbreak. (Guinea-GP). Five vaccines were developed, monovalent vaccines which comprise only a single DNA construct, a bivalent vaccine formulation which comprise either ConEBOVGP #1 with Guinea-GP and a trivalent formulation which comprises all three of ConEBOVGP #1, ConEBOVGP #2, and Guinea-GP (FIG. 10).

Results

A Single Immunization of DNA Vaccine is Immunogenic in Mice

Figure 11:
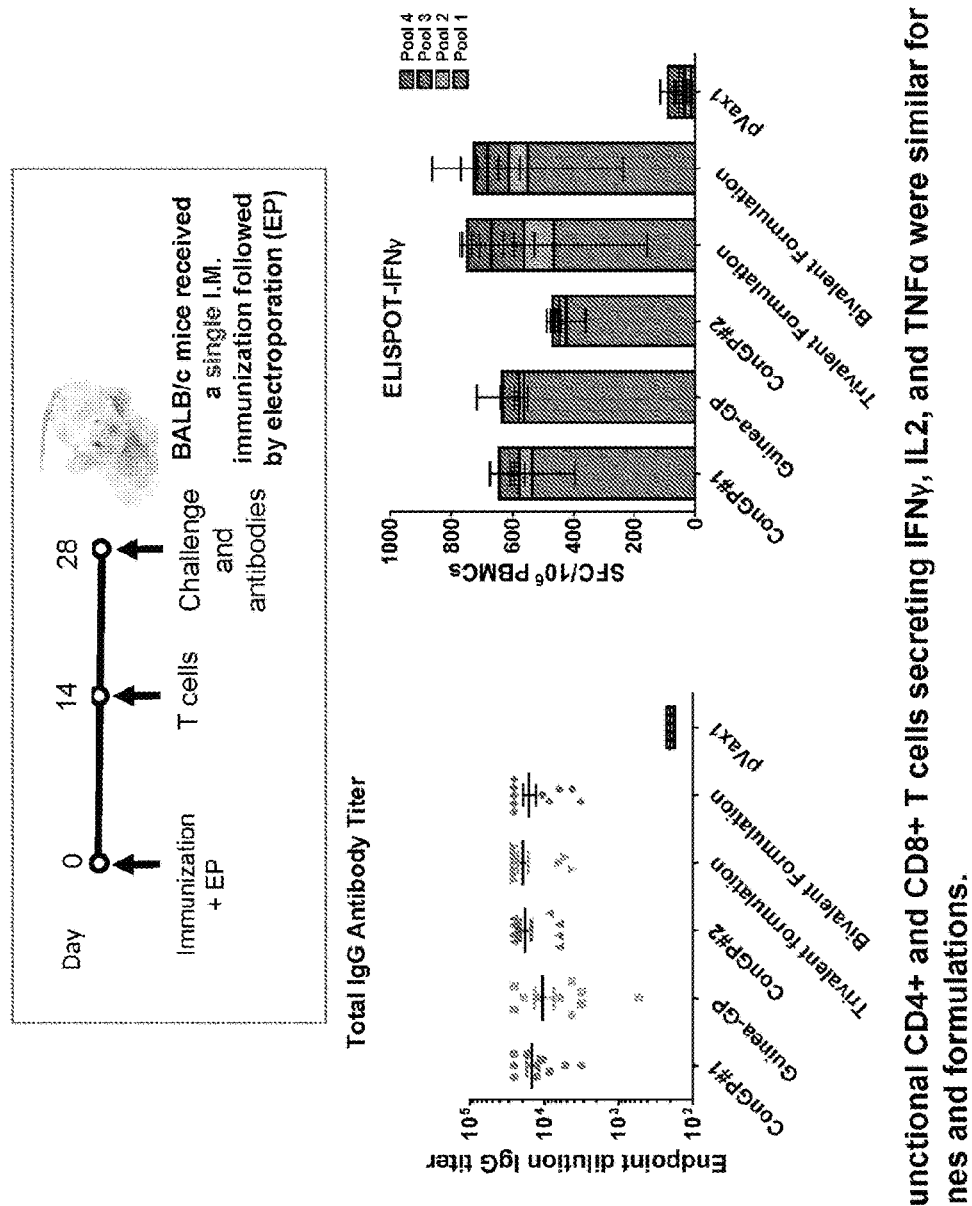

BALB/c mice received a single intramuclular (IM) immunization followed by electroporation (EP) of the vaccine formulation. On day 28, Total IgG antibody titer and ELISPOT-IFNγ were determined. Each vaccine formulation produced a robust IgG response. Polyfunctional CD4+ and CD8+ T cells secreting IFNγ, IL2, and TNFα were similar for all vaccines and formulations. (FIG. 11).

Figure 12:
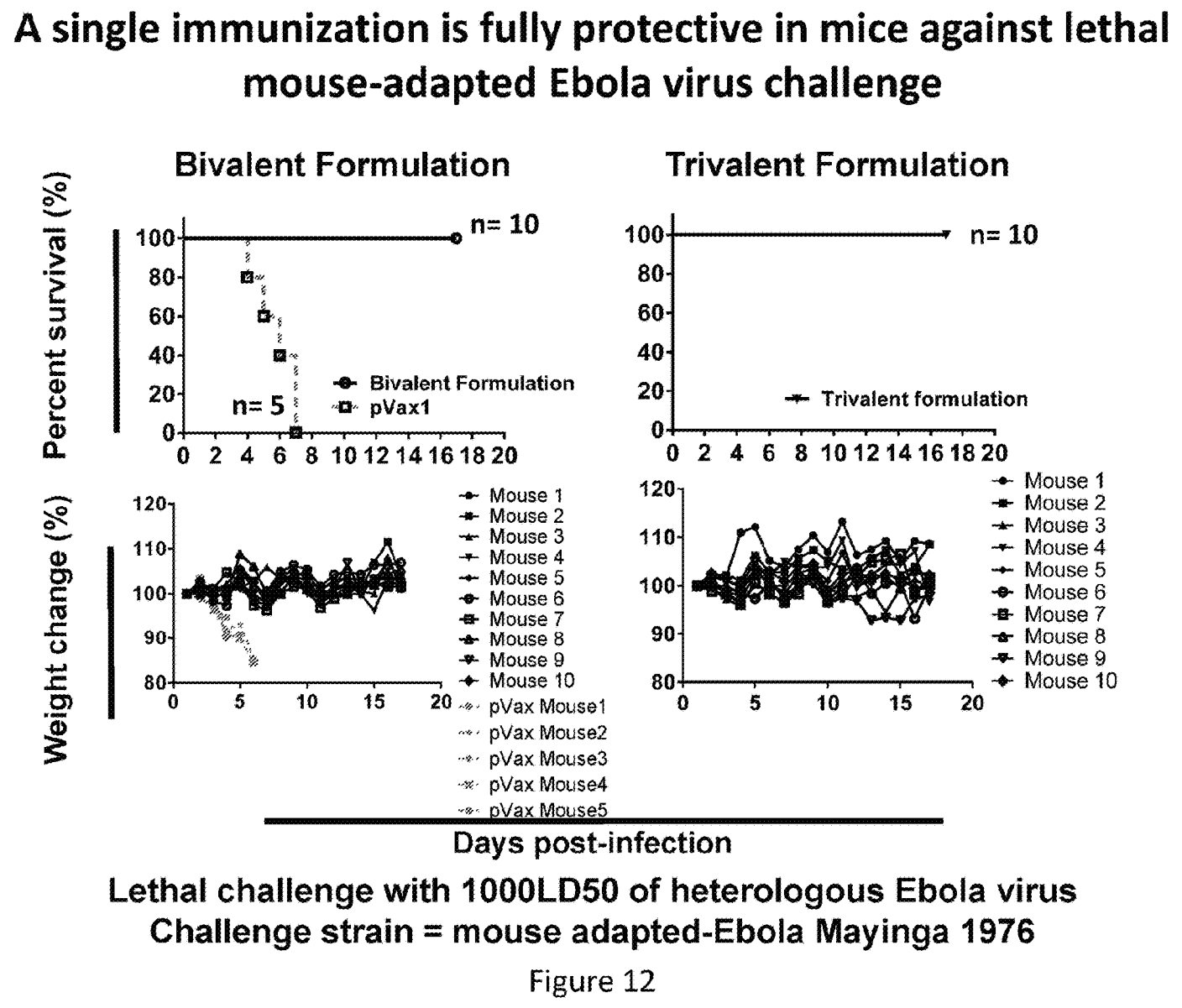

A Single Immunization is Fully Protective in Mice Against Lethal Mouse-Adapted Ebola Virus Challenge BALB/c mice immunized with bivalent or trivalent vaccine formulations were lethal challenged with $1000LD_{50}$ of heterologous Ebolavirus. The challenge strain was mouse adapted-Ebola Mayinga 1976. Mice vaccinated with the control plasmid, pVax1, quickly lost weight and did not survive past day 7. However, both the mice vaccinated with the bivalent and mice vaccinated with the trivalent vaccine formulations maintained their weight and had no deceased mice up to day 20 (FIG. 12).

Individual GP DNA Vaccine Constructs Induce Robust Memory Responses in Mice.

Figure 13:
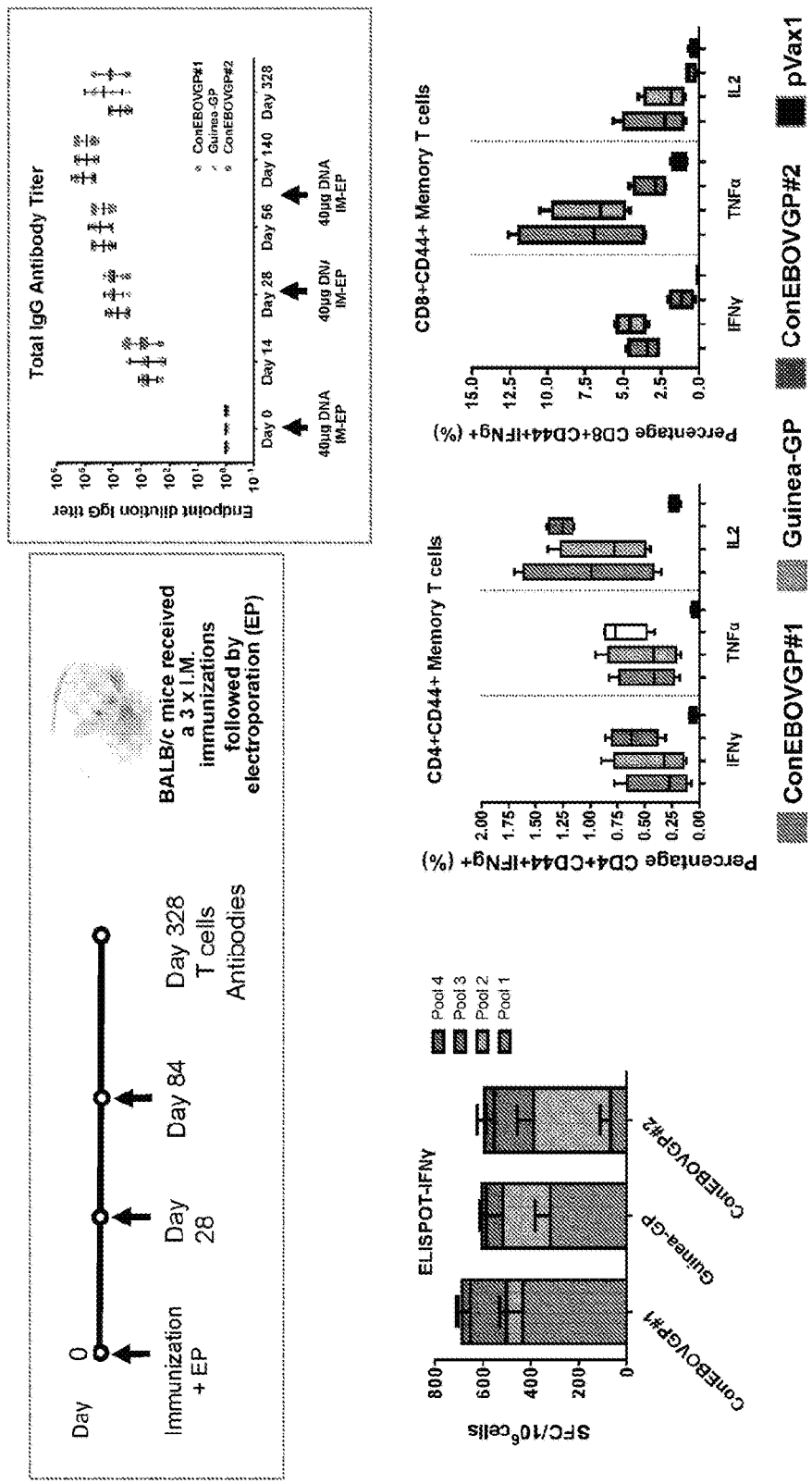

BALB/c mice received a 3×IM 40 µg immunization of a monovalent vaccine followed by electroporation on days 0, 28 and 84. IgG antibody titer, INFγ, CD4+CD44+ memory T cells, and CD8+CD44+ memory T cells were measured. Robust immune responses were detectable months after last injection (FIG. 13).

GP DNA Vaccine Formulations are Immunogenic in NHPs

Figure 6:
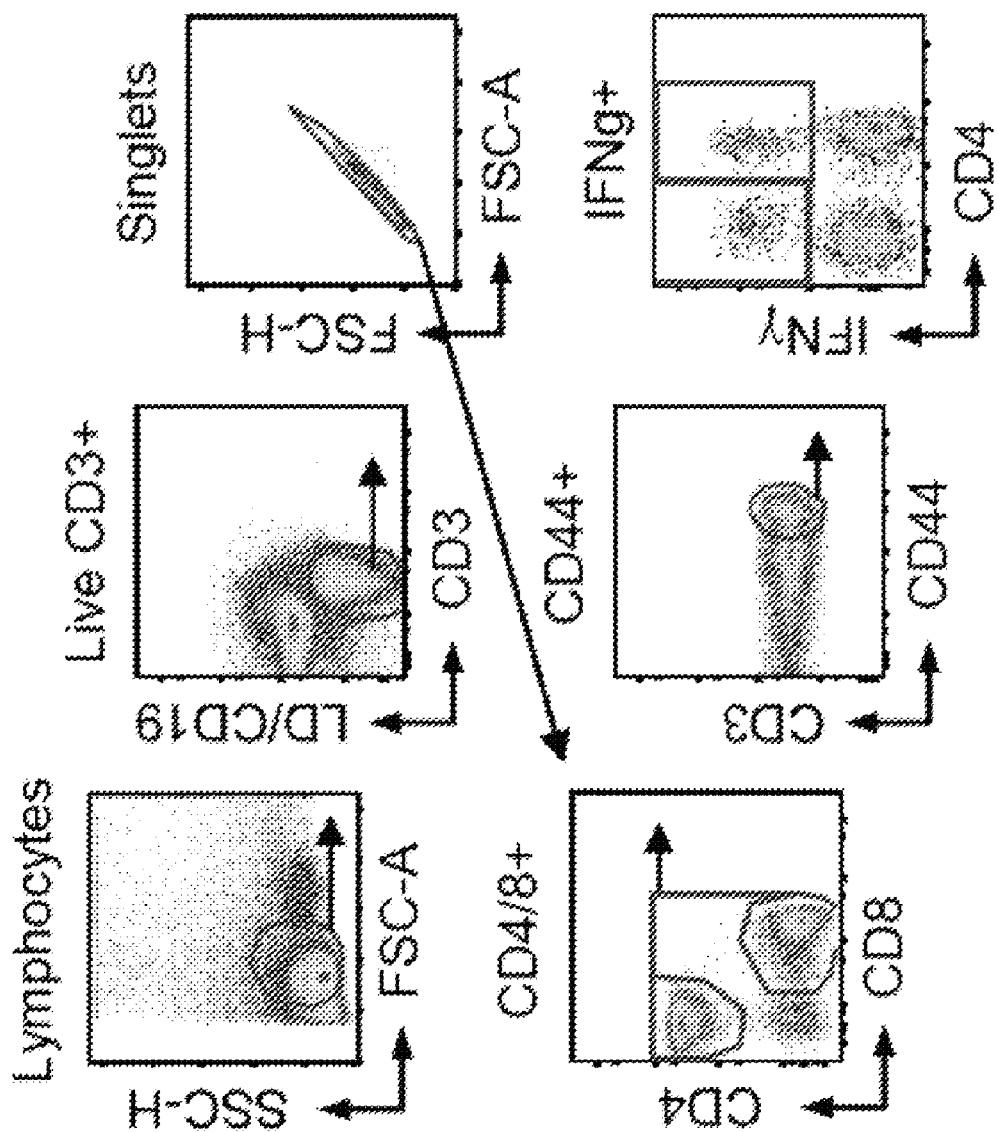
FIG. 6 shows a GP-specific T cell gating disclosed in Example 1.

Cynomolgus macaques were used as a NHP because they are a model for Ebola vaccine efficacy and lethal challenge. Macques were administered either a bivalent formulation with a Rhesus pIL12 adjuvant or a trivalent formulation with a Rhesus pIL12 adjuvant I.M. followed by EP. Different injection regimens in order to understand immunogenicity. Group 1 received 2 IM-EP injections of the bivalent formulation at a 4 week interval. Group 2 received 2 IM-EP injections of the trivalent formulation at a 4 week interval. Group 3 received 3 IM-EP injections of the trivalent formulation. Samples for immunogenicity studies were taken monthly and for one additional month following the last dose. (FIG. 6). Each DNA vaccine formulation induced robust anti-Ebola GP antibody responses (GMT>$10^3$) & anti-GP T-cell responses. The immune responses were boosted following each injection (FIG. 14).

Figure 15:
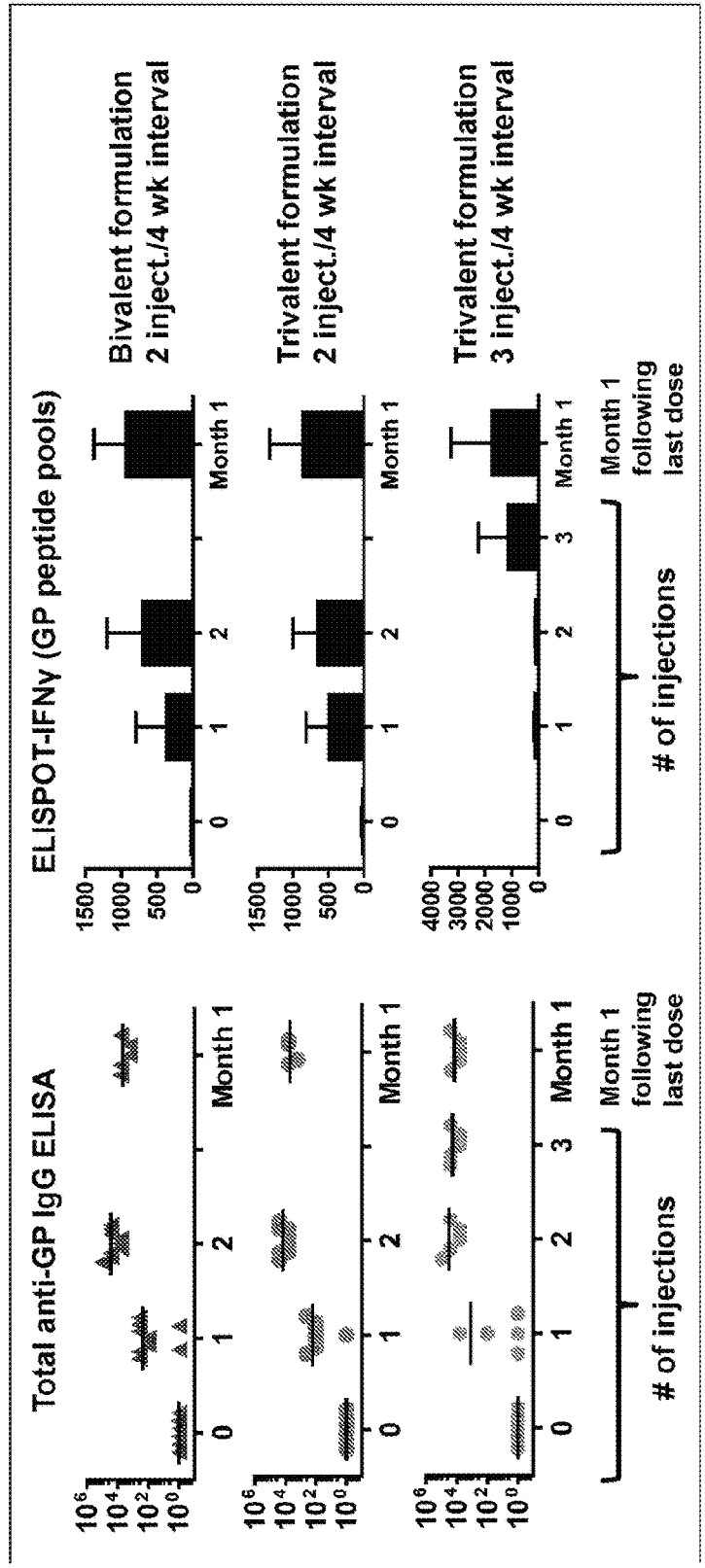
Figure 43:
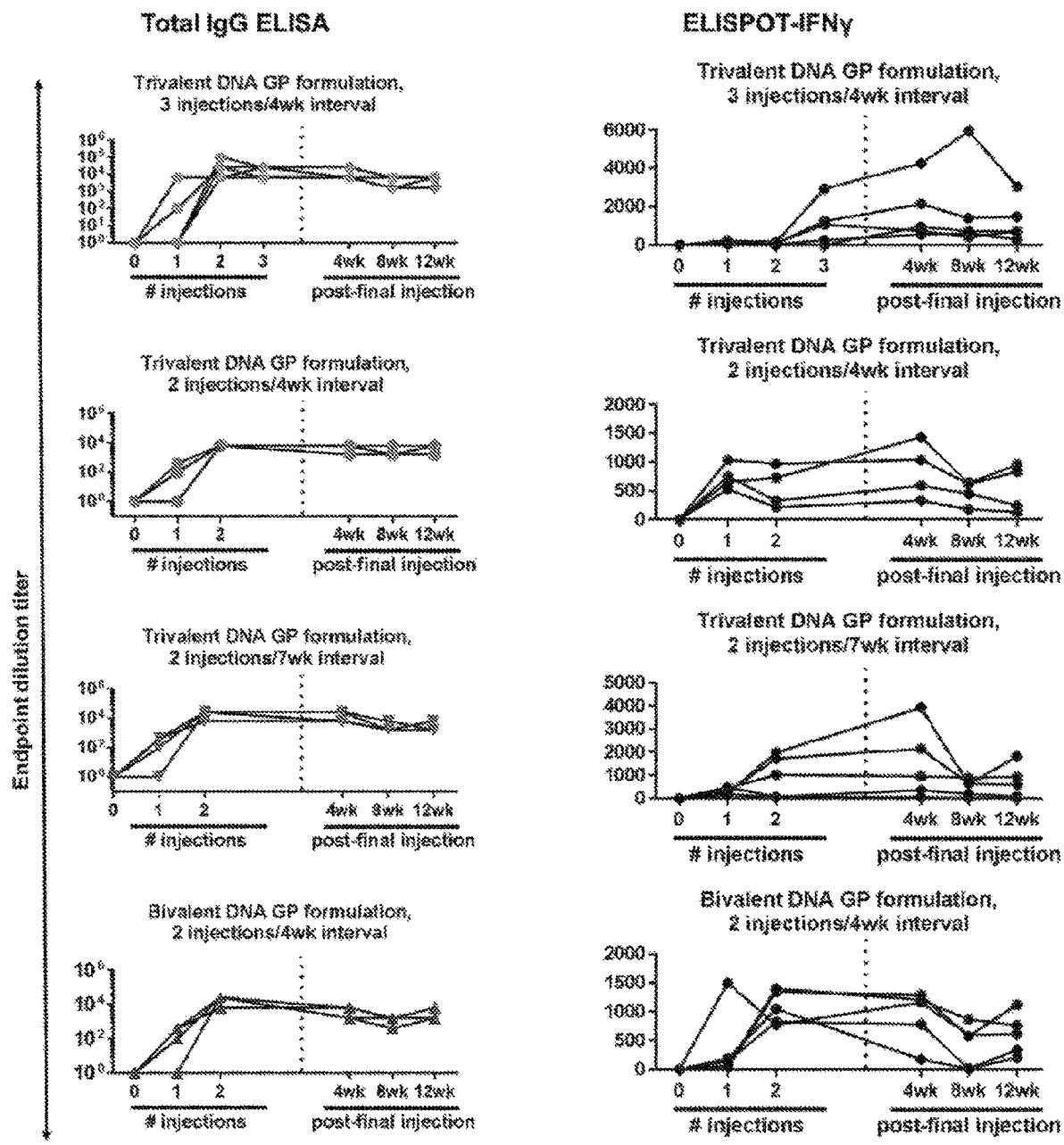

GP DNA Formulation Vaccines Protect Against Lethal Zaire Ebola Virus (Makona) Challenge The Cynomolgus macaques from groups 1, 2 and 3 were challenged with a 1000 TCID50 Guinea-Makona 2014 C07 virus (7-U reference strain) dose 28 days post-final DNA immunization. Animals were monitored for 28 days post-challenge. While none of the control animals survived past day 10 post challenge, 4/4 group 3 animals survived 28 days post challenge, 4/8 group 2 animals survived 28 days post challenge and 3/4 group 1 animals survived 28 days post challenge (FIG. 15). Surviving animals did not have any significant signs of disease. They also maintained normal CBC and enzyme levels. Bivalent and Trivalent DNA vaccines delivered by IM-EP elicit long-term antibody and T cell responses that were detectable >3 months post final DNA injection (FIG. 43).

Three doses of a Trivalent EBOV GP DNA vaccine is 100% protective against lethal EBOV challenge. Two doses of a Bivalent EBOV GP DNA vaccine affords 75% protection. Overall, the data supports further study of DNA vaccines, delivered by IM-EP, for possible administration against Ebola and other infectious pathogens EBOV-001 Phase I Clinical An Open-Label study of INO-4212 (with or without INO-9012 was conducted. INO-4212 was administered IM or ID followed by electroporation in healthy volunteers. Safety and immunological assessments were monitored. Intradermal delivery and intramuscular delivery were compared. There were 69 total subjects. ELISA analysis was performed before immunization (baseline), and at weeks 2, 6, and 14. Seropositive is defined as a positive IgG antibody response to Ebola Zaire glycoprotein.

INO-4201 is a DNA vaccine formulated with the consensus envelope glycoprotein of Zaire Ebolavirus (ConEBOVGP #1) generated by using the envelope glycoprotein sequences of the 1976, 1994, 1995, 1996, 2003, 2005, 2007 and 2008 outbreak strains, driven by a human CMV promoter (hCMV promoter) with the bovine growth hormone 3'end poly-adenylation signal (bGH polyA). pGX4201 was made by cloning the synthetic consensus envelope glycoprotein gene of Zaire Ebolavirus into pGX0001 at the BamHI and XhoI sites.

The ConEBOVGP #1 (ConGP1) sequence was constructed by generating a consensus envelope glycoprotein sequence of Zaire Ebolavirus using the envelope glycoprotein sequences of the 1976, 1994, 1995, 1996, 2003, 2005, 2007 and 2008 outbreak strains. Briefly, a consensus GP sequence was first generated based on six envelope sequences of the 1976, 1994, 1995, 1996, 2003 and 2005 outbreak strains. Then three non-consensus residues at the positions 377, 430 and 440 were weighted towards the 2003, 2005, 2007 and 2008 strains since they were the most recent and lethal outbreaks with published sequence data. The GenBank accession numbers for selected outbreak strain GP sequences are: Q05320, P87671, AAC57989, AEK25495, ABW34743, P87666, AER59718, AER59712, ABW34742, AAL25818. Once the consensus GP1 sequence was obtained, an upstream Kozak sequence was added to the N-terminal. Furthermore, in order to have a higher level of expression, the codon usage of this gene was adapted to the codon bias of Homo sapiens genes. In addition, RNA optimization was also performed: regions of very high (>80%) or very low (<30%) GC content and the cis-acting sequence motifs such as internal TATA boxes, chi-sites and ribosomal entry sites were avoided. The synthesized ConGP1 was digested with BamHI and XhoI, and cloned into the expression vector.

INO-4202 is a DNA vaccine formulated with a DNA plasmid expressing the envelope glycoprotein of Zaire Ebolavirus isolated from the 2014 outbreak in Guinea (GuineaGP), driven by a human CMV promoter (hCMV promoter) with the bovine growth hormone 3' end poly-adenylation signal (bGH polyA).

INO-4212 is a bivalent vaccine of INO-4201 and INO-4202.

Figure 19:
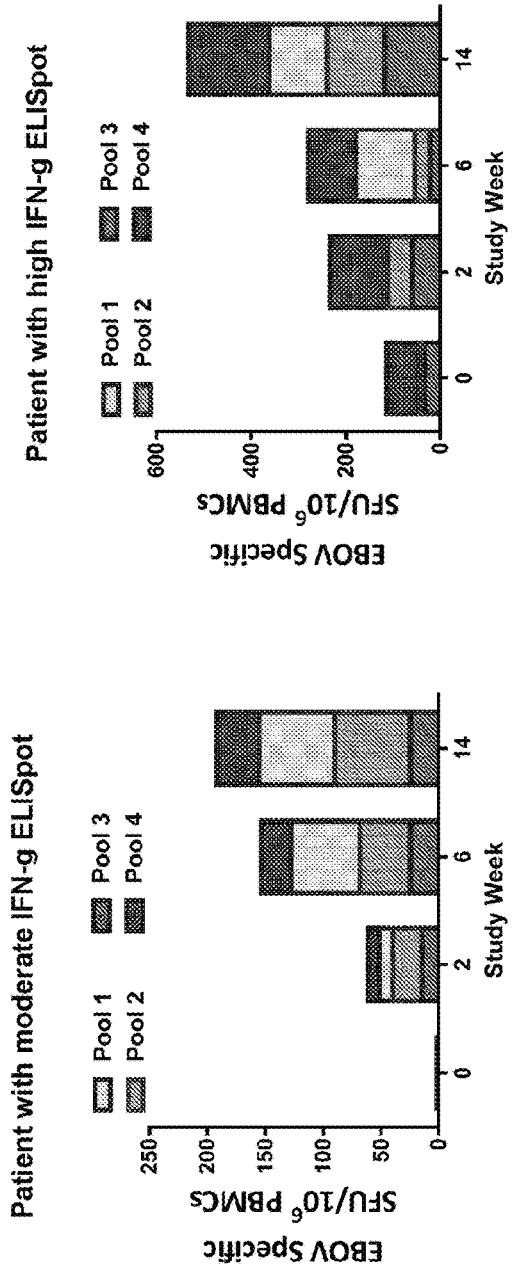

FIG. 17 depicts the vaccine formulation schedule, route and dose for each cohort. After the first injection, 15% or less of the patients was seriopositive. After the second injection, 50-100% of the patients were seriopositive. After the third injection 79-100% of the patients were seriopositive (FIG. 18). Two representative patients with a moderate IFNγ ELISpot, or a high IFNγ ELISpot showed specific T-cell responses (FIG. 19).

While other Ebola vaccines platforms, including NIAID VRC/GSK and rVSV/ZEBOVGP, are currently in clinical trials the present bivalent and trivalent vaccines described herein have advantages not observed in the other vaccine platforms. For example, the bi- or tri-valent vaccines can be administered IM or ID, while the other vaccine platforms are only administered IM. Importantly, NIAID VRC/GSK and rVSV/ZEBOVGP show side effects including fever, fatigue, arthralgia, and lymphopenia while the bi- and tri-valent vaccines do not show any side effects. It should be noted however, that some of the side effects of rVSV/ZEBOVGP and ChAd3/MVAGP overlap with symptoms of Ebola. Further the bi- and tri-valent vaccines give antibody titers one to two orders of magnitude larger than rVSV/ZEBOVGP and ChAd3/MVAGP (FIG. 20).

Figure 22:
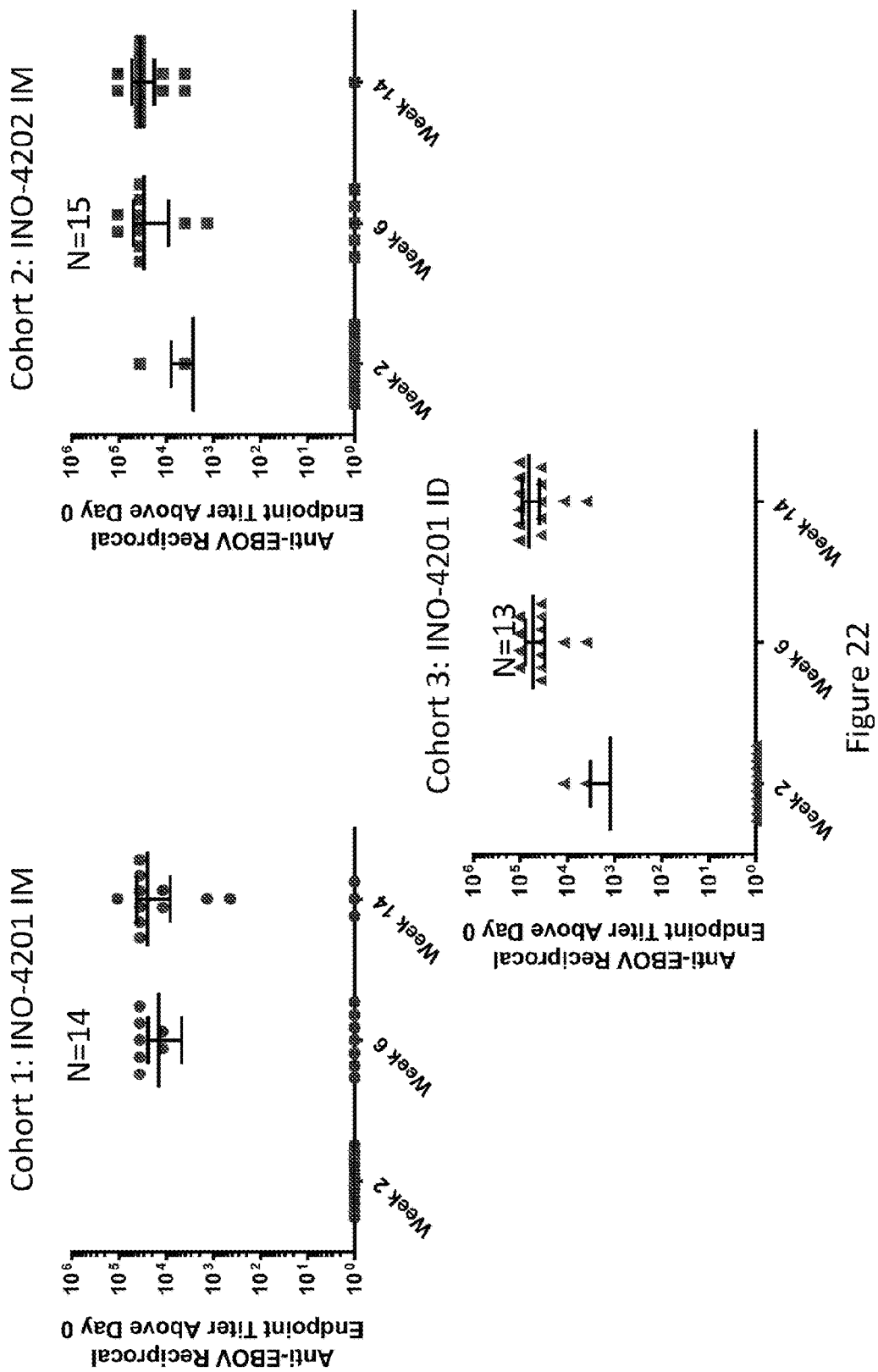
Figure 24:
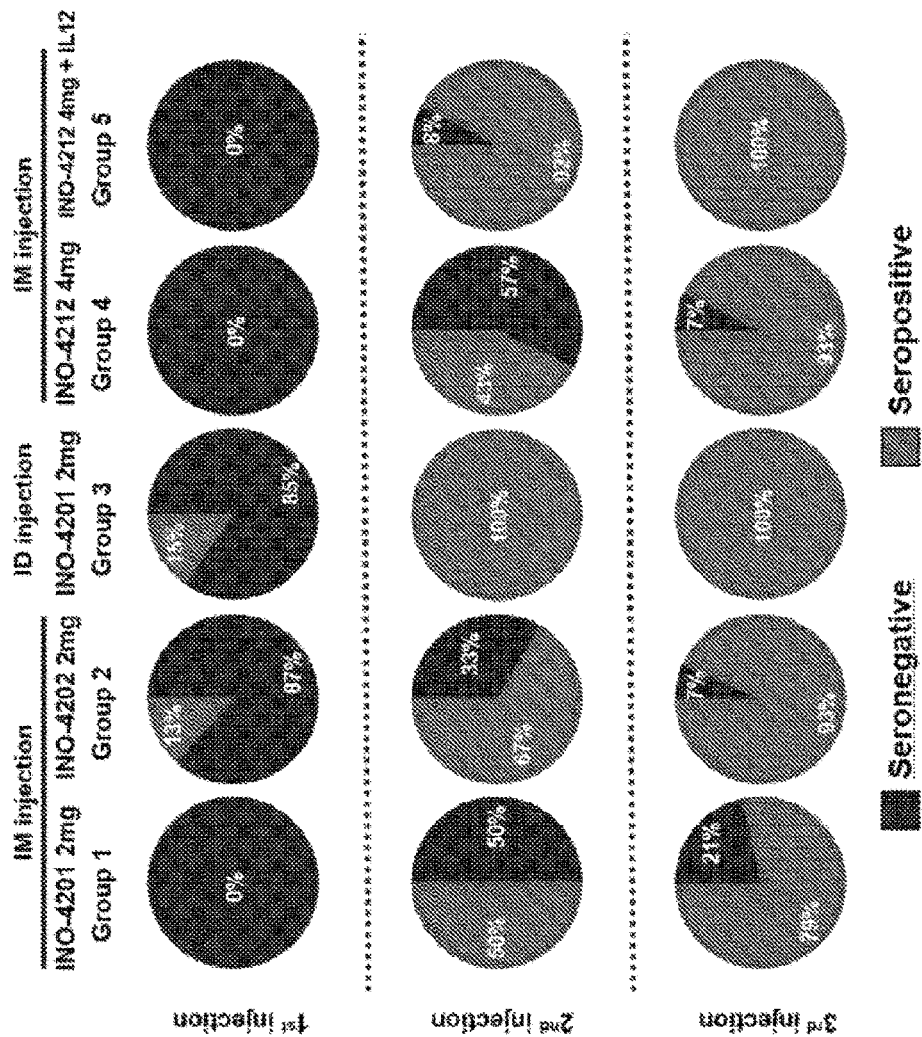
Figure 26:
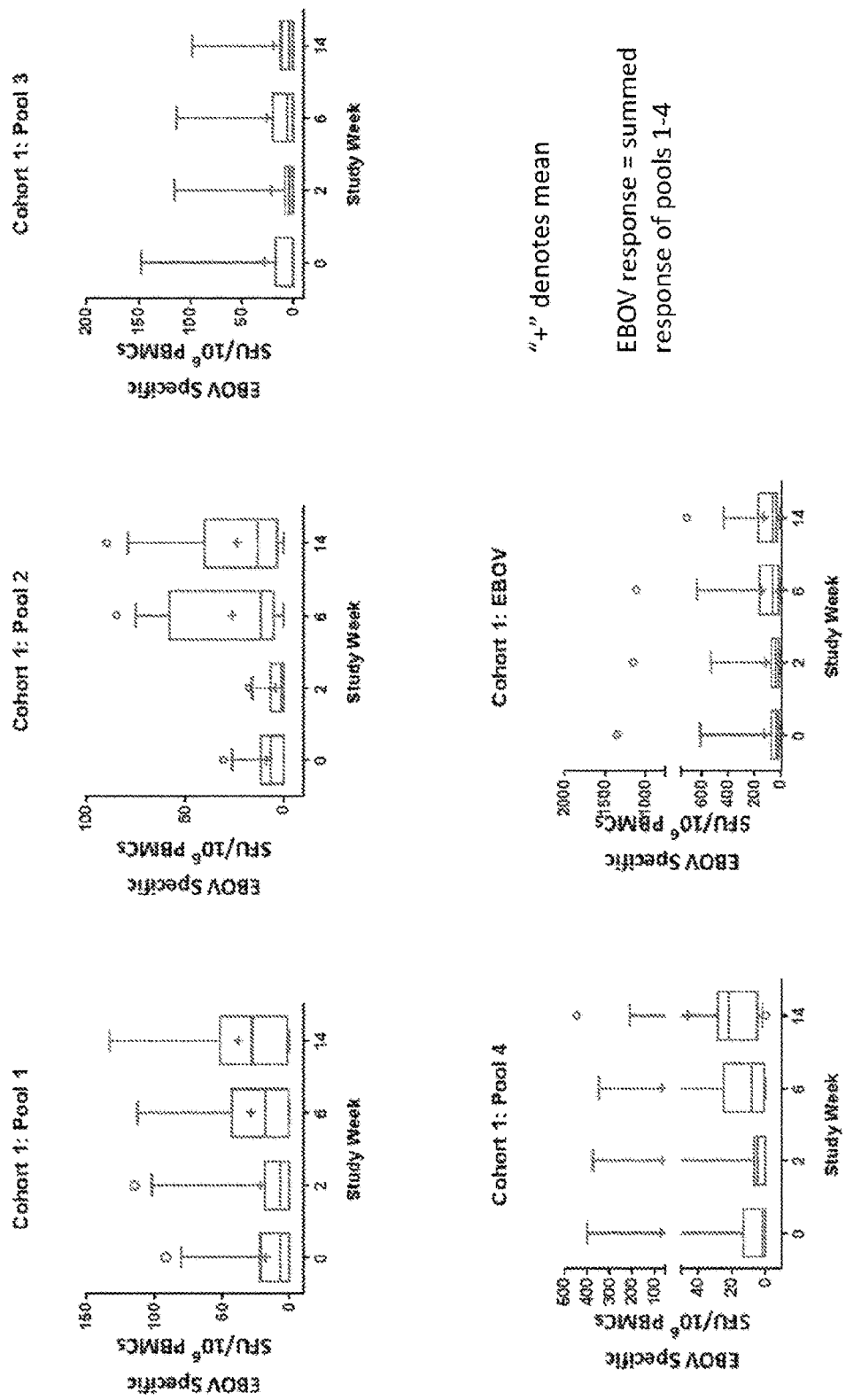
Figure 27:
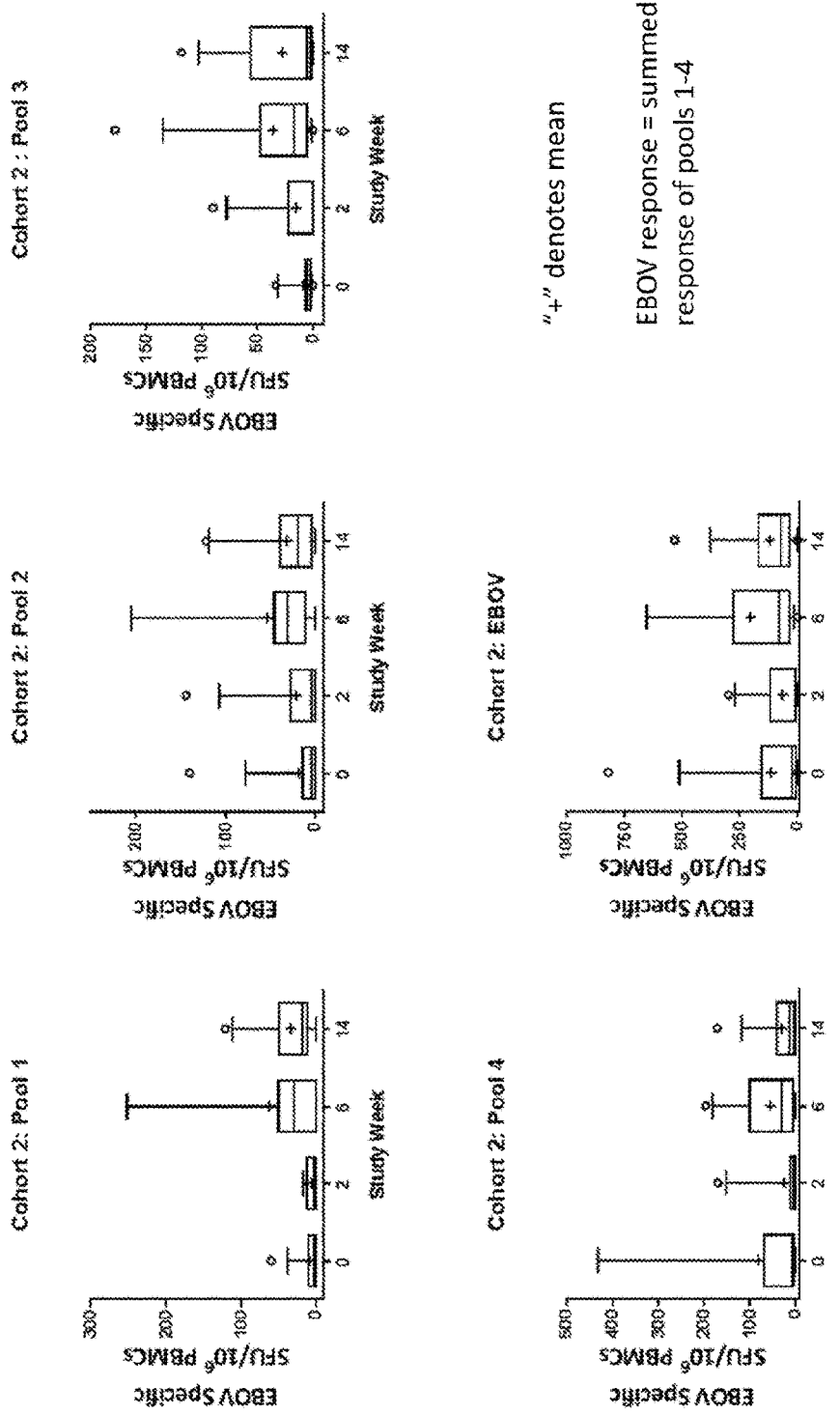
Figure 28:
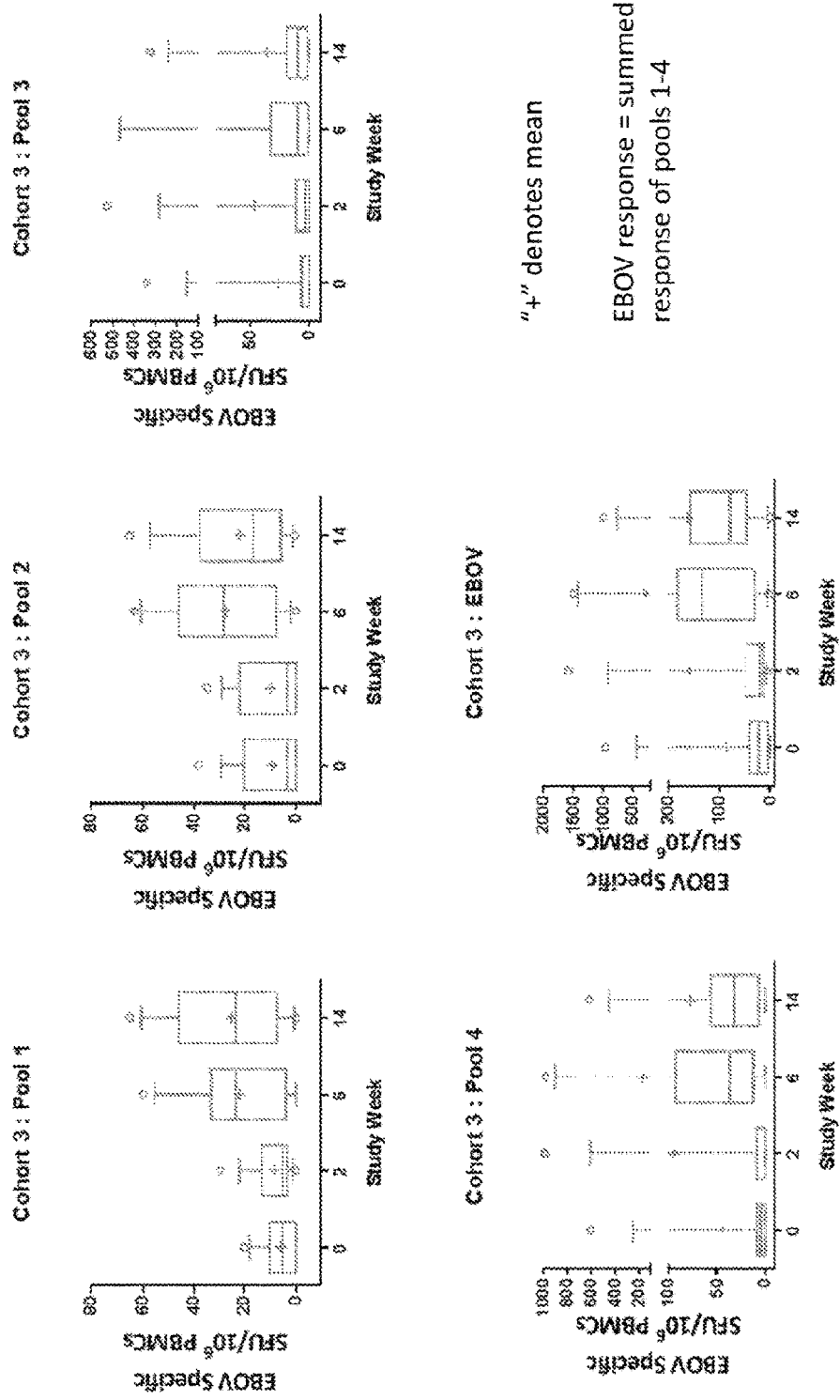
Figure 29:
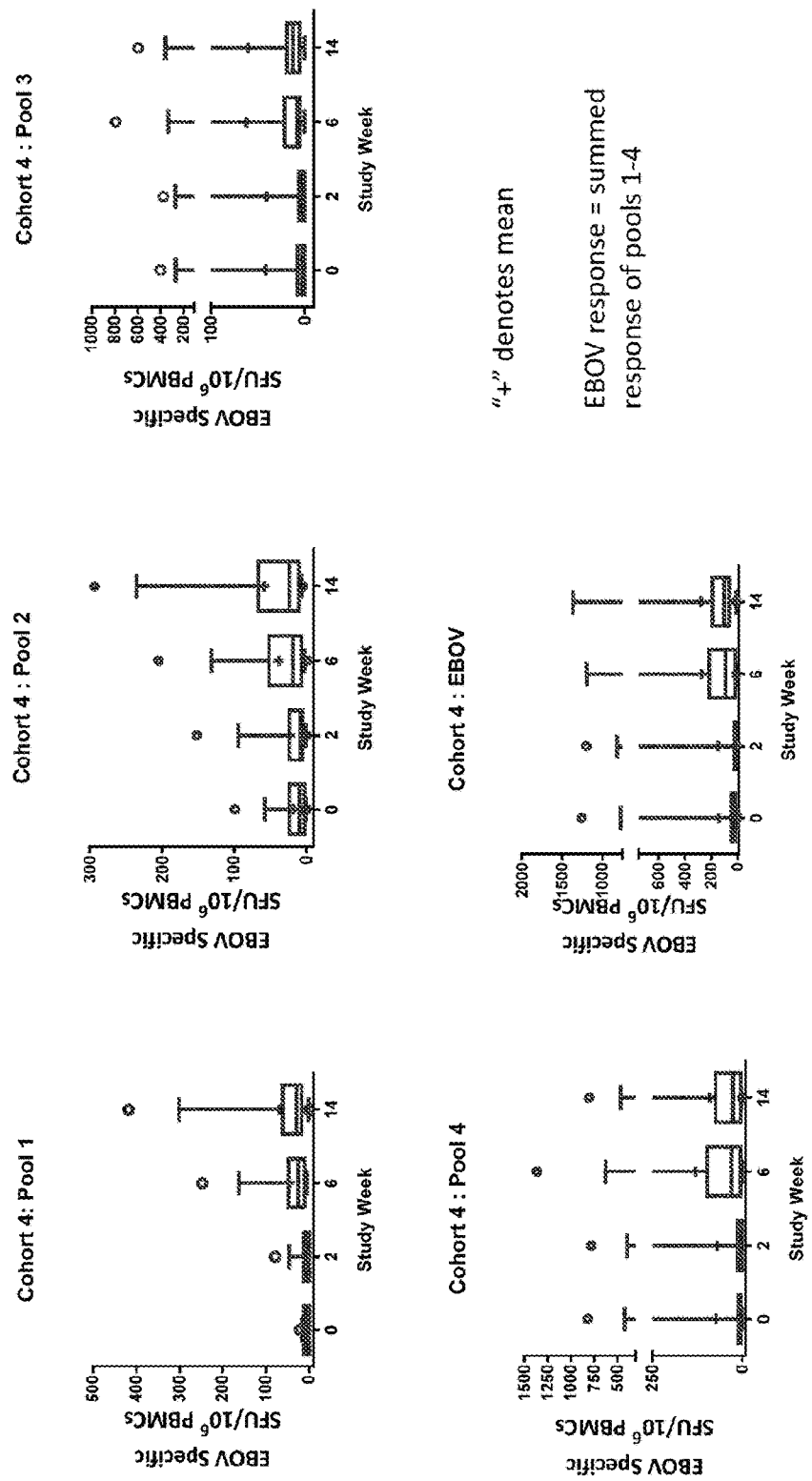
Figure 30:
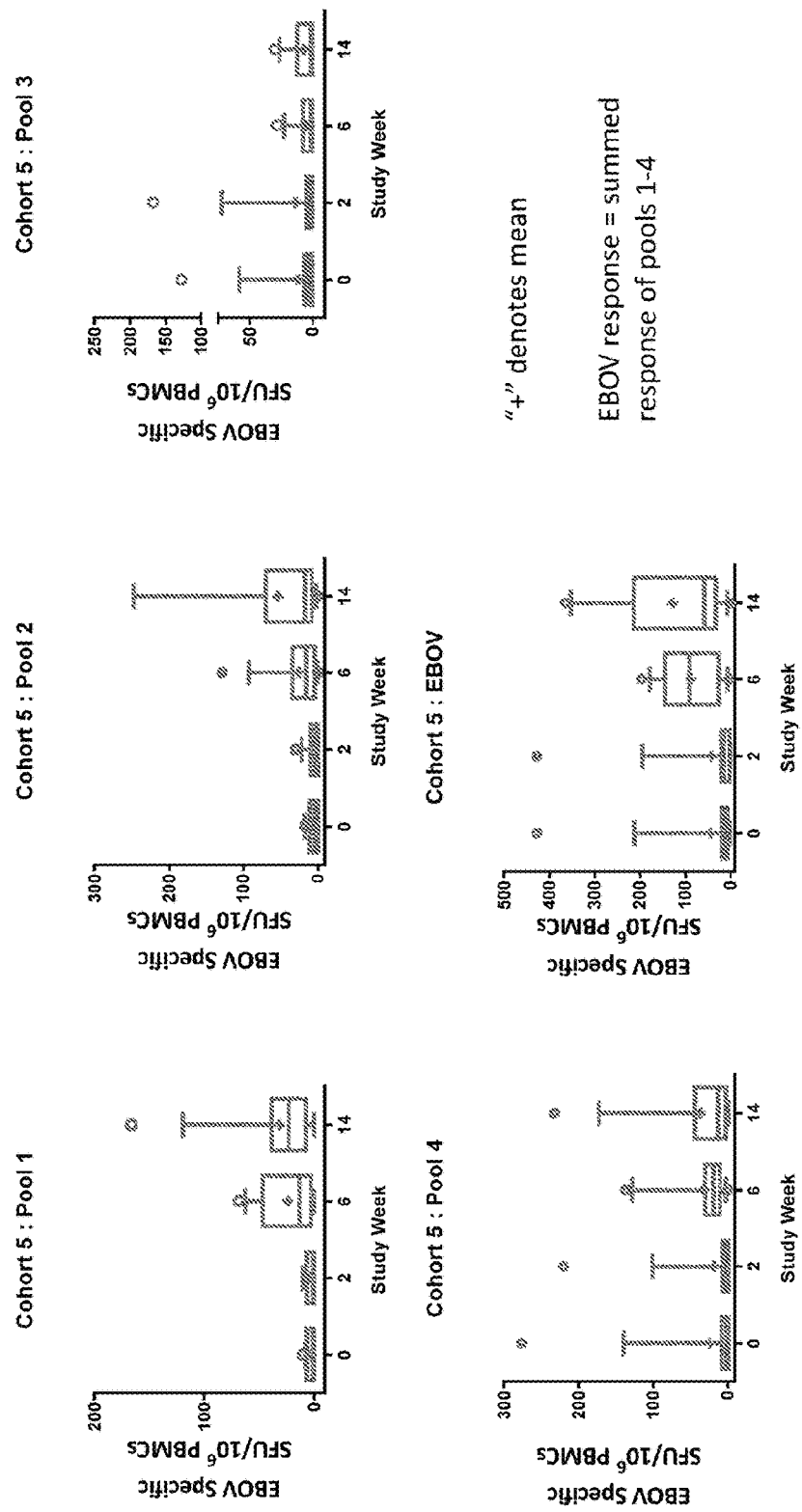
Figure 31:
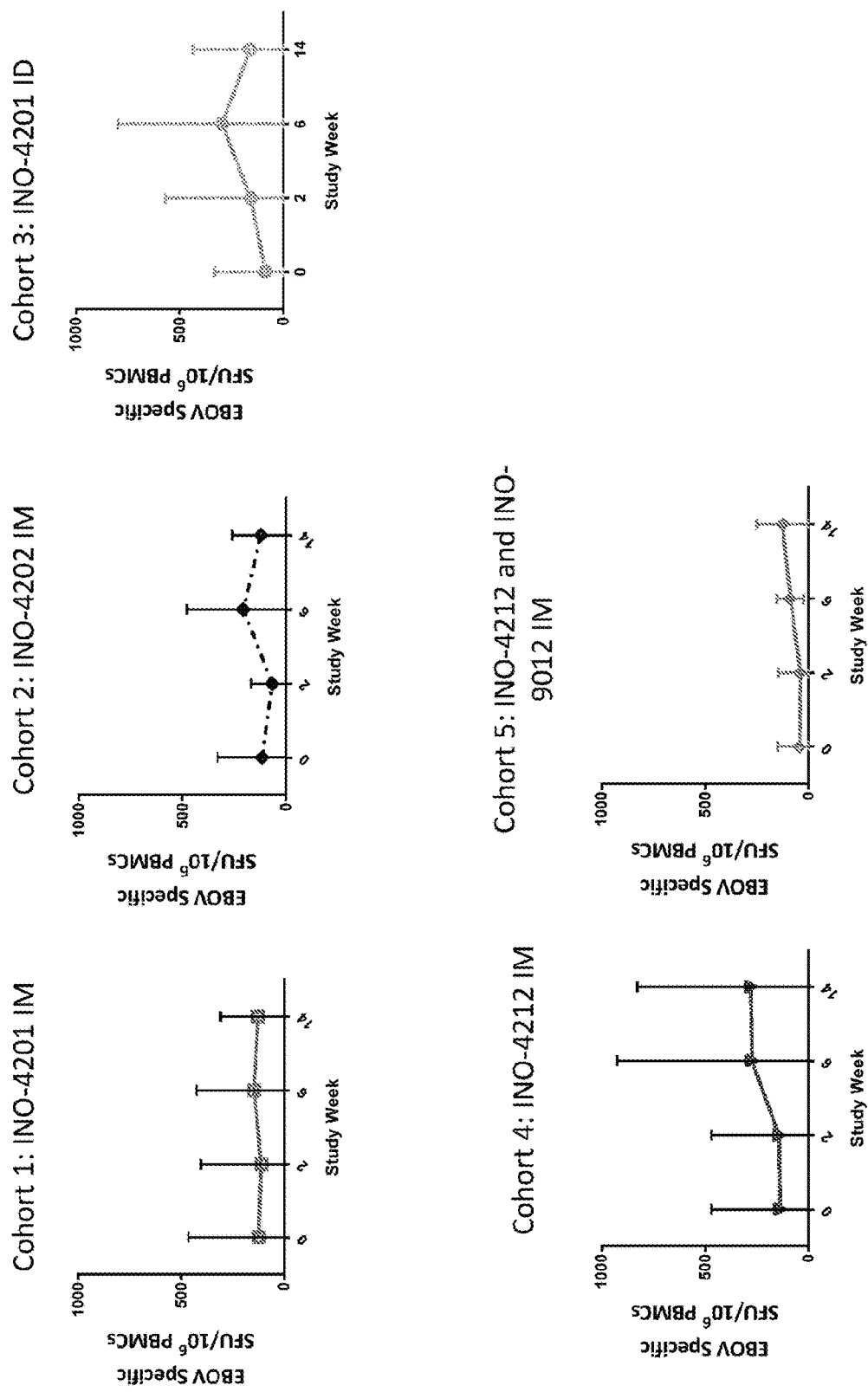
Figure 32:
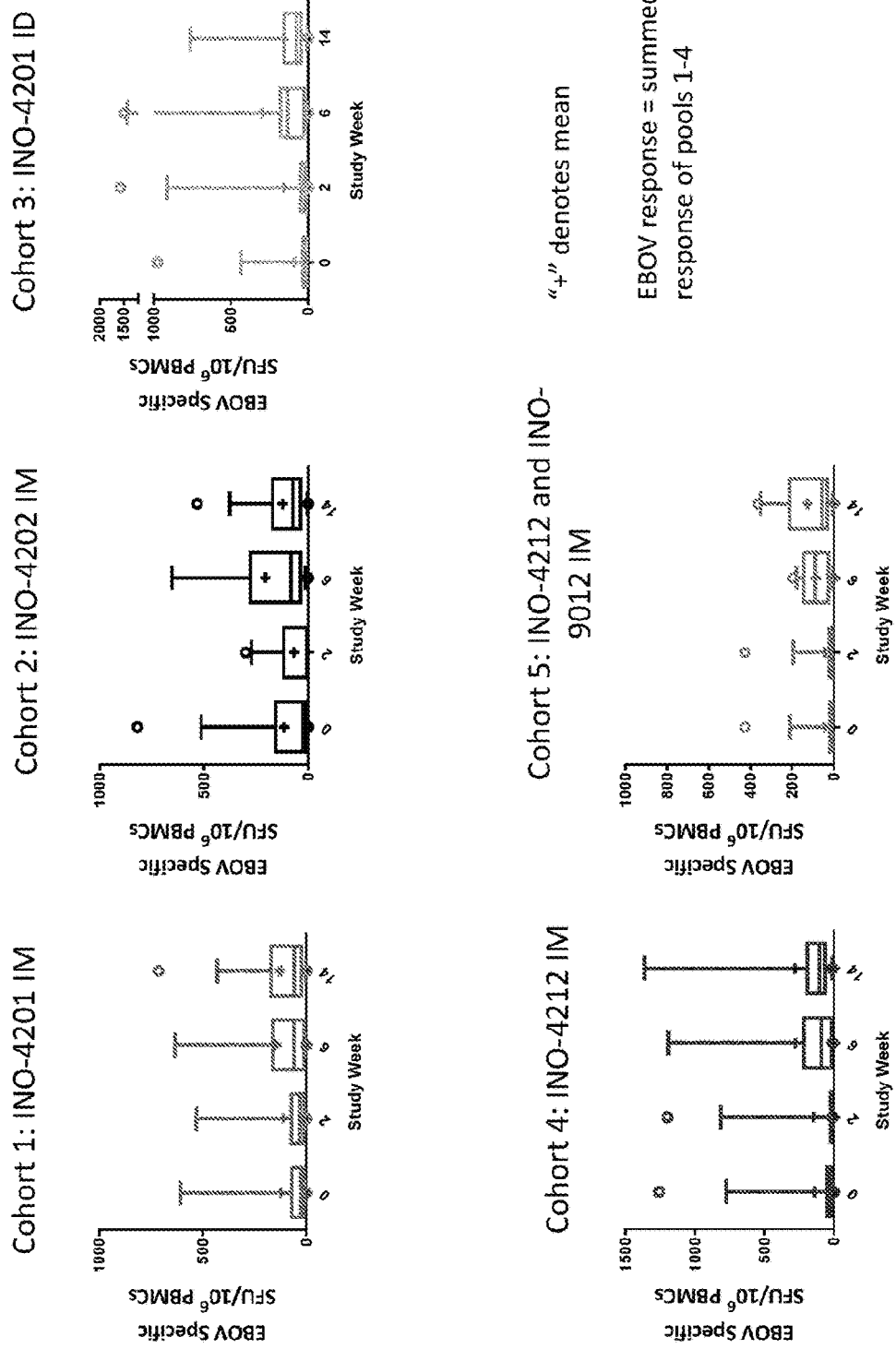
Figure 37:
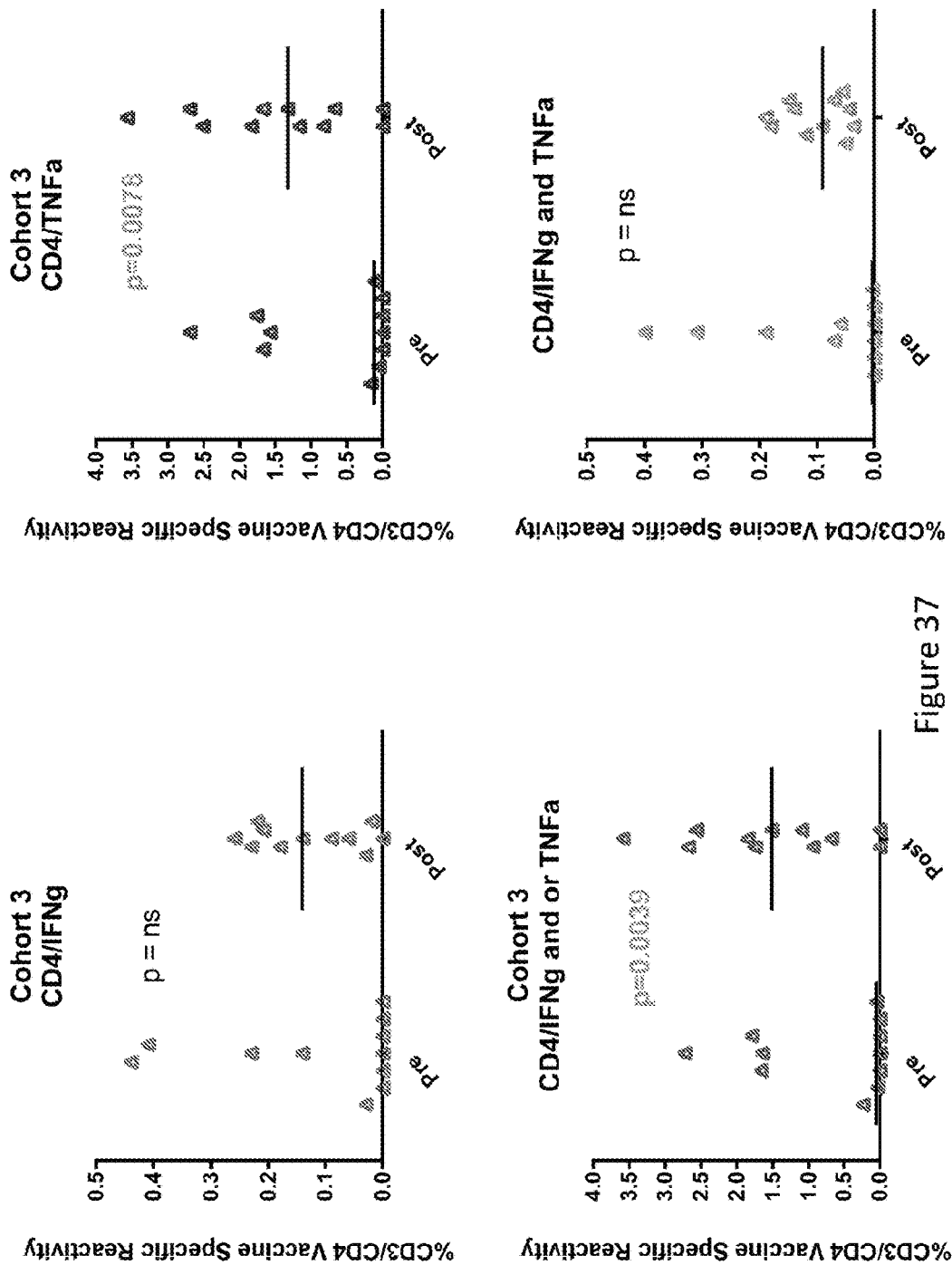
Figure 38:
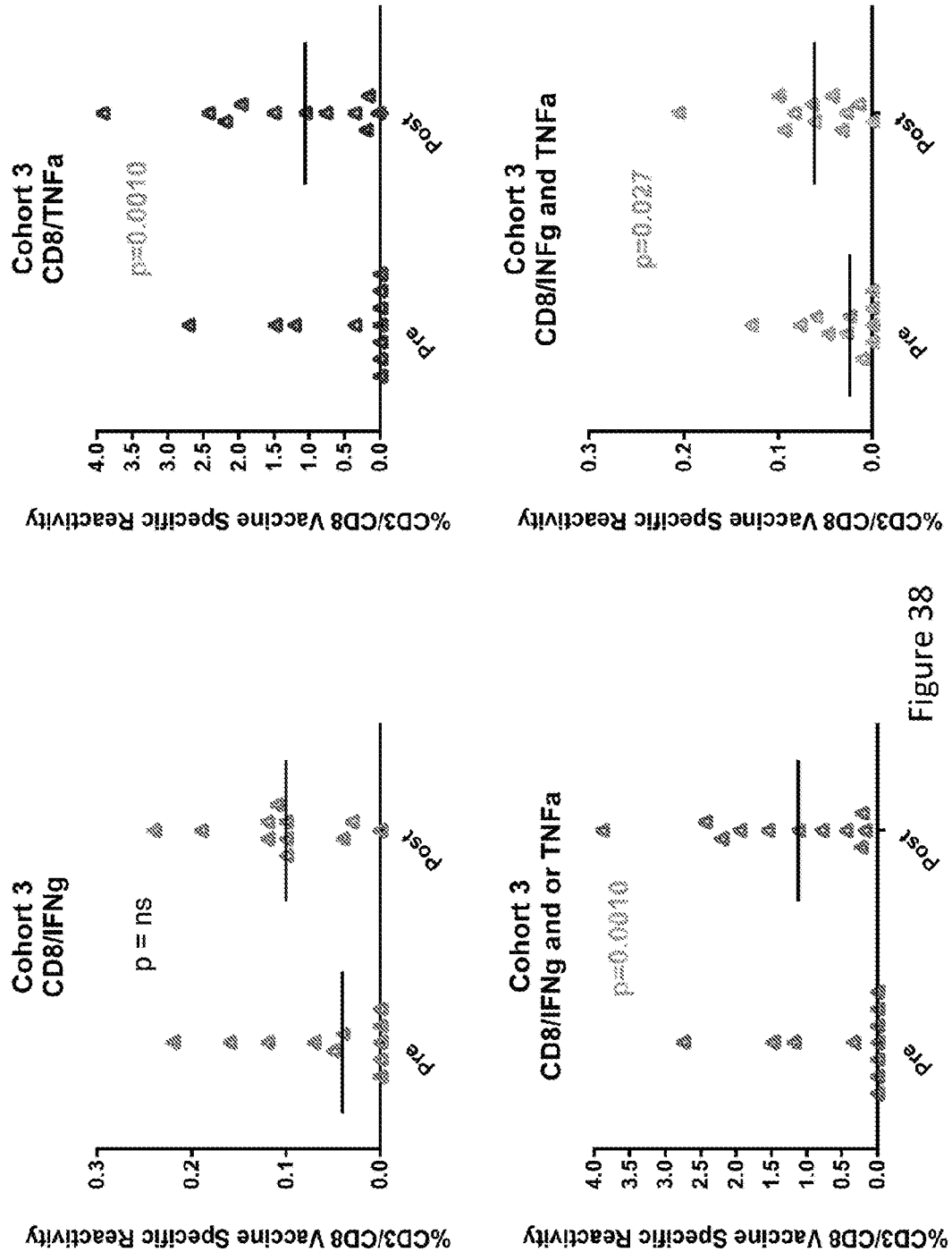

Subjects (n=15) were assigned to receive INO-4201 at a 2 mg DNA/dose given as two separate 1 mg (0.1 mL) ID (Mantoux) injections followed by EP with the CELLECTRA®-3P device. Subjects received a 3-dose series with immunizations at 0, 4 weeks, and 12 weeks (0-4-12 week schedule). Antibodies specific for EBOV glycoprotein (GP) were measured from the sera of vaccinated subjects with a binding ELISA. Reciprocal endpoint titers above Day 0 are shown two weeks post each immunization (FIG. 22). 100% of subjects vaccinated with INO-4201 seroconverted after 2 immunizations (FIG. 22, Cohort 3 and FIG. 24).

Example 8

Described herein is immune response data for the three EBOV DNA constructs described in Example 7: a consensus sequence of ZEBOV (1976-1996) (ConEBOVGP #1 or INO-4201), ZEBOV (2002-2008) (ConEBOVGP #2), and a matched ZEBOV sequence from the 2014 Guinea outbreak. (Guinea-GP). Five vaccines were developed, monovalent vaccines which comprise only a single DNA construct, a bivalent vaccine formulation which comprise either ConEBOVGP #1 with Guinea-GP and a trivalent formulation which comprises all three of ConEBOVGP #1, ConEBOVGP #2, and Guinea-GP. 69 Subjects from cohorts 1-5 were included in analysis of immune response by ELISA and 75 subjects from cohorts 1-5 were included in analysis of immune response by ELISpot (FIGS. 21, 25).

ELISA Titers by Cohort and Timepoint

Figure 23:
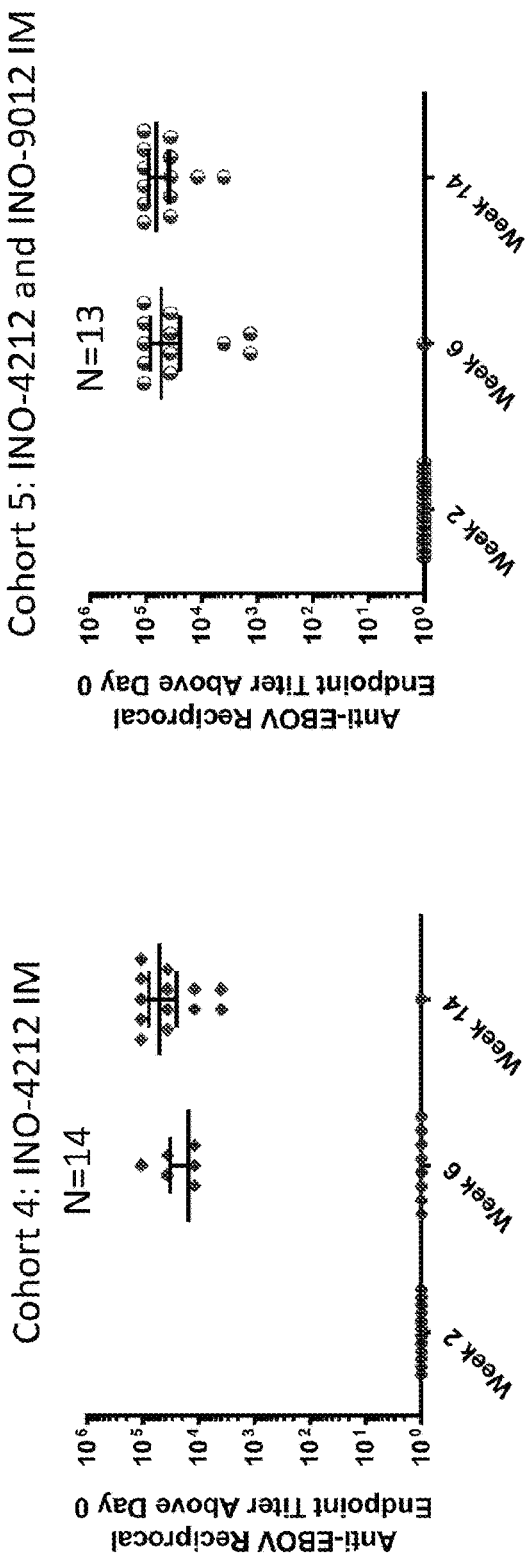

Titers of anti-EBOVR were determined for each cohort at weeks 2, 6 and 14. By week 6, each cohort saw an increase in antibody titer above Day 0 (FIGS. 22-23). There was little to no reactivity for the first dose in each cohort. Dose 2 begins to drive seroconversion, with Cohorts 3 and 5 seeing the largest frequency. Dose three drives >90% serconversion in 4/5 cohorts. Cohorts 3 and 5 show 100% seroconversion at this time point (FIG. 24)

Subject Responses by Peptide Pool

Cohort responses were analyzed by peptide pool (FIGS. 26-33). To analyze ELISpot outliers, day 0 values for each pool and total EBOV responses were used to create an outlier threshold (Mean day 0 values+(3×STDEV of day 0 values)). This threshold should encompass 99% of a normally distributed population. Any subject that displayed baseline values greater than the outlier threshold was removed and a responder criteria was generated with the remaining subjects.

ICS Analysis 47 subjects from all cohorts were included in the analysis, however cohort 5 is underrepresented (FIG. 35). ICS analysis performed at baseline and week 14. A single EBOV peptide pool composed of Pools 1-4 is used for stimulation. Analysis of T cell activity in the form of IFNg or TNFa production from both CD4 and CD8 compartments suggests significant elevation of TNFa in both CD4 and CD8 compartments as well as elevation of TNFa and/or IFNg in Cohort 3 only (Wilcoxon matched paired analysis, two-tailed)

Immunology Summary

100% of Cohort 3 (ID) patients seroconverted after 2 doses. 92% of Cohort 5 (IM+IL12) patients seroconverted after 2 doses and 100% after 3 doses. Other cohorts showed 67% at best after 2 doses and ranged as high as 93% after 3 doses.

When analyzing all patients: the best response frequency were Cohorts 2 and 4 with 53% and 57% respectively. Cohort 3 showed 40% responders. Addition of IL-12 in Cohort 5 did not seem to influence response rates (47%). When analyzing patients with 8 outliers removed the response frequency were Cohorts 2 and 4 with 84.6% and 76.9% respectively. Cohort 3 showed 64.3% responders. Addition of IL-12 in Cohort 5 did not seem to influence response rates (53.3%).

Both CD4 and CD8 T cells showed high expression of TNFa and TNFa and/or IFNg in Cohort 3 (statistically significant to baseline, Wilcoxon matched pairs test, 2 tailed).

Immunization with INO-4201 was well tolerated in healthy volunteers with no Grade 3 or Grade 4 SAEs noted. INO-4201 induced robust Ebola GP-specific antibody (GMT 46,968) and resulted in 100% seroconversion, as gauged by binding ELISA, after only two doses of INO-4201. Administration of INO-4201 generated EBOV GP specific T cell responses as assessed by Interferon gamma (IFN$\gamma$) ELISpot (295.3 SFU per $10^6$ PBMCs) and significant increases in in the production of IFN$\gamma$ or TNF$\alpha$ in both the CD8+ T and CD4+ T cell compartments. Intradermal administration of INO-4201 using the Cellectra device is both well tolerated and immunogenic as assessed by both humoral and cellular EBOV GP-specific immunoassays. These results indicate that INO-4201 is a strong candidate for further clinical development of a prophylactic Ebola vaccine.

Example 9—Lasting Humoral and Cellular Immune Responses in Cynomolgus Macaques Following Administration of a *Zaire* Ebola Virus (EBOV) GP DNA Vaccine Delivered by Intramuscular Electroporation Presented herein are novel Ebola virus disease (EVD) DNA vaccines that have a clean safety profile and are serology independent, allowing for possible repeat vector administration. Three novel synthetic *Zaire* Ebola virus (EBOV) GP DNA vaccines were designed and Bivalent, or Trivalent formulations were developed. Both EBOV-GP DNA vaccines were highly protective (75-100%) against lethal EBOV Makona C07 challenge in cynomolgus macaques. Animals (n=4-5/group) with different regimens were followed to monitor long-term immunogenicity following DNA immunization. All NHPs rapidly seroconverted. NHPs have durable total IgG antibody titers and T cells responses to EBOV GP antigen, including polyfunctional CD4 and CD8 T cells expressing IFN$\gamma$, IL2, and TNF$\alpha$ and responses in memory subset populations (FIGS. 47-59). Together, the data strong support EBOV-GP DNA vaccine delivery for protection and the generation of robust memory immune responses.

The EBOV-GP Dan vaccines elicit long-term immune responses and have a strong recall response following a 1 year boost (FIGS. 49-50). The recall response was remarkably high in the group receiving a single IM injection (FIG. 50).

Example 10

Presented herein are the peptide sequences and the nucleic acid sequences for the peptides.

TABLE 1

| | Plasmid Vaccine pMARV GP sequence MARV ANG | | | | | | |
|---|---|---|---|---|---|---|---|
| Peptide Number | Sequence | SEQ ID NO: | Position | H-2 | ELISPOT AVE | ±SEM | FACS T cell restr. |
| 3 | IQGVKTLPILEIASN | 7 | 13-27 | d | 62 | 34 | 4+ |
| 5 | ASNIQPQNVDSVCSG | 8 | 25-39 | b | 743 | 186 | 8+ |

TABLE 1-continued

Plasmid Vaccine pMARV
GP sequence MARV ANG

| Peptide Number | Sequence | SEQ ID NO: | Position | H-2 | ELISPOT AVE | ±SEM | FACS T cell restr. |
|---|---|---|---|---|---|---|---|
| 12 | SKRWAFRAGVPPKNV | 9 | 67-81 | b | 694 | 204 | 4+ |
| 27 | GKVFTEGNIAAMIVN | 10 | 157-171 | d | 602 | 75 | 4+ |
| 28 | GNIAAMIVNKTVHKM | 11 | 163-177 | b/d | 126 | 28 | 8+ |
|  | GNIAAMIVNKTVHKM | 12 |  | d | 30 | 10 | 4+ |
| 29 | IVNKTVHKMIFSRQG | 13 | 169-183 | d | 92 | 17 | 4+ |
| 30 | HKMIFSRQGQGYRHM | 14 | 175-189 | d | 31 | 10 | 4+ |
| 31 | RQGQGYRHMNLTSTN | 15 | 181-195 | b | 674 | 112 | 8+ |
| 32 | RHMNLTSTNKYWTSS | 16 | 187-201 | b | 44 | 16 | 8+ |
| 65 | LPTENPTTAKSTNST | 17 | 385-399 | b/d | 398/16 | 107/2 | 4+ |
| 71 | PNSTAQHLVYFRRKR | 18 | 421-435 | d | 29 | 6 | 4+ |
| 72 | HLVYFRRKRNILWRE | 19 | 427-441 | d | 145 | 18 | 4+ |
| 89 | GLSWIPFFGPGIEGL | 20 | 529-543 | b | 26 | 8 | 4+ |
| 92 | GLIKNQNNLVCRLRR | 21 | 547-561 | d | 29 | 10 | 4+ |
| 93 | NNLVCRLRRLANQTA | 22 | 553-567 | d | 34 | 13 | 4+ |
| 97 | TTEERTFSLINRHAI | 23 | 577-591 | b | 46 | 18 | 8+ |
| 99 | HAIDFLLARWGGTCK | 24 | 589-603 | d | 63 | 12 | 4+ |
| 101 | TCKVLGPDCCIGIED | 25 | 601-615 | b | 97 | 37 | 4+ |

"Epitope-containing peptides were identified by IFNγ ELISPOT (≥10 SFC/10$^6$ splenocytes AND ≥80% response rate) and then confirmed by FACS (≥3 - 5 x 10$^4$ CD3+ cells were acquired). Responses for each were further characterized by FACS (expression of CD4 and/or CD8 by CD3+/CD44+/IFNγ+ cells). Predicted CD8+ epitopes are underlined (best consensus % rank by IEDB) and previously-described epitopes are referenced. Immunodominant epitopes are displayed (*).

TABLE 2

Plasmid Vaccine pEBOS
GP sequence SUDV CON

| Peptide Number | Sequence | SEQ ID NO: | Position | H-2 | ELISPOT AVE | ±SEM | FACS T cell restr. |
|---|---|---|---|---|---|---|---|
| 4 | FFVWVIILFQKAFSM | 26 | 19-33 | b | 310 | 139 | 8+ |
| 15 | RWGFRSGVPPKVVSY | 27 | 85-99 | b | 108 | 59 | 4+ |
| 19 | YNLEIKKPDGSECLP | 28 | 109-123 | b | 55 | 25 | 4+ |
| 24 | HKAQGTGPCPGDYAF | 29 | 139-153 | d | 13 | 3 | 8+ |
| 27 | GAFFLYDRLASTVIY | 30 | 157-171 | d | 29 | 9 | 8+ |
| 30 | NFAEGVIAFLILAKP | 31 | 175-189 | d | 31 | 6 | 4+ |
| 36 | SYYATSYLEYEIENF | 32 | 211-225 | b | 60 | 16 | 4+ |
| 41 | FVLLDRPHTPQFLFQ | 33 | 241-255 | d | 338 | 55 | 8+ |
| 78 | NITTAVKTVLPQEST | 34 | 463-477 | b/d | 28/105 | 12/18 | 4+ |
| 82 | TGILGSLGLRKRSRR | 35 | 487-501 | d | 82 | 14 | 4+ |

TABLE 2-continued

Plasmid Vaccine pEBOS
GP sequence SUDV CON

| Peptide Number | Sequence | SEQ ID NO: | Position | H-2 | ELISPOT AVE | ±SEM | FACS T cell restr. |
|---|---|---|---|---|---|---|---|
| 83 | LGLRKRSRRQVNTRA | 36 | 493-507 | d | 69 | 12 | 4+ |
| 89 | IAWIPYFGPGAEGIY | 37 | 529-543 | b | 123 | 40 | 8+/4+ |
| 97 | TELRTYTILNRKAID | 38 | 577-591 | d | 12 | 5 | 4+ |
| 101 | CRILGPDCCIEPHDW | 39 | 601-615 | b | 80 | 41 | 4+ |
| 105 | QIIHDFIDNPLPNQD | 40 | 625-639 | b | 28 | 23 | 4+ |
| 110 | GIGITGIIIAIIALL | 41 | 655-669 | b | 27 | 19 | 8+ |

"Epitope-containing peptides were identified by IFNγ ELISPOT (≥10 SFC/10$^6$ splenocytes AND ≥80% response rate) and then confirmed by FACS (≥3 - 5 x 10$^4$ CD3+ cells were acquired). Responses for each were further characterized by FACS (expression of CD4 and/or CD8 by CD3+/CD44+/IFNγ+ cells). Predicted CD8+ epitopes are underlined (best consensus % rank by IEDB) and previously-described epitopes are referenced. Immunodominant epitopes are displayed (*).

TABLE 3

Plasmid Vaccine pEBOZ
GP sequence ZEBOV CON

| Peptide Number | Sequence | SEQ ID NO: | Position | H-2 | ELISPOT AVE | ±SEM | FACS T cell restr. |
|---|---|---|---|---|---|---|---|
| 6 | FSIPLGVIHNSTLQV | 42 | 31-45 | d | 78 | 31 | 8+ |
| 15 | RWGFRSGVPPKVVNY | 43 | 85-99 | b | 44 | 12 | 4+ |
| 19 | YNLEIKKPDGSECLP | 44 | 109-123 | b | 29 | 12 | 4+ |
| 24 | HKVSGTGPCAGDFAF | 45 | 139-153 | d | 484 | 85 | 8+ |
| 27 | GAFFLYDRLASTVIY | 46 | 157-171 | d | 72 | 18 | 8+ |
| 30 | TFAEGVVAFLILPQA | 47 | 175-189 | d | 581 | 85 | 4+ |
| 32 | PQAKKDFFSSHPLRE | 48 | 187-201 | b | 18 | 6 | 4+ |
| 33 | FFSSHPLREPVNATE | 49 | 193-207 | b | 21 | 8 | 4+ |
| 40 | EVDNLTYVQLESRFT | 50 | 235-249 | d | 32 | 17 | 4+ |
| 41 | YVQLESRFTPQFLLQ | 51 | 241-255 | d | 97 | 23 | 4+ |
| 48 | TTIGEWAFWETKKNL | 52 | 283-297 | d | 219 | 70 | 4+ |
| 49 | AFWETKKNLTRKIRS | 53 | 289-303 | d | 32 | 15 | 4+ |
| 50 | KNLTRKIRSEELSFT | 54 | 295-309 | d | 105 | 37 | 4+ |
| 60 | SQGREAAVSHLTTLA | 55 | 355-369 | b | 16 | 7 | 4+ |
| 65 | DNSTHNTPVYKLDIS | 56 | 385-399 | d | 29 | 18 | 4+ |
| 66 | TPVYKLDISEATQVE | 57 | 391-405 | d | 371 | 118 | 4+ |
| 71 | PPATTAAGPPKAENT | 58 | 421-435 | b | 21 | 8 | 4+ |
| 84 | TRREAIVNAQPKCNP | 59 | 499-513 | b | 12 | 5 | 8+ |
| 89 | LAWIPYFGPAAEGIY | 60 | 529-543 | b | 93 | 8 | 8+/4+ |

TABLE 3-continued

Plasmid Vaccine pEBOZ
GP sequence ZEBOV CON

| Peptide Number | Sequence | SEQ ID NO: | Position | H-2 | ELISPOT AVE | ±SEM | FACS T cell restr. |
|---|---|---|---|---|---|---|---|
| 97 | TELRTFSILNRKAID | 61 | 577-591 | b/d | 14/82 | 4/42 | 8+ |
| 101 | CHILGPDCCIEPHDW | 62 | 601-615 | b | 96 | 62 | 4+ |

"Epitope-containing peptides were identified by IFNγ ELISPOT (≥10 SFC/10⁶ splenocytes AND ≥80% response rate) and then confirmed by FACS (≥3 - 5 x 10⁴ CD3+ cells were acquired). Responses for each were further characterized by FACS (expression of CD4 and/or CD8 by CD3+/CD44+/IFNγ+ cells). Predicted CD8+ epitopes are underlined (best consensus % rank by IEDB) and previously-described epitopes are referenced. Immunodominant epitopes are displayed (*).

TABLE 4

Plasmid Vaccine pMARV
GP sequence MARV ANG

| Peptide Number | Sequence | SEQ ID No: | Best con % rank (IEDB) CD8+ (≤0.5) | | | | | CD4+ (<25) | | | Previously defined (80% Blast; Allele |
|---|---|---|---|---|---|---|---|---|---|---|---|
| | | | $D^b$ | $K^b$ | $D^d$ | $K^d$ | $L^d$ | $I-A^b$ | $I-A^d$ | $I-E^d$ | |
| 3 | IQGVKTLPILEIASN | 7 | | | | | | | 12.1 | | |
| 5 | ASNIQPQNVDSVCSG | 8 | 0.4 | | | | | | | | |
| 12 | SKRWAFRAGVPPKNV | 9 | | | | | | | 0.8 | | |
| 27 | GKVFTEGNIAAMIVN | 10 | | | | | | | 12.9 | | |
| 28 | GNIAAMIVNKTVHKM | 11 | 0.2 | | | | | | | 3.9 | $H-2^d$ class I |
| | GNIAAMIVNKTVHKM | 12 | 0.2 | | | | | | | 3.9 | |
| 29 | IVNKTVHKMIFSRQG | 13 | | | | | | | 17.2 | | |
| 30 | HKMIFSRQGQGYRHM | 14 | | | | | | | | | |
| 31 | RQGQGYRHMNLTSTN | 15 | | | 0.1 | | | | 23.9 | | |
| 32 | RHMNLTSTNKYWTSS | 16 | | | | | | | | | |
| 65 | LPTENPTTAKSTNST | 17 | | | | | | 24.0 | | | |
| 71 | PNSTAQHLVYFRRKR | 18 | | | | | | | | 7.5 | |
| 72 | HLVYFRRKRNILWRE | 19 | | | | | 0.3 | | | 8.3 | |
| 89 | GLSWIPFFGPGIEGL | 20 | | | | | | 7.0 | | | |
| 92 | GLIKNQNNLVCRLRR | 21 | | | | | | | | | |
| 93 | NNLVCRLRRLANQTA | 22 | | | | | | | 13.3 | | |
| 97 | TTEERTFSLINRHAI | 23 | 0.1 | | | 0.4 | | | | | |
| 99 | HAIDFLLARWGGTCK | 24 | | | | | | | | 21.8 | |
| 101 | TCKVLGPDCCIGIED | 25 | | | | 0.4 | | | | | |

"Epitope-containing peptides were identified by IFNγ ELISPOT (≥10 SFC/10⁶ splenocytes AND ≥80% response rate) and then confirmed by FACS (≥3 - 5 x 10⁴ CD3+ cells were acquired). Responses for each were further characterized by FACS (expression of CD4 and/or CD8 by CD3+/CD44+/IFNγ+ cells). Predicted CD8+ epitopes are underlined (best consensus % rank by IEDB) and previously-described epitopes are referenced. Immunodominant epitopes are displayed (*).

TABLE 5

Plasmid Vaccine pEBOS
GP sequence SUDV CON

| Peptide Number | Sequence | SEQ ID No: | CD8+ (≤0.5) $D^b$ | $K^b$ | $D^d$ | $K^d$ | $L^d$ | CD4+ (<25) $I-A^b$ | $I-A^d$ | $I-E^d$ | Previously defined (80% Blast; Allele) |
|---|---|---|---|---|---|---|---|---|---|---|---|
| 4 | FFVW<u>VIILFQKAFSM</u> | 26 | 0.4 | | | | | | | | |
| 15 | RWGFRSGVPPKVVSY | 27 | | | | | | 1.2 | | | |
| 19 | YNLEIKKPDGSECLP | 28 | | | | | | | | | |
| 24 | HKAQGTGPCPGDYAF | 29 | | | | | 0.3 | | | | |
| 27 | GAFFLYDRLASTVIY | 30 | | 0.3 | | | | 21.1 | | 23.4 | H-2$^b$ class I |
| 30 | NFAEGVIAFLILAKP | 31 | | | 0.1 | | | | | | |
| 36 | SYYATSYLEYEIENF | 32 | 0.4 | | 0.3 | | 0.1 | | | | |
| 41 | FVLLDRPHTPQFLFQ | 33 | | | | | 0.1 | | | | |
| 78 | NITTAVKTVLPQEST | 34 | | | | | | | 7.2 | | |
| 82 | TGILGSLGLRKRSRR | 35 | | | | | | | | 17.2 | |
| 83 | LGLRKRSRRQVNTRA | 36 | | | | | | | | | |
| 89 | IAWIPYFGPGAEGIY | 37 | | | 0.1 | | | 3.0 | | | |
| 97 | TELRTYTILNRKAID | 38 | 0.1 | | | | | | 18.5 | 21.2 | |
| 101 | CRILGPDCCIEPHDW | 39 | | | | | | | | | |
| 105 | QIIHDFIDNPLPNQD | 40 | 0.3 | | | | | | | | |
| 110 | GIGITGIIAIIALL | 41 | | | | | | | | | |

$^a$Epitope-containing peptides were identified by IFNγ ELISPOT (≥10 SFC/10$^6$ splenocytes AND ≥80% response rate) and then confirmed by FACS (≥3 - 5 x 10$^4$ CD3+ cells were acquired). Responses for each were further characterized by FACS (expression of CD4 and/or CD8 by CD3+/CD44+/IFNγ+ cells). Predicted CD8+ epitopes are underlined (best consensus % rank by IEDB) and previously-described epitopes are referenced. Immunodominant epitopes are displayed (*).

TABLE 6

Plasmid Vaccine pEBOZ
GP sequence ZEBOV CON

| Peptide Number | Sequence | SEQ ID No: | CD8+ (≤0.5) $D^b$ | $K^b$ | $D^d$ | $K^d$ | $L^d$ | CD4+ (<25) $I-A^b$ | $I-A^d$ | $I-E^d$ | Previously defined (80% Blast; Allele) |
|---|---|---|---|---|---|---|---|---|---|---|---|
| 6 | FS<u>IPLGVIHNSTLQV</u> | 42 | | | | | 0.2 | | | | H-2$^d$ class I |
| 15 | RWGFRSGVPPKVVNY | 43 | | | | | | 1.2 | | | H-2$^d$ class I |
| 19 | YNLEIKKPDGSECLP | 44 | | | | | | | | | |
| 24 | HKVSGTGPCAGDFAF | 45 | | | | | 0.1 | 14.9 | | | |
| 27 | GAFFLYDRLASTVIY | 46 | | 0.3 | | | | 21.1 | | 23.4 | |
| 30 | TFAEGVVAFLILPQA | 47 | | | 0.2 | | | | 21.6 | | |
| 32 | PQAKKDFFSSHPLRE | 48 | 0.1 | 0.4 | | | | 16.4 | | | |
| 33 | FFSSHPLREPVNATE | 49 | | | | | | 14.7 | | | |
| 40 | EVDNLTYVQLESRFT | 50 | | | | 0.4 | | | 19.6 | | H-2$^b$ class I |
| 41 | YVQLESRFTPQFLLQ | 51 | | | | | | | | | H-2$^k$ class I |
| 48 | TTIGEWAFWETKKNL | 52 | | | | | | | | 12.9 | |

TABLE 6-continued

Plasmid Vaccine pEBOZ
GP sequence ZEBOV CON

| Peptide Number | Sequence | SEQ ID No: | Best con % rank (IEDB) | | | | | | | | Previously defined (80% Blast; Allele) |
|---|---|---|---|---|---|---|---|---|---|---|---|
| | | | CD8+ (≤0.5) | | | | | CD4+ (<25) | | | |
| | | | $D^b$ | $K^b$ | $D^d$ | $K^d$ | $L^d$ | $I\text{-}A^b$ | $I\text{-}A^d$ | $I\text{-}E^d$ | |
| 49 | AFWETKKNLTRKIRS | 53 | | | | | | | | 22.9 | |
| 50 | KNLTRKIRSEELSFT | 54 | | | | | | | 22.7 | | |
| 60 | SQGREAAVSHLTTLA | 55 | 0.3 | | | | | 23.1 | 3.9 | | |
| 65 | DNSTHNTPVYKLDIS | 56 | | | | | | | | | |
| 66 | TPVYKLDISEATQVE | 57 | | | | | | 22.6 | 5.5 | | |
| 71 | PPATTAAGPPKAENT | 58 | | | | | | 2.1 | | | |
| 84 | TRREAIVNAQPKCNP | 59 | 0.3 | | | | | 14.6 | 7.9 | | |
| 89 | LAWIPYFGPAAEGIY | 60 | | | | 0.1 | | 0.8 | | | |
| 97 | TELRTFSILNRKAID | 61 | 0.1 | | | | | | | 22.2 | |
| 101 | CHILGPDCCIEPHDW | 62 | | | | | | | | | |

"Epitope-containing peptides were identified by IFNγ ELISPOT (≥10 SFC/10^6 splenocytes AND ≥80% response rate) and then confirmed by FACS (≥3 - 5 x 10^4 CD3+ cells were acquired). Responses for each were further characterized by FACS (expression of CD4 and/or CD8 by CD3+/CD44+/IFNγ+ cells). Predicted CD8+ epitopes are underlined (best consensus % rank by IEDB) and previously-described epitopes are referenced. Immunodominant epitopes are displayed (*).

The invention claimed is:

1. An isolated nucleic acid molecule comprising two or more nucleic acid sequences selected from the group consisting of a nucleic acid encoding a first consensus Zaire ebolavirus envelope glycoprotein immunogen (ZE-BOVCON), a nucleic acid encoding a second consensus Zaire ebolavirus envelope glycoprotein immunogen (ZE-BOVCON2), and a nucleic acid encoding a ZEBOV Guinea 2014 Outbreak envelope glycoprotein immunogen (ZE-BOVGUI), wherein the ZEBOVCON is selected from the group consisting of an amino acid sequence of SEQ ID NO: 1, and a fragment comprising at least 600 amino acids of SEQ ID NO:1;

the ZEBOVGUI comprises an amino acid sequence that is at least 95% identical to SEQ ID NO:67, or a fragment of an amino acid sequence that is at least 95% identical to SEQ ID NO:67; and the ZEBOVCON2 is selected from the group consisting of an amino acid sequence of SEQ ID NO:68, and a fragment comprising at least 600 amino acids of SEQ ID NO:68.

2. The isolated nucleic acid molecule of claim 1, wherein the ZEBOVGUI comprises an amino acid sequence that is at least 99% identical to SEQ ID NO: 67, or a fragment of an amino acid sequence that is at least 99% identical to SEQ ID NO: 67.

3. The isolated nucleic acid molecule of claim 1, wherein the ZEBOVGUI comprises an amino acid sequence of SEQ ID NO: 67, or a fragment of SEQ ID NO: 67.

4. The isolated nucleic acid molecule of claim 1, wherein the fragment of SEQ ID NO:1 comprises at least 630 amino acids, or at least 660 amino acids of SEQ ID NO:1.

5. The isolated nucleic acid molecule of claim 1, wherein the fragment of an amino acid sequence that is at least 95% identical to SEQ ID NO:67 comprises at least 600 amino acids, at least 630 amino acids, or at least 660 amino acids.

6. The isolated nucleic acid molecule of claim 1, wherein the fragment of SEQ ID NO:68 comprises at least 630 amino acids, or at least 660 amino acids.

7. The isolated nucleic acid molecule of claim 1, wherein the ZEBOVCON is linked to an IgE signal peptide.

8. The isolated nucleic acid molecule of claim 1, ZEBOVGUI is linked to an IgE signal peptide.

9. The isolated nucleic acid molecule of claim 1, ZEBOVCON2 is linked to an IgE signal peptide.

10. The isolated nucleic acid molecule of claim 1, wherein the nucleic acid encoding ZEBOVGUI comprises a nucleic acid sequence at least 95% identical to SEQ ID NO:69.

11. The isolated nucleic acid molecule of claim 1, wherein the nucleic acid encoding ZEBOVGUI comprises a nucleic acid sequence at least 95% identical to SEQ ID NO:72, or a fragment thereof encoding at least 600 amino acids, at least 630 amino acids, or at least 660 amino acids.

12. The isolated nucleic acid molecule of claim 1, wherein the nucleic acid encoding ZEBOVCON2 comprises a nucleic acid sequence at least 95% identical to SEQ ID NO:70, or a fragment thereof encoding at least 600 amino acids, at least 630 amino acids, or at least 660 amino acids.

13. A composition comprising two or more nucleic acid molecules selected from the group consisting of a nucleic acid molecule encoding a first consensus Zaire ebolavirus envelope glycoprotein immunogen (ZEBOVCON), a nucleic acid molecule encoding a second consensus Zaire ebolavirus envelope glycoprotein immunogen (ZEBOVCON2), and a nucleic acid molecule encoding a ZEBOV Guinea 2014 Outbreak envelope glycoprotein immunogen (ZEBOVGUI), wherein the ZEBOVCON is selected from the group consisting of an amino acid sequence of SEQ ID NO: 1, and a fragment comprising at least 600 amino acids of SEQ ID NO: 1;

the ZEBOVGUI comprises an amino acid sequence that is at least 95% identical to SEQ ID NO:67, or a fragment of an amino acid sequence that is at least 95% identical to SEQ ID NO:67; and the ZEBOVCON2 is selected from the group consisting of an amino acid sequence of SEQ ID NO:68, and a fragment comprising at least 600 amino acids of SEQ ID NO:68.

14. The composition of claim 13, wherein the composition comprises two nucleic acid molecules.

15. The composition of claim 13, wherein the composition comprises three nucleic acid molecules.

16. The isolated nucleic acid molecule of claim 1, wherein the nucleic acid molecule is a plasmid.

17. The composition of claim 13, formulated for delivery to an individual using electroporation.

18. The composition of claim 13, further comprising nucleic acid sequences that encode one or more proteins selected from the group consisting of: IL-12, IL-15 and IL-28.

19. A method of inducing an immune response against an Ebolavirus comprising administering the isolated nucleic acid molecule of claim 1 to an individual in an amount effective to induce an immune response in said individual.

20. A method of inducing an immune response against an Ebolavirus, the method comprising administering the composition of claim 13 to an individual in an amount effective to induce an immune response in said individual.

21. A method of treating a disease associated with Ebolavirus infection in an individual who has been diagnosed with Ebolavirus comprising administering a therapeutically effective amount of the isolated nucleic acid molecule of claim 1 to the individual.

22. A method of treating a disease associated with Ebolavirus infection in an individual who has been diagnosed with Ebolavirus, the method comprising administering a therapeutically effective amount of the composition of claim 13 to the individual.

23. A method of preventing a disease associated with Ebolavirus infection in an individual comprising administering a prophylactically effective amount of the isolated nucleic acid molecule of claim 1 to the individual.

24. A method of preventing a disease associated with Ebolavirus infection in an individual, the method comprising administering a prophylactically effective amount of the composition of claim 13 to the individual.

* * * * *

SEQUENCE LISTING

<160> NUMBER OF SEQ ID NOS: 74

<210> SEQ ID NO 1
<211> LENGTH: 676
<212> TYPE: PRT
<213> ORGANISM: Artificial Sequence
<220> FEATURE:
<223> OTHER INFORMATION: synthetic consensus Zaire ebolavirus
      glycoprotein, pGX4201

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe

-continued

```
            145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
                195                 200                 205
Pro Ser Ser Gly Tyr Tyr Ser Thr Thr Ile Arg Tyr Gln Ala Thr Gly
                210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
                260                 265                 270
Leu Ile Trp Lys Val Asn Pro Glu Ile Asp Thr Thr Ile Gly Glu Trp
                275                 280                 285
Ala Phe Trp Glu Thr Lys Lys Asn Leu Thr Arg Lys Ile Arg Ser Glu
                290                 295                 300
Glu Leu Ser Phe Thr Ala Val Ser Asn Arg Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
                340                 345                 350
Val His Ser Gln Gly Arg Glu Ala Ala Val Ser His Leu Thr Thr Leu
                355                 360                 365
Ala Thr Ile Ser Thr Ser Pro Gln Ser Pro Thr Thr Lys Pro Gly Pro
                370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Pro Ala Thr Thr Ala Ala Gly Pro Pro Lys Ala
                420                 425                 430
Glu Asn Thr Asn Thr Ser Lys Ser Thr Asp Leu Leu Asp Pro Ala Thr
                435                 440                 445
Thr Thr Ser Pro Gln Asn His Ser Glu Thr Ala Gly Asn Asn Asn Thr
                450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
                500                 505                 510
Pro Asn Leu His Tyr Trp Thr Thr Gln Asp Glu Gly Ala Ala Ile Gly
                515                 520                 525
Leu Ala Trp Ile Pro Tyr Phe Gly Pro Ala Ala Glu Gly Ile Tyr Thr
                530                 535                 540
Glu Gly Leu Met His Asn Gln Asp Gly Leu Ile Cys Gly Leu Arg Gln
545                 550                 555                 560
Leu Ala Asn Glu Thr Thr Gln Ala Leu Gln Leu Phe Leu Arg Ala Thr
                565                 570                 575
```

```
Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
            675

<210> SEQ ID NO 2
<211> LENGTH: 676
<212> TYPE: PRT
<213> ORGANISM: Artificial Sequence
<220> FEATURE:
<223> OTHER INFORMATION: synthetic consensus sequence Sudan ebolavirus
      glycoprotein

<400> SEQUENCE: 2

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asn Asn Asn Thr
225                 230                 235                 240

Phe Val Leu Leu Asp Arg Pro His Thr Pro Gln Phe Leu Phe Gln Leu
```

```
                    245                 250                 255
Asn Asp Thr Ile His Leu His Gln Gln Leu Ser Asn Thr Thr Gly Lys
                260                 265                 270

Leu Ile Trp Thr Leu Asp Ala Asn Ile Asn Ala Asp Ile Gly Glu Trp
            275                 280                 285

Ala Phe Trp Glu Asn Lys Lys Asn Leu Ser Glu Gln Leu Arg Gly Glu
        290                 295                 300

Glu Leu Ser Phe Glu Thr Leu Ser Leu Asn Glu Thr Glu Asp Asp
305                 310                 315                 320

Ala Thr Ser Ser Arg Thr Thr Lys Gly Arg Ile Ser Asp Arg Ala Thr
                325                 330                 335

Arg Lys Tyr Ser Asp Leu Val Pro Lys Asp Ser Pro Gly Met Val Ser
                340                 345                 350

Leu His Val Pro Glu Gly Glu Thr Thr Leu Pro Ser Gln Asn Ser Thr
            355                 360                 365

Glu Gly Arg Arg Val Asp Val Asn Thr Gln Glu Thr Ile Thr Glu Thr
        370                 375                 380

Thr Ala Thr Ile Ile Gly Thr Asn Gly Asn Asn Met Gln Ile Ser Thr
385                 390                 395                 400

Ile Gly Thr Gly Leu Ser Ser Ser Gln Ile Leu Ser Ser Ser Pro Thr
                405                 410                 415

Met Ala Pro Ser Pro Glu Thr Gln Thr Ser Thr Thr Tyr Thr Pro Lys
            420                 425                 430

Leu Pro Val Met Thr Thr Glu Glu Pro Thr Thr Pro Arg Asn Ser
        435                 440                 445

Pro Gly Ser Thr Thr Glu Ala Pro Thr Leu Thr Thr Pro Glu Asn Ile
    450                 455                 460

Thr Thr Ala Val Lys Thr Val Leu Pro Gln Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Val Asn Thr Arg Ala Thr Gly Lys Cys Asn
                500                 505                 510

Pro Asn Leu His Tyr Trp Thr Ala Gln Glu Gln His Asn Ala Ala Gly
            515                 520                 525

Ile Ala Trp Ile Pro Tyr Phe Gly Pro Gly Ala Glu Gly Ile Tyr Thr
        530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670
```

Lys Leu Leu Cys
        675

<210> SEQ ID NO 3
<211> LENGTH: 681
<212> TYPE: PRT
<213> ORGANISM: Marburg virus

<400> SEQUENCE: 3

Met Lys Thr Thr Cys Leu Leu Ile Ser Leu Ile Leu Ile Gln Gly Val
1               5                   10                  15

Lys Thr Leu Pro Ile Leu Glu Ile Ala Ser Asn Ile Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Ala Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Thr Leu Gln Glu Tyr Asn Ser Thr Lys Asn Gln
    210                 215                 220

Thr Cys Ala Pro Ser Lys Lys Pro Leu Pro Leu Pro Thr Ala His Pro
225                 230                 235                 240

Glu Val Lys Leu Thr Ser Thr Ser Thr Asp Ala Thr Lys Leu Asn Thr
                245                 250                 255

Thr Asp Pro Asn Ser Asp Asp Glu Asp Leu Thr Thr Ser Gly Ser Gly
            260                 265                 270

Ser Gly Glu Gln Glu Pro Tyr Thr Thr Ser Asp Ala Ala Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Gly Val Val Thr
305                 310                 315                 320

Glu Pro Gly Lys Thr Asn Thr Thr Ala Gln Pro Ser Met Pro Pro His
                325                 330                 335

Asn Thr Thr Thr Ile Ser Thr Asn Asn Thr Ser Lys His Asn Leu Ser
            340                 345                 350

Thr Pro Ser Val Pro Ile Gln Asn Ala Thr Asn Tyr Asn Thr Gln Ser

```
                355                 360                 365
Thr Ala Pro Glu Asn Glu Gln Thr Ser Ala Pro Ser Lys Thr Thr Leu
            370                 375                 380

Leu Pro Thr Glu Asn Pro Thr Thr Ala Lys Ser Thr Asn Ser Thr Lys
385                 390                 395                 400

Ser Pro Thr Thr Thr Val Pro Asn Thr Thr Asn Lys Tyr Ser Thr Ser
                405                 410                 415

Pro Ser Pro Thr Pro Asn Ser Thr Ala Gln His Leu Val Tyr Phe Arg
            420                 425                 430

Arg Lys Arg Asn Ile Leu Trp Arg Glu Gly Asp Met Phe Pro Phe Leu
                435                 440                 445

Asp Gly Leu Ile Asn Ala Pro Ile Asp Phe Asp Pro Val Pro Asn Thr
            450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Lys Val Asn Glu Asn Thr Ala His Ser Gly Glu Asn Glu Asn Asp Cys
            500                 505                 510

Asp Ala Glu Leu Arg Ile Trp Ser Val Gln Glu Asp Asp Leu Ala Ala
                515                 520                 525

Gly Leu Ser Trp Ile Pro Phe Phe Gly Pro Gly Ile Glu Gly Leu Tyr
            530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590

Phe Leu Leu Ala Arg Trp Gly Gly Thr Cys Lys Val Leu Gly Pro Asp
                595                 600                 605

Cys Cys Ile Gly Ile Glu Asp Leu Ser Arg Asn Ile Ser Glu Gln Ile
            610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
                675                 680

<210> SEQ ID NO 4
<211> LENGTH: 681
<212> TYPE: PRT
<213> ORGANISM: Artificial Sequence
<220> FEATURE:
<223> OTHER INFORMATION: synthetic consensus sequence 1 of Marburgvirus
      glycoprotein

<400> SEQUENCE: 4

Met Lys Thr Ile Tyr Phe Leu Ile Ser Leu Ile Leu Ile Gln Ser Ile
1               5                   10                  15

Lys Thr Leu Pro Val Leu Glu Ile Ala Ser Asn Ser Gln Pro Gln Asp
            20                  25                  30
```

```
Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
 50                  55                  60

Glu Ala Ser Lys Arg Trp Ala Phe Arg Thr Gly Val Pro Pro Lys Asn
 65                  70                  75                  80

Val Glu Tyr Thr Glu Gly Glu Ala Lys Thr Cys Tyr Asn Ile Ser
                 85                  90                  95

Val Thr Asp Pro Ser Gly Lys Ser Leu Leu Asp Pro Pro Ser Asn
                100                 105                 110

Ile Arg Asp Tyr Pro Lys Cys Lys Thr Val His His Ile Gln Gly Gln
                115                 120                 125

Asn Pro His Ala Gln Gly Ile Ala Leu His Leu Trp Gly Ala Phe Phe
130                 135                 140

Leu Tyr Asp Arg Val Ala Ser Thr Thr Met Tyr Arg Gly Lys Val Phe
145                 150                 155                 160

Thr Glu Gly Asn Ile Ala Ala Met Ile Val Asn Lys Thr Val His Arg
                165                 170                 175

Met Ile Phe Ser Arg Gln Gly Gln Gly Tyr Arg His Met Asn Leu Thr
                180                 185                 190

Ser Thr Asn Lys Tyr Trp Thr Ser Asn Glu Thr Arg Arg Asn Asp
                195                 200                 205

Thr Gly Cys Phe Gly Ile Leu Gln Glu Tyr Asn Ser Thr Asn Asn Gln
                210                 215                 220

Thr Cys Ser Pro Ser Leu Lys Pro Pro Ser Leu Pro Thr Val Thr Pro
225                 230                 235                 240

Ser Ile His Ser Thr Asn Thr Gln Ile Asn Thr Ala Lys Ser Gly Thr
                245                 250                 255

Met Asn Pro Ser Ser Asp Asp Glu Asp Leu Met Ile Ser Gly Ser Gly
                260                 265                 270

Ser Gly Glu Gln Gly Pro His Thr Thr Leu Asn Val Val Thr Glu Gln
                275                 280                 285

Lys Gln Ser Ser Thr Ile Leu Ser Thr Pro Ser Leu His Pro Ser Thr
290                 295                 300

Ser Gln His Glu Gln Asn Ser Thr Asn Pro Ser Arg His Ala Val Thr
305                 310                 315                 320

Glu His Asn Gly Thr Asp Pro Thr Thr Gln Pro Ala Thr Leu Leu Asn
                325                 330                 335

Asn Thr Asn Thr Thr Pro Thr Tyr Asn Thr Leu Lys Tyr Asn Leu Ser
                340                 345                 350

Thr Pro Ser Pro Pro Thr Arg Asn Ile Thr Asn Asn Asp Thr Gln Arg
                355                 360                 365

Glu Leu Ala Glu Ser Glu Gln Thr Asn Ala Gln Leu Asn Thr Thr Leu
                370                 375                 380

Asp Pro Thr Glu Asn Pro Thr Thr Ala Gln Asp Thr Asn Ser Thr Thr
385                 390                 395                 400

Asn Ile Ile Met Thr Thr Ser Asp Ile Thr Ser Lys His Pro Thr Asn
                405                 410                 415

Ser Ser Pro Asp Ser Ser Pro Thr Thr Arg Pro Pro Ile Tyr Phe Arg
                420                 425                 430

Lys Lys Arg Ser Ile Phe Trp Lys Glu Gly Asp Ile Phe Pro Phe Leu
                435                 440                 445

Asp Gly Leu Ile Asn Thr Glu Ile Asp Phe Asp Pro Ile Pro Asn Thr
```

```
                450               455              460
    Glu Thr Ile Phe Asp Glu Ser Pro Ser Phe Asn Thr Ser Thr Asn Glu
    465                 470                 475                 480

Glu Gln His Thr Pro Pro Asn Ile Ser Leu Thr Phe Ser Tyr Phe Pro
                    485                 490                 495

Asp Lys Asn Gly Asp Thr Ala Tyr Ser Gly Glu Asn Glu Asn Asp Cys
                500                 505                 510

Asp Ala Glu Leu Arg Ile Trp Ser Val Gln Glu Asp Leu Ala Ala
                515                 520                 525

Gly Leu Ser Trp Ile Pro Phe Phe Gly Pro Gly Ile Glu Gly Leu Tyr
                530                 535                 540

Thr Ala Gly Leu Ile Lys Asn Gln Asn Asn Leu Val Cys Arg Leu Arg
    545                 550                 555                 560

Arg Leu Ala Asn Gln Thr Ala Lys Ser Leu Glu Leu Leu Leu Arg Val
                    565                 570                 575

Thr Thr Glu Glu Arg Thr Phe Ser Leu Ile Asn Arg His Ala Ile Asp
                580                 585                 590

Phe Leu Leu Thr Arg Trp Gly Gly Thr Cys Lys Val Leu Gly Pro Asp
                595                 600                 605

Cys Cys Ile Gly Ile Glu Asp Leu Ser Lys Asn Ile Ser Glu Gln Ile
                610                 615                 620

Asp Lys Ile Arg Lys Asp Glu Gln Lys Glu Glu Thr Gly Trp Gly Leu
    625                 630                 635                 640

Gly Gly Lys Trp Trp Thr Ser Asp Trp Gly Val Leu Thr Asn Leu Gly
                    645                 650                 655

Ile Leu Leu Leu Leu Ser Ile Ala Val Leu Ile Ala Leu Ser Cys Ile
                660                 665                 670

Cys Arg Ile Phe Thr Lys Tyr Ile Gly
                675                 680

<210> SEQ ID NO 5
<211> LENGTH: 681
<212> TYPE: PRT
<213> ORGANISM: Artificial Sequence
<220> FEATURE:
<223> OTHER INFORMATION: synthetic consensus sequence 2 of Marburgvirus
      glycoprotein

<400> SEQUENCE: 5

Met Arg Thr Thr Cys Phe Phe Ile Ser Leu Ile Leu Ile Gln Gly Ile
1               5                   10                  15

Lys Thr Leu Pro Ile Leu Glu Ile Ala Ser Asn Asp Gln Pro Gln Asn
                20                  25                  30

Val Asp Ser Val Cys Ser Gly Thr Leu Gln Lys Thr Glu Asp Val His
                35                  40                  45

Leu Met Gly Phe Thr Leu Ser Gly Gln Lys Val Ala Asp Ser Pro Leu
            50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                    85                  90                  95

Val Thr Asp Pro Ser Gly Lys Ser Leu Leu Leu Asp Pro Pro Thr Asn
                100                 105                 110

Val Arg Asp Tyr Pro Lys Cys Lys Thr Ile His His Ile Gln Gly Gln
            115                 120                 125
```

```
Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Asn Gly Thr Gln Thr Asn Asp
        195                 200                 205

Thr Gly Cys Phe Gly Thr Leu Gln Glu Tyr Asn Ser Thr Lys Asn Gln
    210                 215                 220

Thr Cys Ala Pro Ser Lys Thr Pro Pro Pro Thr Ala Arg Pro
225                 230                 235                 240

Glu Ile Lys Pro Thr Ser Thr Pro Thr Asp Ala Thr Arg Leu Asn Thr
                245                 250                 255

Thr Asn Pro Asn Ser Asp Asp Glu Asp Leu Thr Thr Ser Gly Ser Gly
            260                 265                 270

Ser Gly Glu Gln Glu Pro Tyr Thr Thr Ser Asp Ala Val Thr Lys Gln
        275                 280                 285

Gly Leu Ser Ser Thr Met Pro Pro Thr Pro Ser Pro Gln Pro Gly Thr
    290                 295                 300

Pro Gln Gln Gly Gly Asn Asn Thr Asn His Ser Gln Asp Ala Ala Thr
305                 310                 315                 320

Glu Leu Asp Asn Thr Asn Thr Thr Ala Gln Pro Pro Thr Pro Ser His
                325                 330                 335

Asn Thr Thr Thr Ile Ser Thr Asn Asn Thr Ser Lys His Asn Leu Ser
            340                 345                 350

Thr Leu Ser Glu Pro Pro Gln Asn Thr Thr Asn Pro Asn Thr Gln Ser
        355                 360                 365

Met Ala Thr Glu Asn Glu Lys Thr Ser Ala Pro Pro Lys Thr Thr Leu
    370                 375                 380

Pro Pro Thr Glu Ser Pro Thr Thr Glu Lys Ser Thr Asn Asn Thr Lys
385                 390                 395                 400

Ser Pro Thr Thr Met Glu Pro Asn Thr Asn Gly His Phe Thr Ser
                405                 410                 415

Pro Ser Ser Thr Pro Asn Ser Thr Thr Gln His Leu Ile Tyr Phe Arg
            420                 425                 430

Arg Lys Arg Ser Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Gly Ala Ser Ala Glu Glu
465                 470                 475                 480

Asp Gln His Ala Ser Ser Asn Ile Ser Leu Thr Leu Ser Tyr Leu Pro
                485                 490                 495

His Thr Ser Glu Asn Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
```

```
                545                 550                 555                 560
Arg Leu Ala Asn Gln Thr Ala Lys Ser Leu Glu Leu Leu Arg Val
                    565                 570                 575

Thr Thr Glu Glu Arg Thr Phe Ser Leu Ile Asn Arg His Ala Ile Asp
                580                 585                 590

Phe Leu Leu Thr Arg Trp Gly Gly Thr Cys Lys Val Leu Gly Pro Asp
                595                 600                 605

Cys Cys Ile Gly Ile Glu Asp Leu Ser Arg Asn Ile Ser Glu Gln Ile
            610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                    645                 650                 655

Ile Leu Leu Leu Leu Ser Ile Ala Val Leu Ile Ala Leu Ser Cys Ile
                660                 665                 670

Cys Arg Ile Phe Thr Lys Tyr Ile Gly
            675                 680

<210> SEQ ID NO 6
<211> LENGTH: 681
<212> TYPE: PRT
<213> ORGANISM: Artificial Sequence
<220> FEATURE:
<223> OTHER INFORMATION: synthetic consensus sequence 3 of Marburgvirus
      glycoprotein

<400> SEQUENCE: 6

Met Lys Thr Thr Cys Leu Phe Ile Ser Leu Ile Leu Ile Gln Gly Ile
1               5                   10                  15

Lys Thr Leu Pro Ile Leu Glu Ile Ala Ser Asn Asn Gln Pro Gln Asn
                20                  25                  30

Val Asp Ser Val Cys Ser Gly Thr Leu Gln Lys Thr Glu Asp Val His
            35                  40                  45

Leu Met Gly Phe Thr Leu Ser Gly Gln Lys Val Ala Asp Ser Pro Leu
        50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
130                 135                 140

Leu Tyr Asp Arg Ile Ala Ser Thr Thr Met Tyr Arg Gly Arg Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Asn Asn Gly Thr Gln Thr Asn Asp
        195                 200                 205

Thr Gly Cys Phe Gly Ala Leu Gln Glu Tyr Asn Ser Thr Lys Asn Gln
    210                 215                 220
```

```
Thr Cys Ala Pro Ser Lys Ile Pro Ser Pro Leu Pro Thr Ala Arg Pro
225                 230                 235                 240

Glu Ile Lys Pro Thr Ser Thr Pro Thr Asp Ala Thr Lys Leu Asn Thr
                245                 250                 255

Thr Asp Pro Asn Ser Asp Asp Glu Asp Leu Ala Thr Ser Gly Ser Gly
            260                 265                 270

Ser Gly Glu Gln Glu Pro His Thr Thr Ser Asp Ala Val Thr Lys Gln
        275                 280                 285

Gly Leu Ser Ser Thr Met Pro Pro Thr Pro Ser Pro Gln Pro Ser Thr
    290                 295                 300

Pro Gln Gln Glu Gly Asn Asn Thr Asp His Ser Gln Asp Ala Val Thr
305                 310                 315                 320

Glu Pro Asn Lys Thr Asn Thr Thr Ala Gln Pro Ser Met Pro Pro His
                325                 330                 335

Asn Thr Thr Ala Ile Ser Thr Asn Asn Thr Ser Lys His Asn Phe Ser
            340                 345                 350

Thr Leu Ser Ala Pro Leu Gln Asn Thr Thr Asn Tyr Asp Thr Gln Ser
        355                 360                 365

Thr Ala Thr Glu Asn Glu Gln Thr Ser Ala Pro Ser Lys Thr Thr Leu
    370                 375                 380

Pro Pro Thr Gly Asn Leu Thr Thr Ala Lys Ser Thr Asn Asn Thr Lys
385                 390                 395                 400

Gly Pro Thr Thr Thr Ala Pro Asn Met Thr Asn Gly His Leu Thr Ser
                405                 410                 415

Pro Ser Pro Thr Pro Asn Pro Thr Thr Gln His Leu Val Tyr Phe Arg
            420                 425                 430

Lys Lys Arg Ser Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Leu Ala Ala
        515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
                565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Arg Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
```

```
                    645                 650                 655
Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680

<210> SEQ ID NO 7
<211> LENGTH: 15
<212> TYPE: PRT
<213> ORGANISM: Artificial Sequence
<220> FEATURE:
<223> OTHER INFORMATION: Marburg virus epitope fragment 1

<400> SEQUENCE: 7

Ile Gln Gly Val Lys Thr Leu Pro Ile Leu Glu Ile Ala Ser Asn
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Marburg virus epitope fragment 2

<400> SEQUENCE: 8

Ala Ser Asn Ile Gln Pro Gln Asn Val Asp Ser Val Cys Ser Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Marburg virus epitope fragment 3

<400> SEQUENCE: 9

Ser Lys Arg Trp Ala Phe Arg Ala Gly Val Pro Pro Lys Asn Val
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Marburg virus epitope fragment 4

<400> SEQUENCE: 10

Gly Lys Val Phe Thr Glu Gly Asn Ile Ala Ala Met Ile Val Asn
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Marburg virus epitope fragment 5

<400> SEQUENCE: 11

Gly Asn Ile Ala Ala Met Ile Val Asn Lys Thr Val His Lys Met
1               5                   10                  15

<210> SEQ ID NO 12
<211> LENGTH: 15
<212> TYPE: PRT
<213> ORGANISM: Artificial Sequence
<220> FEATURE:
```

-continued

```
<223> OTHER INFORMATION: Marburg virus epitope fragment 6

<400> SEQUENCE: 12

Gly Asn Ile Ala Ala Met Ile Val Asn Lys Thr Val His Lys Met
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Marburg virus epitope fragment 7

<400> SEQUENCE: 13

Ile Val Asn Lys Thr Val His Lys Met Ile Phe Ser Arg Gln Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Marburg virus epitope fragment 8

<400> SEQUENCE: 14

His Lys Met Ile Phe Ser Arg Gln Gly Gln Gly Tyr Arg His Met
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Marburg virus epitope fragment 9

<400> SEQUENCE: 15

Arg Gln Gly Gln Gly Tyr Arg His Met Asn Leu Thr Ser Thr Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Marburg virus epitope fragment 10

<400> SEQUENCE: 16

Arg His Met Asn Leu Thr Ser Thr Asn Lys Tyr Trp Thr Ser Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Marburg virus epitope fragment 11

<400> SEQUENCE: 17

Leu Pro Thr Glu Asn Pro Thr Thr Ala Lys Ser Thr Asn Ser Thr
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Marburg virus epitope fragment 12
```

```
<400> SEQUENCE: 18

Pro Asn Ser Thr Ala Gln His Leu Val Tyr Phe Arg Arg Lys Arg
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Marburg virus epitope fragment 13

<400> SEQUENCE: 19

His Leu Val Tyr Phe Arg Arg Lys Arg Asn Ile Leu Trp Arg Glu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Marburg virus epitope fragment 14

<400> SEQUENCE: 20

Gly Leu Ser Trp Ile Pro Phe Phe Gly Pro Gly Ile Glu Gly Leu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Marburg virus epitope fragment 15

<400> SEQUENCE: 21

Gly Leu Ile Lys Asn Gln Asn Asn Leu Val Cys Arg Leu Arg Arg
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Marburg virus epitope fragment 16

<400> SEQUENCE: 22

Asn Asn Leu Val Cys Arg Leu Arg Arg Leu Ala Asn Gln Thr Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Marburg virus epitope fragment 17

<400> SEQUENCE: 23

Thr Thr Glu Glu Arg Thr Phe Ser Leu Ile Asn Arg His Ala Ile
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Marburg virus epitope fragment 18
```

```
<400> SEQUENCE: 24

His Ala Ile Asp Phe Leu Leu Ala Arg Trp Gly Gly Thr Cys Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Marburg virus epitope fragment 19

<400> SEQUENCE: 25

Thr Cys Lys Val Leu Gly Pro Asp Cys Cys Ile Gly Ile Glu Asp
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Sudan ebolavirus peptide fragment 1

<400> SEQUENCE: 26

Phe Phe Val Trp Val Ile Ile Leu Phe Gln Lys Ala Phe Ser Met
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Sudan ebolavirus peptide fragment 2

<400> SEQUENCE: 27

Arg Trp Gly Phe Arg Ser Gly Val Pro Pro Lys Val Val Ser Tyr
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Sudan ebolavirus peptide fragment 3

<400> SEQUENCE: 28

Tyr Asn Leu Glu Ile Lys Lys Pro Asp Gly Ser Glu Cys Leu Pro
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Sudan ebolavirus peptide fragment 4

<400> SEQUENCE: 29

His Lys Ala Gln Gly Thr Gly Pro Cys Pro Gly Asp Tyr Ala Phe
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Sudan ebolavirus peptide fragment 5

<400> SEQUENCE: 30
```

```
Gly Ala Phe Phe Leu Tyr Asp Arg Leu Ala Ser Thr Val Ile Tyr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Sudan ebolavirus peptide fragment 6

<400> SEQUENCE: 31

Asn Phe Ala Glu Gly Val Ile Ala Phe Leu Ile Leu Ala Lys Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Sudan ebolavirus peptide fragment 7

<400> SEQUENCE: 32

Ser Tyr Tyr Ala Thr Ser Tyr Leu Glu Tyr Glu Ile Glu Asn Phe
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Sudan ebolavirus peptide fragment 8

<400> SEQUENCE: 33

Phe Val Leu Leu Asp Arg Pro His Thr Pro Gln Phe Leu Phe Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Sudan ebolavirus peptide fragment 9

<400> SEQUENCE: 34

Asn Ile Thr Thr Ala Val Lys Thr Val Leu Pro Gln Glu Ser Thr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Sudan ebolavirus peptide fragment 10

<400> SEQUENCE: 35

Thr Gly Ile Leu Gly Ser Leu Gly Leu Arg Lys Arg Ser Arg Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Sudan ebolavirus peptide fragment 11

<400> SEQUENCE: 36
```

Leu Gly Leu Arg Lys Arg Ser Arg Arg Gln Val Asn Thr Arg Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Sudan ebolavirus peptide fragment 12

<400> SEQUENCE: 37

Ile Ala Trp Ile Pro Tyr Phe Gly Pro Gly Ala Glu Gly Ile Tyr
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Sudan ebolavirus peptide fragment 13

<400> SEQUENCE: 38

Thr Glu Leu Arg Thr Tyr Thr Ile Leu Asn Arg Lys Ala Ile Asp
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Sudan ebolavirus peptide fragment 14

<400> SEQUENCE: 39

Cys Arg Ile Leu Gly Pro Asp Cys Cys Ile Glu Pro His Asp Trp
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Sudan ebolavirus peptide fragment 15

<400> SEQUENCE: 40

Gln Ile Ile His Asp Phe Ile Asp Asn Pro Leu Pro Asn Gln Asp
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Sudan ebolavirus peptide fragment 16

<400> SEQUENCE: 41

Gly Ile Gly Ile Thr Gly Ile Ile Ile Ala Ile Ile Ala Leu Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Zaire ebolavirus consensus fragment 1

<400> SEQUENCE: 42

Phe Ser Ile Pro Leu Gly Val Ile His Asn Ser Thr Leu Gln Val

```
                   1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Zaire ebolavirus consensus fragment 2

<400> SEQUENCE: 43

Arg Trp Gly Phe Arg Ser Gly Val Pro Pro Lys Val Val Asn Tyr
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Zaire ebolavirus consensus fragment 3

<400> SEQUENCE: 44

Tyr Asn Leu Glu Ile Lys Lys Pro Asp Gly Ser Glu Cys Leu Pro
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: Zaire ebolavirus consensus fragment 4

<400> SEQUENCE: 45

Gly Ala Phe Phe Leu Tyr Asp Arg Leu Ala Ser Thr Val Ile Tyr
 1               5                  10                  15

<210> SEQ ID NO 46
<211> LENGTH: 15
<212> TYPE: PRT
<213> ORGANISM: Artificial Sequence
<220> FEATURE:
<223> OTHER INFORMATION: Zaire ebolavirus consensus fragment 5

<400> SEQUENCE: 46

Gly Ala Phe Phe Leu Tyr Asp Arg Leu Ala Ser Thr Val Ile Tyr
 1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: Zaire ebolavirus consensus fragment 6

<400> SEQUENCE: 47

Thr Phe Ala Glu Gly Val Val Ala Phe Leu Ile Leu Pro Gln Ala
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: Zaire ebolavirus consensus fragment 7

<400> SEQUENCE: 48

Pro Gln Ala Lys Lys Asp Phe Phe Ser Ser His Pro Leu Arg Glu
 1               5                  10                  15
```

```
<210> SEQ ID NO 49
<211> LENGTH: 15
<212> TYPE: PRT
<213> ORGANISM: Artificial Sequence
<220> FEATURE:
<223> OTHER INFORMATION: Zaire ebolavirus consensus fragment 8

<400> SEQUENCE: 49

Phe Phe Ser Ser His Pro Leu Arg Glu Pro Val Asn Ala Thr Glu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Zaire ebolavirus consensus fragment 9

<400> SEQUENCE: 50

Glu Val Asp Asn Leu Thr Tyr Val Gln Leu Glu Ser Arg Phe Thr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Zaire ebolavirus consensus fragment 10

<400> SEQUENCE: 51

Tyr Val Gln Leu Glu Ser Arg Phe Thr Pro Gln Phe Leu Leu Gln
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Zaire ebolavirus consensus fragment 11

<400> SEQUENCE: 52

Thr Thr Ile Gly Glu Trp Ala Phe Trp Glu Thr Lys Lys Asn Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Zaire ebolavirus consensus fragment 12

<400> SEQUENCE: 53

Ala Phe Trp Glu Thr Lys Lys Asn Leu Thr Arg Lys Ile Arg Ser
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Zaire ebolavirus consensus fragment 13

<400> SEQUENCE: 54

Lys Asn Leu Thr Arg Lys Ile Arg Ser Glu Glu Leu Ser Phe Thr
1               5                   10                  15
```

<210> SEQ ID NO 55
<211> LENGTH: 15
<212> TYPE: PRT
<213> ORGANISM: Artificial Sequence
<220> FEATURE:
<223> OTHER INFORMATION: Zaire ebolavirus consensus fragment 14

<400> SEQUENCE: 55

Ser Gln Gly Arg Glu Ala Ala Val Ser His Leu Thr Thr Leu Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Zaire ebolavirus consensus fragment 15

<400> SEQUENCE: 56

Asp Asn Ser Thr His Asn Thr Pro Val Tyr Lys Leu Asp Ile Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Zaire ebolavirus consensus fragment 16

<400> SEQUENCE: 57

Thr Pro Val Tyr Lys Leu Asp Ile Ser Glu Ala Thr Gln Val Glu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Zaire ebolavirus consensus fragment 17

<400> SEQUENCE: 58

Pro Pro Ala Thr Thr Ala Ala Gly Pro Pro Lys Ala Glu Asn Thr
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Zaire ebolavirus consensus fragment 18

<400> SEQUENCE: 59

Thr Arg Arg Glu Ala Ile Val Asn Ala Gln Pro Lys Cys Asn Pro
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Zaire ebolavirus consensus fragment 19

<400> SEQUENCE: 60

Leu Ala Trp Ile Pro Tyr Phe Gly Pro Ala Ala Glu Gly Ile Tyr
1               5                   10                  15

-continued

```
<210> SEQ ID NO 61
<211> LENGTH: 15
<212> TYPE: PRT
<213> ORGANISM: Artificial Sequence
<220> FEATURE:
<223> OTHER INFORMATION: Zaire ebolavirus consensus fragment 20

<400> SEQUENCE: 61

Thr Glu Leu Arg Thr Phe Ser Ile Leu Asn Arg Lys Ala Ile Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Zaire ebolavirus consensus fragment 21

<400> SEQUENCE: 62

Cys His Ile Leu Gly Pro Asp Cys Cys Ile Glu Pro His Asp Trp
1               5                   10                  15

<210> SEQ ID NO 63
<211> LENGTH: 15
<212> TYPE: PRT
<213> ORGANISM: Human

<400> SEQUENCE: 63

Cys His Ile Leu Gly Pro Asp Cys Cys Ile Glu Pro His Asp Trp
1               5                   10                  15

<210> SEQ ID NO 64
<211> LENGTH: 2034
<212> TYPE: DNA
<213> ORGANISM: Artificial Sequence
<220> FEATURE:
<223> OTHER INFORMATION: synthetic Zaire ebolavirus glycoprotein
      consensus, pGX4201

<400> SEQUENCE: 64
atgggggtca ctgggattct gcagctgcct agagatcgct tcaagcgaac ctctttcttt      60
ctgtgggtca tcattctgtt ccagaggact tttagtatcc ctctgggcgt cattcacaat     120
tctaccctgc aggtgagtga cgtcgataag ctggtgtgtc gggacaaact gagctccacc     180
aaccagctga gatctgtcgg cctgaatctg aggggaacg gagtggctac cgatgtccca     240
agtgcaacaa agagatgggg gtttcgctca ggagtgcccc ctaaagtggt caattacgag     300
gccgggggaat gggctgagaa ttgctataac ctggaaatca gaaacccga cggatcagag     360
tgtctgccag ccgctcccga tgggattcgc ggattcccta atgcagata cgtgcacaag     420
gtcagcggca ccgggccatg tgcaggagac ttcgccttc ataaagaagg cgccttcttt     480
ctgtacgata actggcttc accgtgatc tatagggga ccacattcgc cgagggagtg     540
gtcgcttttc tgattctgcc tcaggccaag aaagacttct tttctagtca tcctctgcgg     600
gaaccagtga acgctaccga ggaccccagc agcggctact attccactac catcagatac     660
caggccacag gattcggcac caatgagaca gaatacctgt tgaagtgga caacctgaca     720
tatgtccagc tggagtctag gttcactccc cagtttctgc tgcagctgaa tgaaactatc     780
tataccagtg gcaagcgctc aaatacaact gggaagctga tttggaaagt gaaccctgag     840
atcgatacca caattggcga atgggccttt tgggagacca gaaaaaacct gacacggaag     900
atcagaagcg aggaactgtc cttcaccgca gtgagtaata gggccaaaaa catttcaggc     960
```

| | |
|---|---|
| cagagcccag cacgaacttc ctctgacccc gggaccaata ctaccacaga agatcacaag | 1020 |
| atcatggcca gcgagaacag ttcagctatg gtgcaggtcc actcccaggg aagggaggca | 1080 |
| gccgtgtctc atctgactac cctggccaca atctctacta gtccccagag ccccacaact | 1140 |
| aagcccgggc ctgacaatag cacccataac acacctgtgt acaaactgga tatctccgaa | 1200 |
| gccacccagg tcgagcagca ccatcggaga acagacaatg attccactgc atctgacacc | 1260 |
| cctccagcaa ccacagctgc aggacccccc aaggctgaga atactaacac cagcaaaagc | 1320 |
| accgacctgc tggaccccgc aactaccaca tcaccacaga accacagcga gacagccggg | 1380 |
| aacaataaca ctcaccatca ggacaccgga gaggaatccg ccagctccgg caagctgggg | 1440 |
| ctgatcacaa atactattgc tggagtggca ggactgatca caggcgggag gcgaactcga | 1500 |
| cgagaagcta ttgtgaacgc acagcccaaa tgcaatccta acctgcacta ttggactacc | 1560 |
| caggacgagg gagcagctat cggactggca tggattccat actttgggcc cgcagccgaa | 1620 |
| ggaatctata ccgagggcct gatgcataat caggatggac tgatctgtgg cctgcggcag | 1680 |
| ctggctaacg aaacaactca ggcactgcag ctgttcctgc gagctaccac agagctgcgg | 1740 |
| acctttagca tcctgaatcg caaggcaatt gacttcctgc tgcagcgatg gggaggcaca | 1800 |
| tgccacatcc tgggaccaga ctgctgtatt gagcctcatg attggacaaa gaacatcact | 1860 |
| gacaaaattg atcagatcat tcacgacttc gtggataaaa cactgccaga tcagggggac | 1920 |
| aatgataact ggtggactgg atggagacag tggattcccg ccggcattgg cgtcaccggc | 1980 |
| gtcattattg ccgtcattgc tctgttctgt atttgtaagt tcgtgttctg ataa | 2034 |

<210> SEQ ID NO 65
<211> LENGTH: 2034
<212> TYPE: DNA
<213> ORGANISM: Artificial Sequence
<220> FEATURE:
<223> OTHER INFORMATION: synthetic Sudan ebolavirus glycoprotein consensus

<400> SEQUENCE: 65

| | |
|---|---|
| atggagggac tgtcactgct gcagctgcct agagataagt tcaggaaaag ctccttcttt | 60 |
| gtgtgggtca tcattctgtt ccagaaggcc ttttcaatgc ccctgggcgt ggtcactaat | 120 |
| agcaccctgg aagtgacaga gatcgatcag ctggtctgta aggaccacct ggcttcaact | 180 |
| gatcagctga aaagcgtggg gctgaacctg gagggatcag cgtcagcac tgatattcct | 240 |
| tctgcaacca gagatgggg atttcgcagc ggagtgcccc taaagtggt ctcctacgaa | 300 |
| gcaggggagt gggccgaaaa ttgctataac ctggagatca agaaaccaga tggcagcgaa | 360 |
| tgtctgccac cccctccaga cggggtgcgc ggattcccca gatgcagata cgtccacaag | 420 |
| gcccagggga ccgaccttg tccaggagac tatgcctttc ataaagatgg cgctttcttt | 480 |
| ctgtacgacc gcctggctag tacagtgatc tatcgaggcg tcaatttcgc cgagggcgtg | 540 |
| atcgcttttc tgattctggc aaagccaaaa gaaaccttcc tgcagagccc tcccattagg | 600 |
| gaggccgtga actacacaga aaacacttct agttactacg ctacatccta cctggagtat | 660 |
| gaaatcgaga actttggcgc tcagcactct accacactgt tcaagattaa caataacacc | 720 |
| tttgtgctgc tggatcgccc tcatacacca cagttcctgt tcagctgaa cgacactatc | 780 |
| cacctgcatc agcagctgag caatactacc ggaaaactga tttggacact ggacgctaat | 840 |
| atcaacgcag atattggcga gtgggccttc tgggaaaata agaaaaacct gtccgagcag | 900 |
| ctgcggggag aggaactgag ctttgaaaca ctgtccctga tgaaactga ggacgatgac | 960 |

```
gccacctcaa gccgaacaac taagggccgg atctctgatc gggctaccag aaagtacagt   1020
gatctggtgc caaaagactc tcccggcatg gtgagtctgc acgtccctga aggggagacc   1080
acactgccat cccagaactc tactgagggc cggagagtgg acgtcaatac ccaggagact   1140
atcaccgaaa ctaccgcaac aatcattggc actaacggga ataacatgca gatcagcacc   1200
attggcacag ggctgtcctc tagtcagatt ctgtcaagct ccctaccat ggcccctcc    1260
cctgagacac agacttctac aacttataca cccaagctgc ctgtgatgac acagaggaa    1320
cccactaccc cacccagaaa cagtcctggg tcaacaactg aggcacccac cctgaccaca   1380
cctgaaaata tcactaccgc cgtgaaaaca gtcctgcctc aggagtctac tagtaacgga   1440
ctgatcacca gcacagtgac tggaattctg ggcagtctgg ggctgcgcaa gcgatcaagg   1500
cgccaagtga atactcgggc taccggcaaa tgcaatccaa acctgcacta ctggaccgca   1560
caggagcagc ataacgccgc tgggatcgct tggattcctt acttcggacc aggcgcagag   1620
gggatctata ccgaaggact gatgcataat cagaacgccc tggtgtgtgg cctgagacag   1680
ctggcaaatg agacaactca ggccctgcag ctgttcctga gcaaccac agaactgagg    1740
acctatacaa tcctgaaccg gaaggccatt gattttctgc tgcgacgatg gggcgggacc   1800
tgcagaatcc tgggaccaga ctgctgtatt gagccccacg attggaccaa gaacatcaca   1860
gacaagatca accagatcat tcatgatttc atcgacaacc cactgcccaa tcaggacaac   1920
gatgacaatt ggtggaccgg atggcgacag tggattcccg caggaattgg aatcaccgga   1980
attattattg ccattattgc tctgctgtgt gtctgtaagc tgctgtgttg ataa          2034
```

<210> SEQ ID NO 66
<211> LENGTH: 2049
<212> TYPE: DNA
<213> ORGANISM: Artificial Sequence
<220> FEATURE:
<223> OTHER INFORMATION: synthetic Marburgvirus glycoprotein consensus
      sequence

<400> SEQUENCE: 66

```
atgaaaacca cttgtctgct gatctcactg attctgattc agggcgtcaa aacactgccc    60
attctggaaa ttgcctctaa catccagcca cagaacgtgg actccgtctg ttctgggacc   120
ctgcagaaga cagaggatgt gcacctgatg ggcttcaccc tgagcgggca gaaggtcgca   180
gactcacccc tggaagccag caaacgatgg gcatttcggg ccggagtgcc ccctaagaac   240
gtcgagtaca ccgaaggcga ggaagccaaa acatgctata atatctccgt gactgatcct   300
agtggcaagt cactgctgct ggacccaccc ccaacacatt gggattaccc taagtgtaaa   360
acaatccacc atattcaggg ccagaatcca cacgctcagg ggatcgcact gcatctgtgg   420
ggagccttct ttctgtacga caggattgct agcaccacaa tgtatcgcgg aaagtgttc    480
accgagggaa acatcgccgc tatgattgtg aataagacag tccacaaaat gatctttct    540
cgccagggcc agggtaccg acatatgaac ctgaccagta caaataagta ttggaccagc    600
tccaacggca ctcagaccaa tgacactggg tgcttcggaa ccctgcagga gtacaacagt   660
actaaaaatc agacctgtgc tccatcaaag aaaccactgc cactgcctac cgcacaccca   720
gaggtgaagc tgacaagtac ttcaaccgac gccacaaaac tgaacactac cgaccccaat   780
agtgacgatg aagatctgac aactagcgga tccggctctg gggagcagga accttatacc   840
acatccgatg cagccaccaa gcagggcctg tctagtacaa tgcctccaac tccatctccc   900
cagcctagta ctccccagca gggcgggaac aataccaacc attcccaggg cgtggtcaca   960
```

-continued

```
gagccaggga agactaacac taccgcccag ccctctatgc cccctcacaa tacaactacc    1020
atctccacca acaatacatc taaacataac ctgagcacac cttccgtgcc aatccagaac    1080
gctactaact acaacactca gtctaccgca cccgagaatg aacagacttc tgcccctagt    1140
aagacaactc tgctgcccac cgagaaccct accacagcca agtcaacaaa tagcactaaa    1200 tccctacta ccacagtgcc aaacactacc aataagtaca gtacctcacc aagccccacc     1260
cctaactcca cagcacagca cctggtctat ttccggagaa aaagaaatat cctgtggagg    1320
gagggcgaca tgttcccttt tctggatggg ctgatcaacg ctccaattga cttcgatcca    1380
gtgcccaata caaagactat ctttgacgaa tcaagctcct ctggcgcctc tgctgaggaa    1440
gatcagcacg cctcacccaa cattagcctg acactgtcct actttcctaa agtgaacgag    1500
aatactgccc atagcgggga gaacgaaaat gactgcgatg ctgagctgcg gatctggagc    1560
gtccaggaag acgatctggc tgcaggactg tcctggatcc cattctttgg acccggcatt    1620
gagggactgt ataccgccgg cctgattaag aaccagaaca acctggtgtg cagactgagg    1680
cgcctggcca atcagaccgc taaatcactg gaactgctgc tgcgggtcac aactgaggaa    1740
agaacattca gcctgatcaa ccgacatgct attgactttc tgctggcacg ctggggaggc    1800
acctgcaagg tgctgggacc agactgctgt atcggcattg aggatctgtc tcgcaatatc    1860
agtgaacaga tcgaccagat taagaaagat gagcagaagg aaggaaccgg atggggactg    1920
ggcggcaagt ggtggaccag cgattggggc gtgctgacaa acctgggaat cctgctgctg    1980
ctgtccatcg ccgtcctgat tgctctgtcc tgtatttgtc ggattttcac taagtatatt    2040
gggtgataa                                                          2049
```

<210> SEQ ID NO 67
<211> LENGTH: 676
<212> TYPE: PRT
<213> ORGANISM: Artificial Sequence
<220> FEATURE:
<223> OTHER INFORMATION: ZEBOV GUI, pGX4202

<400> SEQUENCE: 67

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
```

```
                165                 170                 175
Ala Glu Gly Val Val Ala Phe Leu Ile Leu Pro Gln Ala Lys Lys Asp
                    180                 185                 190

Phe Phe Ser Ser His Pro Leu Arg Glu Pro Val Asn Ala Thr Glu Asp
                195                 200                 205

Pro Ser Ser Gly Tyr Tyr Ser Thr Thr Ile Arg Tyr Gln Ala Thr Gly
            210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
                260                 265                 270

Leu Ile Trp Lys Val Asn Pro Glu Ile Asp Thr Thr Ile Gly Glu Trp
                275                 280                 285

Ala Phe Arg Glu Thr Lys Lys Asn Leu Thr Arg Lys Ile Arg Ser Glu
                290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
                340                 345                 350

Val His Ser Gln Gly Arg Lys Ala Ala Val Ser His Leu Thr Thr Leu
                355                 360                 365

Ala Thr Ile Ser Thr Ser Pro Gln Pro Pro Thr Thr Lys Thr Gly Pro
                370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
                420                 425                 430

Glu Asn Thr Asn Thr Ser Lys Ser Ala Asp Ser Leu Asp Leu Ala Thr
                435                 440                 445

Thr Thr Ser Pro Gln Asn Tyr Ser Glu Thr Ala Gly Asn Asn Asn Thr
                450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
                500                 505                 510

Pro Asn Leu His Tyr Trp Thr Thr Gln Asp Glu Gly Ala Ala Ile Gly
                515                 520                 525

Leu Ala Trp Ile Pro Tyr Phe Gly Pro Ala Ala Glu Gly Ile Tyr Ile
                530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590
```

```
Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
            675

<210> SEQ ID NO 68
<211> LENGTH: 676
<212> TYPE: PRT
<213> ORGANISM: Artificial Sequence
<220> FEATURE:
<223> OTHER INFORMATION: ZEBOV CON2, p

```
Leu Ile Trp Lys Val Asn Pro Glu Ile Asp Thr Thr Ile Gly Glu Trp
            275                 280                 285

Ala Phe Trp Glu Thr Lys Lys Thr Ser Leu Gly Lys Ile Arg Ser Glu
        290                 295                 300

Glu Leu Ser Phe Thr Ala Val Ser Asn Gly Ala Lys Asp Ile Ser Gly
305                 310                 315                 320

Gln Ser Pro Ala Arg Thr Ser Ser Asp Pro Glu Thr Tyr Thr Thr Thr
                325                 330                 335

Glu Asp His Lys Ile Met Ala Ser Glu Asn Ser Ser Thr Met Val Gln
            340                 345                 350

Val His Asn Gln Gly Arg Glu Ala Ala Val Ser His Leu Ile Thr Leu
        355                 360                 365

Ala Thr Ile Ser Thr Ser Pro Gln Ser Pro Thr Thr Lys Pro Gly Gln
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Pro Ala Thr Thr Ala Ala Gly Pro Pro Lys Ala
            420                 425                 430

Glu Asn Ile Asn Thr Ser Lys Ser Ala Asp Ser Leu Asp Pro Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Gly Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675
```

<210> SEQ ID NO 69
<211> LENGTH: 4991
<212> TYPE: DNA
<213> ORGANISM: Artificial Sequence
<220> FEATURE:
<223> OTHER INFORMATION: plasmid pZEBOV-GUI, pGX4202

<400> SEQUENCE: 69

```
gctgcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccgc caccatgggg gtcaccggga ttctgcagct gccaagagat    780
agattcaagc gcacctcctt tttcctgtgg gtcatcatcc tgtttcagag aacctttttct    840
atccccctgg gagtgattca caattcaaca ctgcaggtga gcgacgtcga taagctggtg    900
tgtcgcgaca aactgagctc caccaaccag ctgcgaagcg tcgggctgaa tctggaggga    960
aacggagtgg caaccgatgt cccaagcgca acaaagagat ggggctttag atccggagtg   1020
ccccctaaag tggtcaacta cgaggcaggc gaatgggccg agaattgcta taacctggaa   1080
atcaagaaac ctgacggatc agagtgtctg cccgccgctc ctgatggcat taggggattc   1140
ccaagatgca gatacgtgca caaggtcagc ggcacaggac cctgtgctgg cgacttcgca   1200
tttcataaag aaggagcttt ctttctgtac gatcgactgg caagcaccgt gatctatagg   1260
ggcaccacat tcgccgaggg agtggtcgct tttctgattc tgccccaggc taagaaagac   1320
ttcttttcta gtcacccact gagggaaccc gtgaacgcca cagaggaccc cagcagcggc   1380
tactatagta ctaccatcag ataccaggcc actgggttcg gcactaatga gaccgaatac   1440
ctgtttgaag tggacaacct gacatatgtc cagctggaga gccggttcac tcctcagttt   1500
ctgctgcagc tgaatgaaac catctatgct agcggaaagc gctccaatac aactgggaag   1560
ctgatttgga aagtgaaccc agagatcgat accacaattg gcgaatgggc ctttcgggag   1620
accaagaaaa acctgacacg caagatccga tctgaggaac tgagtttcac cgccgtgagc   1680
aatgggccaa aaaacatttc cggccagtct cctgctagga cttcctctga cccagaaacc   1740
aatactacca acgaggatca caagatcatg gcttccgaga acagttcagc aatggtgcag   1800
gtccacagtc agggcagaaa agcagccgtg tcacatctga caactctggc cacaatctct   1860
actagtcctc agccacccac cacaaagaca gggcccgaca attctaccca taacacacct   1920
gtgtacaaac tggatatcag tgaggccacc caggtcggcc agcaccatag gagagccgac   1980
aatgatagta ctgcttcaga caccccctcca gcaactaccg ctgcaggccc actgaaggcc   2040
gaaaatacaa acacttcaaa aagcgccgac tccctggatc tggctacaac tacctccccc   2100
```

| | |
|---|---|
| cagaactatt ctgagaccgc tggaaacaat aacactcacc atcaggacac cggggaggaa | 2160 |
| tctgcaagct ccgggaagct gggcctgatc accaatacaa ttgctggagt ggcaggactg | 2220 |
| atcacaggag gacgcgaac tcgaagagaa gtgattgtca acgctcagcc taaatgcaat | 2280 |
| ccaaacctgc actactggac aactcaggac gagggagcag ctatcggact ggcatggatt | 2340 |
| ccctacttcg gccctgcagc cgaaggaatc tatattgagg ggctgatgca taatcaggat | 2400 |
| ggactgatct gtgggctgcg gcagctggca acgaaaccca caggccct gcagctgttc | 2460 |
| ctgcgggcaa ctaccgagct gcgcacattt ccatcctga atagaaaggc cattgacttc | 2520 |
| ctgctgcagc gatggggagg aacctgccac atcctgggac cagactgctg tattgagccc | 2580 |
| catgattgga caaagaacat cactgacaaa attgatcaga tcattcacga ctttgtggat | 2640 |
| aagactctgc ctgatcaggg ggacaatgat aactggtgga ccggatggcg acagtggatt | 2700 |
| cccgcaggaa ttggggtgac cggcgtcatc attgccgtga tcgctctgtt ctgcatttgt | 2760 |
| aagttcgtct tttgataact cgagtctaga ggggcccgttt aaacccgctg atcagcctcg | 2820 |
| actgtgcctt ctagttgcca gccatctgtt gtttgcccct ccccgtgcc ttccttgacc | 2880 |
| ctggaaggtg ccactcccac tgtccttttcc taataaaatg aggaaattgc atcgcattgt | 2940 |
| ctgagtaggt gtcattctat tctgggggt ggggtgggc aggacagcaa ggggagat | 3000 |
| tgggaagaca atagcaggca tgctgggat gcggtgggct ctatggcttc tactgggcgg | 3060 |
| ttttatggac agcaagcgaa ccggaattgc cagctgggc gccctctggt aaggttggga | 3120 |
| agccctgcaa agtaaactgg atggctttct tgccgccaag gatctgatgg cgcaggggat | 3180 |
| caagctctga tcaagagaca ggatgaggat cgtttcgcat gattgaacaa gatggattgc | 3240 |
| acgcaggttc tccggccgct tgggtggaga ggctattcgg ctatgactgg gcacaacaga | 3300 |
| caatcggctg ctctgatgcc gccgtgttcc ggctgtcagc gcaggggcgc ccggttcttt | 3360 |
| ttgtcaagac cgacctgtcc ggtgccctga atgaactgca agacgaggca gcgcggctat | 3420 |
| cgtggctggc cacgacgggc gttccttgcg cagctgtgct cgacgttgtc actgaagcgg | 3480 |
| gaagggactg gctgctattg ggcgaagtgc cggggcagga tctcctgtca tctcaccttg | 3540 |
| ctcctgccga gaaagtatcc atcatggctg atgcaatgcg gcggctgcat acgcttgatc | 3600 |
| cggctacctg cccattcgac caccaagcga aacatcgcat cgagcgagca cgtactcgga | 3660 |
| tggaagccgg tcttgtcgat caggatgatc tggacgaaga gcatcagggg ctcgcgccag | 3720 |
| ccgaactgtt cgccaggctc aaggcgagca tgcccgacgg cgaggatctc gtcgtgaccc | 3780 |
| atggcgatgc ctgcttgccg aatatcatgg tggaaaatgg ccgcttttct ggattcatcg | 3840 |
| actgtggccg gctgggtgtg gcggaccgct atcaggacat agcgttggct acccgtgata | 3900 |
| ttgctgaaga gcttggcggc gaatgggctg accgcttcct cgtgctttac ggtatcgccg | 3960 |
| ctcccgattc gcagcgcatc gccttctatc gccttcttga cgagttcttc tgaattatta | 4020 |
| acgcttacaa tttcctgatg cggtattttc tccttacgca tctgtgcggt atttcacacc | 4080 |
| gcatcaggtg gcacttttcg ggaaatgtg cgcggaaccc ctatttgttt attttttctaa | 4140 |
| atacattcaa atatgtatcc gctcatgaga caataaccct gataaatgct tcaataatag | 4200 |
| cacgtgctaa aacttcattt ttaatttaaa aggatctagg tgaagatcct ttttgataat | 4260 |
| ctcatgacca aaatccctta acgtgagttt tcgttccact gagcgtcaga ccccgtagaa | 4320 |
| aagatcaaag gatcttcttg agatcctttt tttctgcgcg taatctgctg cttgcaaaca | 4380 |
| aaaaaaccac cgctaccagc ggtggtttgt ttgccggatc aagagctacc aactcttttt | 4440 |

-continued

| | |
|---|---|
| ccgaaggtaa ctggcttcag cagagcgcag ataccaaata ctgttcttct agtgtagccg | 4500 |
| tagttaggcc accacttcaa gaactctgta gcaccgccta catacctcgc tctgctaatc | 4560 |
| ctgttaccag tggctgctgc cagtggcgat aagtcgtgtc ttaccgggtt ggactcaaga | 4620 |
| cgatagttac cggataaggc gcagcggtcg ggctgaacgg ggggttcgtg cacacagccc | 4680 |
| agcttggagc gaacgaccta caccgaactg agatacctac agcgtgagct atgagaaagc | 4740 |
| gccacgcttc ccgaagggag aaaggcggac aggtatccgg taagcggcag gtcggaaca | 4800 |
| ggagagcgca cgagggagct ccaggggga aacgcctggt atctttatag tcctgtcggg | 4860 |
| tttcgccacc tctgacttga gcgtcgattt tgtgatgct cgtcaggggg gcggagccta | 4920 |
| tggaaaaacg ccagcaacgc ggccttttta cggttcctgg ccttttgctg gccttttgct | 4980 |
| cacatgttct t | 4991 |

<210> SEQ ID NO 70
<211> LENGTH: 2034
<212> TYPE: DNA
<213> ORGANISM: Artificial Sequence
<220> FEATURE:
<223> OTHER INFORMATION: pEBOZ CON2 DNA Coding Sequence, pGX4203

<400> SEQUENCE: 70

| | |
|---|---|
| atggggatta ctgggattct gcagctgccc cgagataggt tcaagcgcac ttcattcttc | 60 |
| ctgtgggtca ttattctgtt tcagagaacc tttagcatcc cctgggagt gattcacaat | 120 |
| tcaacactgc aggtgagcga cgtcgataag ctggtgtgta gagacaaact gagctccacc | 180 |
| aaccagctgc gatccgtcgg cctgaatctg gagggaaacg gggtggccac agatgtccca | 240 |
| agtgctacta gcgctgggg ctttcgatca ggagtgcccc ctaaagtggt caactacgag | 300 |
| gcaggcgaat gggccgagaa ttgctataac ctggaaatca gaaacctga cggcagcgag | 360 |
| tgtctgccag cagctcctga tgggattcgg ggattcccca gatgcagata tgtgcacaag | 420 |
| gtctctggca caggaccttg tgctggcgac ttcgcatttc ataaagaagg agcattctt | 480 |
| ctgtacgatc ggctggccag caccgtgatc tatcgcggca ccacattcgc agaggagtg | 540 |
| gtcgcctttc tgattctgcc tcaggcaaag aaagacttct tttctagtca ccctctgcgc | 600 |
| gaaccagtga atgctacaga ggaccccagc agcggctact atagtactac catccgatac | 660 |
| caggccactg ggttcggcac taatgagacc gaatacctgt ttgaagtgga caacctgact | 720 |
| tatgtccagc tggagagcag gttcaccccc cagtttctgc tgcagctgaa cgaaaccatc | 780 |
| tatgccagcg gaaagagatc caatacaact gggaagctga tttggaaagt gaaccctgag | 840 |
| atcgacacca caattggaga atgggctttt tgggagacaa agaaaacttc tctggggaag | 900 |
| atccggtctg aggaactgag tttcacagct gtgagtaacg gggcaaaaga tatctcagga | 960 |
| cagagcccag cacgaacctc ctctgacccc gaaacataca ctaccacaga ggatcacaag | 1020 |
| atcatggctt cagaaaatag ttcaaccatg gtgcaggtcc acaaccaggg acgagaggca | 1080 |
| gccgtgagcc atctgacac cctggccaca attagcactt ccccacagag ccccactacc | 1140 |
| aagcctggcc aggacaattc cacccataac acaccagtgt ataaactgga tatctctgaa | 1200 |
| gccacacagg tcgagcagca ccataggaga actgacaatg attccactgc atctgacacc | 1260 |
| ccaccagcaa caactgctgc aggacctcca aaggccgaga atatcaacac ttctaaaagt | 1320 |
| gctgacagcc tggaccccgc aaccacaact tccccacaga actactctga gaccgccgga | 1380 |
| aacaataaca cccaccatca ggacacaggg gaagaaagtg ctggatcagg gaagctgggc | 1440 |
| ctgatcacca atacaattgc tggagtggca ggactgatca ctggaggacg acgaacccga | 1500 |

```
agggaagcca ttgtgaacgc tcagcccaaa tgcaatccta acctgcacta ctggaccaca    1560
caggacgagg gagcagctat cggactggca tggattccat acttcggccc cgcagccgaa    1620
ggaatctata cagaggggct gatgcataat caggatggac tgatttgtgg gctgaggcag    1680
ctggccaacg aaactaccca ggctctgcag ctgttcctga gggctacaac tgagctgaga    1740
acctttccca tcctgaatcg aaaggcaatt gacttcctgc tgcagagatg gggaggaaca    1800
tgccacatcc tgggaccaga ctgctgtatt gagcctcatg attggacaaa gaacatcact    1860
gacaaaattg atcagatcat tcacgacttt gtggataaga ctctgccaga tcaggggggac   1920 aatgataact ggtggaccgg ctggagacag tggattcccg ccggcattgg agtgaccggc    1980
gtcatcattg ccgtgatcgc tctgttctgc atttgtaagt tcgtcttttg ataa           2034
```

<210> SEQ ID NO 71
<211> LENGTH: 4991
<212> TYPE: DNA
<213> ORGANISM: Artificial Sequence
<220> FEATURE:
<223> OTHER INFORMATION: plasmid pEBOZ CON2, pGX4203

<400> SEQUENCE: 71

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccgc caccatgggg attactggga ttctgcagct gccccgagat    780
aggttcaagc gcacttcatt cttcctgtgg gtcattattc tgtttcagag aacctttagc    840
atccccctgg gagtgattca caattcaaca ctgcaggtga gcgacgtcga taagctggtg    900
tgtagagaca aactgagctc caccaaccag ctgcgatccg tcggcctgaa tctggaggga    960 aacgggggtgg ccacagatgt cccaagtgct actaagcgct ggggctttcg atcaggagtg   1020
ccccctaaag tggtcaacta cgaggcaggc gaatgggccg agaattgcta taacctggaa   1080
atcaagaaac ctgacggcag cgagtgtctg ccagcagctc ctgatgggat cggggattc     1140 cccagatgca gatatgtgca caaggtctct ggcacaggac cttgtgctgg cgacttcgca   1200
tttcataaag aaggagcatt ctttctgtac gatcggctgg ccagcaccgt gatctatcgc   1260
ggcaccacat tcgcagaggg agtggtcgcc tttctgattc tgcctcaggc aaagaaagac    1320 ttctttttcta gtcaccctct gcgcgaacca gtgaatgcta cagaggaccc cagcagcggc   1380
tactatagta ctaccatccg ataccaggcc actgggttcg gcactaatga gaccgaatac   1440 ctgttttgaag tggacaacct gacttatgtc cagctggaga gcaggttcac ccccagttt   1500
```

```
ctgctgcagc tgaacgaaac catctatgcc agcggaaaga gatccaatac aactgggaag    1560
ctgatttgga aagtgaaccc tgagatcgac accacaattg gagaatgggc tttttgggag    1620
acaaagaaaa cttctctggg gaagatccgg tctgaggaac tgagtttcac agctgtgagt    1680
aacggggcaa aagatatctc aggacagagc ccagcacgaa cctcctctga ccccgaaaca    1740
tacactacca cagaggatca caagatcatg gcttcagaaa atagttcaac catggtgcag    1800
gtccacaacc agggacgaga ggcagccgtg agccatctga tcaccctggc cacaattagc    1860
acttccccac agagcccac taccaagcct ggccaggaca attccaccca taacacacca    1920
gtgtataaac tggatatctc tgaagccaca caggtcgagc agcaccatag gagaactgac    1980
aatgattcca ctgcatctga cacccccacca gcaacaactg ctgcaggacc tccaaaggcc    2040
gagaatatca acacttctaa aagtgctgac agcctggacc ccgcaaccac aacttcccca    2100
cagaactact ctgagaccgc cggaaacaat aacacccacc atcaggacac aggggaagaa    2160
agtgctggat cagggaagct gggcctgatc accaatacaa ttgctggagt ggcaggactg    2220
atcactggag gacgacgaac ccgaagggaa gccattgtga acgctcagcc caaatgcaat    2280
cctaacctgc actactggac cacacaggac gagggagcag ctatcggact ggcatggatt    2340
ccatacttcg gccccgcagc cgaaggaatc tatacagagg ggctgatgca taatcaggat    2400
ggactgattt gtgggctgag gcagctggcc aacgaaacta cccaggctct gcagctgttc    2460
ctgagggcta caactgagct gagaacccttt tccatcctga atcgaaaggc aattgacttc    2520
ctgctgcaga gatggggagg aacatgccac atcctgggac cagactgctg tattgagcct    2580
catgattgga caaagaacat cactgacaaa attgatcaga tcattcacga ctttgtggat    2640
aagactctgc cagatcaggg ggacaatgat aactggtgga ccggctggag acagtggatt    2700
cccgccggca ttggagtgac cggcgtcatc attgccgtga tcgctctgtt ctgcatttgt    2760
aagttcgtct tttgataact cgagtctaga gggcccgttt aaacccgctg atcagcctcg    2820
actgtgcctt ctagttgcca gccatctgtt gtttgcccct cccccgtgcc ttccttgacc    2880
ctggaaggtg ccactcccac tgtcctttcc taataaaatg aggaaattgc atcgcattgt    2940
ctgagtaggt gtcattctat tctggggggt ggggtgggc aggacagcaa ggggaggat    3000 tgggaagaca atagcaggca tgctggggat gcggtgggct ctatggcttc tactgggcgg    3060
ttttatggac agcaagcgaa ccggaattgc cagctgggc gccctctggt aaggttggga    3120
agccctgcaa agtaaactgg atggcttcct tgccgccaag gatctgatgg cgcaggggat    3180
caagctctga tcaagagaca ggatgaggat cgtttcgcat gattgaacaa gatggattgc    3240
acgcaggttc tccggccgct tgggtggaga ggctattcgg ctatgactgg gcacaacaga    3300
caatcggctg ctctgatgcc gccgtgttcc ggctgtcagc gcaggggcgc ccggttcttt    3360
ttgtcaagac cgacctgtcc ggtgccctga atgaactgca agacgaggca gcgcggctat    3420
cgtggctggc cacgacgggc gttccttgcg cagctgtgct cgacgttgtc actgaagcgg    3480
gaagggactg gctgctattg ggcgaagtgc cggggcagga tctcctgtca tctcaccttg    3540
ctcctgccga gaaagtatcc atcatggctg atgcaatgcg gcggctgcat acgcttgatc    3600
cggctacctg cccattcgac caccaagcga aacatcgcat cgagcgagca cgtactcgga    3660
tggaagccgg tcttgtcgat caggatgatc tggacgaaga gcatcagggg ctcgcgccag    3720
ccgaactgtt cgccaggctc aaggcgagca tgcccgacgg cgaggatctc gtcgtgaccc    3780
atggcgatgc ctgcttgccg aatatcatgg tggaaaatgg ccgcttttct ggattcatcg    3840
actgtggccg gctgggtgtg gcggaccgct atcaggacat agcgttggct acccgtgata    3900
```

-continued

```
ttgctgaaga gcttggcggc gaatgggctg accgcttcct cgtgctttac ggtatcgccg   3960
ctcccgattc gcagcgcatc gccttctatc gccttcttga cgagttcttc tgaattatta   4020
acgcttacaa tttcctgatg cggtattttc tccttacgca tctgtgcggt atttcacacc   4080
gcatcaggtg gcacttttcg gggaaatgtg cgcggaaccc ctatttgttt atttttctaa   4140
atacattcaa atatgtatcc gctcatgaga caataaccct gataaatgct tcaataatag   4200
cacgtgctaa aacttcattt ttaatttaaa aggatctagg tgaagatcct ttttgataat   4260
ctcatgacca aaatccctta acgtgagttt tcgttccact gagcgtcaga ccccgtagaa   4320
aagatcaaag gatcttcttg agatcctttt tttctgcgcg taatctgctg cttgcaaaca   4380
aaaaaaccac cgctaccagc ggtggtttgt ttgccggatc aagagctacc aactcttttt   4440
ccgaaggtaa ctggcttcag cagagcgcag ataccaaata ctgttcttct agtgtagccg   4500
tagttaggcc accacttcaa gaactctgta gcaccgccta catacctcgc tctgctaatc   4560
ctgttaccag tggctgctgc cagtggcgat aagtcgtgtc ttaccgggtt ggactcaaga   4620
cgatagttac cggataaggc gcagcggtcg ggctgaacgg ggggttcgtg cacacagccc   4680
agcttggagc gaacgaccta caccgaactg agatacctac agcgtgagct atgagaaagc   4740
gccacgcttc ccgaagggag aaaggcggac aggtatccgg taagcggcag ggtcggaaca   4800
ggagagcgca cgagggagct tccaggggga aacgcctggt atctttatag tcctgtcggg   4860
tttcgccacc tctgacttga gcgtcgattt ttgtgatgct cgtcaggggg gcggagccta   4920
tggaaaaacg ccagcaacgc ggccttttta cggttcctgg ccttttgctg gccttttgct   4980
cacatgttct t                                                        4991
```

<210> SEQ ID NO 72
<211> LENGTH: 2036
<212> TYPE: DNA
<213> ORGANISM: Artificial Sequence
<220> FEATURE:
<223> OTHER INFORMATION: pZEBOV-GUI DNA Coding Sequence, pGX4202

<400> SEQUENCE: 72

```
atgggggtca ccgggattct gcagctgcca agagatagat tcaagcgcac ctccttttc      60 ctgtgggtca tcatcctgtt tcagagaacc ttttctatcc ccctgggagt gattcacaat    120
tcaacactgc aggtgagcga cgtcgataag ctggtgtgtc gcgacaaact gagctccacc    180
aaccagctgc gaagcgtcgg gctgaatctg gagggaaacg gagtggcaac cgatgtccca    240
agcgcaacaa agagatgggg ctttagatcc ggagtgcccc ctaaagtggt caactacgag    300
gcaggcgaat gggccgagaa ttgctataac ctggaaatca agaaacctga cggatcagag    360
tgtctgcccg ccgctcctga tggcattagg ggattcccaa gatgcagata cgtgcacaag    420
gtcagcggca caggaccctg tgctggcgac ttcgcatttc ataaagaagg agctttcttt    480
ctgtacgatc gactggcaag caccgtgatc tataggggca ccacattcgc cgagggagtg    540
gtcgcttttc tgattctgcc ccaggctaag aaagacttct tttctagtca cccactgagg    600
gaacccgtga acgccacaga ggaccccagc agcggctact atagtactac catcagatac    660
caggccactg ggttcggcac taatgagacc gaatacctgt ttgaagtgga caacctgaca    720
tatgtccagc tggagagccg gttcactcct cagtttctgc tgcagctgaa tgaaaccatc    780
tatgctagcg gaaagcgctc caatacaact gggaagctga tttggaaagt gaacccagag    840
atcgatacca caattggcga atgggccttt cgggagacca agaaaaacct gacacgcaag    900
```

-continued

```
atccgatctg aggaactgag tttcaccgcc gtgagcaatg ggccaaaaaa catttccggc    960
cagtctcctg ctaggacttc ctctgaccca gaaaccaata ctaccaacga ggatcacaag   1020
atcatggctt ccgagaacag ttcagcaatg gtgcaggtcc acagtcaggg cagaaaagca   1080
gccgtgtcac atctgacaac tctggccaca atctctacta gtcctcagcc acccaccaca   1140
aagacagggc ccgacaattc tacccataac acacctgtgt acaaactgga tatcagtgag   1200
gccacccagg tcggccagca ccataggaga gccgacaatg atagtactgc ttcagacacc   1260
cctccagcaa ctaccgctgc aggcccactg aaggccgaaa atacaaacac ttcaaaaagc   1320
gccgactccc tggatctggc tacaactacc tcccccaga actattctga gaccgctgga   1380
aacaataaca ctcaccatca ggacaccggg gaggaatctg caagctccgg aagctgggc    1440 ctgatcacca atacaattgc tggagtggca ggactgatca caggaggacg acgaactcga   1500
agagaagtga ttgtcaacgc tcagcctaaa tgcaatccaa acctgcacta ctggacaact   1560
caggacgagg gagcagctat cggactggca tggattccct acttcggccc tgcagccgaa   1620
ggaatctata ttgaggggct gatgcataat caggatggac tgatctgtgg gctgcggcag   1680
ctggcaaacg aaaccacaca ggccctgcag ctgttcctgc gggcaactac cgagctgcgc   1740
acattttcca tcctgaatag aaaggccatt gacttcctgc tgcagcgatg gggaggaacc   1800
tgccacatcc tgggaccaga ctgctgtatt gagccccatg attggacaaa gaacatcact   1860
gacaaaattg atcagatcat tcacgacttt gtggataaga ctctgcctga tcaggggac    1920 aatgataact ggtggaccgg atggcgacag tggattcccg caggaattgg ggtgaccggc   1980
gtcatcattg ccgtgatcgc tctgttctgc atttgtaagt tcgtcttttg ataact       2036
```

<210> SEQ ID NO 73
<211> LENGTH: 25
<212> TYPE: PRT
<213> ORGANISM: Artificial Sequence
<220> FEATURE:
<223> OTHER INFORMATION: Chemically synthesized

<400> SEQUENCE: 73

```
Glu Thr Ile Tyr Thr Ser Gly Lys Arg Ser Asn Thr Thr Gly Lys Leu
1               5                   10                  15

Ile Trp Lys Val Asn Pro Glu Ile Asp
            20                  25
```

<210> SEQ ID NO 74
<211> LENGTH: 25
<212> TYPE: PRT
<213> ORGANISM: Artificial Sequence
<220> FEATURE:
<223> OTHER INFORMATION: Chemically synthesized

<400> SEQUENCE: 74

```
Glu Thr Ile Tyr Ala Ser Gly Lys Arg Ser Asn Thr Thr Gly Lys Leu
1               5                   10                  15

Ile Trp Lys Val Asn Pro Glu Ile Asp
            20                  25
```